(12) United States Patent
Revazova et al.

(10) Patent No.: US 7,732,202 B2
(45) Date of Patent: Jun. 8, 2010

(54) OXYGEN TENSION FOR THE PARTHENOGENIC ACTIVATION OF HUMAN OOCYTES FOR THE PRODUCTION OF HUMAN EMBRYONIC STEM CELLS

(75) Inventors: Elena S. Revazova, Pacific Palisades, CA (US); Marina V. Pryzhkova, Moscow (RU); Leonid N. Kuzmichev, Moscow (RU); Jeffrey D. Janus, Frederick, MD (US)

(73) Assignee: International Stem Cell Corporation, Oceanside, CA (US)

( * ) Notice: Subject to any disclaimer, the term of this patent is extended or adjusted under 35 U.S.C. 154(b) by 452 days.

(21) Appl. No.: 11/505,260

(22) Filed: Aug. 15, 2006

(65) Prior Publication Data

US 2007/0141702 A1    Jun. 21, 2007

Related U.S. Application Data

(60) Provisional application No. 60/733,309, filed on Nov. 2, 2005, provisional application No. 60/758,443, filed on Jan. 11, 2006, provisional application No. 60/813,799, filed on Jun. 14, 2006, provisional application No. 60/729,177, filed on Oct. 21, 2005.

(51) Int. Cl.
*C12N 15/00* (2006.01)
(52) U.S. Cl. .................................. 435/373; 435/325
(58) Field of Classification Search .................. None
See application file for complete search history.

(56) References Cited

U.S. PATENT DOCUMENTS

| | | | |
|---|---|---|---|
| 5,496,720 A | 3/1996 | Susko-Parrish et al. | 435/240.2 |
| 5,843,754 A | 12/1998 | Susko-Parrish et al. | 435/240 |
| 6,077,710 A | 6/2000 | Susko-Parrish et al. | 435/375 |
| 6,194,202 B1 | 2/2001 | Susko-Parrish et al. | 435/325 |
| 6,271,436 B1 | 8/2001 | Piedrahita et al. | 800/21 |
| 6,369,294 B1 | 4/2002 | Piedrahita et al. | 800/14 |
| 6,673,987 B1 | 1/2004 | King | 800/21 |
| 6,680,199 B1 | 1/2004 | Susko-Parrish et al. | 435/375 |

FOREIGN PATENT DOCUMENTS

| | | |
|---|---|---|
| WO | WO 01/30978 A1 | 5/2001 |
| WO | WO 03/046141 A2 | 6/2003 |

OTHER PUBLICATIONS

Rhoton-Vlasak et al. Efficacy of Calcium Ionophore A23187 Oocyte Activation for Generating Parthenotes for Human Embryo Research. Jounal of Assisted Reproduction and Genetics. 1996, vol. 12, pp. 793-796.*
Thomson et al. Embryonic Stem Cell Lines Derived from Human Blastocyts. Science, 1998, vol. 282, pp. 1145-1147.*
Edgar et al. A Quantitative Analysis of the Impact of Cryopreservation on the Implantation Potential of Human Early Cleavage Stage Embryos. Human Reproduction. 2000, vol. 15, pp. 175-179.*
Bichet et al., "Oxygen tension modulates β-globin switching in embryoid bodies", *FASEB J.*, 13:285-295 (1999).
Gassmann et al., "Oxygen supply and oxygen-dependent gene expression in differentiating embryonic stem cells", *Proc. Natl. Acad. Sci. USA.*, Physiology, 93:2867-2872 (1996).
Iwamoto et al., "Low oxygen tension during in vitro maturation of porcine follicular oocytes improves parthenogenetic activation and subsequent development to the blastocyst stage", *Theriogenology*, 63:1277-1289 (2005).
Booth et al., "The Effect of Oxygen Tension on Porcine Embryonic Development Is Dependent on Embryo Type," *Theriogenology* (2005), 63:2040-2052, Elsevier Inc.

* cited by examiner

*Primary Examiner*—Deborah Crouch
(74) *Attorney, Agent, or Firm*—DLA Piper LLP (US)

(57) ABSTRACT

Methods of producing human stem cells are disclosed for parthenogenetically activating human oocytes by manipulation of $O_2$ tension, including manipulation of $Ca^{2+}$ under high $O_2$ tension and contacting oocytes with serine threonine kinase inhibitors under low $O_2$ tension, isolating inner cell masses (ICMs) from the activated oocytes, and culturing the cells of the isolated ICMs under high $O_2$ tension. Moreover, methods are described for the production of stems cells from activated oocytes in the absence of non-human animal products, including the use of human feeder cells/products for culturing ICM/stem cells. Stem cells produced by the disclosed methods are also described.

26 Claims, 18 Drawing Sheets

OXYGEN TENSION FOR THE PARTHENOGENIC ACTIVATION OF HUMAN OOCYTES FOR THE PRODUCTION OF HUMAN EMBRYONIC STEM CELLS

RELATED APPLICATIONS

This application claims benefit of U.S. Provisional Application No. 60/733,309, filed Nov. 2, 2005; U.S. Provisional Application No. 60/758,443, filed Jan. 11, 2006, U.S. Provisional Application No. 60/813,799, filed Jun. 14, 2006, and U.S. Provisional Application No. 60/729,177, filed Oct. 21, 2005, all of which are herein incorporated by reference in their entirety.

BACKGROUND OF THE INVENTION

1. Field of the Invention

The present invention relates generally to embryonic stems cells, and more specifically to a process for obtaining human embryonic stem cells using parthenogenically activated oocytes.

2. Background Information

Human embryonic stem cells (ES) cells are pluripotent cells that can differentiate into a large array of cell types. When injected into immune-deficient mice, embryonic stem cells form differentiated tumors (teratomas). However, embryonic stem cells that are induced in vitro to form embryoid bodies (EBs) provide a source of embryonic stem cell lines that are amenable to differentiation into multiple cell types characteristic of several tissues under certain growth conditions. For example, ES cells become differentiated into neurons in the presence of nerve growth factor and retinoic acid.

Human ES cells and their differentiated progeny are important sources of normal human cells for therapeutic transplantation and for drug testing and development. Required by both of these goals is the provision of sufficient cells that are differentiated into tissue types suitable for a patient's needs or the appropriate pharmacological test. Associated with this is a need for an efficient and reliable method of producing differentiated cells from embryonic stem cells.

Currently, human embryonic stem cells (hES) are derived from three sources: blastocysts remaining after infertility treatments and donated for research, blastocysts generated from donated gametes (oocytes and sperm), and the products of nuclear transfer (NT). Cadaveric fetal tissue is the only source of human embryonic germ cells (hEG). hES and hEG cells offer remarkable scientific and therapeutic possibilities, involving potential for generating more specialized cells or tissues. Ethical concerns about the sources of hES and hEG cells, however, and fears that use of NT for research could lead to use of NT to produce a human being, have fostered a great deal of public discussion and debate.

Parthenogenic activation of mammalian oocytes may be used as an alternative to fertilization by sperm/NT to prepare oocytes for embryonic stem cell generation. Parthenogenic activation is the production of embryonic cells, with or without eventual development into an adult, from a female gamete in the absence of any contribution from a male gamete.

Parthenogenetic activation of mammalian oocytes has been induced in a number of ways. Using an electrical stimulus to induce activation is of particular interest because electrofusion is part of the current nuclear transfer procedure. Parthenogenetic activation in vitro by electrical stimulation with electrofusion apparatus used for embryonic cell-oocyte membrane fusion has been reported.

Mouse oocytes have been activated by exposure to $Ca^{+2}$—$Mg^{+2}$ free medium, medium containing hyaluronidase, exposure to ethanol, $Ca^{+2}$ ionophores or chelators, inhibitors of protein synthesis, and electrical stimulation. These procedures have led to high rates of parthenogenic activation and development of mouse oocytes, but did not activate and/or lead to a lower development rate of young bovine oocytes. Further, fertilization and parthenogenic activation of mouse oocytes is also dependent on post ovulatory aging.

Activation of bovine oocytes has been reported by ethanol, electrical stimulation, exposure to room temperature, and a combination of electrical stimulation and protein inhibition with cycloheximide. While these processes are thought to raise intracellular $Ca^{+2}$, they are most successful when the oocytes have been aged for more than 28 hours.

SUMMARY OF THE INVENTION

The present invention is based on the seminal discovery that certain conditions are optimal for parthenogenically activating human oocytes.

In one embodiment, a method of producing human stem cells is provided including parthenogenetically activating an oocyte, where activation includes contacting the oocyte with an ionophore at high oxygen ($O_2$) tension and contacting the oocyte with a serine-threonine kinase inhibitor under low $O_2$ tension, cultivating the activated oocyte at low $O_2$ tension until blastocyst formation, transferring the blastocyst to a layer of feeder cells, and culturing the transferred blastocyst under high $O_2$ tension, mechanically isolating an inner cell mass (ICM) from trophectoderm of the blastocyst, and culturing the cells of the ICM on a layer of feeder cells, where culturing the ICM cells is carried out under high $O_2$ tension. Preferably, the oocyte is human.

In a related aspect, low $O_2$ tension is maintained by incubation in a gas mixture environment comprising an $O_2$ concentration of about 2% $O_2$ to about 5% $O_2$, where the gas mixture environment further comprises about 5% $CO_2$ and about 90% nitrogen ($N_2$) to 93% $N_2$.

In another embodiment, a method of activating human metaphase II oocytes is provided including incubating human metaphase II oocytes in in vitro fertilization (IVF) media under high $O_2$ tension, activating by incubating the cells in IVF media comprising an ionophore under high $O_2$ tension, and subsequently incubating the cells in IVF media comprising a serine-threonine kinase inhibitor (STKI) under low $O_2$ tension, and incubating the STKI treated cells until blastocyst formation under low $O_2$ tension, where inner cell masses (ICM) obtained from the blastocyst produce culturable stem cells. High $O_2$ tension may be maintained by incubating the cells in a gas mixture environment having about 5% $CO_2$, about 20% $O_2$, and about 75% $N_2$.

In a related aspect, the $O_2$ tension for the incubating steps subsequent to activation is maintained by incubating the cells in a gas mixture environment comprising an $O_2$ concentration of about 2% $O_2$ to about 5% $O_2$, where the gas mixture environment further includes about 5% $CO_2$ and about 90% $N_2$ to about 93% $N_2$.

In another related aspect, the IVF media is essentially free of non-human products.

In a further related aspect, isolated oocytes prepared by the invention methods are provided, including isolated inner cell masses (ICM) prepared from such oocytes and corresponding stem cells isolated therefrom.

In another embodiment, human parthenogenic activation of mammalian oocytes resulting in embryogenic stem cells and their differentiated progeny is provided. Such cells and progeny are substantially isogenic to the oocyte donor, thus allowing for autologous transplantation of cells relative to the oocyte donor, and rejection by the oocyte donor's immune system is typically avoided.

In a related aspect, a cell bank of hES cell lines derived from parthenogenically activated oocytes is provided.

In one embodiment, a method for producing human stem cells from a cryopreserved oocyte or parthenote is provided, including microinjecting into the cytoplasm of the oocyte or parthenote a cryopreservation agent, freezing the oocyte or parthenote to a cryogenic temperature to cause it to enter a dormant state, storing the oocyte or parthenote in the dormant state, thawing the oocyte or parthenote, parthenogenically activating the oocyte, where the activation includes contacting the oocyte with an ionophore at high $O_2$ tension and contacting the oocyte with a serine-threonine kinase inhibitor under low $O_2$ tension, cultivating the parthenote or activated oocyte under low $O_2$ tension until blastocyst formation, isolating an inner cell mass (ICM) from the trophectoderm of the blastocyst, and culturing the cells of the ICM on a layer of feeder cells, where culturing is carried out under high $O_2$ tension.

In another embodiment, autologous stem cells derived from parthenogenetically activated oocytes from a human donor are provided. In one aspect, the stem cells possess a substantially identical haplotype as the donor cell. In a related aspect, stem cells are substantially identical genetically to the donor cell.

In one aspect, a stem cell is identified as a full sibling of the donor according to single nucleotide polymorphism (SNP) markers. In another aspect, a stem cell is genomically imprinted according to donor origin.

In one embodiment, a differentiated cell derived from a stem cell obtained from a parthenogenetically activated oocyte from a human donor is disclosed. In a related aspect, the differentiated cell includes, but is not limited to, a neuronal cell, a cardiac cell, a smooth muscle cell, a striated muscle cell, an endothelial cell, an osteoblast, an oligodendrocyte, a hematopoietic cell, an adipose cell, a stromal cell, a chondrocyte, an astrocyte, a dendritic cell, a keratinocyte, a pancreatic islet, a lymphoid precursor cell, a mast cell, a mesodermal cell, and an endodermal cell. In a further related aspect, the differentiated cell expresses one or more markers, including but not limited to, neurofiliment 68, NCAM, beta III-tubulin, GFAP, alpha-actinin, desmin, PECAM-1, VE-Cadherin, alpha-fetoprotein, or a combination thereof.

In another embodiment, a cell line comprising autologous stem cells is disclosed, where the stem cells are derived from parthenogenetically activated oocytes from a human donor. In one aspect, the cells do not express SSEA-1. In another aspect, the cells of the cell line give rise to ectodermal, mesodermal, and endodermal germ lines.

In one embodiment, a cell bank is disclosed including cryopreserved parthenotes, where the parthenotes are derived from parthenogenetically activated oocytes from one or more human donors. In a related aspect, the parthenotes have been cultivated under low $O_2$ tension until blastocyst formation.

In one embodiment, a cell bank is disclosed including cryopreserved autologous stem cells, where the stem cells are derived from parthenogenetically activated oocytes from one or more human donors.

In another embodiment, a method of treating a subject in need thereof, comprising administering a cellular composition comprising differentiated cells, wherein the differentiated cells are derived from a stem cell obtained from a parthenogenetically activated oocyte from a human donor. In one aspect, the differentiated cell is selected from the group consisting of a neuronal cell, cardiac cell, smooth muscle cell, striated muscle cell, endothelial cell, osteoblast, oligodendrocyte, hematopoietic cell, adipose cell, stromal cell, chondrocyte, astrocyte, dendritic cell, keratinocyte, pancreatic islet, lymphoid precursor cell, mast cell, mesodermal cell, and endodermal cell.

In a related aspect, the subject presents a disease selected from the group consisting of Parkinson's disease, Huntington's disease, Alzheimer's disease, ALS, spinal cord defects or injuries, multiple sclerosis, muscular dystrophy, cystic fibrosis, liver disease, diabetes, heart disease, retinal disease (such as macular degeneration and retinitis pigmentosa), cartilage defects or injuries, burns, foot ulcers, vascular disease, urinary tract disease, AIDS, and cancer.

In one embodiment, a method of generating cloned human embryonic stem cells is disclosed, including removing a first pronuclei from a previously fertilized human oocyte, transferring a second pro-nuclei into the enucleated oocyte, where the second pro-nuclei is derived from a donor oocyte or an oocyte from the mother of the donor, or a parthenogenetically activated oocyte, where the pro-nuclei of the oocyte has been replaced by the nucleus of a donor somatic cell prior to activation, and cultivating the resulting oocyte until blastocyst formation, where an inner cell mass from the blastocyst contains the embryonic stem cells.

Exemplary methods and compositions according to this invention are described in greater detail below.

DETAILED DESCRIPTION OF THE INVENTION

Figure 1A:
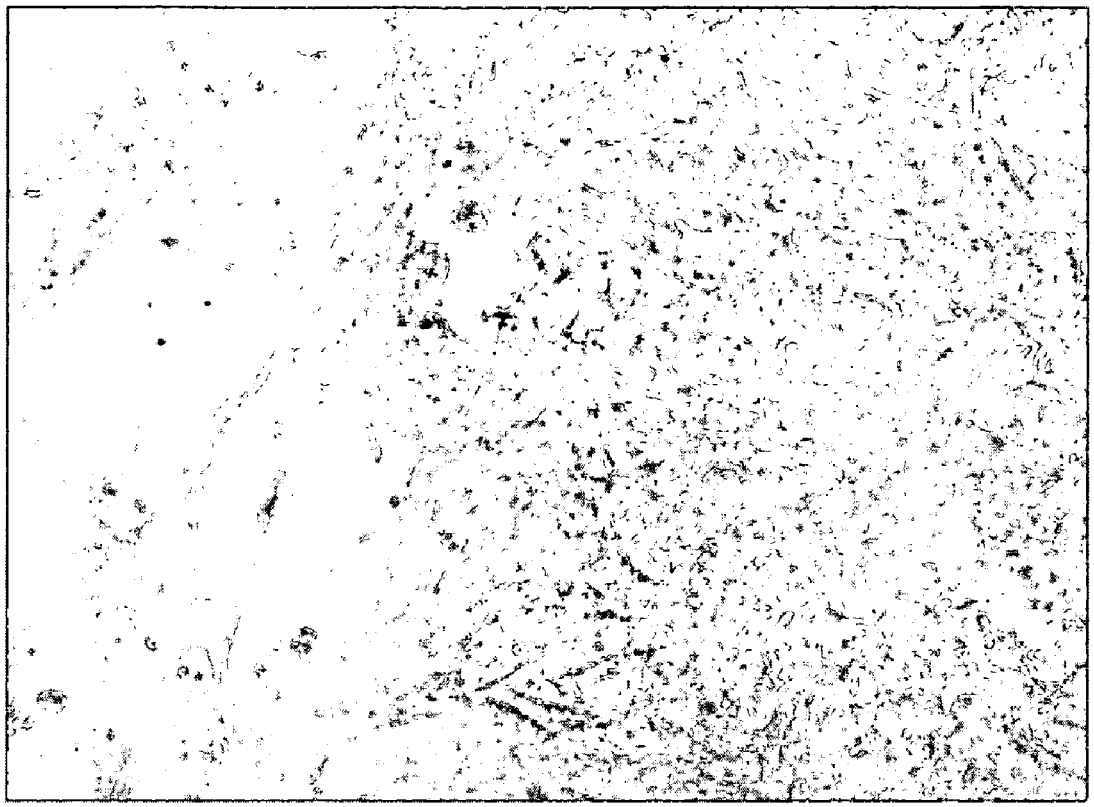
FIG. 1A shows a micrograph of the surface marker expression of alkaline phosphatase for the parthenogenically derived hES cells.

Before the present composition, methods, and culturing methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

"Differentiation" refers to a change that occurs in cells to cause those cells to assume certain specialized functions and to lose the ability to change into certain other specialized functional units. Cells capable of differentiation may be any of totipotent, pluripotent or multipotent cells. Differentiation may be partial or complete with respect to mature adult cells.

Gynogenesis refers to the production of an embryo containing a discernible trophectoderm and inner cell mass that results upon activation of a cell, such as an oocyte, or other embryonic cell type, containing mammalian DNA of all female origin, preferably human female origin, e.g., human or non-human primate oocyte DNA. Such female mammalian DNA may be genetically modified, e.g., by insertion, deletion or substitution of at least one DNA sequence, or may be unmodified. For example, the DNA may be modified by the insertion or deletion of desired coding sequences, or sequences that promote or inhibit embryogenesis. Typically, such an embryo will be obtained by in vitro activation of an oocyte that contains DNA of all female origin. Gynogenesis is inclusive of parthenogenesis which is defined below. It also includes activation methods where the spermatozoal DNA does not contribute to the DNA in the activated oocyte.

In a related aspect, oocytes are obtained from superovulating subjects prepared for IVF. "Superovulation" techniques, such as treatment of a female subject with hormones, used in IVF are designed to stimulate the ovaries to produce several eggs (oocytes) rather than the usual single egg as in a natural cycle.

The medications required to boost egg production may include, but are not limited to the following: Lupron (gonadotropin releasing hormone-agonist), Orgalutran, Antagon or Cetrotide (gonadotropin releasing hormone-antagonist), Follistim, Bravelle or Gonal-F (FSH, follicle stimulating hormone), Repronex (combination of FSH and LH, luteinizing hormone), and Pregnyl or Novarel (hCG, human chorionic gonadotropin).

In a related aspect, collection of eggs can be performed under transvaginal ultrasound guidance. To accomplish this, a needle is inserted (e.g., under IV sedation) through the vaginal wall into the ovaries using ultrasound to locate each follicle. The follicular fluid is drawn up into a test tube to obtain the eggs.

"Parthenogenesis" ("parthenogenically activated" and "parthenogenetically activated" is used interchangeably) the process by which activation of the oocyte occurs in the absence of sperm penetration, and refers to the development of an early stage embryo comprising trophectoderm and inner cell mass that is obtained by activation of an oocyte or embryonic cell, e.g., blastomere, comprising DNA of all female origin. In a related aspect, a "parthenote" refers to the resulting cell obtained by such activation. In another related aspect, "blastocyst" refers to a cleavage stage of a fertilized or activated oocyte comprising a hollow ball of cells made of outer trophoblast cells and an inner cell mass (ICM). In a further related aspect, "blastocyst formation" refers to the process, after oocyte fertilization or activation, where the oocyte is subsequently cultured in media for a time to enable it to develop into a hollow ball of cells made of outer trophoblast cells and ICM (e.g., 5 to 6 days).

In one embodiment, the process of creating cloned human embryonic stem cell line by parthenogenetically activated oocytes is disclosed. While pathogenesis is not an uncommon form of reproduction in nature, mammals are not known to be capable of this form of reproduction. However, a 10% rate of spontaneous parthenogenesis can be found in oocytes from females of the inbred mouse strain LT/Sv (Ozil and Huneau, Development (2001) 128:917-928; Vrana et al., Proc Natl Acad Sci USA (2003) 100(Suppl 1):11911-11916; Berkowitz and Goldstein, New Eng J Med (1996) 335(23):1740-1748). Oocytes from placental mammals can be induced to undergo parthenogenesis in vitro; however, embryonic development is unsuccessful.

Following parthenogenic activation of mammalian oocytes and transfer of the activated oocyte into a surrogate mother, there is limited embryonic survival: ten days in mice; 21 days in sheep; 29 days in pigs; and 11.5 days in rabbits (Kurebayashi et al., Theriogenology (2000) 53:1105-1119; Hagemann et al., Mol Reprod Dev (1998) 50:154-162; Surani and Barton, Science (1983) 222:1034-1036). The reason for this arrested development is likely due to genetic imprinting. It has been shown that maternal and paternal genomes are epigentically different and that both sets are required for successful embryonic development (Surani, Cell (1998) 93:309-312; Sasaki et al., (1992) 6:1843-1856). In parthenotes, all of the genetic material should be of maternal origin, a therefore should lack paternal imprinting. Paternal imprinting is thought to be responsible for extra-embryo tissue development, thus the development of trophoblastic tissue following fertilization of an enucleated oocyte (Stevens, Nature (1978) 276:266-267). In animals, therefore, enucleated zygotes may be useful for nuclear transfer with subsequent parthenogenic activation.

In another embodiment, the nucleus from a donor's somatic cell can be transferred into a fertilized enucleated human oocyte with subsequent parthenogenetic activation. The three embodiments above are illustrated by the following flow diagrams:

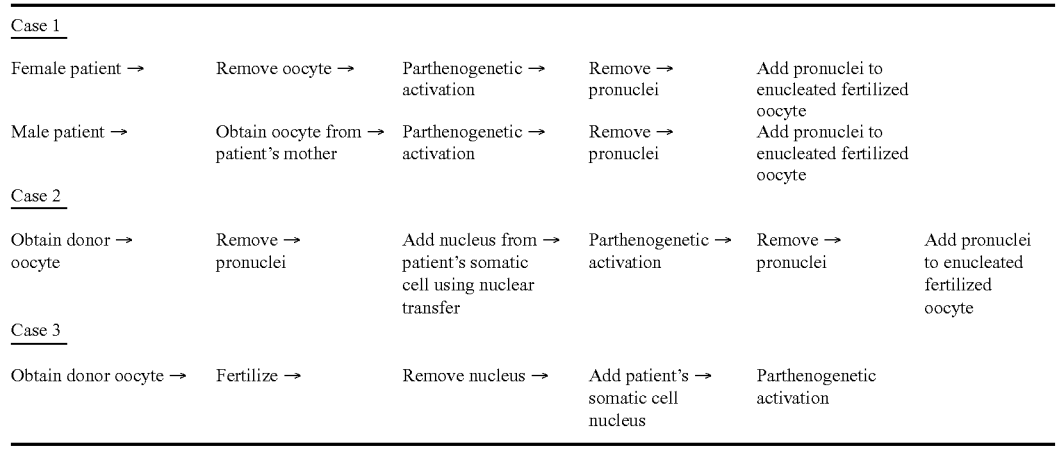

Mammalian parthenotes undergo only limited development with eventual death of the embryo. In Macac fascicularis, only 14 percent of oocytes in stage II metaphase following in vitro Parthenogenetic activation developed to the blastocyst stage following 8 days of culture (Monk, Genes Dev (1988) 2:921-925). Similarly, 12 percent of human oocytes that were parthenogenetically activated in vitro following nuclear transfer developed to the blastocyst state (Monk, 1988). In both cases, one stem cell line was created.

Embryos formed in spontaneously activated parthenotes in virgin females of the LT/Sv inbred mouse strain die within a few days. When nuclear transfer is performed from cells comprising the inner cell mass (ICM) of these embryos into fertilized enucleated C57BL/6j mouse oocytes, cloned mice with the LT/Sv genome are obtained (Kaufman et al., Nature (1977) 265:53-55). Thus, the use of a fertilized oocyte allows for full-term development of a parthenote. In one aspect, a fertilized enucleated human oocyte can be used to support development of a parthenogenetic embryo containing a donor's nuclei until the blastocyst stage.

In one embodiment, the pronuclei of a donor's oocyte or from the oocyte of the mother of a donor, following parthenogenetic activation, can be transferred into a fertilized human oocyte from which the male and female pronuclei have been extracted.

In another embodiment, a two stage process is disclosed for generating human stem cells including transferring the nucleus of a donor's somatic cell into a donor oocyte, where the oocyte is subsequently activated by parthenogenesis and transferring the pronuclei of the activated oocyte into a fertilized oocyte, where the male and female pronuclei have been extracted.

"Pluripotent cell" refers to a cell derived from an embryo produced by activation of a cell containing DNA of all female or male origin that can be maintained in vitro for prolonged, theoretically indefinite period of time in an undifferentiated state, that can give rise to different differentiated tissue types, i.e., ectoderm, mesoderm, and endoderm. The pluripotent state of the cells is preferably maintained by culturing inner cell mass or cells derived from the inner cell mass of an embryo produced by androgenetic or gynogenetic methods under appropriate conditions, for example, by culturing on a fibroblast feeder layer or another feeder layer or culture that includes leukemia inhibitory factor (LIF). The pluripotent state of such cultured cells can be confirmed by various methods, e.g., (i) confirming the expression of markers characteristic of pluripotent cells; (ii) production of chimeric animals that contain cells that express the genotype of the pluripotent cells; (iii) injection of cells into animals, e.g., SCID mice, with the production of different differentiated cell types in vivo; and (iv) observation of the differentiation of the cells (e.g., when cultured in the absence of feeder layer or LIF) into embryoid bodies and other differentiated cell types in vitro.

"Diploid cell" refers to a cell, e.g., an oocyte or blastomere, having a diploid DNA content of all male or female origin.

"Haploid cell" refers to a cell, e.g., an oocyte or blastomere, having a haploid DNA content, where the haploid DNA is of all male or female origin.

Activation refers to a process where a fertilized or unfertilized oocyte, for example, but not limited to, in metaphase II of meiosis, undergoes a process typically including separation of the chromatid pairs, extrusion of the second polar body, resulting in an oocyte having a haploid number of chromosomes, each with one chromatid. Activation includes methods whereby a cell containing DNA of all male or female origin is induced to develop into an embryo that has a discernible inner cell mass and trophectoderm, which is useful for producing pluripotent cells but which is itself is likely to be incapable of developing into a viable offspring. Activation may be carried out, for example, under one of the following conditions: (1) conditions that do not cause second polar body extrusion; (ii) conditions that cause polar body extrusion but where the polar body extrusion is inhibited; or (iii) conditions that inhibit first cell division of the haploid oocyte.

"Metaphase II" refers to a stage of cell development where the DNA content of a cell consists of a haploid number of chromosomes with each chromosome represented by two chromatids.

In one embodiment, metaphase II oocytes are activated by incubating oocytes under various $O_2$ tension gas environments. In a related aspect, the low $O_2$ tension gas environment is created by a gas mixture comprising an $O_2$ concentration of about 2%, 3%, 4%, or 5%. In a further related aspect, the gas mixture comprises about 5% $CO_2$. Further, the gas mixture comprises about 90% $N_2$, 91% $N_2$, or 93% $N_2$. This gas mixture is to be distinguished from 5% $CO_2$ air, which is approximately about 5% $CO_2$, 20% $O_2$, and 75% $N_2$.

"$O_2$ tension" refers to the partial pressure (pressure exerted by a single component of a gas mixture) of oxygen in a fluid (i.e., liquid or gas). Low tension is when the partial pressure of oxygen ($pO_2$) is low and high tension is when the $pO_2$ is high.

"Defined-medium conditions" refer to environments for culturing cells where the concentration of components therein required for optimal growth are detailed. For example, depending on the use of the cells (e.g., therapeutic applications), removing cells from conditions that contain xenogenic proteins is important; i.e., the culture conditions are animal-free conditions or free of non-human animal proteins. In a related aspect, "in vitro fertilization (IVF) media" refers to a nutrient system which contains chemically defined substances on or in which fertilized oocytes can be grown.

"Extracellular matrix (ECM) substrates" refer to a surface beneath cells which supports optimum growth. For example, such ECM substrates include, but are not limited to, Matrigel, laminin, gelatin, and fibronectin substrates. In a related aspect, such substrates may comprise collagen IV, entactin, heparin sulfate proteoglycan, to include various growth factors (e.g., bFGF, epidermal growth factor, insulin-like growth factor-1, platelet derived growth factor, nerve growth factor, and TGF-β-1).

"Embryo" refers to an embryo that results upon activation of a cell, e.g., oocyte or other embryonic cells containing DNA of all male or female origin, which optionally may be modified, that comprises a discernible trophectoderm and inner cell mass, which cannot give rise to a viable offspring and where the DNA is of all male or female origin. The inner cell mass or cells contained therein are useful for the production of pluripotent cells as defined previously.

"Inner cell mass (ICM)" refers to the inner portion of an embryo which gives rise to fetal tissues. Herein, these cells are used to provide a continuous source of pluripotent cells in vitro. Further, the ICM includes the inner portion of the embryo that results from androgenesis or gynogenesis, i.e., embryos that result upon activation of cells containing DNA of all male or female origin. Such DNA, for example, will be human DNA, e.g., human oocyte or spermatozoal DNA, which may or may not have been genetically modified.

"Trophectoderm" refers to another portion of early stage embryo which gives rise to placental tissues, including that tissue of an embryo that results from androgenesis or gynogenesis, i.e., embryos that result from activation of cells that contain DNA of all male or female origin, e.g., human ovarian or spermatozoan.

"Differentiated cell" refers to a non-embryonic cell that possesses a particular differentiated, i.e., non-embryonic, state. The three earliest differentiated cell types are endoderm, mesoderm, and ectoderm.

"Substantially identical" refers to a quality of sameness regarding a particular characteristic that is so close as to be essentially the same within the ability to measure difference (e.g., by HLA typing, SNP analysis, and the like).

"Histocompatible" refers to the extent to which an organism will tolerate a graft of a foreign tissue.

"Genomic imprinting" refers to the mechanism by which a number of genes throughout the genome are monoallelically expressed according to their parental origin.

"Homoplasmy," including grammatical variations thereof, refers to the presence of the same type of the mitochondrial DNA (mtDNA) within a cell or individual.

"Heteroplasmy," including grammatical variations thereof, refers to the presence of a mixture of more than one type of mitochondrial DNA (mtDNA) within a cell or individual.

"Uniparental" refers to one or more cells or individuals from which another arises and to which it remains subsidiary.

"Mechanically isolating" refers to the process of separating cell aggregates by physical forces. For example, such a process would exclude the use of enzymes (or other cell cleavage products) which might contain non-human materials.

In the native environment, immature oocytes (eggs) from the ovary undergo a process of maturation which results in the progression through meiosis to metaphase II of meiosis. The oocytes then arrest at metaphase II. In metaphase II, the DNA content of the cell consists of a haploid number of chromosomes, each represented by two chromatids.

Such oocytes may be maintained indefinitely by cryopreserving by, for example, but not limited to, microinjection with a sugar.

In one embodiment, a method for producing human stem cells from a cryopreserved oocyte or parthenote is provided, including microinjecting into the cytoplasm of the oocyte or parthenote a cryopreservation agent, freezing the oocyte or parthenote to a cryogenic temperature to cause it to enter a dormant state, storing the oocyte or parthenote in the dormant state, thawing the oocyte or parthenote, parthenogenically activating the oocyte under high $O_2$ tension in the presence or an ionophore followed by contacting the oocyte with a serine-threonine kinase inhibitor under low $O_2$ tension, culturing the activated oocyte or parthenote until blastocyst formation, isolating an inner cell mass (ICM) from the blastocyst, and culturing the cells of the ICM on a layer of human feeder cells, where culturing the ICM cells is carried out under high $O_2$ tension.

In one aspect, oocytes obtained as described are transferred to modified, isotonic IVF covered with embryo-tested mineral oil (Sigma), or any other suitable medium. If desired, the oocytes may be incubated with an extracellular sugar at the same concentration as the amount planned for microinjection. For example, to inject 0.1 M sugar, oocytes may be equilibrated in DMEM/F-12 with 0.1 M sugar. In one aspect, the cryopreservation agent comprises a lower $Na^+$ concentration than standard DMEM (i.e., $Na^+$ low media). In a related aspect, the cryopreservation agent comprises a higher $K^+$ concentration than standard DMEM (i.e., $K^+$ high). In a further related aspect, the cryopreservation agent comprises both a lower $Na^+$ and higher $K^+$ concentration than standard DMEM (i.e., $Na^+$ low/$K^+$ high media). In one aspect, the cryopreservation agent comprises an organic buffer, including but not limited to, HEPES. In another aspect, the cryopreservation agent comprises moieties that inhibit apoptotic protein (e.g., capases).

Alternatively, the oocytes may be optionally equilibrated with any other substantially non-permeable solute, such a NaCl, to decrease their cell volume prior to microinjection. This initial decrease in cell volume may result in a smaller final volume of the microinjected oocytes compared to oocytes not incubated in a hypertonic media prior to microinjection. This smaller final volume may minimize any potential adverse effect from the swelling of the oocytes. This general procedure for the preparation of cells for microinjection may also be used for other cell types (e.g., activated oocytes, hES cells, and the like).

The oocytes are then microinjected with a cryopreservation agent. Microinjection equipment and procedures are well characterized in the art and microinjection equipment known for use in injecting small molecules into cells may be used with the invention. In an exemplary microinjection step, oocytes can be microinjected at a pressure of 10 psi for 30 milliseconds. Another example of a standard microinjection technique is the method described by Nakayama and Yanagimachi (Nature Biotech. 16:639-642, 1998).

A cryopreservation agent useful in this process includes any chemical that has cryo-protective properties and is ordinarily non-permeable. In particular, the cryopreservation agent can include sugars either alone or mixed together with other traditional cryopreservation agents. Carbohydrate sugars such as trehalose, sucrose, fructose, and raffinose, may be microinjected to concentrations less than or equal to about 1.0 M, and more preferably, less than or equal to about 0.4 M. In one aspect, the concentration is between 0.05 and 0.20 M, inclusive. Additionally, an extracellular sugar or traditional cryopreservation agent may be added prior to storage. If the cells were incubated in a hypertonic solution prior to microinjection, the substantially non-permeable solute may be allowed to remain in the media after microinjection or may be removed from the media by washing the cells with media containing a lower concentration, or none, of this solute.

Certain sugars or polysaccharides which ordinarily do not permeate cell membranes because they are too large to pass through the membrane have superior physiochemical and biological properties for cryopreservation purposes. While these sugars ordinarily do not permeate cell membranes on their own, using the method as described, these ordinarily non-permeating sugars may be microinjected intracellularly to result in a beneficial effect.

Non-permeating sugars having a stabilizing or preserving effect on cells that are especially useful as the cryopreservation agent in the present method include sucrose, trehalose, fructose, dextran, and raffinose. Among these sugars, trehalose, a non-reducing disaccharide of glucose, has been shown to be exceptionally effective in stabilizing cell structures at low concentrations. The addition of extracellular glycolipids or glycoproteins may also stabilize the cell membrane.

Following the microinjection of the cryopreservation agent, the cells are prepared for storage. A variety of methods for freezing and/or drying may be employed to prepare the cells for storage. In particular, three approaches are described herein: vacuum or air drying, freeze drying, and freeze-thaw protocols. Drying processes have the advantage that the stabilized biological material may be transported and stored at ambient temperatures.

Typically, oocytes loaded with 1 to 2M DMSO are cooled at a very slow cooling rate (0.3 to 0.5° C./min) to an intermediate temperature (−60° C. to −80° C.) before plunging in liquid nitrogen for storage. The sample can then be stored at this temperature.

The suspended material can then be stored at cryopreservation temperatures, for example, by leaving the vials in liquid nitrogen ($LN_2$), for the desired amount of time.

Protocols for vacuum or air drying and for freeze drying proteins are well characterized in the art (Franks et al., "Materials Science and the Production of Shelf-Stable Biologicals," BioPharm, October 1991, p. 39; Shalaev et al., "Changes in the Physical State of Model Mixtures during Freezing and Drying: Impact on Product Quality," Cryobiol. 33, 14-26 (1996)) and such protocols may be used to prepare cell suspensions for storage with the method as described. In addition to air drying, other convective drying methods that may be used to remove water from cell suspensions include the convective flow of nitrogen or other gases.

An exemplary evaporative vacuum drying protocol useful with the method of the invention may include placing 20 μl each into wells on 12 well plates and vacuum drying for 2 hours at ambient temperature. Of course, other drying methods could be used, including drying the cells in vials. Cells prepared in this manner may be stored dry, and rehydrated by diluting in DMEM or any other suitable media.

A method of the invention using freeze drying to prepare the cells for storage begins with freezing the cell suspension. While methods of freezing known in the art may be employed, the simple plunge freezing method described herein for the freeze-thaw method may also be used for the freezing step in the freeze drying protocol.

After freezing, a two stage drying process may be employed. In the first stage, energy of sublimation is added to vaporize frozen water. Secondary drying is performed after the pure crystalline ice in the sample has been sublimated. Freeze dried cells can be stored and hydrated in the same manner as described above for vacuum drying. Viable cells may then be recovered.

After the recovery of cells from a frozen or dried state, any external cryopreservation agent may be optionally removed from the culture media. For example, the media may be diluted by the addition of the corresponding media with a lower concentration of cryopreservation agent. For example, the recovered cells may be incubated for approximately five minutes in media containing a lower concentration of sugar than that used for cell storage. For this incubation, the media may contain the same sugar that was used as the cryopreservation agent; a different cryopreservation agent, such as galactose; or any other substantially non-permeable solute. To minimize any osmotic shock induced by the decrease in the osmolarity of the media, the concentration of the extracellular cryopreservation agent may be slowly decreased by performing this dilution step multiple times, each time with a lower concentration of cryopreservation agent. These dilution steps may be repeated until there is no extracellular cryopreservation agent present or until the concentration of cryopreservation agent or the osmolarity of the media is reduced to a desired level.

The parthenogenetically activated oocytes, blastocysts, ICM, and autologous stem cells can be stored or "banked" in a manner that allows the cells to be revived as needed in the future. An aliquot of the parthenogenetically activated oocytes and autologous stem cells can be removed at any time, to be grown into cultures of many undifferentiated cells and then differentiated into a particular cell type or tissue type, and may then be used to treat a disease or to replace malfunctioning tissues in a subject. Since the cells are parthenogenetically derived from the donor, the cells can be stored so that an individual or close relative can have access to cells for an extended period of time.

In one embodiment, a cell bank is provided for storing parthenogenetically activated oocytes, blastocysts, ICM, and/or autologous stem cell samples. In another embodiment, methods for administering such a cell bank are provided. U.S. Published Patent Application No. 20030215942, which is incorporated by reference herein in its entirety, provides an example of a stem cell bank system.

Using methods such as those described above, the isolation and in vitro propagation of parthenogenetically activated oocytes, blastocysts, ICM, and autologous stem cell samples and their cryopreservation facilitates the establishment of a "bank" of transplantable human stem cells. Because it is possible to store smaller aliquots of cells, the banking procedure could take up a relatively small space. Therefore, the cells of many individuals could be stored or "banked" on a short term or long term basis, with relatively little expense.

In one embodiment, a portion of the sample is made available for testing, either before or after processing and storage.

This invention also provides methods of recording or indexing the parthenogenetically activated oocyte, blastocyst, ICM, and/or autologous stem cell samples so that when a sample needs to be located, it can be easily retrieved. Any indexing and retrieval system can be used to fulfill this purpose. Any suitable type of storage system can be used so that the parthenogenetically activated oocytes, blastocysts, ICM, and/or autologous stem cells can be stored. The samples can be designed to store individual samples, or can be designed to store hundreds, thousands, and even millions of different cell samples.

The stored parthenogenetically activated oocyte, blastocyst, ICM, and/or autologous stem cell samples can be indexed for reliable and accurate retrieval. For example, each sample can be marked with alphanumeric codes, bar codes, or any other method or combinations thereof. There may also be an accessible and readable listing of information enabling identification of each parthenogenetically activated oocyte, blastocyst, ICM, and/or autologous stem cell sample and its location in the bank and enabling identification of the source and/or type the cell sample, which is outside of the bank. This indexing system can be managed in any way known in the art, e.g., manually or non-manually, e.g. a computer and conventional software can be used.

In one embodiment, the cell samples are organized using an indexing system so that the sample will be available for the donor's use whenever needed. In other embodiments, the cell samples can be utilized by individuals related to the original donor. Once recorded into the indexing system, the cell sample can be made available for matching purposes, e.g., a matching program will identify an individual with matching type information and the individual will have the option of being provided the matching sample.

The storage banking system can comprise a system for storing a plurality of records associated with a plurality of individuals and a plurality of cell samples. Each record may contain type information, genotypic information or phenotypic information associated with the cell samples or specific individuals. In one embodiment, the system will include a cross-match table that matches types of the samples with types of individuals who wish to receive a sample.

In one embodiment, the database system stores information for each parthenogenetically activated oocyte, blastocyst, ICM, and/or autologous stem cell sample in the bank. Certain information is stored in association with each sample. The information may be associated with a particular donor, for example, an identification of the donor and the donor's medical history. For example, each sample may be HLA typed and the HLA type information may be stored in association with each sample. The information stored may also be availability information. The information stored with each sample is searchable and identifies the sample in such a way that it can be located and supplied to the client immediately.

Accordingly, embodiments of the invention utilize computer-based systems that contain information such as the donor, date of submission, type of cells submitted, types of cell surface markers present, genetic information relating to the donor, or other pertinent information, and storage details such as maintenance records and the location of the stored samples, and other useful information.

The term "a computer-based system" refers to the hardware, software, and any database used to store, search, and retrieve information about the stored cells. The computer-based system preferably includes the storage media described above, and a processor for accessing and manipulating the data. The hardware of the computer-based systems of this embodiment comprises a central processing unit (CPU) and a database. A skilled artisan can readily appreciate that any one of the currently available computer-based systems are suitable.

In one embodiment, the computer system includes a processor connected to a bus that is connected to a main memory (preferably implemented as RAM) and a variety of secondary storage devices, such as a hard drive and removable medium storage device. The removable medium storage device can represent, for example, a floppy disk drive, a DVD drive, an optical disk drive, a compact disk drive, a magnetic tape drive, etc. A removable storage medium, such as a floppy disk, a compact disk, a magnetic tape, etc. containing control logic and/or data recorded therein can be inserted into the removable storage device. The computer system includes appropriate software for reading the control logic and/or the data from the removable medium storage device once inserted in the removable medium storage device. Information relating to the parthenogenetically activated oocyte, blastocyst, ICM, and/or autologous stem cell can be stored in a well known manner in the main memory, any of the secondary storage devices, and/or a removable storage medium. Software for accessing and processing these data (such as search tools, compare tools, etc.) reside in main memory during execution.

As used herein, "a database" refers to memory that can store any useful information relating to the parthenogenetically activated oocyte and/or autologous stem cell collections and the donors.

The data relating to the stored parthenogenetically activated oocyte, blastocyst, ICM, and/or autologous stem cell can be stored and manipulated in a variety of data processor programs in a variety of formats. For example, the data can be stored as text in a word processing file, such as Microsoft WORD or WORDPERFECT, an ASCII file, an html file, or a pdf file in a variety of database programs familiar to those of skill in the art, such as DB2, SYBASE, or ORACLE.

A "search program" refers to one or more programs that are implemented on the computer-based system to search for details or compare information relating to the cryopreserved samples within a database. A "retrieval program" refers to one or more programs that can be implemented on the computer-based system to identify parameters of interest in the database. For example, a retrieval program can be used to find samples that fit a particular profile, samples having specific markers or DNA sequences, or to find the location of samples corresponding to particular individuals.

There is no upper limit on the number of cell samples that can be stored in one cell bank. In one embodiment, hundreds of products from different individuals will be stored at one bank or storage facility. In another embodiment, up to millions of products may be stored in one storage facility. A single storage facility may be used to store parthenogenetically activated oocyte and/or autologous stem cell samples, or multiple storage facilities may be used.

In some embodiments of the present invention, the storage facility may have a means for any method of organizing and indexing the stored cell samples, such as, for example, automated robotic retrieval mechanisms and cell sample manipulation mechanisms. The facility may include micromanipulation devices for processing cell samples. Known conventional technologies can be used for efficient storage and retrieval of the cell samples. Exemplary technologies include but are not limited to Machine Vision, Robotics, Automated Guided Vehicle System, Automated Storage and Retrieval Systems, Computer Integrated Manufacturing, Computer Aided Process Planning, Statistical Process Control, and the like.

The type information or other information associated with the individual in need of a sample may be recorded into a system that can be used to identify an appropriate matching product, such as, for example, a database system, an indexing system, and the like. Once recorded in the system, a match can be made between the type of the individual and a donor cell sample. In preferred embodiments, the donor sample is from the same individual as the individual in need of the sample. However, similar but not identical donor/recipient matches can also be used. The matching sample is available for the individual possessing the matching type identifier. In one embodiment of this invention, the individual's identification information is stored in connection with the cell sample. In some embodiments, the matching process occurs around the time of harvesting the sample, or can occur at any time during processing, storage, or when a need arises. Accordingly, in some embodiments of the invention, the matching process occurs before the individual is in actual need of the cell sample.

When the parthenogenetically activated oocyte, blastocyst, ICM, and/or autologous stem cell sample is needed by an individual, it may be retrieved and made available for research, transplantation or other purposes within minutes, if desired. The sample may also be further processed to prepare it for transplantation or other needs.

Normally, the oocyte is ovulated at this stage and fertilized by the sperm. The sperm initiates the completion of meiosis in a process called activation. During activation, the pairs of chromatids separate, the second polar body is extruded, and the oocyte retains a haploid number of chromosomes, each with one chromatid. The sperm contributes the other haploid complement of chromosomes to make a full diploid cell with single chromatids. The chromosomes then progress through DNA synthesis during the first cell cycle. These cells then develop into embryos.

By contrast, embryos described herein are developed by artificial activation of cells, typically mammalian oocytes or blastomeres containing DNA of all male or female origin. As discussed in the background of the invention, many methods have been reported in the literature for artificial activation of unfertilized oocytes. Such methods include physical methods, e.g., mechanical methods such as pricking, manipulation or oocytes in culture, thermal methods such as cooling and heating, repeated electric pulses, enzymatic treatments, such as trypsin, pronase, hyaluronidase, osmotic treatments, ionic treatments such as with divalent cations and calcium ionophores, such as ionomycin and A23187, the use of anesthetics such as ether, ethanol, tetracaine, lignocaine, procaine, phenothiazine, tranquilizers such as thioridazine, trifluoperazine, fluphenazine, chlorpromazine, the use of protein synthesis inhibitors such as cycloheximide, puromycin, the use of phosphorylation inhibitors, e.g., protein kinase inhibitors such as staurosporine, 2-aminopurine, sphingosine, and DMAP, combinations thereof, as well as other methods.

Such activation methods are well known in the art and are discussed U.S. Pat. No. 5,945,577, incorporated herein by reference.

In one embodiment, a human cell in metaphase II, typically an oocyte or blastomere comprising DNA of all male or female origin, is artificially activated for effecting artificial activation of oocytes.

In a related aspect, the activated cell, e.g., oocyte, which is diploid, is allowed to develop into an embryo that comprises a trophectoderm and an inner cell mass. This can be effected using known methods and culture media that facilitate blastocyst development.

After the gynogenetic embryos have been cultured to produce a discernable trophectoderm and inner cell mass, the cells of the inner cell mass are then used to produce the desired pluripotent cell lines. This can be accomplished by transferring cells derived from the inner cell mass or the entire inner cell mass onto a culture that inhibits differentiation. This can be effected by transferring the inner cell mass cells onto a feeder layer that inhibits differentiation, e.g., fibroblasts or epithelial cells, such as fibroblasts derived from postnatal human tissues, etc., or other cells that produce LIF. Other factors/components may be employed to provide appropriate culture conditions for maintaining cells in the undifferentiated state including, but not limited to, addition of conditioned media (Amit et al., Developmental Biol (2000) 227:271-278), bFGF and TGF-$\beta$1 (with or without LIF) (Amit et al., Biol Reprod (2004) 70:837-845), factors which activate the gp130/STAT3 pathway (Hoffman and Carpenter, Nature Biotech (2005) 23(6):699-708), factors which activate the PI3K/Akt, PKB pathway (Kim et al., FEBS Lett (2005) 579:534-540), factors that are members of the bone morphogenetic protein (BMP) super family (Hoffman and Carpenter (2005), supra), and factors which activate the canonical/$\beta$-catenin Wnt signaling pathway (e.g., GSK-3-specific inhibitor; Sato et al., Nat Med (2004) 10:55-63). In a related aspect, such factors may comprise culture conditions that include feeder cells and/or ECM substrates (Hoffman and Carpenter (2005), supra).

In one aspect, the inner cell mass cells are cultured on human postnatal foreskin or dermal fibroblast cells or other cells which produce leukemia inhibitory factor, or in the presence of leukemia inhibitory factor. In a related aspect, feeder cells are inactivated prior to seeding with the ICM. For example, the feeder cells can be mitotically inactivated using an antibiotic. In a related aspect, the antibiotic can be, but is not limited to, mitomycin C.

Culturing will be effected under conditions that maintain the cells in an undifferentiated, pluripotent state, for prolonged periods, theoretically indefinitely. In one embodiment, oocytes are parthenogenically activated with calcium ionophores under high $O_2$ tension followed by contacting the oocytes with a serine-threonine kinase inhibitor under low $O_2$ tension. The resulting ICM from the parthenogenically activated oocytes is cultured under high $O_2$ tension, where the cells, for example, are maintained using a gas mixture comprising 20% $O_2$. In one aspect, culturable refers to being capable of, or fit for, being cultivated. In a related aspect, ICM isolation is carried out mechanically after four days of blastocyst cultivation, where the cultivation is carried out on feeder cells. Such cultivation, for example, eliminates the need to use materials derived from animal sources, as would be the case for immunosurgery.

In a related aspect, culture media for the ICM is supplemented with non-animal sera, including but not limited to, human umbilical cord serum, where the serum is present in defined media (e.g., IVF, available from MediCult A/S, Denmark; Vitrolife, Sweden; or Zander IVF, Inc., Vero Beach, Fla.). In another aspect, the media and processes as provided are free of animal products. In a related aspect, animal products are those products, including serum, interferons, chemokines, cytokines, hormones, and growth factors, that are from non-human sources.

The pluripotent state of the cells produced by the present invention can be confirmed by various methods. For example, the cells can be tested for the presence or absence of characteristic ES cell markers. In the case of human ES cells, examples of such markers are identified supra, and include SSEA-4, SSEA-3, TRA-1-60, TRA-1-81 and OCT 4, and are known in the art.

Also, pluripotency can be confirmed by injecting the cells into a suitable animal, e.g., a SCID mouse, and observing the production of differentiated cells and tissues. Still another method of confirming pluripotency is using the subject pluripotent cells to generate chimeric animals and observing the contribution of the introduced cells to different cell types. Methods for producing chimeric animals are well known in the art and are described in U.S. Pat. No. 6,642,433, incorporated by reference herein.

Yet another method of confirming pluripotency is to observe ES cell differentiation into embryoid bodies and other differentiated cell types when cultured under conditions that favor differentiation (e.g., removal of fibroblast feeder layers). This method has been utilized and has been confirmed that the subject pluripotent cells give rise to embryoid bodies and different differentiated cell types in tissue culture.

The resultant pluripotent cells and cell lines, preferably human pluripotent cells and cell lines, which are derived from DNA of entirely female original, have numerous therapeutic and diagnostic applications. Such pluripotent cells may be used for cell transplantation therapies or gene therapy (if genetically modified) in the treatment of numerous disease conditions.

In this regard, it is known that mouse embryonic stem (ES) cells are capable of differentiating into almost any cell type. Therefore, human pluripotent (ES) cells produced according to the invention should possess similar differentiation capacity. The pluripotent cells according to the invention will be induced to differentiate to obtain the desired cell types according to known methods. For example, human ES cells produced according to the invention may be induced to differentiate into hematopoietic stem cells, muscle cells, cardiac muscle cells, liver cells, islet cells, retinal cells, cartilage cells, epithelial cells, urinary tract cells, etc., by culturing such cells in differentiation medium and under conditions which provide for cell differentiation. Medium and methods which result in the differentiation of ES cells are known in the art as are suitable culturing conditions.

For example, Palacios et al, Proc. Natl. Acad. Sci., USA, 92:7530-7537 (1995) teach the production of hematopoietic stem cells from an embryonic cell line by subjecting stem cells to an induction procedure comprising initially culturing aggregates of such cells in a suspension culture medium lacking retinoic acid followed by culturing in the same medium containing retinoic acid, followed by transferal of cell aggregates to a substrate which provides for cell attachment.

Moreover, Pedersen, J. Reprod. Fertil. Dev., 6:543-552 (1994) is a review article which references numerous articles disclosing methods for in vitro differentiation of embryonic stem cells to produce various differentiated cell types including hematopoietic cells, muscle, cardiac muscle, nerve cells, among others.

Further, Bain et al, Dev. Biol., 168:342-357 (1995) teach in vitro differentiation of embryonic stem cells to produce neural cells which possess neuronal properties. These references are exemplary of reported methods for obtaining differentiated cells from embryonic or stem cells. These references and in particular the disclosures therein relating to methods for differentiating embryonic stem cells are incorporated by reference in their entirety herein. Thus, using known methods and culture medium, one skilled in the art may culture the subject ES cells, including genetically engineered or transgenic ES cells, to obtain desired differentiated cell types, e.g., neural cells, muscle cells, hematopoietic cells, etc. Pluripotent cells produced by the methods described herein may be used to obtain any desired differentiated cell type. Therapeutic usages of differentiated human cells are unparalleled. For example, human hematopoietic stem cells may be used in medical treatments requiring bone marrow transplantation. Such procedures are used to treat many diseases, e.g., late stage cancers such as ovarian cancer and leukemia, as well as diseases that compromise the immune system, such as AIDS. Hematopoietic stem cells can be obtained, e.g., by incorporating male or female DNA derived from a male or female cancer or AIDS patient with an enucleated oocyte, obtaining pluripotent cells as described above, and culturing such cells under conditions which favor differentiation, until hematopoietic stem cells are obtained. Such hematopoietic cells may be used in the treatment of diseases including cancer and AIDS.

Alternatively, the subject pluripotent cells may be used to treat a patient with a neurological disorder by culturing such cells under differentiation conditions that produce neural cell lines. Specific diseases treatable by transplantation of such human neural cells include, by way of example, Parkinson's disease, Alzheimer's disease, ALS and cerebral palsy, among others. In the specific case of Parkinson's disease, it has been demonstrated that transplanted fetal brain neural cells make the proper connections with surrounding cells and produce dopamine. This can result in long-term reversal of Parkinson's disease symptoms. In a related aspect, nerve precursors can be used to reanneal severed/damaged nerve fibers to restore movement after hand, leg, and spinal cord injuries.

One object of the subject invention is that it provides an essentially limitless supply of pluripotent, human cells that can be used to produce differentiated cells suitable for autologous transplantation for the oocyte donor. Human embryonic stem cells and their differentiated progeny derived from blastocysts remaining after infertility treatments, or created using NT, will likely be rejected by a recipient's immune system when used in allogenic cell transplantation therapy. Parthenogenically derived stem cells should result in differentiated cells that could alleviate the significant problem associated with current transplantation methods, i.e., rejection of the transplanted tissue which may occur because of host-vs-graft or graft-vs-host rejection relative to the oocyte donor. Conventionally, rejection is prevented or reduced by the administration of anti-rejection drugs such as cyclosporin. However, such drugs have significant adverse side-effects, e.g., immunosuppression, carcinogenic properties, as well as being very expensive. Cells produced by the methods as disclosed should eliminate, or at least greatly reduce, the need for anti-rejection drugs relative to the oocyte donor.

Another object of the subject invention is that it provides an essentially limitless supply of pluripotent, human cells that can be used to produce differentiated cells suitable for allogenic transplantation to members of the oocyte donor's family (e.g., siblings). The cells will be immunologically and genetically similar to those of the oocytes donor's direct family members and thus less likely to be rejected by the donor's family members.

Another object of this method is that parthenogenic activation of mammalian oocytes is a relatively simple procedure when compared to SCNT and results in the creation of stem cells with less cell manipulation.

Parthenogenic activation of mammalian oocytes has shown to be more efficient in the creation of stem cells than methods requiring mechanical manipulation of the oocyte (e.g., SCNT).

One drawback of SCNT is that subjects with deficient mitochondrial respiratory chain activity present phenotypes with striking similarities to abnormalities commonly encountered in SCNT fetuses and offspring (Hiendleder et al, Repro Fertil Dev (2005) 17(1-2):69-83). Cells normally contain only one type of mitochondrial DNA (mtDNA), termed homoplasmy, however, heteroplasmy does exist, usually as a combination of mutant and wild-type mt DNA molecules or form a combination of wild-type variants (Spikings et al., Hum Repro Update (2006) 12(4):401-415). As heteroplasmy can result in mitochondrial disease, various mechanisms exist to ensure maternal-only transmission. However, with the increasing use of protocols which bypass normal mechanisms for homoplasmy maintenance (e.g., cytoplasmic transfer (CT) and SCNT), perturbed mitochondrial function may be intrinsic to stem cells derived from these sources.

In one aspect, as the parthenotes are uniparental, the possibility of heteroplasmy is minimized.

Other diseases and conditions treatable by cell therapy include, by way of example, spinal cord injuries, multiple sclerosis, muscular dystrophy, diabetes, liver diseases Including acute diseases (viral hepatitis, drug overdoses (acetaminophen) and others), chronic diseases (chronic hepatitis and others (generally leading to cirrhosis)), heritable liver defects (hemophilia B, factor IX deficiency, bulirubin metabolism defects, urea cycle defects, lysosomal storage disease, a1-antitrypsin deficiency and others), heart diseases, cartilage replacement, burns, foot ulcers, gastrointestinal diseases, vascular diseases, kidney disease, retinal disease, urinary tract disease, and aging related diseases and conditions.

This methodology can be used to replace defective genes, e.g., defective immune system genes, cystic fibrosis genes, or to introduce genes which result in the expression of therapeutically beneficial proteins such as growth factors, lymphokines, cytokines, enzymes, etc.

For example, the gene encoding brain derived growth factor may be introduced into human pluripotent cells produced according to the invention, the cells differentiated into neural cells and the cells transplanted into a Parkinson's patient to retard the loss of neural cells during such disease.

Also, the subject pluripotent human ES cells, may be used as an in vitro model of differentiation, in particular for the study of genes which are involved in the regulation of early development. Also, differentiated cell tissues and organs produced using the subject ES cells may be used in drug studies.

Further, the subject ES cells or differentiated cells derived therefrom may be used as nuclear donors for the production of other ES cells and cell colonies.

Still further, pluripotent cells obtained according to the present disclosure may be used to identify proteins and genes that are involved in embryogenesis. This can be effected, e.g., by differential expression, i.e., by comparing mRNAs that are expressed in pluripotent cells provided according to the invention to mRNAs that are expressed as these cells differentiate into different cell types, e.g., neural cells, myocardiocytes, other muscle cells, skin cells, etc. Thereby, it may be possible to determine what genes are involved in differentiation of specific cell types.

Further, ES cells and/or their differentiated progeny that have specific genetic defects, such as the genetic defect that leads to Duchene's Muscular Dystrophy, may be used as models to study the specific disease associated with the genetic defect.

Also, it is another object of the present disclosure to expose pluripotent cell lines produced according to the described methods to cocktails of different growth factors, at different concentrations and under different cell culture conditions such as cultured on different cell matrices or under different partial pressures of gases so as to identify conditions that induce the production and proliferation of desired differentiated cell types.

The following examples are intended to illustrate but not limit the invention.

EXAMPLE 1

Production of Human Parthenogenic Embryogenic Stem Cells

Materials and Methods

Donors voluntarily donated oocytes, cumulous cells, and blood (for DNA analysis) with no financial payment. Donors signed comprehensive informed consent documents and were informed that all donated materials were to be used for research and not for reproductive purposes. Before ovarian stimulation, oocyte donors underwent medical examination for suitability according to FDA eligibility determination guidelines for donors of human cells, tissues, and cellular and tissue-based products (Food and Drug Administration. (Draft) Guidance for Industry: Eligibility Determination for Donors of Human Cells, Tissues, and Cellular and Tissue Based Products (HCT/Ps) dated May 2004) and order N 67 (02.26.03) of Russian Public Health Ministry. It included X-ray, blood and urine analysis, and liver function test. Donors were also screened for syphilis, HIV, HBV, and HCV.

Oocytes were obtained using standard hormonal stimulation to produce superovulation in the subject donor. Each donor egg underwent ovarian stimulation by FSH from the 3rd to the 13th days of their menstrual cycle. A total of 1500IU of FSh was given. From the 10th to the 14th day of the donor's menstrual cycle, gonadoliberin antagonist Orgalutran (Organon, Holland) was injected at 0.25 mg/day. From the 12th to the 14th day of the donor's menstrual cycle a daily injection of 75IU FSH+75IU LH (Menopur, Ferring GmbH, Germany(was given, If an ultrasound examination displayed follicles between 18 and 20 mm in diameter, a single 8000IU dose of hGC (Choragon, Ferring GmbH, Germany) was administered on the 14th day of the donor's menstrual cycle. Trans-vaginal punction was performed 35 hours after hCG injection on approximately the 16th day. Follicular fluid was collected from the antral follicles of anesthetized donors by ultrasound-guided needle aspiration into sterile tubes.

Cumulus oocyte complexes (COCs) were picked from the follicular fluid, washed in Flushing Medium (MediCult) and then incubated in Universal IVF medium (MediCult, see Table 1) with a Liquid Paraffin (MediCult) overlay for 2 hours in a 20% $O_2$, 5% $CO_2$, at 37° C. humidified atmosphere.

TABLE 1

| IVF media. COMPOSITION |
|---|
| Calcium Chloride |
| EDTA |
| Glucose |
| Human Serum Albumin |

TABLE 1-continued

IVF media.
COMPOSITION

Magnesium Sulfate
Penicillin G
Potassium Chloride
Potassium di-Hydrogen Phosphate
Sodium Bicarbonate
Sodium Chloride
Sodium Lactate
Sodium Pyruvate
Water Before activation, cumulus-oocyte complexes (COCs) were treated with SynVitro Hyadase (MediCult, A/S, Denmark) to remove cumulus cells followed by incubation in Universal IVF medium with a paraffin overlay for 30 minutes.

From this point onward, the culture of oocytes and embryos was performed in a humidified atmosphere at 37° C. using $O_2$-reduced gas mixture (90% $N_2$+5% $O_2$+5% $CO_2$), with the exception of the ionomycin treatment. The oocytes were activated by incubation in 5 μM ionomycin for 5 minutes in a $CO_2$ incubator at 37° C. in a gas environment of 20% $O_2$, 5% $CO_2$, followed by culture with 1 mM 6-dimethylaminopurine (DMAP) for 4 hours in IVF medium, with paraffin overlay, in a gas environment of 90% $N_2$, 5% $O_2$, and 5% $CO_2$ at 37° C. The oocytes were then washed 3 times in IVF. Activation and cultivation were carried out in 4-well plates (Nunclon, A/S, Denmark) in 500 μl of medium overlaid with liquid paraffin oil (MediCult, A/S, Denmark).

Activated oocytes were cultivated in IVF medium in a gas environment comprising 5% $O_2$, 5% $CO_2$, and 90% $N_2$, and embryos generated from the activated oocytes were cultured in the same gas mixture.

Activated oocytes were allowed to incubate in IVF under the above conditions (i.e., low $O_2$ tension) until fully expanded blastocysts containing an inner cell mass (ICM) at a Blastocyst Scoring Modification of 1AA or 2AA (Shady Grove Fertility Center, Rockville, Md., and Georgia Reproductive Specialists, Atlanta, Ga.) was observed.

The zona pellucida was removed by 0.5% pronase (Sigma, St. Louis) treatment. The ICM from blastocysts was isolated by immuno-surgery where the blastocysts were incubated with horse antiserum to human spleen cells followed by exposure to guinea pig complement. Trophoectodern cells were removed from the ICM by gently pipetting the treated blastocysts.

For the derivation of ICM from whole blastocysts, the blastocysts were placed on a feeder layer in medium designed for culture of phESC (i.e., VitroHES™ media (e.g., DMEM/ high glucose medium, VitroLife, Sweden) supplemented with 10% human umbilical cord blood serum, 5 ng/ml human recombinant LIF (Chemicon Int'l, Inc., Temecula, Calif.), 4 ng/ml recombinant human FGF (Chemicon Int'l, Inc., Temecula, Calif.) and penicillin-streptomycin (100 U/ 100 μg)). When blastocysts attached and trophoplast cells spread, the ICM became visible. Through three to four days of additional culture, the ICM was isolated through mechanical slicing of the ICM from the trophoectoderm outgrowth using a finely drawn glass pipette. Further, the IMC cells were cultured on a feeder cell layer of mitotically inactivated post natal human dermal fibroblasts, in VirtroHES™ media (as formulated above) in a 96-well plate in 5% $CO_2$ and 20% $O_2$ at 37° C. This gas mixture was used to culture stem cells. Human fibroblast cultures were made using non-animal materials. Inactivation of fibroblasts was carried out using 10 μg/ml mitomycin C (Sigma, St. Louis, Mo.) for 3 hours.

In a separate method, immuno-surgery was performed by incubating blastocysts with horse antiserum to human spleen cells followed by exposure to rabbit complement. The trophectoderm cells were removed from the ICM through gentle pipetting of the treated blastocyts. Further culturing of the isolated ICMs was performed on a feeder layer of neonatal human skin fibroblasts (HSF) obtained from a genetically unrelated individual (with parental consent) derived using medium containing human umbilical cord blood serum. The HSF feeder layer was mitotically inactivated using mitomycin C.

The medium for the culture of HSF consisted of 90% DMEM (high glucose, with L-glutamaine (Invitrogen), 10% human umbilical cord blood serum and penicillin-streptomycin (100 U/100 mg) Invitrogen).

For the culture of ICM and phESC, VitroHES™ (Vitrolife) supplemented with 4 ng/ml hrbFGF, 5 ng/ml hrLIF and 10% human umbilical cord blood serum was used. The ICM was mechanically plated on a fresh feeder layer and cultured for three to four days. The first colony was mechanically cut and replated after five days of culture. All subsequent passages were made after five to six days in culture. For early passages, colonies were mechanically divided into clumps and replated. Further passing of phESC was performed with collagenase IV treatment and mechanical dissociation. The propagation of phESC was performed at 37° C., 5% $CO_2$ in a humidified atmosphere.

Oocyte Activation

From the initial donor, four oocytes were activated, and the activated oocytes were cultivated in IVF medium in a gas environment comprising 5% $O_2$, 5% $CO_2$, and 90% $N_2$ and followed over five (5) days. Table 2 shows the progress of maturation of the activated oocytes. Each oocyte was separated in a 4-well plate.

TABLE 2

Cultured Activated Oocytes.*

| | Day 1 | Day 2 | Day 3 | Day 5 |
|---|---|---|---|---|
| N1 | 1 pronucleus (pn), 1 polar body (pb) | 2 blastomers (bl) equal, fragmentation (fr)-0% | 4 bl equal, fr-2% | 1 morula, fr-15% |
| N2 | 0 pn, 1 pb | 4 bl not equal, fr-4% | 5 bl not equal, fr-20% | 4 bl not equal, fr-40% |
| N3 | 1 pn, 1 pb | 2 bl not equal, fr-0% | 6 bl equal, fr-0% | early blastocysts |
| N4 | 1 pn, 1 pb | 4 bl equal, fr-10% | 4 bl equal, fr-20% | Fully expanded blastocyst with good ICM 1AA |

*Cells were incubated in M1 ™ media (MediCult) on the first day and M2 ™ media (MediCult) on days 2-5. Media was changed everyday. M1 ™ and M2 ™ contain human serum albumin, glucose and derived metabolites, physiological salts, essential amino acids, non-essential amino acids, vitamins, nucleotides, sodium bicarbonate, streptomycin (40 mg/l), penicillin (40.000 IU/l) and phenol red.

Inner cell masses were isolated from N4 and transferred to human fibroblast feeder cells as outlined above. N1 and N2 degenerated on Day 6. Further, on Day 6, N3 produced fully expanded blastocyst with ICM 2AB. N3 was then transferred to human fibroblast feeder cells on Day 6. ICM from N4 was unchanged. N3 was used to isolate stem cells.

ICM cells were cultivated in VitroHES™ medium in a gas environment comprising 5% $CO_2$, and 95% $N_2$ and followed over forty-five (45) days. Table 2a shows the progress of N3 ICM cell cultivation.

TABLE 2a

Progress of N3-ICM Cultivation.*

| Day | |
|---|---|
| Day 3 | ICM transplanted on fresh feeder cells. |
| Day 8 | Colony of cells divided mechanically into 6 pieces and cultivated in 3 wells of a 96-well plate-1st passage. |
| Day 14 | From five (5) colonies of 1st passage, cells were mechanically divided, and 20 colonies of a 2nd passage were cultivated in 3 wells of a 24-well plate. |
| Day 20 | Cells were plated in 35 mm dish-3rd passage. |
| Day 24 | Five (5) 35 mm dishes were seeded with cells-4th passage. One dish was divided chemically with 5% pronase (Sigma) at room temperature. |
| Day 30 | Twenty-five (25) 35 mm were seeded with cells-5th** passage. |
| Day 34 | 6th** cell passage. |
| Day 35 | 11 ampules were frozen from the 6th passage. |
| Day 37 | 7th** cell passage. |
| Day 44 | 12 ampules were frozen from the 7th passage. |
| Day 45 | 8th cell passage. |

*Cells were grown on M2 ™ media (MediaCult).
**These passages were made with pronase digestion.

Stem Cell Isolation.

From the oocytes from 5 donors, the use of MediCult media followed by a culture under reduced oxygen allowed for the production of 23 blastocysts on the fifth or sixth day of culture. Eleven of the blastocysts had visible ICMs (Table 3).

minutes at room temperature (RT). Monoclonal antibodies were diluted in blocking solution and used for one hour at RT: SSEA-1 (MAB4301) (1:30), SSEA-3 (MAB4303) (1:10), SSEA-4 (MAB4304) (1:50), OCT-4 (MAB4305) (1:30), TRA-1-60 (MAB4360) (1:50), and TRA-1-81 (MAB4381) (1:50) from Chemicon. After the cells were washed, secondary antibodies Alexa Fluor 546 (orange-fluorescent) and 488 (green-fluorescent) (Molecular Probes, Invitrogen) were diluted 1:1000 in PBS+0.05% Tween-20 and applied for one hour at RT. Cells were washed and nuclei were stained with DAPI (Sigma) 0.1 μg/ml in PBS+0.05% Tween-20 during ten minutes at RT. Cells were washed and mounted on slides with Mowiol (Calbiochem). Fluorescence images were visualized with a fluorescence microscope.

For the detection of mesodermal markers in three week old embryoid bodies or in contractile embryoid bodies, monoclonal mouse anti-desmina antibody anti-human alpha actinin antibody (Chemicon) as the muscle specific markers, and anti-human CD31/PECAM-1 antibody (R&D Systems), anti-human VE Cadherin (DC144) antibody (R&D Systems) as the endothelial markers were used.

For detection of the endodermal markers in embryoid bodies, monoclonal mouse anti-human alpha-fetoprotein antibody (R&D Systems) was used.

TABLE 3

Generation of Parthenotes and Parthenogenetic Embryonic Stem Cell Lines.

| Donor Number | Oocytes harvested | Oocytes donated | Normally activated oocytes | Parthenotes created | Blastocysts derived With ICM | Blastocysts derived Without visible ICM | Lines generated |
|---|---|---|---|---|---|---|---|
| 1 | 8 | 4 | 4 | 4 | 2 | — | phESC-1 immunosurgery |
| 2 | 15 | 8 | 8 | 8 | 3 | 3 | phESC-3 phESC-4 phESC-5 all from whole blastocysts |
| 3 | 27 | 14 | 12[1] | 11[2] | 3 | 2 | phESC-6 from whole blastocysts |
| 4 | 22 | 11 | 10[3] | 10 | 2 | 3 | phESC-7 from whole blastocysts |
| 5 | 20 | 9[4] | 7 | 7 | 1 | 4 | No cell line generated |

[1] two oocytes were not activated;
[2] one oocyte degenerated after activation;
[3] one oocyte was not activated;
[4] two oocytes were at metaphase stage I and were discarded.

These results indicate an approximate 57.5% success rate in the formation of blastocysts from parthenogenetically activated oocytes.

Immunohistochemical Staining

For immunostaining, hES cell colonies and phESC cells on feeder layers were seeded onto micro cover glass, washed twice with PBS and fixed with 100% methanol for 5 minutes at −20° C. Cells were washed twice with PBS+0.05% Tween-20 and permeabilized with PBS+0.1% Triton X-100 for 10 minutes at room temperature. After cell washing, non-specific binding was blocked by incubation with blocking solution (PBS+0.05% Tween-20+four percent goat serum plus three percent human umbilical cord blood serum) for 30

Alkaline Phosphatase and Telomerase Activity

Alkaline phosphatase and telomerase activity were performed according to the manufacturer's specifications with AP kit and TRAPEZE™ Kit (Chemicon).

Karyotyping

To analyse the karyotype, hES cells were treated with 10 μg/ml Demecolcine (Sigma) for two hours, harvested with 0.05% trypsin/EDTA (Invitrogen) and centrifuged at 700× rpm for three minutes. The pellet was resuspended in 5 ml of 0.56% KCl, and incubated for 15 minutes at RT. After repeated centrifugation, the supernatant was removed and cells were resuspended and fixed with 5 ml of an ice cold mixture of methanol/acetic acid (3:1) for five minutes at +4° C. The fixation of the cells was repeated twice, after that the cell suspension was placed onto microscope slides and the preparations were stained with Giemsa Modified Stain (Sigma). Metaphases from cells prepared in this manner were analyzed by a standard G-banding method. Quantity of 5/1000 metaphase spreads were revealed and 63 metaphases were analyzed.

Embryoid Body Formation hES and phESC cell colonies were mechanically divided into clumps and placed in wells of a 24 well plate precoated with 1.5% agarose (Sigma) in medium containing 85% Knockout DMEM, 15% human umbilical cord blood serum, 1×MEM NEAA, 1 mM Glutamax, 0.055 mM β-mercaptoethanol, penicillin-streptomycin (50 U/50 mg), 4 ng/ml hrbFGF (all from Invitrogen, except serum). Human EBs were cultured for 14 days in suspension culture and placed on a culture dish to give outgrowth or cultivated in suspension for an additional week.

Neural differentiation was induced by the cultivation of two week old embryoid bodies attached to a culture dish surface over a period of a week in differentiation medium: DMEM/F12, B27, 2 mM Glutamax, penicillin-streptomycin (100 U/100 μg) and 20 ng/ml hrbFGF (all from Invitrogen). Some embryoid bodies gave rise to differentiated cells with neural morphology, others were dissected and additionally cultured to produce neurospheres.

Rhythmically beating embryoid bodies appeared spontaneously following five days of culture after plating on an adhesive surface in the same medium as was used for embryoid body generation.

HLA Typing

Genomic DNA was extracted from donor blood, hES, phESC cells, and human newborn skin fibroblasts (NSFs) with Dynabeads DNA Direct Blood from Dynal (Invitrogen). HLA typing was performed by PCR with allele-specific sequencing primers (PCR-SSP, Protrans) according to the manufacturer's specifications. HLA class I genes (HLA A*,B*,Cw*) were typed with PROTRANS HLA A*B*Cw* defining A*01-A*80, B*07-B*83, Cw*01-Cw*18 regions. HLA class II genes (HLA DRB1*, DRB3*, DRB4*, DRB5*, DQA1*, DQB1*) were analysed with PROTRANS HLA DRB1* defining DRB1*01-DRB1*16 (DR1-DR18), DRB3*, DRB4*, DRB5* regions and PROTRANS HLA DQB1* DQA1* defining DQB1*02-DQB1*06 (DQ2-DQ9), DQA1*0101-DQA1*0601 regions. PCR amplification was achieved: at 94° C. for 2 min; 10 cycles at 94° C. for 10 sec, 65° C. for 1 min; 20 cycles at 94° C. for 10 sec, 61° C. for 50 sec, 72° C. for 30 sec. Amplified products were detected in 2% agarose gel.

Affimetrix SNP Microarray Analysis

Genomic DNA was isolated from blood, cumulus cells, phESC and NSF by phenol/chloroform extraction method. These DNA samples obtained from four Caucasian subjects were genotyped with Affimetrix Mapping 50K Hind 240 Array (part of Affimetrix GeneChip Mapping 100K kit). Initially, the dataset contained 57,244 binary SNP markers. Since the number of markers is more than would be necessary to identify the equivalency of genomic samples and to study heterozygosity, 15 (chromosomes 1-15) out of 22 autosomal chromosomes were chosen. The shorter seven chromosomes were removed to reduce the chance that no marker, or only a single marker for a given chromosome, is selected during random sampling. The 1,459 markers were analyzed by Relcheck (version 0.67, Copyright © 2000 Karl W. Broman, Johns Hopkins University, Licensed under GNU General Public License version 2 (June 1991)).

Genomic Imprinting Analysis

Total nucleic acid was prepared as described Li et al. (J Biol Chem (2002) 277(16):13518-13527). RNA and DNA were extracted from cells using Tri-reagent (Sigma) or by using an RNA preparation kit from Qiagen (Valencia, Calif.).

Northern blots containing RNA from the various samples (see FIG. 3) were blotted onto filters by standard methods (See, e.g., Sambrook et al., Molecular Cloning: A Laboratory Manual, 1989, 2nd ed, Cold Spring Harbor Press). The Northern filter was hybridized with single stranded oligonucleotide probes that hybridized specifically to the mRNAs. The oligonucleotide probes were end-labeled with $[\gamma^{32}P]ATP$ (Amersham Biosciences). The filters were subsequently washed three times for 10 min each with 0.2×SSC (1×SSC=0.15 M NaCl and 0.015 M sodium citrate) containing 0.1% SDS at 60° C. and analyzed by PhosphorImager (Molecular Dynamics). The sequences of the oligonucleotide probes were obtained from sequences based on the following Accession Nos.: NP002393 (Peg1_2 and Peg1_A; for these genes, human PEG1 is transcribed from two alternative promoters, resulting in the transcription of two isoforms, of which only one (isoform 1_2) is imprinted. Paternal expression isoform 1 occurs in conjunction with an unmethylated CpG island in exon 1 of the paternal allele, whereas the corresponding CpG island in the maternal gene (isoform 1_A) is fully methylated. See, e.g., Li et al. (2002), supra); CAG29346 (SNRPN); AF087017 (H19); NR_001564 (inactive X specific transcripts-XIST); and P04406 (GAPDH).

DNA Fingerprinting Analysis

Genomic DNA was isolated from blood, hES cells, and NSFs through a phenol/chloroform extraction, digested with HinfI restriction enzyme (Fermentas) and loaded in a 0.8% agarose gel. Following electrophoresis, denatured DNA was transferred to a nylon membrane (Hybond N, Amersham) by Southern blotting and hybridized with $^{32}$P-labeled (CAC) 5 oligonucleotide probe. mData were analysed after membrane exposition on X-ray film (Kodak XAR) using Cronex intensifying screens.

Monolocus PCR Genotyping

In order to determine allelic identities for minisatellite loci between blood donor DNA and stem cell DNA, 11 polymorphic sites ((1) 3' Apolipoprotein B hypervariable minisatellite locus (3'ApoB); (2) D1S80 (PMCT118) hypervariable minisatellite locus (D1S80); (3) D6S366; (4) D16S359; (5) D7S820; (6) Human von Willebrand factor gene hypervariable minisatellite locus II (vWFII); (7) D13S317; (8) Human von Willebrand factor gene hypervariable microsatellite locus (vWA); (9) Human c-fms proto-oncogene for CFS-1 receptor gene microsatellite locus (CSF1PO); (10) Human thyroid peroxidase gene microsatellite locus (TPOX); and (11) Human tyrosine hydroxylase gene microsatellite locus (TH01)) were analyzed by PCR genotyping. Allele frequencies for known populations (i.e., Russian and Caucasian-American populations) determined for the above polymorphic sites were compared to allele frequencies of these sites in test samples (i.e., hES, NSF, and donor blood DNA). Chromosomal location, Genbank locus and locus definition, repeat sequence data, allelic ladder range, VNTR ladder size range, other known alleles, allele sizes, PCR protocols, and allele frequency results for the 11 minisatellite loci of the disclosed populations analyzed are provided below.

(1) 3' Apolipoprotein B hypervariable minisatellite locus (3'ApoB VNTR)

Chromosomal location: 2p23-p23

GenBank locus and locus definition: APOB, apolipoprotein B (including Ag(x) antigen) untranslated region Repeat sequence 5'-3': (TATAATTAAATATT TTATAAT-TAAAATATT)n (SEQ ID NO: 1)

Allelic ladder size range (bases): 450+10+2 primer+links

VNTR ladder size range (# of repeats, according to Ludwig et al, 1989): 30, 32, 34, 36, 38, 40, 42, 44, 46, 48, 50, 52

Other known alleles (# of repeats): 25, 27, 28, 31, 33, 35, 37, 39, 41, 43, 45, 47, 49, 51, 53, 54, 55

Promega K562 DNA® Allele sizes (# of repeats): 36/36

PCR protocol:

| | |
|---|---|
| Thermal cycler: | DNA Technology Ltd., Russia |
| Initial Incubation: | 95° C., 2' |
| Cycling for 30 cycles: | |
| Denaturation | 94° C., 1' |
| Elongation and primer linking | 60° C., 2' |
| Extension step: | 72° C., 5' |
| Hold step: | 4° C., unlimited time |

The analysis may be done as described in Verbenko et al. (Apolipoprotein B 3'-VNTR polymorphism in Eastern European populations. Eur J Hum Gen (2003) 11(1):444-451). See Table 4.

TABLE 4

Allele Frequencies for Russian Populations

| Allele | Allele frequency | Number of Alleles observed |
|---|---|---|
| 25 | 0.001 | 1 |
| 30 | 0.079 | 75 |
| 32 | 0.071 | 68 |
| 33 | 0.001 | 1 |
| 34 | 0.238 | 227 |
| 35 | 0.004 | 4 |
| 36 | 0.393 | 375 |
| 37 | 0.001 | 1 |
| 38 | 0.036 | 36 |
| 39 | 0.001 | 1 |
| 40 | 0.014 | 13 |
| 42 | 0.001 | 1 |
| 44 | 0.042 | 41 |
| 45 | 0.006 | 6 |
| 46 | 0.033 | 31 |
| 48 | 0.067 | 64 |
| 50 | 0.011 | 10 |
| 52 | 0.001 | 1 |

| | |
|---|---|
| Homozygotes | 94 |
| Heterozygotes | 333 |
| Total samples | 427 |

(2) D1S80 (pMCT118) hypervariable minisatellite locus (D1S80 VNTR)

Chromosomal location: 1p35-36

GenBank locus and locus definition: Human D1S80 and MCT118 gene

Repeat sequence 5'-3': (GAAGACAGACCACAG)n (SEQ ID NO: 2)

Allelic ladder size range (bases): 387-762

VNTR ladder size range (# of repeats): 16, 17, 18, 19, 20, 21, 22, 23, 24, 25, 26, 27, 28, 29, 30, 31, 34, 35, 36, 37, 40, 41

Other known alleles (# of repeats): 13, 14, 15, 38, 39, >41

Promega K562 DNA® Allele sizes (# of repeats): 18/29

PCR protocol:

| | |
|---|---|
| Thermal cycler: | DNA Technology Ltd., Russia |
| Initial Incubation: | 95° C., 2' |
| Cycling for 30 cycles: | |
| Denaturation | 94° C., 45" |
| Primer linking | 60° C., 30" |
| Elongation | 72° C., 45" |
| Extension step: | 72° C., 5' |
| Hold step: | 4° C., unlimited time |

The analysis may be done as described in Verbenko et al. (Allele frequencies for D1S80 (pMCT118) locus in some Eastern European populations. J Forensic Sci (2003) 48(1): 207-208). See Table 5.

TABLE 5

Allele Frequencies for Russian Populations

| Allele | Allele frequency | Number of Alleles observed |
|---|---|---|
| 18 | 0.280 | 33 |
| 20 | 0.017 | 2 |
| 21 | 0.009 | 1 |
| 22 | 0.042 | 5 |
| 23 | 0.017 | 2 |
| 24 | 0.390 | 46 |
| 25 | 0.017 | 2 |
| 26 | 0.025 | 3 |
| 28 | 0.068 | 8 |
| 29 | 0.009 | 1 |
| 30 | 0.034 | 4 |
| 31 | 0.059 | 7 |
| 33 | 0.017 | 2 |
| 34 | 0.008 | 1 |
| 36 | 0.008 | 1 |

| | |
|---|---|
| Homozygotes | 15 |
| Heterozygotes | 44 |
| Total samples | 59 |

(3) D6S366

Chromosomal location: 6q21-qter

GenBank locus and locus definition: NA

Allelic ladder size range (bases): 150-162

STR ladder size range (# of repeats): 12, 13, 15

Other known alleles (# of repeats): 10, 11, 14, 16, 17

Promega K562 DNA® Allele sizes (# of repeats): 13/14

PCR protocol:

| | |
|---|---|
| Thermal cycler: | DNA Technology Ltd., Russia |
| Initial Incubation: | 95° C., 2' |
| Cycling for 30 cycles: | |
| Denaturation | 94° C., 1' |
| Elongation and primer linking | 60° C., 2' |
| Extension step: | 72° C., 5' |
| Hold step: | 4° C., unlimited time |

The analysis may be done as described in Efremov et al. (An expert evaluation of molecular genetic individualizing systems based on the HUMvWFII and D6S366 tetranucleotide tandem repeats. Sud Med Ekspert (1998) 41(2):33-36). See Table 6.

TABLE 6

Allele Frequencies for Russian Populations

| Allele | Allele frequency | Number of Alleles observed |
|---|---|---|
| 10 | 0.008 | 3 |
| 11 | 0.059 | 21 |
| 12 | 0.316 | 112 |
| 13 | 0.251 | 89 |
| 14 | 0.085 | 30 |
| 15 | 0.175 | 62 |
| 16 | 0.015 | 7 |
| 17 | 0.011 | 4 |
| Total samples | | 177 |

(4) D16S539

Chromosomal location: 16q24-qter

GenBank locus and locus definition: NA

Repeat sequence 5'-3': (AGAT)n (SEQ ID NO:3)

Allelic ladder size range (bases): 264-304

STR ladder size range (# of repeats): 5, 8, 9, 10, 11, 12, 13, 14, 15

Promega K562 DNA™ Allele sizes (# of repeats): 11/12

PCR protocol:

| | |
|---|---|
| Thermal cycler: | DNA Technology Ltd., Russia |
| Initial Incubation: | 95° C., 2' |
| Cycling for 30 cycles: | |
| Denaturation | 94° C., 45" |
| Primer linking | 64° C., 30" |
| Elongation | 72° C., 30" |
| Extension step: | 72° C., 5' |
| Hold step: | 4° C., unlimited time |

The analysis has been done as described in GenePrint™ STR Systems (Silver Stain Detection) Technical Manual No. D004. Promega Corporation, Madison, Wis. USA: 1993-2001. See Table 7.

TABLE 7

Allele Frequencies for Caucasian-Americans

| Allele | Allele frequency | Number of Alleles observed |
|---|---|---|
| 6 | 0.000 | 0 |
| 7 | 0.000 | 0 |
| 8 | 0.026 | 11 |
| 9 | 0.107 | 45 |
| 10 | 0.079 | 33 |
| 11 | 0.319 | 134 |

TABLE 7-continued

Allele Frequencies for Caucasian-Americans

| Allele | Allele frequency | Number of Alleles observed |
|---|---|---|
| 12 | 0.269 | 113 |
| 13 | 0.167 | 70 |
| 14 | 0.031 | 13 |
| 15 | 0.002 | 1 |
| Homozygotes | | 57 |
| Heterozygotes | | 153 |
| Total samples | | 210 |

(5) D7S820

Chromosomal location: 7q11.21-22

GenBank locus and locus definition: NA

Repeat sequence 5'-3': (AGAT)n (SEQ ID NO:4)

Allelic ladder size range (bases): 215-247

VNTR ladder size range (# of repeats): 6, 7, 8, 9, 10, 11, 12, 13, 14

Promega K562 DNA® Allele sizes (# of repeats): 9/11

PCR protocol:

| | |
|---|---|
| Thermal cycler: | DNA Technology Ltd., Russia |
| Initial Incubation: | 95° C., 2' |
| Cycling for 30 cycles: | |
| Denaturation | 94° C., 45" |
| Primer linking | 64° C., 30" |
| Elongation | 72° C., 30" |
| Extension step: | 72° C., 5' |
| Hold step: | 4° C., unlimited time | analysis has been done as described in GenePrint® STR Systems (Silver Stain Detection) Technical Manual No. D004. Promega Corporation, Madison, Wis. USA: 1993-2001. See Table 8.

TABLE 8

Allele Frequencies for D7S820 in Different Populations

| Allele | Allele frequency for Caucasian-Americans | Number of Alleles observed | Allele frequency for Russians | Number of Alleles observed |
|---|---|---|---|---|
| 6 | 0.002 | 1 | 0.0012 | 1 |
| 7 | 0.010 | 4 | 0.0087 | 7 |
| 8 | 0.155 | 65 | 0.1928 | 155 |
| 9 | 0.152 | 64 | 0.1480 | 119 |
| 10 | 0.295 | 124 | 0.2524 | 203 |
| 11 | 0.195 | 82 | 0.2040 | 164 |
| 12 | 0.121 | 51 | 0.1580 | 127 |
| 13 | 0.057 | 24 | 0.0299 | 24 |
| 14 | 0.012 | 5 | 0.0050 | 4 |
| Homozygotes | 43 | | 92 | |
| Heterozygotes | 167 | | 310 | |
| Total samples | 210 | | 402 | |

(6) Human von Willebrand factor gene hypervariable microsatellite locus II (vWFII)
Chromosomal location: 12p13.3-12p13.2
GenBank locus and locus definition: HUMvWFII, Human von Willebrand factor gene
Repeat sequence 5'-3': (ATCT)n/(AGAT)n (SEQ ID NO'S 3&5)
Allelic ladder size range (bases): 154-178
STR ladder size range (# of repeats): 9, 11, 12, 13
Other known alleles (# of repeats): 8, 10, 14, 15
Promega K562 DNA® Allele sizes (# of repeats): 13/13
PCR protocol:

| Thermal cycler: | DNA Technology Ltd., Russia |
|---|---|
| Initial Incubation: | 95° C., 2' |
| Cycling for 30 cycles: | |
| Denaturation | 94° C., 1' |
| Elongation and primer linking | 60° C., 2' |
| Extension step: | 72° C., 5' |
| Hold step: | 4° C., unlimited time |

The analysis has been done as described in Efremov et al. (An expert evaluation of molecular genetic individualizing systems based on the HUMvWFII and D6S366 tetranucleotide tandem repeats. Sud Med Ekspert (1998) 41(2):33-36). See Table 9.

TABLE 9

Allele Frequencies for Russian Populations

| Allele | Allele frequency | Number of Alleles observed |
|---|---|---|
| 9 | 0.082 | 37 |
| 10 | 0.088 | 40 |
| 11 | 0.392 | 177 |
| 12 | 0.296 | 134 |
| 13 | 0.069 | 31 |
| 14 | 0.058 | 26 |
| 15 | 0.015 | 7 |
| Total samples | | 226 |

(7) D13S317
Chromosomal location: 13q22-q31
GenBank locus and locus definition: NA
Repeat sequence 5'-3': (AGAT)n (SEQ ID NO:3)
Allelic ladder size range (bases): 165-197
STR ladder size range (# of repeats): 8, 9, 10, 11, 12, 13, 14, 15
Other known alleles (# of repeats): 7
Promega K562 DNA® Allele sizes (# of repeats): 8/8
PCR protocol:

| Thermal cycler: | DNA Technology Ltd., Russia |
|---|---|
| Initial Incubation: | 95° C., 2' |
| Cycling for 30 cycles: | |
| Denaturation | 94° C., 45" |
| Primer linking | 64° C., 30" |
| Elongation | 72° C., 30" |
| Extension step: | 72° C., 5'. |
| Hold step: | 4° C., unlimited time |

The analysis has been done as described in GenePrint® STR Systems (Silver Stain Detection) Technical Manual No. D004. Promega Corporation, Madison, Wis. USA: 1993-2001. See Table 10.

TABLE 10

Allele Frequencies for D13S317 in Different Populations

| Allele | Allele frequency for Caucasian-Americans | Number of Alleles observed | Allele frequency for Russians | Number of Alleles observed |
|---|---|---|---|---|
| 7 | 0.000 | 0 | 0 | 0 |
| 8 | 0.143 | 60 | 0.1393 | 112 |
| 9 | 0.052 | 22 | 0.0883 | 71 |
| 10 | 0.052 | 22 | 0.0684 | 55 |
| 11 | 0.305 | 128 | 0.3706 | 298 |
| 12 | 0.307 | 129 | 0.2040 | 164 |
| 13 | 0.083 | 35 | 0.0871 | 70 |
| 14 | 0.057 | 24 | 0.0423 | 34 |
| 15 | 0.000 | 0 | 0 | 0 |
| Homozygotes | | 61 | | 90 |
| Heterozygotes | | 149 | | 312 |
| Total samples | | 210 | | 402 |

(8) Human von Willebrand factor gene hypervariable microsatellite locus (vWA)
  Chromosomal location: 12p 12pter
  GenBank locus and locus definition: HUMVWFA31, Human von Willebrand factor gene
  Repeat sequence 5'-3': (AGAT)n (SEQ ID NO:7)
  Allelic ladder size range (bases): 139-167
  STR ladder size range (# of repeats): 14, 16, 17, 18
  Other known alleles (# of repeats): 11, 12, 13, 15, 19, 20, 21
  Promega K562 DNA® Allele sizes (# of repeats): 16/16
  PCR protocol:

| Thermal cycler: | DNA Technology Ltd., Russia |
| --- | --- |
| Initial Incubation: | 95° C., 2' |
| Cycling for 30 cycles: | |
| Denaturation | 94° C., 1' |
| Elongation and primer linking | 60° C., 2' |
| Extension step: | 72° C., 5' |
| Hold step: | 4° C., unlimited time |

The analysis has been done as described in GenePrint® STR Systems (Silver Stain Detection) Technical Manual No. D004. Promega Corporation, Madison, Wis. USA: 1993-2001. See Table 11.

TABLE 11

Allele Frequencies for HUMVWFA31 in Different Populations

| Allele | Allele frequency for Caucasian-Americans | Number of Alleles observed | Allele frequency for Russians | Number of Alleles observed |
| --- | --- | --- | --- | --- |
| 13 | 0.000 | 0 | 0.0025 | 2 |
| 14 | 0.131 | 56 | 0.0796 | 64 |
| 15 | 0.082 | 35 | 0.0920 | 74 |
| 16 | 0.211 | 90 | 0.2127 | 171 |
| 17 | 0.265 | 113 | 0.2836 | 228 |
| 18 | 0.202 | 86 | 0.2251 | 181 |
| 19 | 0.087 | 37 | 0.0833 | 67 |
| 20 | 0.021 | 9 | 0.0199 | 16 |
| 21 | 0.000 | 0 | 0.0012 | 1 |
| Homozygotes | | 38 | | 70 |
| Heterozygotes | | 175 | | 332 |
| Total samples | | 213 | | 402 |

(9) Human c-fms proto-oncogene for CSF-1 receptor gene microsatellite locus (CSF1PO)
  Chromosomal location: 5q33.3-34
  GenBank locus and locus definition: HUMCSF1PO, Human c-fms proto-oncogene
  Repeat sequence 5'-3': (AGAT)n (SEQ ID NO:3)
  Allelic ladder size range (bases): 295-327
  STR ladder size range (# of repeats): 7, 8, 9, 10, 11, 12, 13, 14, 15
  Other known alleles (# of repeats): 6
  Promega K562 DNA® Allele sizes (# of repeats): 9/10
  PCR protocol:

| Thermal cycler: | DNA Technology Ltd., Russia |
| --- | --- |
| Initial Incubation: | 95° C., 2' |
| Cycling for 30 cycles: | |
| Denaturation | 94° C., 45" |
| Primer linking | 64° C., 30" |
| Elongation | 72° C., 30" |
| Extension step: | 72° C., 5' |
| Hold step: | 4° C., unlimited time |

The analysis has been done as described in GenePrint® STR Systems (Silver Stain Detection) Technical Manual No. D004. Promega Corporation, Madison, Wis. USA: 1993-2001. See Table 12.

TABLE 12

Allele Frequencies for Caucasian-Americans

| Allele | Allele frequency | Number of Alleles observed |
| --- | --- | --- |
| 6 | 0.000 | 0 |
| 7 | 0.000 | 0 |
| 8 | 0.002 | 1 |
| 9 | 0.033 | 14 |
| 10 | 0.251 | 108 |
| 11 | 0.309 | 133 |
| 12 | 0.330 | 142 |
| 13 | 0.060 | 26 |
| 14 | 0.014 | 6 |
| 15 | 0.000 | 0 |

TABLE 12-continued

Allele Frequencies for Caucasian-Americans

| Allele | Allele frequency | Number of Alleles observed |
| --- | --- | --- |
| Homozygotes | | 47 |
| Heterozygotes | | 168 |
| Total samples | | 215 |

(10) Human thyroid peroxidase gene microsatellite locus (TPOX)
  Chromosomal location: 2p25.1-pter
  GeneBank locus and locus definition: HUMTPOX, Human thyroid peroxidase gene
  Repeat sequence 5'-3': (AATG)n (SEQ ID NO:7)
  Allelic ladder size range (bases): 224-252
  STR ladder size range (# of repeats): 6, 7, 8, 9, 10, 11, 12, 13

Other known alleles (# of repeats): none
Promega K562 DNA® Allele sizes (# of repeats): 8/9
PCR protocol:

| Thermal cycler: | DNA Technology Ltd., Russia |
|---|---|
| Initial Incubation: | 95° C., 2' |
| Cycling for 30 cycles: | |
| Denaturation | 94° C., 45" |
| Primer linking | 64° C., 30" |
| Elongation | 72° C., 30" |
| Extension step: | 72° C., 5' |
| Hold step: | 4° C., unlimited time |

The analysis has been done as described in GenePrint® STR Systems (Silver Stain Detection) Technical Manual No. D004. Promega Corporation, Madison, Wis. USA: 1993-2001. See Table 13.

TABLE 13

Allele Frequencies for Caucasian-Americans

| Allele | Allele frequency | Number of Alleles observed |
|---|---|---|
| 6 | 0.002 | 1 |
| 7 | 0.000 | 0 |
| 8 | 0.528 | 227 |
| 9 | 0.093 | 40 |
| 10 | 0.056 | 24 |
| 11 | 0.284 | 122 |
| 12 | 0.037 | 16 |
| 13 | 0.000 | 0 |
| Homozygotes | | 76 |
| Heterozygotes | | 139 |
| Total samples | | 215 |

(11) Human tyrosine hydroxylase gene microsatellite locus (TH01)

Chromosomal location: 5q33.3-34

GenBank locus and locus definition: HUMTHO1, Human tyrosine hydroxylase gene

Repeat sequence 5'-3': (AATG)n (SEQ ID NO:8)

Allelic ladder size range (bases): 179-203

STR ladder size range (# of repeats): 5, 6, 7, 8, 9, 10, 11

Other known alleles (# of repeats): 9.3

Promega K562 DNA® Allele sizes (# of repeats): 9.3/9.3

PCR protocol:

| Thermal cycler: | DNA Technology Ltd., Russia |
|---|---|
| Initial Incubation: | 95° C., 2' |
| Cycling for 30 cycles: | |
| Denaturation | 94° C., 45" |
| Primer linking | 64° C., 30" |
| Elongation | 72° C., 30" |
| Extension step: | 72° C., 5' |
| Hold step: | 4° C., unlimited time |

The analysis has been done as described in GenePrint® STR Systems (Silver Stain Detection) Technical Manual No. D004. Promega Corporation, Madison, Wis. USA: 1993-2001. See Table 14.

TABLE 14

Allele Frequencies for Caucasian-Americans

| Allele | Allele frequency | Number of Alleles observed |
|---|---|---|
| 5 | 0.007 | 3 |
| 6 | 0.237 | 101 |
| 7 | 0.148 | 63 |
| 8 | 0.117 | 50 |
| 9 | 0.155 | 66 |
| 9.3 | 0.331 | 141 |
| 10 | 0.005 | 2 |
| 11 | 0.000 | 0 |
| Homozygotes | | 50 |
| Heterozygotes | | 163 |
| Total samples | | 213 |

Results

Figure 1B:
FIG. 1B shows a micrograph of the expression for the surface marker Oct4.
Figure 1C:
FIG. 1C shows a micrograph of the expression for the surface marker SSEA-1.
Figure 1D:
FIG. 1D shows a micrograph of the expression for the surface marker SSEA-3.
Figure 1E:
FIG. 1E shows a micrograph of the expression for the surface marker SSEA-4.
Figure 1F:
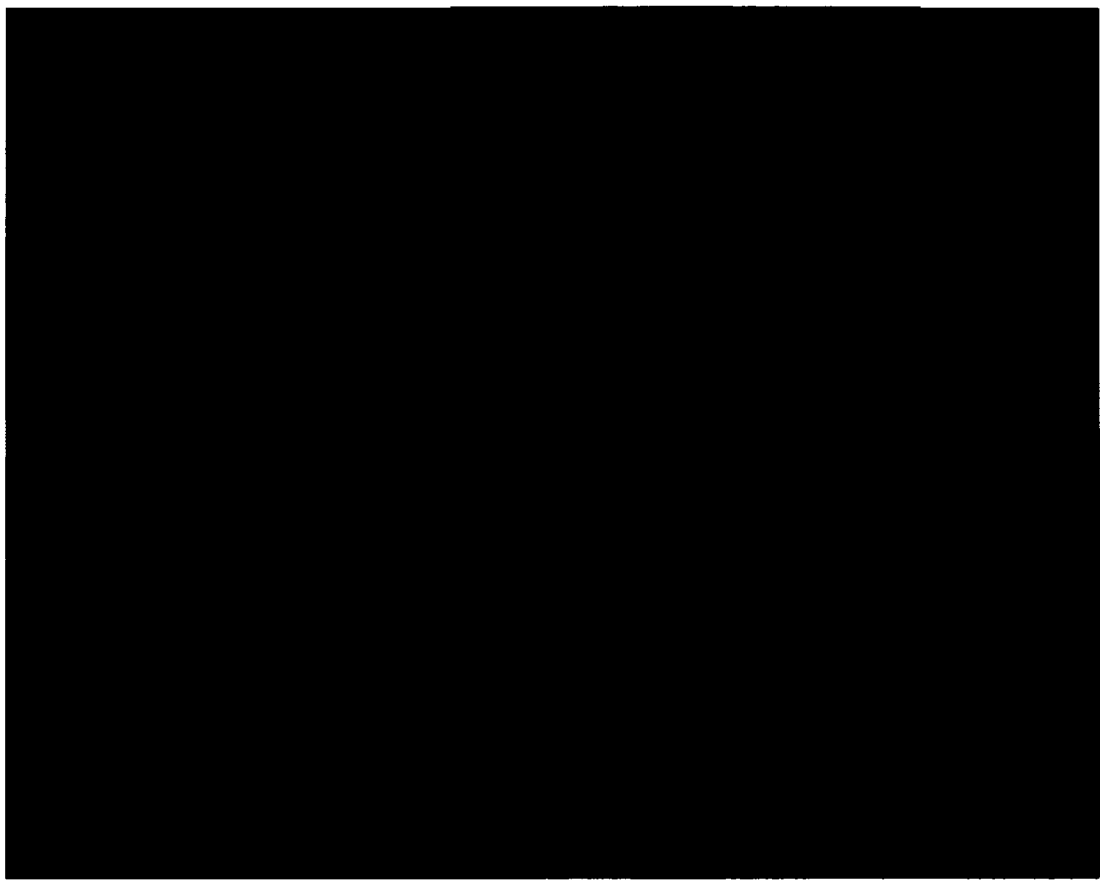
FIG. 1F shows a micrograph of the expression for the surface marker TRA-1-60.
Figure 1G:
FIG. 1G shows a micrograph of the expression for the surface marker TRA-1-81.
Figure 2A:
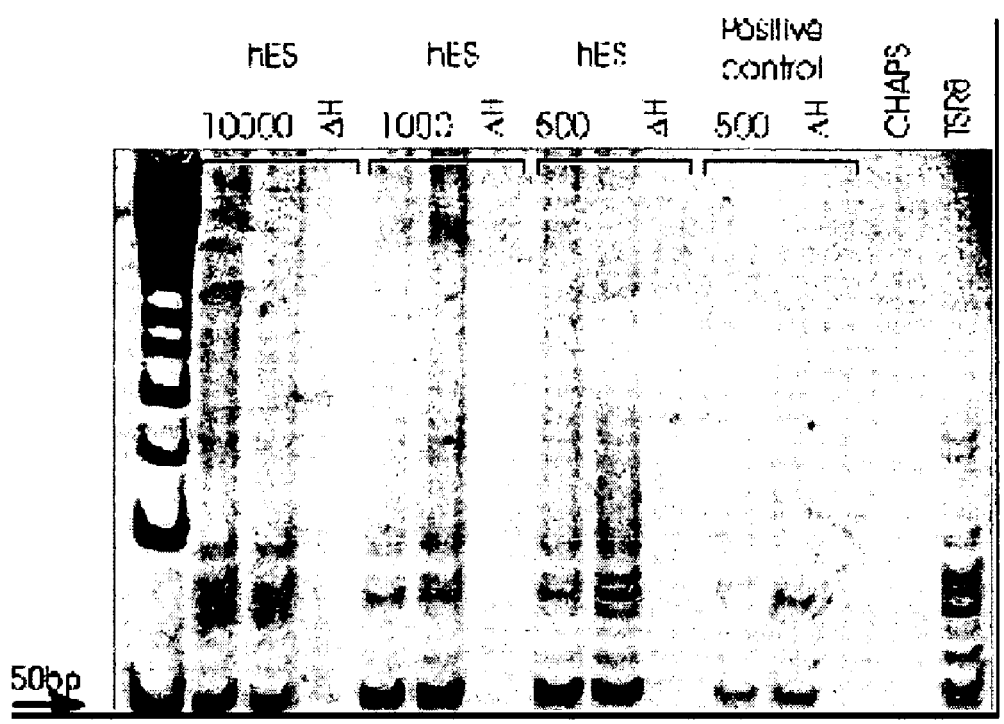
FIG. 2A shows the analysis of telomerase activity for the parthenogenically derived hES cells. 500, 1000, and 10000 (units) of extract was used to perform the analysis. ΔH-heat treated test extract (negative control); positive control-telomerase positive cells; CHAPS-lysis buffer; TSR8-control template.
Figure 2B:
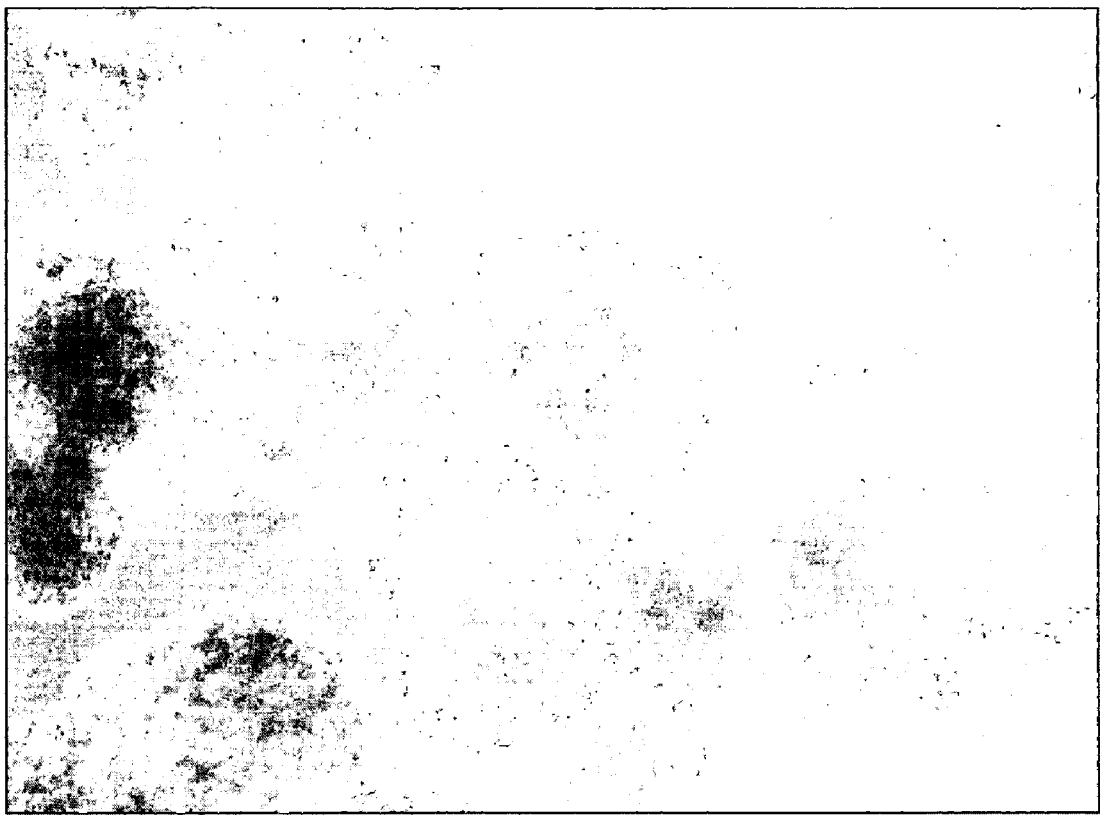
FIG. 2B shows a micrograph of embryoid body formation from parthenogenically derived hES cells, 9 day culture.
Figure 2C:
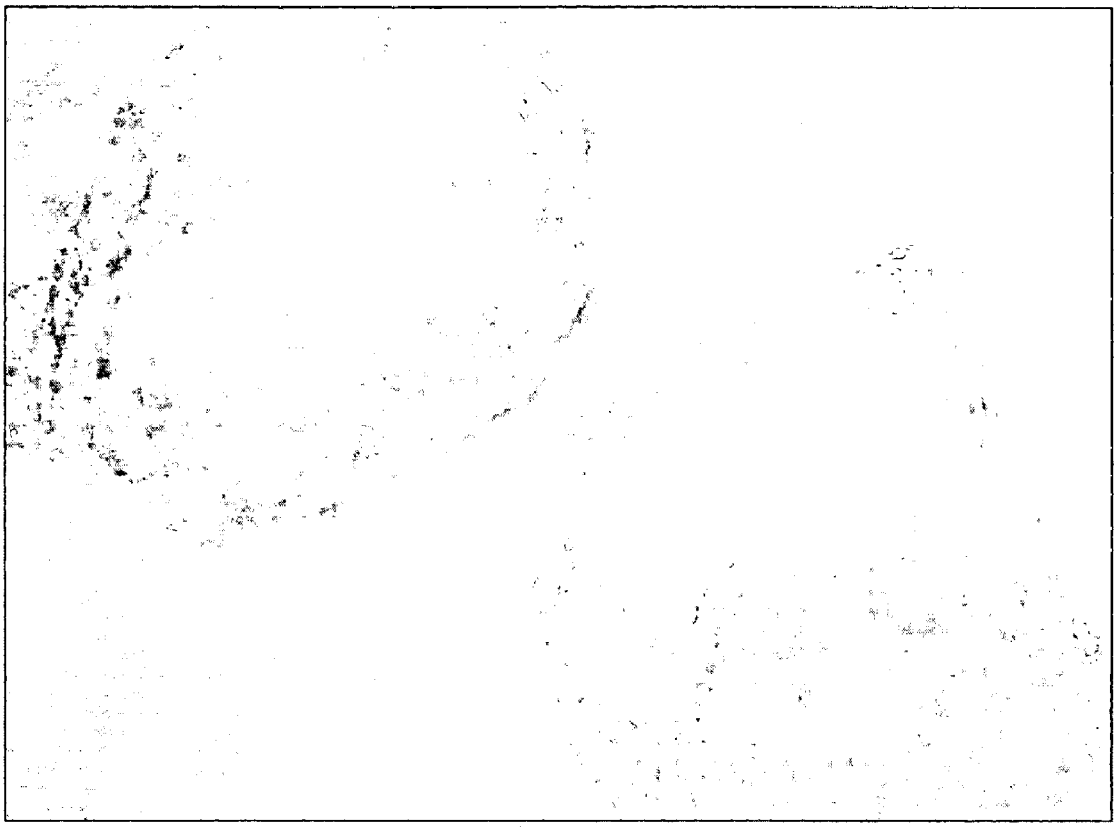
FIG. 2C shows a micrograph of embryoid body formation from parthenogenically derived hES cells, 10 day culture.
Figure 2D:
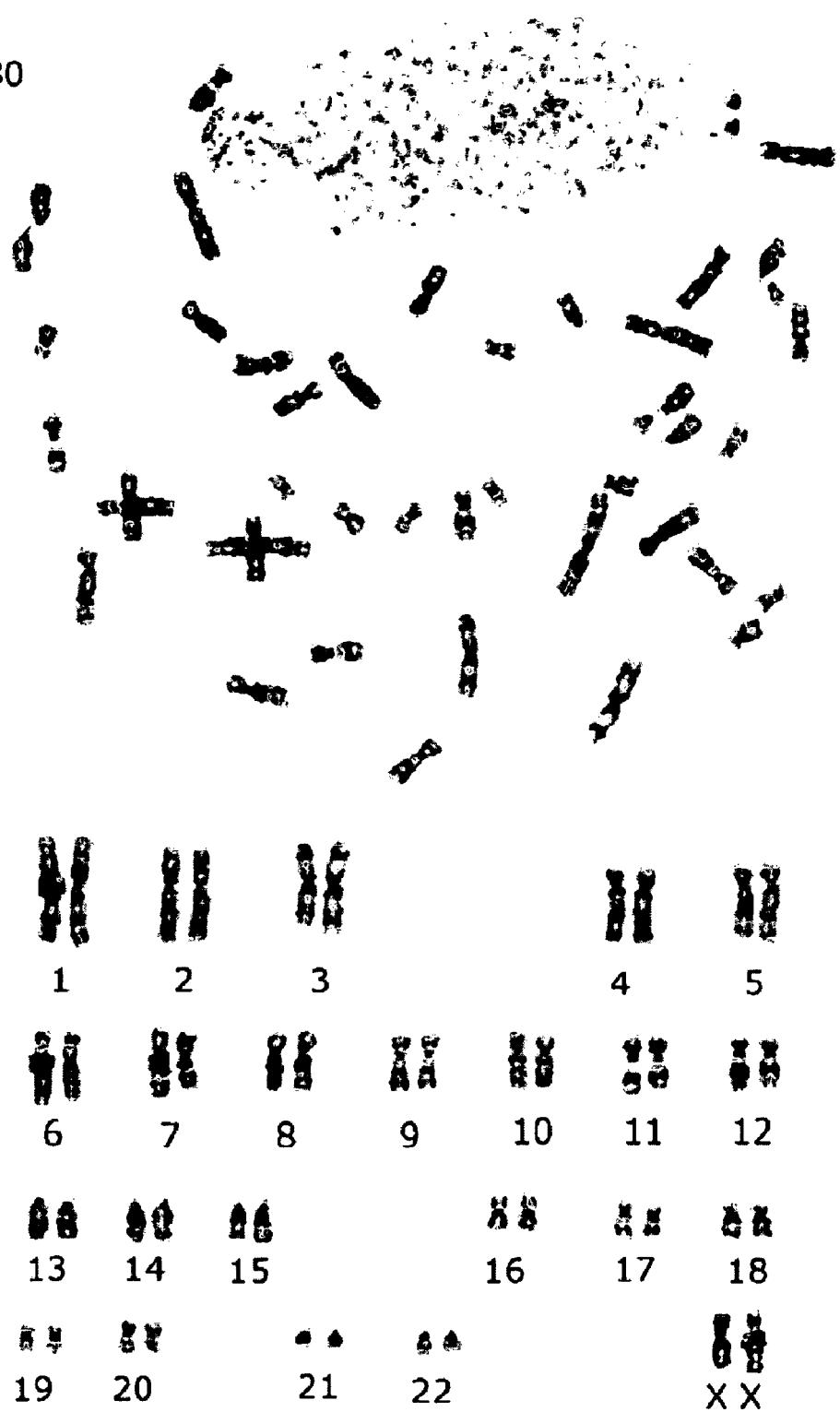
FIG. 2D illustrates the karyotype of parthenogenically derived hES cells.

The hES cells from this method display many features that are typical for embryonic stem cells: cytoplasmic lipid bodies, small cytoplasmic/nuclear ratio and clearly distinguishable nucleoli. The hES cell colonies display similar morphology to that reported previously for human embryonic stem cells derived after in vitro fertilization. The cells were immunoreactively positive for alkaline phosphatase (FIG. 1A), octamer-binding transcription factor 4 mRNA (Oct-4) (FIG. 1B), stage-specific embryonic antigen 1 (SSEA-1) (FIG. 1C), stage-specific embryonic antigen 3 (SSEA-3) (FIG. 1D), stage-specific embryonic antigen 4 (SSEA-4) (FIG. 1E), tumor rejection antigen 1-60 (TRA-1-60) (FIG. 1F), tumor rejection antigen 1-81 (TRA-1-81) (FIG. 1G), and negative for stage-specific embryonic antigen 1 (SSEA-1) (FIG. 1C), (which is positive for mouse embryonic stem cells, but not for human). Telomerase activity is often correlated with replicative immortality and is typically expressed in germ cells, cancer cells, and a variety of stem cells, including stem cells, but absent in most somatic cell types. The cells prepared by this method after three months in in vitro proliferation maintained their undifferentiated morphology and displayed high levels of telomerase activity (FIG. 2A). The pluripotency of the cells was investigated in vitro by embryoid body formation (FIGS. 2B, 2C), G-banded karyotyping shows that cells have normal human 46XX karyotype (FIG. 2D).

DNA fingerprinting analysis was performed on the blood of the oocyte donor, on the ES cells, and on the HNSF feeder cells by Southern blotting and hybridization with a $^{32}$P-labeled (CAC)s oligonucleotide probe (FIG. 2E), and monolocus polymerase chain reaction (PCR) with different locuses.

For monolocus PCR, genotyping revealed identical alleles for all loci (but one, D7S820) between blood (donor) DNA and OL1 DNA. See Table 15.

TABLE 15

Monolocus PCR genotyping.

| NN | Locus definition | Chromosomal location | hES | NSF | Blood |
|---|---|---|---|---|---|
| 1. | 3'ApoB | 2p24-p23 | 36/48 | 36/36 | 36/48 |
| 2. | D1S80 | 1p35-36 | 18/24 | 22/31 | 18/24 |
| 3. | D6S366 | 6q21-qter | 13/15 | 17/17 | 13/15 |
| 4. | D16S359 | 16q24-qter | 8/13 | 12/13 | 8/13 |
| 5. | D7S820 | 7q11.21-22 | 11/11 | 9/10 | 10/11 |
| 6. | vWFII | 12p13.3-12p13.2 | 11/13 | 9/11 | 11/13 |

TABLE 15-continued

Monolocus PCR genotyping.

| NN | Locus definition | Chromosomal location | hES | NSF | Blood |
|---|---|---|---|---|---|
| 7. | D13S317 | 13q22-q31 | 9/12 | 11/12 | 9/12 |
| 8. | vWA | 12p12pter | 14/18 | 17/18 | 14/18 |
| 9. | CSF1PO | 5q33.3-34 | 12/12 | 12/13 | 12/12 |
| 10. | TPOX | 2p25.1-pter | 8/11 | 8/11 | 8/11 |
| 11. | TH01 | 5q33.3-34 | 6/6 | 6/9.3 | 6/6 |

Heterozygosity (heterozygosis) of all heterozygous donor loci (but one, D7S820) was not changed in hES loci. Homozygosity (homozygosis) of D7S820 locus in hES DNA is a result of mutation (insertion of one AGAT monomer in microsatellite repeat) due to slipped-strand mispairing during DNA replication and DNA repair.

These results are in accordance with those obtained with multilocus DNA fingerprinting (when substantially identical fingerprint patterns for donor DNA and hES DNA were found).

Figure 2E:
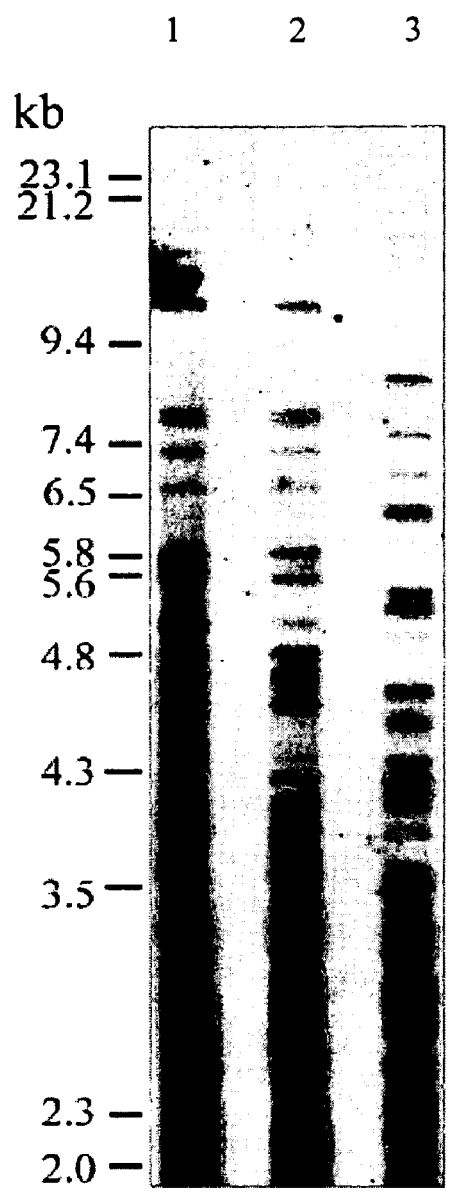
FIG. 2E shows the results from DNA finger printing analysis of parthenogenically derived hES cells. 1—DNA from the blood of the oocyte donor; 2—DNA from the parthenogenic hES cells derived from the same donor; 3—DNA from human feeder fibroblasts.

FIG. 2E demonstrated heterozygosity of hES cells and their identity with the oocyte donor's blood, and there was no similarity between the hES cells and the feeder cells. The DNA profile of hES cell line was confirmed by PCR-based haplotype analysis using polymorphic genes within the MHC class I and class II. Total genomic DNA from the oocyte donor blood cells, from hES cells, and feeder HNSFs were genotyped and compared. The data demonstrated that hES cells and cells from donor blood were indistinguishable from each other and therefore should be considered autologous, and both distinguished from DNA of the feeder cells (Table 16).

Natl Acad Sci USA (2003) 100(Suppl 1): 11911-11916), and do not coincide with data from parthenogenetic mouse stem cell lines (Lin et al., Stem Cells (2003) 21:153-161), which contains half of the donor genetic material.

Figure 4:
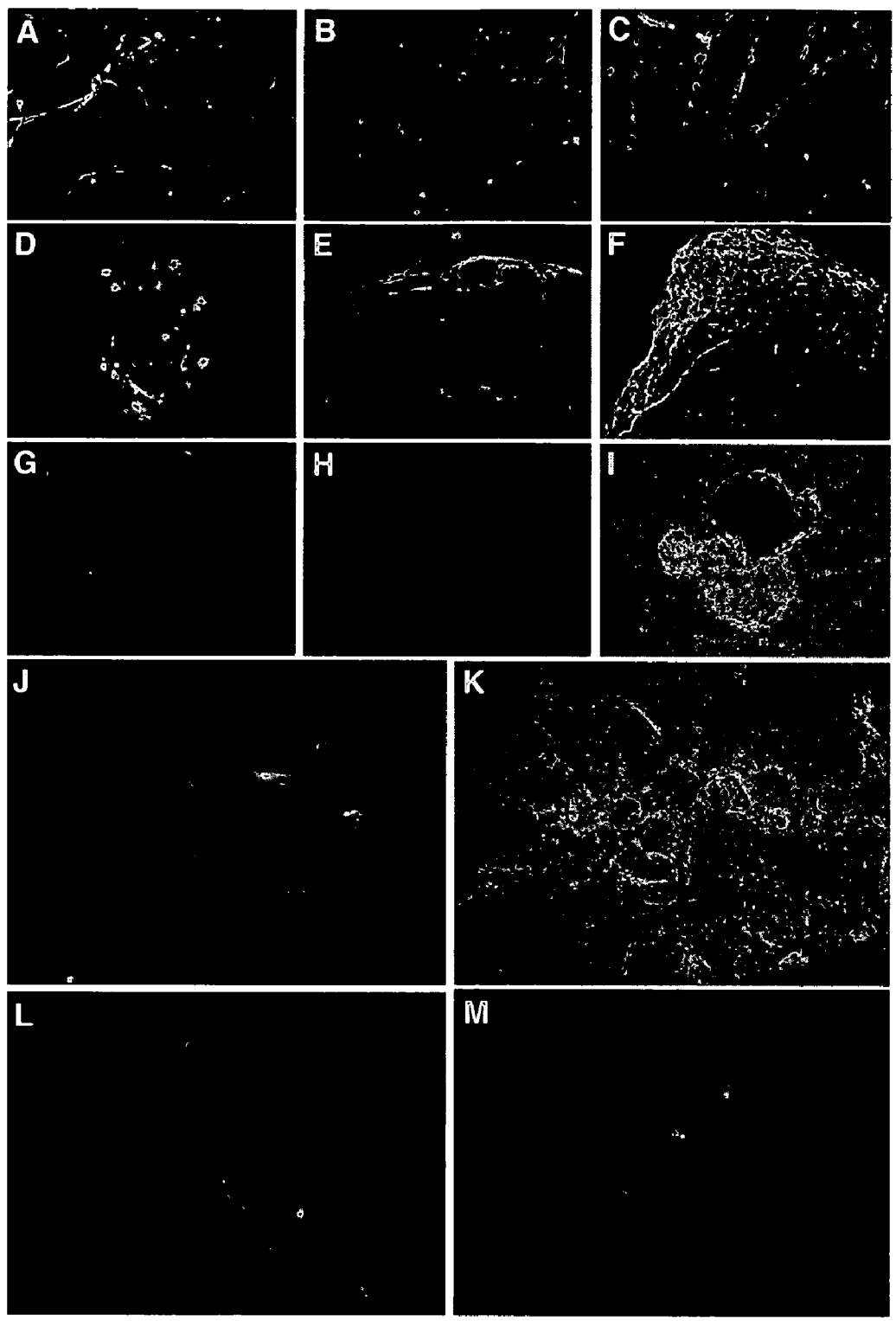
FIG. 4 shows the differentiation of phESC into derivatives of all three germ layers. Ectoderm differentiation is presented by positive immunocytochemical staining for neuron specific markers 68 (A), NCAM (B), beta III-tubulin (C) and glial cell marker GFAP (D, M). Differentiated cells were positive for mesodermal markers: muscle specific alpha actinin (G) and desmin (J), endothelial markers PECAM-1 (E) and VE-Cadherin (F). Endoderm differentiation is presented by positive staining for alpha-fetoprotein (H, L). The phESC produce pigmented epithelial-like cells (I, K). Magnification (I)×100; (A-H, J-M),×400.
Figure 5:
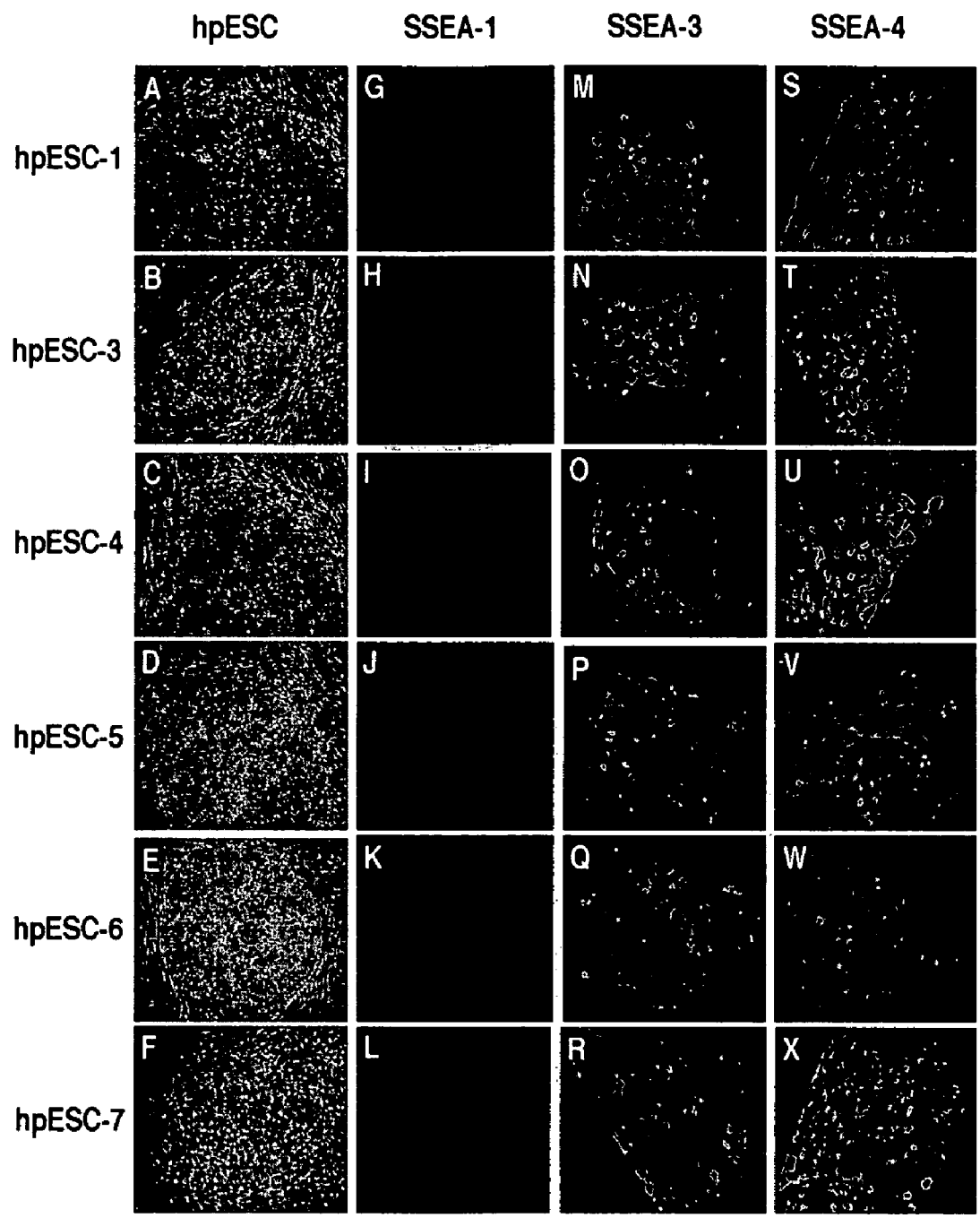
FIG. 5 shows the characterization of phESC lines for specific markers. Undifferentiated colonies of phESC on human feeder layer cells (A-F), negative staining for SSEA-1 (G-L), expression of cell surface markers SSEA-3 (M-R), SSEA-4 (S—X). Magnification (A) to (E)×100; (F)×200; (G) to (X)× 400. Alkaline phosphatase positive staining of phESC colonies on feeder cells (A-F), OCT-4 (G-L), TRA-1-60 (K—R) and TRA-1-81 (S—X). Magnification (A, B, O, R)×100; (C—F, M, S, X)×200; (G-L, N, P, Q, T-W)×400.
Figure 5:
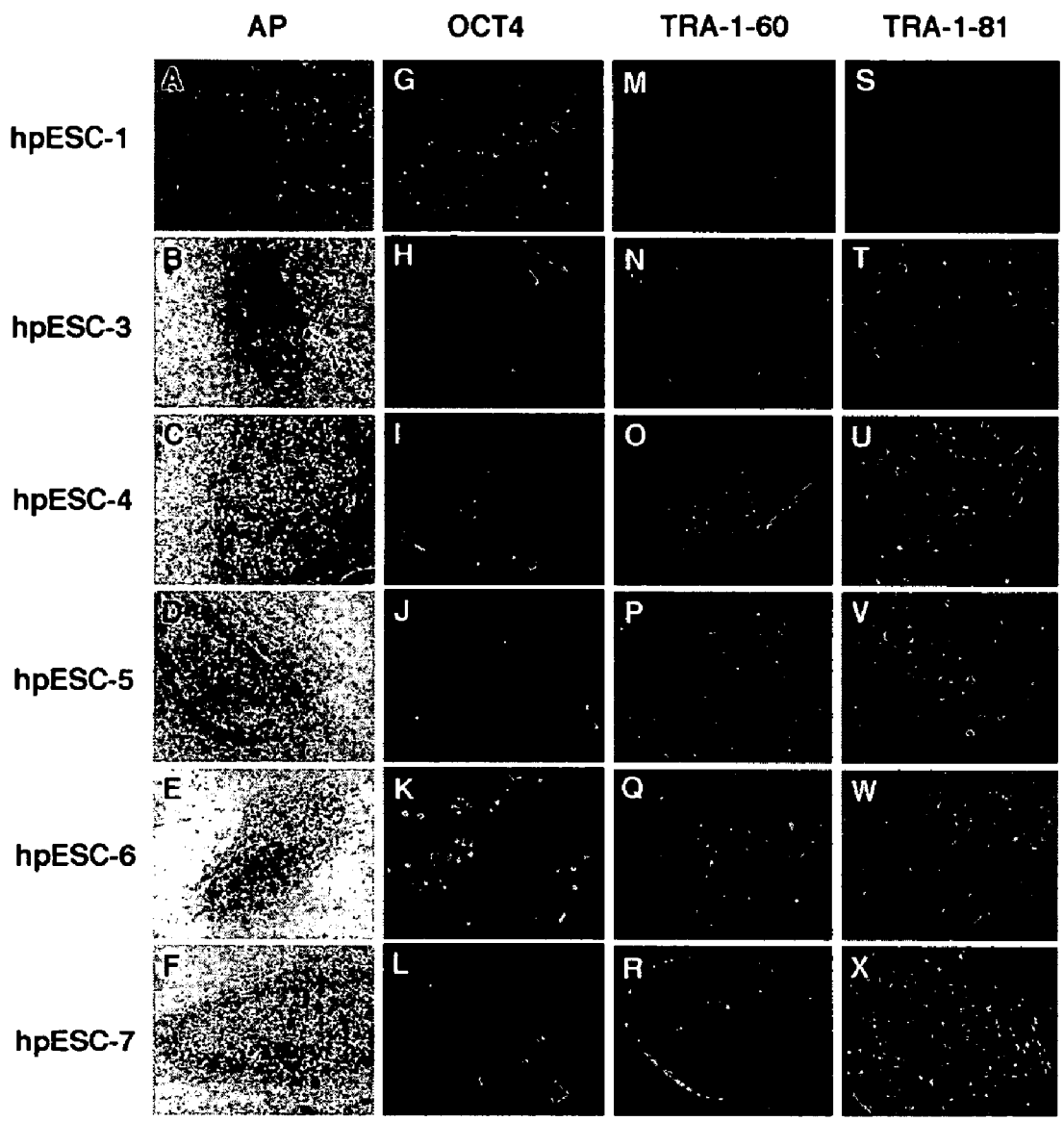
Figure 6:
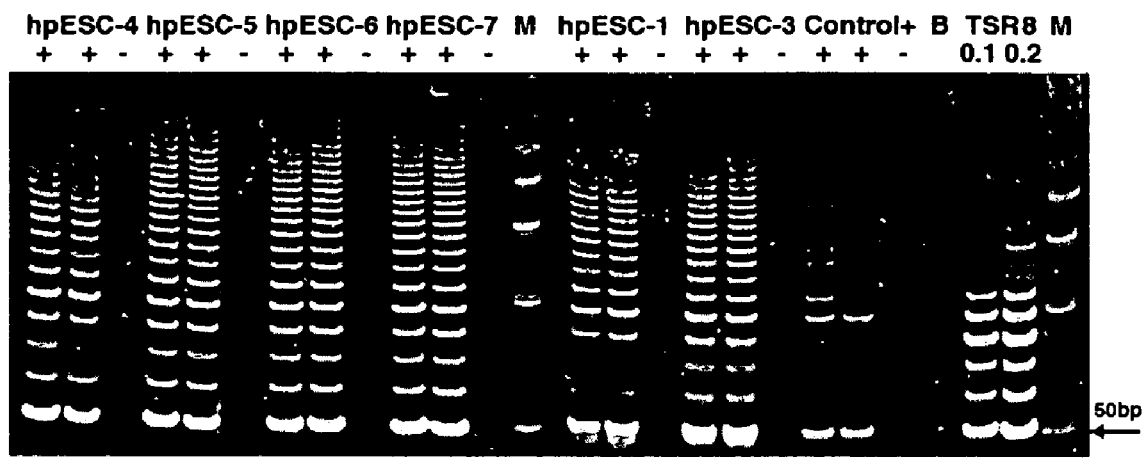
FIG. 6 demonstrates that phESC cells possess high levels of telomerase activity by comparison with positive control cells: "+"-extract from 500 cells; "–"-heat treated cell extract with inactivated telomerase; "Control +"-telomerase positive cell extract (applied with TRAPEZE Kit); "B"-CHAPS lysis buffer, primer-dimer/PCR contamination control; TSR8-telomerase quantitative control template (0.1 and 0.2 amole/µl); "M"-marker, DNA ladder.
Figure 7:
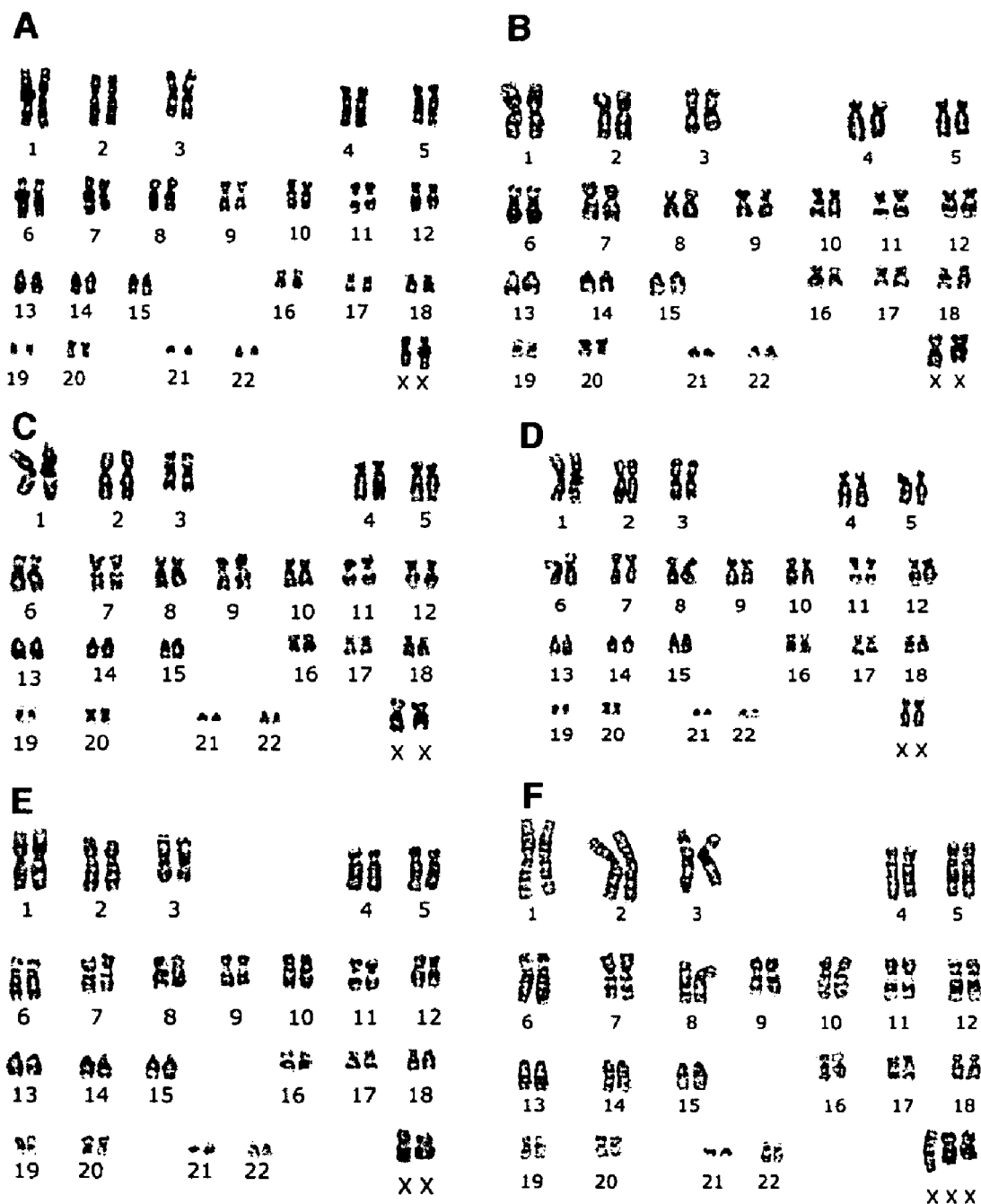
FIG. 7 shows the G-banded karyotyping of phESC lines. The phESC-1 (A), phESC-3 (B), phESC-4 (C), phESC-5 (D) and phESC-6 (E) lines have normal 46, XX karyotype. The phESC-7 line has 47, XXX karyotype (F).

The phESC lines display a morphology expected in hES cells, forming colonies with tightly packed cells, prominent nucleoli and a small cytoplasm to nucleus ratio (FIG. 4). These cells express traditional hES markers SSEA-3, SSEA-4, TRA-1-60, TRA-1-81, and OCT-4, and do not express SSEA-1, a positive marker for undifferentiated mouse embryonic stem cells (FIG. 4). The cells derived from all lines demonstrate high levels of alkaline phosphatase and telomerase activity (FIG. 5 and FIG. 6). G-banded karyotyping showed that phESC lines have a normal human 46,XX karyotype, with the exception of the phESC-7 line (FIG. 7). Approximately 91% of cells from the phESC-7 line have a 47,XXX karyotype and 9% of the cells have a 48,XXX,+6 karyotype. A different degree of X chromosome heteromorphism was observed in the lines; approximately 12% of the phESC-1 and phESC-6 lines; 42% for the phESC-5 line; and 70, 80, and 86% for the cell lines phESC7, phESC-3, and phESC-4, respectively (FIG. 7).

Comparative DNA profiling of was performed on all the phESC lines, the donor somatic cells and the feeder cells. These studies used Affimetrix SNP microarrays (Mapping 50K Hind 240 Arrays) to study chromosome changes and to confirm the genetic similarity of the phESC to the donor's somatic cells. All paired genotype relationships between phESC lines and their associated donor somatic cells were identified as "full siblings", and all other combinations of

TABLE 16

HLA Typing.

| | MHC I | | | MHC II | | |
|---|---|---|---|---|---|---|
| | HLA-A | HLA-B | HLA-C | DRB1 | DQB1 | DQA1 |
| pHES-1 | A*01 | B*15(63) | Cw*04 | DRB1*12 | DQB1*06 | DQA1*01 |
| | A*02 | B*35 | Cw*0708 | DRB1*13 | DQB1*03 | DQA1*0505 |
| Donor | A*01 | B*15(63) | Cw*04 | DRB1*12 | DQB1*06 | DQA1*01 |
| | A*02 | B*35 | Cw*0708 | DRB1*13 | DQB1*03 | DQA1*0505 |
| HNSF | A*25 | B*15(62) | Cw*12 | DRB1*04 | DQB1*06 | DQA1*01 |
| | A*32 | B*18 | Cw*12 | DRB1*15 | DQB1*03 | DQA1*03 |

DNA fingerprinting and HLA typing analysis confirmed that the hES cells are heterozygous and contain the whole donor genetic material. These results coincide with data from parthenogenetic monkey stem cell lines (Vrana et al., Proc pairs were identified as "unrelated". Internal controls identified the paired genotype relationship between split cultures derived from the same phESC line as "monozygotic twins" (Table 17, Database S1).

TABLE 17

Database S1.
Database S1 Identifying DNA samples from phESC and related donors

| genotype 1 | genotype 2 | putative relationship | inferred relationship | IBS 0 | IBS 1 | IBS 2 | n_typed | MZtwins | LOD par/off | LOD fullsibs | LOD halfsibs | LOD unrelated |
|---|---|---|---|---|---|---|---|---|---|---|---|---|
| 1 | 2 | unrelated | unrelated | 166 | 662 | 631 | 1459 | −1503.03 | −300.45 | −23.15 | −8.41 | 0 |
| 1 | 3 | unrelated | unrelated | 241 | 616 | 602 | 1459 | −1560.65 | −434.85 | −28.04 | −12.22 | 0 |
| 1 | 4 | unrelated | unrelated | 225 | 623 | 611 | 1459 | −1535.94 | −400.61 | −31.39 | −14.39 | 0 |
| 1 | 5 | unrelated | unrelated | 225 | 623 | 611 | 1459 | −1535.94 | −400.61 | −31.39 | −14.39 | 0 |
| 1 | 6 | unrelated | unrelated | 243 | 644 | 572 | 1459 | −1642.35 | −445.78 | −31.74 | −14.54 | 0 |
| 1 | 7 | unrelated | unrelated | 252 | 638 | 569 | 1459 | −1641.11 | −453.5 | −29.25 | −12.86 | 0 |
| 1 | 8 | unrelated | unrelated | 250 | 643 | 566 | 1459 | −1656.02 | −460.02 | −32.86 | −15.32 | 0 |
| 1 | 9 | unrelated | unrelated | 219 | 657 | 583 | 1459 | −1605.31 | −382.39 | −27.37 | −11.58 | 0 |
| 1 | 10 | unrelated | unrelated | 158 | 707 | 594 | 1459 | −1591.43 | −279.21 | −26.37 | −10..89 | 0 |
| 1 | 11 | unrelated | unrelated | 193 | 668 | 598 | 1459 | −1584.71 | −354.76 | −29.65 | −13..31 | 0 |
| 1 | 12 | unrelated | unrelated | 166 | 671 | 622 | 1459 | −1523.1 | −300.5 | −30.53 | −13..92 | 0 |
| 2 | 3 | unrelated | full sibs | 0 | 282 | 1177 | 1459 | −440.02 | −146.3 | 0 | −167.42 | −363.63 |
| 2 | 4 | unrelated | unrelated | 233 | 627 | 599 | 1459 | −1569.66 | −423.24 | −28.24 | −12.91 | 0 |
| 2 | 5 | unrelated | unrelated | 233 | 627 | 599 | 1459 | −1569.66 | −423.24 | −28.24 | −12.91 | 0 |
| 2 | 6 | unrelated | unrelated | 217 | 650 | 592 | 1459 | −1584.75 | −388.44 | −22.62 | −8.53 | 0 |
| 2 | 7 | unrelated | unrelated | 243 | 650 | 566 | 1459 | −1645.94 | −437.91 | −23.23 | −8.72 | 0 |
| 2 | 8 | unrelated | unrelated | 225 | 649 | 585 | 1459 | −1603.18 | −404.41 | −27.04 | −11.97 | 0 |
| 2 | 9 | unrelated | unrelated | 210 | 639 | 610 | 1459 | −1532.75 | −360.46 | −24.72 | −9.89 | 0 |
| 2 | 10 | unrelated | unrelated | 144 | 683 | 632 | 1459 | −1491.18 | −243.56 | −16.82 | −4.51 | 0 |
| 2 | 11 | unrelated | unrelated | 172 | 680 | 607 | 1459 | −1556.46 | −310.03 | −23.5 | −9.7 | 0 |
| 2 | 12 | unrelated | unrelated | 176 | 667 | 616 | 1459 | −1538.57 | −327.95 | −27.31 | −12..06 | 0 |
| 3 | 4 | unrelated | unrelated | 336 | 457 | 666 | 1459 | −1391.57 | −599.92 | −30.6 | −14.62 | 0 |
| 3 | 5 | unrelated | unrelated | 336 | 457 | 666 | 1459 | −1391.57 | −599.92 | −30.6 | −14.62 | 0 |
| 3 | 6 | unrelated | unrelated | 322 | 482 | 655 | 1459 | −1415.98 | −571.23 | −26.08 | −11.86 | 0 |
| 3 | 7 | unrelated | unrelated | 369 | 442 | 648 | 1459 | −1432.05 | −664.95 | −27.39 | −11.93 | 0 |
| 3 | 8 | unrelated | unrelated | 334 | 483 | 642 | 1459 | −1449.86 | −597.75 | −31.68 | −15.14 | 0 |
| 3 | 9 | unrelated | unrelated | 307 | 493 | 659 | 1459 | −1395.19 | −530.45 | −24.56 | −10 | 0 |
| 3 | 10 | unrelated | unrelated | 215 | 623 | 621 | 1459 | −1503.92 | −364.97 | −17.26 | −4.43 | 0 |
| 3 | 11 | unrelated | unrelated | 264 | 582 | 613 | 1459 | −1531.91 | −473.48 | −28.41 | −12..81 | 0 |
| 3 | 12 | unrelated | unrelated | 254 | 595 | 610 | 1459 | −1544.73 | −460.57 | −29.92 | −13..88 | 0 |
| 4 | 5 | unrelated | MZ twins | 0 | 0 | 1459 | 1459 | 0 | −379.58 | −45.47 | −401.67 | −677.74 |
| 4 | 6 | unrelated | unrelated | 334 | 475 | 650 | 1459 | −1436.59 | −599.55 | −32.73 | −15.19 | 0 |
| 4 | 7 | unrelated | unrelated | 365 | 439 | 655 | 1459 | −1418.34 | −656.01 | −31.6 | −14.56 | 0 |
| 4 | 8 | unrelated | unrelated | 329 | 486 | 644 | 1459 | −1450.75 | −586.4 | −32.06 | −14.88 | 0 |
| 4 | 9 | unrelated | unrelated | 332 | 466 | 661 | 1459 | −1395.18 | −590.12 | −28.69 | −12.94 | 0 |
| 4 | 10 | unrelated | unrelated | 245 | 606 | 608 | 1459 | −1542.32 | −438.93 | −28.75 | −12..74 | 0 |
| 4 | 11 | unrelated | unrelated | 273 | 569 | 617 | 1459 | −1530.97 | −492.84 | −29.03 | −12..34 | 0 |
| 4 | 12 | unrelated | full sibs | 0 | 224 | 1235 | 1459 | −326.17 | −162.34 | 0 | −183.44 | −393.46 |
| 5 | 6 | unrelated | unrelated | 334 | 475 | 650 | 1459 | −1436.59 | −599.55 | −32.73 | −15.19 | 0 |
| 5 | 7 | unrelated | unrelated | 365 | 439 | 655 | 1459 | −1418.34 | −656.01 | −31.6 | −14.56 | 0 |
| 5 | 8 | unrelated | unrelated | 329 | 486 | 644 | 1459 | −1450.75 | −586.4 | −32.06 | −14.88 | 0 |
| 5 | 9 | unrelated | unrelated | 332 | 466 | 661 | 1459 | −1395.18 | −590.12 | −28.69 | −12.94 | 0 |
| 5 | 10 | unrelated | unrelated | 245 | 606 | 608 | 1459 | −1542.32 | −438.93 | −28.75 | −12..74 | 0 |
| 5 | 11 | unrelated | unrelated | 273 | 569 | 617 | 1459 | −1530.97 | −492.84 | −29.03 | −12..34 | 0 |
| 5 | 12 | unrelated | full sibs | 0 | 224 | 1235 | 1459 | −326.17 | −162.34 | 0 | −183.44 | −393.46 |
| 6 | 7 | unrelated | full sibs | 45 | 176 | 1238 | 1459 | −277.78 | −217.21 | 0 | −165.72 | −390.62 |
| 6 | 8 | unrelated | full sibs | 44 | 187 | 1228 | 1459 | −289.8 | −201.32 | 0 | −153.75 | −365.51 |
| 6 | 9 | unrelated | unrelated | 333 | 481 | 645 | 1459 | −1436.5 | −595.4 | −30.3 | −13.77 | 0 |
| 6 | 10 | unrelated | unrelated | 240 | 601 | 618 | 1459 | −1518.17 | −425.03 | −27.11 | −11..53 | 0 |
| 6 | 11 | unrelated | full sibs | 0 | 164 | 1295 | 1459 | −209.27 | −191.66 | 0 | −213.25 | −440.56 |
| 6 | 12 | unrelated | unrelated | 234 | 615 | 610 | 1459 | −1547.15 | −416.14 | −30.21 | −13..64 | 0 |
| 7 | 8 | unrelated | full sibs | 38 | 225 | 1196 | 1459 | −326.62 | −150.16 | 0 | −121.55 | −334.09 |
| 7 | 9 | unrelated | unrelated | 359 | 473 | 627 | 1459 | −1479.28 | −642.41 | −30.61 | −14.47 | 0 |
| 7 | 10 | unrelated | unrelated | 252 | 623 | 584 | 1459 | −1598.35 | −443.81 | −28.88 | −13..09 | 0 |
| 7 | 11 | unrelated | full sibs | 0 | 230 | 1229 | 1459 | −318.49 | −137.93 | 0 | −159.55 | −389.58 |
| 7 | 12 | unrelated | unrelated | 265 | 583 | 611 | 1459 | −1539.33 | −472.91 | −30.55 | −13..87 | 0 |
| 8 | 9 | unrelated | unrelated | 347 | 480 | 632 | 1459 | −1472.41 | −625.68 | −30.93 | −14.31 | 0 |
| 8 | 10 | unrelated | unrelated | 244 | 614 | 601 | 1459 | −1561.3 | −434 | −28.07 | −12..37 | 0 |
| 8 | 11 | unrelated | full sibs | 0 | 175 | 1284 | 1459 | −223.73 | −178.56 | 0 | −200.12 | −428.04 |
| 8 | 12 | unrelated | unrelated | 236 | 610 | 613 | 1459 | −1539.08 | −417.14 | −29.32 | −13..14 | 0 |
| 9 | 10 | unrelated | full sibs | 0 | 228 | 1231 | 1459 | −315.15 | −152.88 | 0 | −174.27 | −392.91 |
| 9 | 11 | unrelated | unrelated | 269 | 567 | 623 | 1459 | −1502.69 | −479.57 | −28.47 | −12..55 | 0 |
| 9 | 12 | unrelated | unrelated | 245 | 612 | 602 | 1459 | −1557.25 | −438.53 | −26.07 | −11..15 | 0 |

TABLE 17-continued

Database S1.
Database S1 Identifying DNA samples from phESC and related donors

| genotype 1 | genotype 2 | putative relationship | inferred relationship | IBS 0 | IBS 1 | IBS 2 | n_typed | MZtwins | LOD par/off | LOD fullsibs | LOD halfsibs | LOD unrelated |
|---|---|---|---|---|---|---|---|---|---|---|---|---|
| 10 | 11 | unrelated | unrelated | 187 | 635 | 637 | 1459 | −1478.7 | −328.06 | −25.52 | −10.6 | 0 |
| 10 | 12 | unrelated | unrelated | 181 | 662 | 616 | 1459 | −1534.36 | −329 | −25.2 | −10.6 | 0 |

DNA samples were numbered as follows: 1-human neonatal skin fibroblasts; 2-phESC-7 line donor; 3-phESC-7 line; 4-phESC-1 line; 5-phESC-1 line; 6-phESC-3 line; 7-phESC-4 line; 8-phESC-5 line; 9-phESC-6 line; 10-phESC-6 line donor; 11-phESC-3 to phESC-5 lines donor; and 12-phESC-1 line donor.
The result shows that only one pair (sample 4-5), has been identified as monozygotic (MZ) twins. Ten other pairs (samples 2-3, 4-12, 5-12, 6-7, 6-11, 7-8, 7-11, 8-11, 9-10) have been identified as full siblings, and all the other combination of pairs have been identified as unrelated. The IBS columns in the output display the number of markers at which the pair are both typed and share 0, 1, or 2 alleles identical by state (For MZ twins under ideal conditions of no genotyping errors, all markers must be placed under IBS = 2). The output does not display P (observed markers | given relationship) directly, but it displays LOD score —$\log_{10}$ {P(observed markers | putative relationship/P(observed markers | relationship for which maximum likelihood was obtained and thus the call was made)} as a measure of similarity. The smaller the LOD score is, the less likely the putative relationship between two samples it.

Comparative analysis of 1,459 SNP markers revealed phESC heterozygosity and showed that changes had occurred in the phESC cell genotype in comparison to the related donor somatic cell genotype. Some segments of the somatic cell genome that had formerly been heterozygous became homozygous in the related phESC line genome. This heterozygous to homozygous pattern occurred in 11-15% of the phESC-1, phESC-3, phESC-4, phESC-5 and phESC-6 lines, and was 19% for the phESC7 line (Database S2). Moreover, genetic differences were observed between the phESC and phESC-5 lines that had been derived from the same oocyte donor (Table 18, Database S2).

TABLE 18

Database S2.
Database S2 Heterozygosity or phESC (Abbreviated as "pC") Lines

| chromosome | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 1 | SNP_A-1697748 | rs10752719 | 3744122 | 3.744122 | 0.436 | AB | AB | BB | AB | AB | AB | BB | BB | BB | BB |
| 1 | SNP_A-1743594 | rs806104 | 5977200 | 5.9772 | 0.631 | AB | AB | AA | AB | AB | AB | AB | AB | AA | AA |
| 1 | SNP_A-1687843 | rs301791 | 8402638 | 8.402638 | 0.274 | AB | AB | BB | BB | BB | BB | AB | AB | AA | AB |
| 1 | SNP_A-1647681 | rs1474868 | 11978430 | 11.97843 | 0.333 | BB | BB | AA | AA | AA | AA | AA | AA | AA | AA |
| 1 | SNP_A-1673737 | rs1417144 | 14211391 | 14.211391 | 0.548 | AA | AA | AB | AB | AB | AB | AA | AA | AB | AB |
| 1 | SNP_A-1747116 | rs860379 | 18414756 | 18.414756 | 0.25 | BB | BB | BB | BB | BB | BB | BB | BB | BB | BB |
| 1 | SNP_A-1662223 | rs10492997 | 19514677 | 19.514677 | 0.631 | AA | AA | BB | BB | BB | BB | AB | AB | AA | AA |
| 1 | SNP_A-1662225 | rs559346 | 28077956 | 28.077956 | 0.583 | BB | AB | AB | AB | AB | AB | AB | AB | AA | AB |
| 1 | SNP_A-1646469 | rs4949455 | 31783886 | 31.783886 | 0.382 | AA | AB | AB | BB | AB | AB | AB | AB | AA | AA |
| 1 | SNP_A-1695076 | rs6661190 | 33872782 | 33.872782 | 0.274 | BB | BB | BB | BB | BB | BB | BB | BB | BB | AB |
| 1 | SNP_A-1679571 | rs4653029 | 34558585 | 34.558585 | 0.274 | BB | BB | BB | BB | BB | BB | BB | BB | BB | BB |
| 1 | SNP_A-1675060 | rs7531479 | 36798680 | 36.79868 | 0.714 | AA | AA | AA | AA | AA | AA | AA | AA | AA | AA |
| 1 | SNP_A-1753902 | rs1010805 | 37858235 | 37.858235 | 0.738 | AA | AA | AB | AA | BB | AB | AA | AA | BB | BB |
| 1 | SNP_A-1691977 | rs6693076 | 39972196 | 39.972196 | 0.441 | AA | AA | AB | AA | BB | AB | AB | AB | BB | BB |
| 1 | SNP_A-1723259 | rs407752 | 40472948 | 40.472948 | 0.333 | BB | BB | AB | AA | BB | AB | BB | BB | BB | BB |
| 1 | SNP_A-1692103 | rs7515340 | 41055964 | 41.055964 | 0.381 | AB | AB | AA | AA | AA | AA | AA | AA | BB | BB |
| 1 | SNP_A-1696731 | rs4660575 | 41902429 | 41.902429 | 0.429 | BB | BB | BB | BB | BB | BB | AA | AA | BB | AB |
| 1 | SNP_A-1701070 | rs1408412 | 42787470 | 42.78747 | 0.679 | AA | AA | AA | AA | AA | AA | AA | AA | AA | AA |
| 1 | SNP_A-1729559 | rs1771551 | 45552736 | 45.552736 | 0.738 | AA | AA | AA | AA | AA | AA | AA | AA | BB | AB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 1 | SNP_A-1670587 | rs2245122 | 47358015 | 47.358015 | 0.598 | AA | AA | AA | AA | AA | AA | BB | BB | BB | AB |
| 1 | SNP_A-1711898 | rs1875645 | 50501900 | 50.5019 | 0.524 | AB | AB | BB | BB | BB | BB | BB | BB | BB | BB |
| 1 | SNP_A-1645411 | rs625643 | 54349188 | 54.349188 | 0.25 | BB | BB | BB | BB | BB | BB | BB | BB | BB | BB |
| 1 | SNP_A-1718210 | rs10493206 | 56531172 | 56.531172 | 0.488 | AA | AA | BB | BB | BB | BB | AB | AB | AA | AB |
| 1 | SNP_A-1752670 | rs1831870 | 57339224 | 57.339224 | 0.524 | AB | AB | AB | AB | BB | AB | BB | BB | BB | AB |
| 1 | SNP_A-1669308 | rs852766 | 57998529 | 57.998529 | 0.564 | AA | AA | AA | AA | AA | AA | AA | AA | BB | AB |
| 1 | SNP_A-1681141 | rs1969772 | 58917123 | 58.917123 | 0.738 | AA | AA | AA | AA | AA | AA | AB | AB | AA | AB |
| 1 | SNP_A-1690420 | rs10489908 | 61576784 | 61.576784 | 0.738 | AA | AA | AA | AA | AA | AA | AA | AA | AA | AA |
| 1 | SNP_A-1727043 | rs2765249 | 62441479 | 62.441479 | 0.75 | AA | AA | AA | AA | AA | AA | BB | BB | AA | AB |
| 1 | SNP_A-1646105 | rs3861943 | 63439667 | 63.439667 | 0.405 | BB | BB | BB | BB | BB | BB | AB | AB | AA | AB |
| 1 | SNP_A-1654674 | rs592298 | 64000081 | 64.000081 | 0.25 | BB | BB | BB | BB | BB | BB | AB | AB | BB | AB |
| 1 | SNP_A-1708628 | rs746633 | 64503887 | 64.503887 | 0.692 | AA | AA | BB | BB | BB | BB | BB | BB | AA | AB |
| 1 | SNP_A-1713897 | rs1171279 | 65700514 | 65.700514 | 0.345 | BB | BB | BB | BB | BB | BB | BB | BB | BB | AB |
| 1 | SNP_A-1717648 | rs1280310 | 66928844 | 66.928844 | 0.655 | AB | AB | AB | BB | AA | AB | AB | AB | AA | AB |
| 1 | SNP_A-1712508 | rs1408956 | 67849084 | 67.849084 | 0.536 | AB | AB | AB | AA | BB | AB | AB | AB | BB | BB |
| 1 | SNP_A-1688631 | rs1413953 | 70834525 | 70.834525 | 0.571 | AB | AB | AA | AA | AA | AA | AB | AB | AA | AB |
| 1 | SNP_A-1720162 | rs1338655 | 73569634 | 73.569634 | 0.429 | AB | AB | AA | AA | AA | AA | AA | AA | BB | BB |
| 1 | SNP_A-1697494 | rs10493539 | 74427598 | 74.427598 | 0.25 | AA | AA | BB | BB | BB | BB | BB | BB | AA | AB |
| 1 | SNP_A-1649261 | rs277355 | 75002805 | 75.002805 | 0.345 | BB | BB | BB | BB | BB | BB | AB | AB | BB | AB |
| 1 | SNP_A-1744876 | rs1250876 | 75905253 | 75.905253 | 0.345 | AB | AB | AB | BB | AA | AB | AB | AB | BB | BB |
| 1 | SNP_A-1739854 | rs3928852 | 76926021 | 76.926021 | 0.607 | AA | AA | AA | AA | AA | AA | AB | AB | AA | AA |
| 1 | SNP_A-1687047 | rs10493596 | 77438262 | 77.438262 | 0.718 | AA | AA | AA | AA | AA | AA | AB | AB | AA | AA |
| 1 | SNP_A-1732619 | rs1248480 | 79071260 | 79.07126 | 0.357 | BB | BB | AA | AA | AA | AA | AB | AB | BB | BB |
| 1 | SNP_A-1664985 | rs2127436 | 79792017 | 79.792017 | 0.488 | AB | AB | BB | AB | AA | AB | BB | BB | AA | AB |
| 1 | SNP_A-1644541 | rs2389016 | 80511350 | 80.51135 | 0.738 | AA | AA | AB | BB | AA | AB | AB | AB | AA | AB |
| 1 | SNP_A-1645927 | rs10518660 | 82094088 | 82.094088 | 0.738 | AB | AB | AA | AA | AA | AA | AA | AA | AA | AA |
| 1 | SNP_A-1693780 | rs6598991 | 82697988 | 82.697988 | 0.524 | BB | BB | AB | AA | AB | AB | AA | AA | AA | AA |
| 1 | SNP_A-1674234 | rs2268667 | 85505767 | 85.505767 | 0.321 | BB | BB | AB | AA | AB | AB | BB | BB | BB | AB |
| 1 | SNP_A-1752288 | rs306322 | 88673430 | 88.67343 | 0.726 | AA | AA | AA | AA | AA | AA | AB | AB | BB | AB |
| 1 | SNP_A-1736094 | rs1831298 | 90211840 | 90.21184 | 0.262 | AB | AB | BB | BB | BB | BB | AA | AA | BB | AB |
| 1 | SNP_A-1711115 | rs4233429 | 90811924 | 90.811924 | 0.25 | BB | BB | AB | BB | AB | AB | BB | BB | BB | BB |
| 1 | SNP_A-1714794 | rs665484 | 91375951 | 91.375951 | 0.512 | AB | AB | AA | AA | AA | AA | AA | AA | BB | BB |
| 1 | SNP_A-1675488 | rs490800 | 92304926 | 92.304926 | 0.369 | BB | BB | AB | BB | AB | AB | AB | AB | BB | AB |
| 1 | SNP_A-1656572 | rs6703310 | 93500761 | 93.500761 | 0.393 | AB | AB | AA | AA | AA | AA | BB | BB | BB | BB |
| 1 | SNP_A-1755223 | rs223237 | 96276742 | 96.276742 | 0.476 | BB | BB | BB | BB | BB | BB | AA | AA | AA | AA |
| 1 | SNP_A-1691383 | rs1911500 | 98291841 | 98.291841 | 0.738 | AA | AA | AA | AA | AA | AA | AB | AB | AA | AB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 1 | SNP_A-1725993 | rs1838587 | 101983453 | 101.983453 | 0.525 | AA | AA | AB | AA | AB | AB | AB | AB | AA | AB |
| 1 | SNP_A-1689489 | rs7521799 | 102944538 | 102.944538 | 0.619 | BB | BB | AB | AA | AB | AB | AA | AB | BB | BB |
| 1 | SNP_A-1684273 | rs1576516 | 104210964 | 104.210964 | 0.452 | AB | AB | AA | AA | AA | AA | BB | BB | AA | AA |
| 1 | SNP_A-1733369 | rs1919894 | 107240697 | 107.240697 | 0.381 | BB | BB | BB | BB | BB | BB | AA | AB | BB | BB |
| 1 | SNP_A-1715038 | rs10494081 | 108114145 | 108.114145 | 0.667 | AA | AA | AA | AA | AA | AA | AA | BB | AB | AB |
| 1 | SNP_A-1699288 | rs2026485 | 108978565 | 108.978565 | 0.333 | BB | BB | AB | BB | AB | AB | BB | BB | BB | AB |
| 1 | SNP_A-1750726 | rs6682717 | 110527665 | 110.527665 | 0.441 | AA | AA | AB | BB | AB | AB | AB | AA | AA | AA |
| 1 | SNP_A-1648811 | rs694180 | 111438255 | 111.438255 | 0.464 | AB | AB | BB | BB | BB | BB | BB | BB | AA | AB |
| 1 | SNP_A-1753842 | rs1936061 | 112187978 | 112.187978 | 0.595 | AA | AA | AA | AA | AA | AA | BB | AB | BB | BB |
| 1 | SNP_A-1689065 | rs2359417 | 113685242 | 113.685242 | 0.452 | BB | BB | BB | BB | BB | BB | AA | AB | BB | BB |
| 1 | SNP_A-1746401 | rs3767824 | 118152606 | 118.152606 | 0.429 | BB | BB | BB | BB | BB | BB | BB | BB | BB | BB |
| 1 | SNP_A-1688653 | rs1766803 | 119095860 | 119.09586 | 0.366 | BB | AB | BB | BB | BB | BB | BB | BB | BB | BB |
| 1 | SNP_A-1708513 | rs477992 | 119969618 | 119.969618 | 0.286 | AA | AB | BB | BB | BB | AB | BB | BB | BB | AB |
| 1 | SNP_A-1701244 | rs10494240 | 143040559 | 143.040559 | 0.321 | AB | AB | AA | AA | AA | AA | BB | AB | AA | AB |
| 1 | SNP_A-1706430 | rs10494267 | 148366991 | 148.366991 | 0.321 | BB | BB | BB | BB | BB | BB | AB | AB | BB | BB |
| 1 | SNP_A-1680305 | rs2879490 | 149760236 | 149.760236 | 0.381 | BB | BB | BB | BB | BB | AB | AA | AA | AA | AA |
| 1 | SNP_A-1723421 | rs10494303 | 150706096 | 150.706096 | 0.571 | BB | BB | AA | AA | AA | AB | AB | AB | AA | AA |
| 1 | SNP_A-1681003 | rs884664 | 151516798 | 151.516798 | 0.702 | AA | AA | AA | AA | AA | AB | AA | AA | AA | AA |
| 1 | SNP_A-1667931 | rs10494315 | 154072954 | 154.072954 | 0.655 | AB | AB | AA | AA | AA | AB | BB | BB | BB | AB |
| 1 | SNP_A-1647211 | rs919477 | 155585918 | 155.585918 | 0.25 | BB | BB | BB | BB | BB | BB | BB | BB | BB | AB |
| 1 | SNP_A-1662451 | rs1149392 | 157241261 | 157.241261 | 0.286 | BB | BB | BB | BB | BB | BB | BB | BB | BB | BB |
| 1 | SNP_A-1695012 | rs6683968 | 158923070 | 158.92307 | 0.571 | AA | AA | BB | BB | BB | BB | AA | AA | AA | AA |
| 1 | SNP_A-1716490 | rs869513 | 159832184 | 159.832184 | 0.607 | AA | AA | AA | AA | AA | AA | AA | AA | AA | AA |
| 1 | SNP_A-1727494 | rs4656422 | 161688624 | 161.688624 | 0.25 | AB | AB | AA | AA | AB | AB | BB | BB | BB | BB |
| 1 | SNP_A-1646555 | rs4657482 | 162563307 | 162.563307 | 0.405 | AB | AB | BB | BB | BB | BB | AB | AB | BB | BB |
| 1 | SNP_A-1743854 | rs2093658 | 164086850 | 164.08685 | 0.317 | AA | AA | AA | AA | AB | AB | AA | AA | AA | AA |
| 1 | SNP_A-1681011 | rs1358948 | 165590931 | 165.590931 | 0.31 | BB | BB | BB | BB | BB | BB | AB | AB | AA | AB |
| 1 | SNP_A-1751990 | rs2205848 | 166407951 | 166.407951 | 0.31 | BB | BB | BB | BB | BB | BB | BB | BB | BB | AB |
| 1 | SNP_A-1736240 | rs10494487 | 167046739 | 167.046739 | 0.298 | AB | AB | BB | BB | BB | BB | BB | BB | BB | BB |
| 1 | SNP_A-1674510 | rs3753538 | 168481215 | 168.481215 | 0.691 | AA | AA | AA | AA | AA | AA | AA | AA | BB | AB |
| 1 | SNP_A-1719434 | rs10489280 | 169204277 | 169.204277 | 0.488 | AA | AA | BB | BB | BB | BB | AA | AA | BB | BB |
| 1 | SNP_A-1753950 | rs989423 | 171514180 | 171.51418 | 0.75 | AA | AA | AA | AA | AA | AA | AA | AA | AA | AA |
| 1 | SNP_A-1722081 | rs1359587 | 172487558 | 172.487558 | 0.691 | AB | AB | BB | BB | AB | AB | AB | AB | AA | AB |
| 1 | SNP_A-1694706 | rs2861746 | 173128066 | 173.128066 | 0.452 | AB | AB | AB | AB | AB | AB | AB | AB | BB | BB |
| 1 | SNP_A-1733825 | rs2493119 | 175995013 | 175.995013 | 0.333 | BB | BB | BB | BB | BB | BB | BB | BB | AA | AB |
| 1 | SNP_A-1671505 | rs1281294 | 178629596 | 178.629596 | 0.714 | AA | AA | AA | AA | AA | AA | AA | AA | AA | AA |

TABLE 18-continued

Database S2.
Database S2 Heterozygosity or phESC (Abbreviated as "pC") Lines

| chromosome | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 1 | SNP_A-1694118 | rs2274984 | 179839103 | 179.839103 | 0.524 | AB | AB | AB | BB | AB | AB | AA | AA | BB | BB |
| 1 | SNP_A-1644471 | rs1184639 | 180355276 | 180.355276 | 0.357 | BB | BB | BB | BB | BB | BB | BB | BB | BB | AB |
| 1 | SNP_A-1711261 | rs2840274 | 180942462 | 180.942462 | 0.429 | AA | AA | BB | BB | BB | AA | AB | BB | BB | BB |
| 1 | SNP_A-1706912 | rs170885 | 181673406 | 181.673406 | 0.512 | AB | AB | AA | AA | AA | AA | BB | AB | BB | AB |
| 1 | SNP_A-1703470 | rs10489701 | 182242226 | 182.242226 | 0.595 | AA | AA | AB | BB | AB | AB | AA | AA | AA | AA |
| 1 | SNP_A-1696277 | rs10489756 | 182835425 | 182.835425 | 0.262 | BB | BB | AB | AA | AB | AB | AA | AA | BB | AB |
| 1 | SNP_A-1744486 | rs726706 | 183604111 | 183.604111 | 0.429 | AB | AB | BB | BB | BB | BB | BB | BB | AA | AB |
| 1 | SNP_A-1693312 | rs7543266 | 184360480 | 184.36048 | 0.595 | AA | AA | AA | AA | AA | AA | AA | AA | AA | AA |
| 1 | SNP_A-1739170 | rs6665263 | 185050414 | 185.050414 | 0.452 | BB | BB | BB | BB | BB | BB | BB | BB | AA | AA |
| 1 | SNP_A-1726093 | rs10494626 | 186275233 | 186.275233 | 0.464 | AA | AA | BB | BB | BB | BB | BB | BB | BB | AB |
| 1 | SNP_A-1658415 | rs815160 | 186988747 | 186.988747 | 0.427 | AB | AB | AA | AA | AA | AA | AA | AA | AA | AA |
| 1 | SNP_A-1666089 | rs1563191 | 187849406 | 187.849406 | 0.333 | AB | AB | AB | BB | AB | AB | BB | BB | BB | BB |
| 1 | SNP_A-1753798 | rs1338034 | 188358939 | 188.358939 | 0.393 | BB | BB | BB | BB | BB | BB | BB | BB | BB | BB |
| 1 | SNP_A-1688981 | rs4657868 | 190164348 | 190.164348 | 0.524 | AB | AB | BB | BB | BB | BB | BB | AB | BB | BB |
| 1 | SNP_A-1723115 | rs10494707 | 191296870 | 191.29687 | 0.357 | BB | BB | BB | BB | BB | BB | AA | AB | BB | BB |
| 1 | SNP_A-1651749 | rs822456 | 191826836 | 191.826836 | 0.439 | BB | BB | BB | BB | BB | BB | BB | BB | AA | AB |
| 1 | SNP_A-1642592 | rs10494728 | 192402426 | 192.402426 | 0.25 | AB | AB | BB | BB | BB | BB | AA | AB | BB | BB |
| 1 | SNP_A-1658925 | rs3762271 | 193802099 | 193.802099 | 0.6 | AB | AB | AA | AA | AA | AA | BB | BB | AA | AB |
| 1 | SNP_A-1687705 | rs1927246 | 195048356 | 195.048356 | 0.702 | AB | AB | AB | BB | AB | AB | AA | AA | AA | AB |
| 1 | SNP_A-1725025 | rs10494808 | 196821529 | 196.821529 | 0.548 | AB | AB | AA | AA | AA | AA | BB | BB | BB | AB |
| 1 | SNP_A-1665029 | rs6667172 | 197375495 | 197.375495 | 0.5 | BB | BB | AA | AA | AA | AA | AA | AB | AA | AB |
| 1 | SNP_A-1747494 | rs832174 | 197990176 | 197.990176 | 0.25 | AA | AA | BB | BB | BB | BB | BB | BB | BB | BB |
| 1 | SNP_A-1651207 | rs7555556 | 199822633 | 199.822633 | 0.293 | AB | AB | AB | AB | AB | AB | AA | AB | BB | AB |
| 1 | SNP_A-1714962 | rs10494844 | 200501548 | 200.501548 | 0.75 | AA | AA | AA | AA | AA | AA | AA | AB | AA | AA |
| 1 | SNP_A-1724123 | rs10494852 | 201189443 | 201.189443 | 0.655 | BB | BB | BB | BB | BB | BB | AA | AB | AA | AA |
| 1 | SNP_A-1673439 | rs311286 | 203999303 | 203.999303 | 0.286 | AB | AB | BB | BB | BB | BB | BB | BB | BB | BB |
| 1 | SNP_A-1669116 | rs684431 | 204553812 | 204.553812 | 0.381 | BB | BB | AA | AB | AA | AB | BB | BB | AB | AB |
| 1 | SNP_A-1650733 | rs2358452 | 208747444 | 208.747444 | 0.707 | AA | AA | AA | AA | AA | AA | BB | BB | AA | AA |
| 1 | SNP_A-1651975 | rs340840 | 210516282 | 210.516282 | 0.393 | AB | AB | BB | BB | BB | BB | BB | BB | AA | AA |
| 1 | SNP_A-1683565 | rs10494987 | 211525052 | 211.525052 | 0.691 | AB | AB | AA | AA | AA | AA | AA | AA | AA | AA |
| 1 | SNP_A-1750462 | rs10495003 | 212237742 | 212.237742 | 0.417 | AB | AB | BB | AB | BB | AB | AA | AB | AA | AA |
| 1 | SNP_A-1683969 | rs6604634 | 213109650 | 213.10965 | 0.524 | BB | BB | AA | AA | AA | AA | BB | BB | AA | AA |
| 1 | SNP_A-1731002 | rs10495045 | 213806233 | 213.806233 | 0.714 | AA | AA | AA | AB | AA | AB | BB | BB | AB | AB |
| 1 | SNP_A-1677675 | rs618171 | 215537693 | 215.537693 | 0.631 | AB | AB | AA | AA | AA | AA | AA | AB | AB | AB |
| 1 | SNP_A-1703136 | rs10495156 | 217494419 | 217.494419 | 0.298 | BB | BB | BB | BB | BB | BB | AA | AA | AB | AB |
| 1 | SNP_A-1711849 | rs1338077 | 218118775 | 218.118775 | 0.321 | BB | BB | BB | AB | BB | AB | BB | BB | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 1 | SNP_A-1755399 | rs4481859 | 219121051 | 219.121051 | 0.512 | AB | AB | AA | AA | AA | AA | BB | BB | BB | BB |
| 1 | SNP_A-1739524 | rs10495236 | 221802391 | 221.802391 | 0.691 | AB | AB | AA | AB | AA | AB | AB | AB | AB | AB |
| 1 | SNP_A-1710164 | rs710805 | 225430849 | 225.430849 | 0.429 | AB | AB | BB | AB | BB | AB | AB | AB | AA | AA |
| 1 | SNP_A-1688357 | rs1998067 | 226545242 | 226.545242 | 0.298 | BB | BB | AA | AA | AA | AA | BB | BB | BB | BB |
| 1 | SNP_A-1732138 | rs9286801 | 229119361 | 229.119361 | 0.476 | AA | AA | AA | AA | AA | AA | AA | AA | AA | AA |
| 1 | SNP_A-1747040 | rs1892298 | 230387334 | 230.387334 | 0.714 | AA | AA | AA | AA | AA | AA | AA | AB | AA | AA |
| 1 | SNP_A-1717898 | rs2463190 | 232711157 | 232.711157 | 0.441 | AB | AB | BB | AB | BB | AB | AA | AA | AA | AA |
| 1 | SNP_A-1710935 | rs819639 | 233219640 | 233.21964 | 0.56 | AB | AB | AA | AA | AA | AA | BB | AB | AA | AA |
| 1 | SNP_A-1755297 | rs2819774 | 234214896 | 234.214896 | 0.691 | AA | AA | AA | AA | AA | AA | BB | AA | AB | AB |
| 1 | SNP_A-1677233 | rs6685861 | 235621137 | 235.621137 | 0.357 | BB | BB | AA | AA | AA | AA | AA | AB | AA | AA |
| 1 | SNP_A-1679485 | rs732160 | 236262770 | 236.26277 | 0.298 | BB | BB | BB | BB | BB | BB | BB | BB | AB | AB |
| 1 | SNP_A-1679759 | rs1039529 | 238918670 | 238.91867 | 0.619 | AA | AA | AA | AA | AA | AA | AA | AA | AA | AA |
| 1 | SNP_A-1664943 | rs879725 | 240732087 | 240.732087 | 0.464 | BB | AB | AA | AA | AA | AA | AB | AB | AB | AB |
| 1 | SNP_A-1724627 | rs1093961 | 241902498 | 241.902498 | 0.415 | BB | AB | AB | BB | AB | AB | AA | AB | AB | AB |
| 1 | SNP_A-1672603 | rs3844080 | 243632874 | 243.632874 | 0.655 | BB | BB | AA | AA | AA | AA | BB | AB | AA | AA |
| 2 | SNP_A-1753456 | rs10519439 | 108913 | 0.108913 | 0.274 | BB | BB | BB | BB | BB | BB | AB | AB | BB | BB |
| 2 | SNP_A-1746820 | rs6759198 | 2342478 | 2.342478 | 0.56 | AA | AA | BB | BB | BB | BB | AB | AB | BB | BB |
| 2 | SNP_A-1697325 | rs2119075 | 4395806 | 4.395806 | 0.607 | AA | AA | AA | AB | AB | AB | AB | AB | AB | AB |
| 2 | SNP_A-1740868 | rs963964 | 5206872 | 5.206872 | 0.321 | BB | BB | BB | BB | BB | BB | BB | BB | AB | AB |
| 2 | SNP_A-1677893 | rs1429220 | 5881639 | 5.881639 | 0.369 | BB | BB | BB | BB | BB | BB | BB | BB | BB | BB |
| 2 | SNP_A-1650909 | rs6727796 | 7605796 | 7.605796 | 0.512 | BB | BB | AA | AA | AA | AA | BB | BB | AB | AB |
| 2 | SNP_A-1663651 | rs9287698 | 8437894 | 8.437894 | 0.281 | BB | BB | BB | BB | BB | BB | AB | AB | AA | AA |
| 2 | SNP_A-1647101 | rs2271333 | 9323848 | 9.323848 | 0.5 | AB | AB | AA | AA | AA | AA | BB | BB | BB | BB |
| 2 | SNP_A-1717786 | rs2241113 | 10226344 | 10.226344 | 0.31 | BB | BB | AB | AB | AB | AB | AB | AB | BB | BB |
| 2 | SNP_A-1706150 | rs1686426 | 10899146 | 10.899146 | 0.5 | BB | BB | AB | AB | AB | AB | BB | BB | BB | BB |
| 2 | SNP_A-1676173 | rs4669806 | 12151350 | 12.15135 | 0.619 | BB | BB | AA | AA | AA | AA | AA | AA | AA | AB |
| 2 | SNP_A-1664687 | rs625842 | 12779571 | 12.779571 | 0.583 | BB | BB | AA | AA | AA | AA | BB | BB | AB | AB |
| 2 | SNP_A-1696327 | rs7568703 | 15041402 | 15.041402 | 0.571 | AA | AA | AB | AB | AB | AB | BB | BB | AA | AA |
| 2 | SNP_A-1683239 | rs4668968 | 15835884 | 15.835884 | 0.369 | BB | BB | BB | BB | BB | BB | BB | BB | BB | BB |
| 2 | SNP_A-1677981 | rs9306902 | 16971747 | 16.971747 | 0.631 | AA | AA | AA | AA | AA | AA | AA | AA | AA | AA |
| 2 | SNP_A-1714454 | rs10495699 | 19918971 | 19.918971 | 0.56 | AB | AB | AB | AB | AA | AB | AB | AA | AB | AB |
| 2 | SNP_A-1668860 | rs10495705 | 20662972 | 20.662972 | 0.564 | AA | AA | AA | AA | AA | AA | BB | BB | AA | AA |
| 2 | SNP_A-1693698 | rs7594267 | 23344557 | 23.344557 | 0.571 | AA | AA | BB | BB | BB | BB | BB | BB | AA | AA |
| 2 | SNP_A-1751070 | rs1275963 | 26804398 | 26.804398 | 0.643 | AB | AB | AA | AA | AA | AA | AA | AA | AA | AA |
| 2 | SNP_A-1684619 | rs2014701 | 30210694 | 30.210694 | 0.631 | AA | AA | AA | AA | AA | AA | BB | AB | BB | BB |
| 2 | SNP_A-1648557 | rs10490360 | 32207919 | 32.207919 | 0.441 | BB | BB | AA | AA | AA | AA | BB | BB | AB | AB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 2 | SNP_A-1671421 | rs219145 | 33123165 | 33.123165 | 0.634 | AA | AA | AA | AA | AA | AA | AA | AA | BB | BB |
| 2 | SNP_A-1696185 | rs10495796 | 34029149 | 34.029149 | 0.274 | BB | BB | BB | BB | BB | BB | BB | BB | BB | BB |
| 2 | SNP_A-1642658 | rs2049638 | 34866446 | 34.866446 | 0.738 | AA | AA | AA | AA | AA | AA | AA | AB | AB | AB |
| 2 | SNP_A-1696029 | rs1401242 | 35923474 | 35.923474 | 0.417 | AB | AB | AB | AB | AA | AB | AA | AB | AB | AB |
| 2 | SNP_A-1748242 | rs2161905 | 36427824 | 36.427824 | 0.286 | BB | BB | BB | BB | BB | BB | AA | AB | BB | BB |
| 2 | SNP_A-1660238 | rs975315 | 38407251 | 38.407251 | 0.631 | AB | AB | AA | AA | AA | AA | AA | AB | AA | AA |
| 2 | SNP_A-1719460 | rs9309043 | 39939220 | 39.93922 | 0.643 | BB | BB | AB | AB | BB | AB | BB | BB | BB | BB |
| 2 | SNP_A-1714203 | rs2059338 | 41186539 | 41.186539 | 0.714 | AB | AB | AB | AB | BB | AB | AA | AB | BB | BB |
| 2 | SNP_A-1690204 | rs10495900 | 43528810 | 43.52881 | 0.369 | AB | AB | BB | BB | BB | BB | BB | BB | BB | BB |
| 2 | SNP_A-1740164 | rs4276071 | 44121457 | 44.121457 | 0.417 | BB | BB | AA | AA | AA | AA | AB | AB | BB | BB |
| 2 | SNP_A-1685265 | rs6708061 | 44721790 | 44.72179 | 0.357 | BB | BB | BB | BB | BB | BB | AA | AA | AB | AB |
| 2 | SNP_A-1680505 | rs6737073 | 45442330 | 45.44233 | 0.286 | BB | BB | BB | BB | BB | BB | AA | AA | AB | AB |
| 2 | SNP_A-1680749 | rs935661 | 45967008 | 45.967008 | 0.56 | AB | AB | AB | AA | AB | AB | AB | AB | AB | AB |
| 2 | SNP_A-1721531 | rs7589621 | 46494033 | 46.494033 | 0.738 | AB | AB | AA | AA | AA | AA | AA | AA | AA | AA |
| 2 | SNP_A-1734011 | rs6544955 | 47235732 | 47.235732 | 0.643 | AA | AA | AA | AA | AA | AA | AA | AA | AA | AA |
| 2 | SNP_A-1699364 | rs10495972 | 49412546 | 49.412546 | 0.298 | AB | AB | BB | BB | BB | BB | BB | BB | BB | BB |
| 2 | SNP_A-1696353 | rs10495987 | 50064931 | 50.064931 | 0.286 | AB | AB | AA | AA | AA | AA | BB | BB | BB | BB |
| 2 | SNP_A-1646009 | rs10490176 | 50979585 | 50.979585 | 0.738 | AB | AB | AA | AA | AA | AA | AA | AA | AA | AA |
| 2 | SNP_A-1676509 | rs1160297 | 53148971 | 53.148971 | 0.321 | AB | AB | BB | BB | BB | BB | BB | BB | AB | AB |
| 2 | SNP_A-1742892 | rs843622 | 54460133 | 54.460133 | 0.524 | BB | BB | AA | AA | AA | AA | BB | BB | AA | AA |
| 2 | SNP_A-1704006 | rs5008666 | 59390639 | 59.390639 | 0.65 | AA | AA | BB | BB | BB | BB | AA | AA | AA | AB |
| 2 | SNP_A-1673301 | rs1517401 | 63452358 | 63.452358 | 0.738 | AA | AA | BB | BB | BB | BB | AB | AB | AA | AA |
| 2 | SNP_A-1711471 | rs2581047 | 64219699 | 64.219699 | 0.286 | BB | BB | BB | BB | BB | BB | BB | BB | BB | BB |
| 2 | SNP_A-1652253 | rs2971828 | 66466238 | 66.466238 | 0.667 | BB | BB | AA | AA | AA | AA | AA | AA | AA | AA |
| 2 | SNP_A-1722279 | rs9309400 | 67746695 | 67.746695 | 0.738 | AB | AB | AA | AA | AA | AA | BB | BB | AA | AA |
| 2 | SNP_A-1656216 | rs10496165 | 68531740 | 68.53174 | 0.333 | BB | BB | BB | BB | BB | BB | BB | BB | AA | AB |
| 2 | SNP_A-1703772 | rs2312209 | 69633766 | 69.633766 | 0.524 | BB | BB | AA | AA | AB | AB | BB | BB | BB | BB |
| 2 | SNP_A-1753748 | rs10489986 | 70719802 | 70.719802 | 0.75 | AA | AA | AA | AA | AA | AA | AA | AB | AA | AA |
| 2 | SNP_A-1723065 | rs6724782 | 73591645 | 73.591645 | 0.286 | AA | AB | BB | BB | BB | BB | AB | AB | BB | BB |
| 2 | SNP_A-1665193 | rs730148 | 76269470 | 76.26947 | 0.408 | BB | BB | AA | AA | AB | AB | AA | AA | BB | BB |
| 2 | SNP_A-1718918 | rs1446707 | 77141310 | 77.14131 | 0.429 | BB | BB | AA | AA | AA | AA | AA | AA | BB | BB |
| 2 | SNP_A-1749208 | rs4852483 | 79513076 | 79.513076 | 0.75 | AA | AB | BB | BB | BB | BB | AA | AA | AA | AA |
| 2 | SNP_A-1745171 | rs216616 | 80715814 | 80.715814 | 0.298 | BB | BB | AA | AA | AA | AA | BB | BB | BB | BB |
| 2 | SNP_A-1750234 | rs9309572 | 81381197 | 81.381197 | 0.321 | BB | BB | BB | BB | AA | AA | BB | BB | BB | AB |
| 2 | SNP_A-1728812 | rs7577293 | 85846940 | 85.84694 | 0.274 | AA | AB | BB | BB | BB | BB | BB | BB | AA | AB |
| 2 | SNP_A-1676217 | rs9308826 | 99738211 | 99.738211 | 0.738 | AA | AA | AA | AA | AA | AA | AA | AA | AA | AA |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 2 | SNP_A-1655416 | rs9308849 | 101983905 | 101.983905 | 0.714 | AA | AA | AA | AA | AA | AA | AA | AA | AB | BB | AB |
| 2 | SNP_A-1655538 | rs956966 | 103046093 | 103.046093 | 0.512 | AA | AA | BB | BB | BB | AB | BB | BB | BB | BB |
| 2 | SNP_A-1690274 | rs1869070 | 106074094 | 106.074094 | 0.714 | AA | AA | AA | AA | AA | AA | AB | AB | AB | AB |
| 2 | SNP_A-1742362 | rs1398132 | 106705516 | 106.705516 | 0.607 | AB | AB | AA | AA | AA | AA | BB | BB | AB | AB |
| 2 | SNP_A-1654768 | rs826690 | 108705477 | 108.705477 | 0.429 | BB | BB | AA | AA | AB | AB | AB | AB | AB | AB |
| 2 | SNP_A-1709888 | rs1469529 | 109207139 | 109.207139 | 0.583 | AB | AB | AA | AA | AB | AB | AB | AB | AA | AA |
| 2 | SNP_A-1671489 | rs3961919 | 112959552 | 112.959552 | 0.298 | BB | BB | AA | AA | AB | AB | AB | AB | AB | AB |
| 2 | SNP_A-1720080 | rs2166965 | 114191141 | 114.191141 | 0.679 | AA | AA | AA | AA | AB | AB | AA | AA | AA | AA |
| 2 | SNP_A-1712138 | rs1346762 | 114988791 | 114.988791 | 0.72 | AA | AA | AA | AA | AA | AA | AA | AA | AA | AA |
| 2 | SNP_A-1752188 | rs9284719 | 118395025 | 118.395025 | 0.595 | AB | AB | AA | AA | AA | AA | AA | AA | AA | AA |
| 2 | SNP_A-1685413 | rs1370380 | 120731125 | 120.731125 | 0.286 | AB | AB | AA | AA | AA | AA | BB | BB | AB | AB |
| 2 | SNP_A-1721631 | rs4848174 | 122659698 | 122.659698 | 0.655 | AA | AA | AA | AA | AB | AB | AB | AB | AA | AA |
| 2 | SNP_A-1707304 | rs1215318 | 125809045 | 125.809045 | 0.536 | AA | AA | BB | BB | BB | BB | BB | BB | AB | AB |
| 2 | SNP_A-1673583 | rs548032 | 127461866 | 127.461866 | 0.631 | AA | AA | AA | AA | AA | AA | AA | AA | AB | AB |
| 2 | SNP_A-1671177 | rs2124432 | 128900396 | 128.900396 | 0.61 | AB | AB | AA | AA | AA | AA | AA | AA | AA | AA |
| 2 | SNP_A-1676259 | rs10496731 | 135431360 | 135.43136 | 0.488 | BB | BB | AB | BB | AB | AB | AB | AB | BB | BB |
| 2 | SNP_A-1689435 | rs10496750 | 137176540 | 137.17654 | 0.667 | AB | AB | AB | AA | AB | AB | AA | AA | AB | AB |
| 2 | SNP_A-1695208 | rs10490739 | 137712397 | 137.712397 | 0.287 | BB | BB | BB | BB | BB | BB | BB | BB | BB | BB |
| 2 | SNP_A-1651715 | rs3884566 | 139082237 | 139.082237 | 0.357 | AB | AB | BB | BB | BB | BB | AB | AB | AB | AB |
| 2 | SNP_A-1665733 | rs3922799 | 139592638 | 139.592638 | 0.476 | BB | BB | BB | BB | BB | BB | BB | BB | AA | AA |
| 2 | SNP_A-1713885 | rs838042 | 140153918 | 140.153918 | 0.262 | AA | AA | AB | AA | AB | AB | BB | BB | BB | BB |
| 2 | SNP_A-1663529 | rs1518441 | 140908218 | 140.908218 | 0.286 | AA | AA | BB | BB | BB | BB | AB | AB | AB | AB |
| 2 | SNP_A-1643152 | rs10496859 | 141502410 | 141.50241 | 0.536 | BB | BB | AA | AA | AA | AA | AA | AA | BB | BB |
| 2 | SNP_A-1689866 | rs355562 | 142245134 | 142.245134 | 0.321 | BB | BB | BB | BB | BB | BB | BB | BB | BB | BB |
| 2 | SNP_A-1688373 | rs7560400 | 143121832 | 143.121832 | 0.75 | AA | AA | AB | BB | AB | AB | AB | AB | AA | AA |
| 2 | SNP_A-1725903 | rs1437717 | 146329325 | 146.329325 | 0.571 | AB | AB | BB | BB | AB | AB | AA | AA | AA | AA |
| 2 | SNP_A-1729119 | rs1528842 | 148291308 | 148.291308 | 0.75 | AB | AB | AB | BB | AB | AB | AA | AA | AA | AA |
| 2 | SNP_A-1716616 | rs6734792 | 151450390 | 151.45039 | 0.738 | AA | AA | AA | AA | AA | AA | BB | BB | AA | AA |
| 2 | SNP_A-1645341 | rs9287956 | 151979514 | 151.979514 | 0.464 | BB | BB | AA | AA | AA | AA | AB | AB | AB | AB |
| 2 | SNP_A-1711079 | rs1370502 | 153235438 | 153.235438 | 0.667 | BB | BB | BB | BB | BB | AA | AA | AA | AB | AB |
| 2 | SNP_A-1751360 | rs10497129 | 153977886 | 153.977886 | 0.31 | AB | AB | AA | AA | AA | AA | BB | BB | BB | BB |
| 2 | SNP_A-1682179 | rs1469155 | 155088509 | 155.088509 | 0.726 | AA | AA | AA | AA | AA | AA | AB | AB | AB | AB |
| 2 | SNP_A-1729675 | rs6750583 | 159423695 | 159.423695 | 0.738 | BB | BB | AB | BB | AA | AB | AB | AB | AB | AB |
| 2 | SNP_A-1710753 | rs997163 | 161593412 | 161.593412 | 0.366 | AA | AA | BB | BB | BB | BB | AA | AA | BB | BB |
| 2 | SNP_A-1657420 | rs1227921 | 162517707 | 162.517707 | 0.512 | BB | BB | AB | BB | AA | AB | AB | AB | BB | BB |
| 2 | SNP_A-1681353 | rs1446471 | 164812395 | 164.812395 | 0.345 | BB | BB | AB | AA | BB | AB | AA | AA | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 2 | SNP_A-1755647 | rs10497261 | 166152395 | 166.152395 | 0.702 | AB | AB | AA | AA | AA | AA | AB | AB | BB | AB |
| 2 | SNP_A-1656096 | rs9287874 | 167411538 | 167.411538 | 0.738 | AA | AA | AA | AA | AA | AA | AB | AB | BB | AB |
| 2 | SNP_A-1673653 | rs2278785 | 168822282 | 168.822282 | 0.381 | BB | BB | BB | BB | BB | BB | AA | AA | BB | BB |
| 2 | SNP_A-1702574 | rs830995 | 169955143 | 169.955143 | 0.702 | AA | AA | AA | AA | AA | AA | AB | AB | AA | AB |
| 2 | SNP_A-1645337 | rs961313 | 170759024 | 170.759024 | 0.274 | BB | BB | BB | BB | BB | BB | AB | AB | BB | BB |
| 2 | SNP_A-1687817 | rs731693 | 171622741 | 171.622741 | 0.667 | AA | AA | AA | AA | AA | AA | AB | AB | BB | BB |
| 2 | SNP_A-1749036 | rs4095835 | 172330518 | 172.330518 | 0.429 | BB | BB | BB | BB | BB | BB | BB | BB | BB | AB |
| 2 | SNP_A-1683223 | rs7575189 | 173840675 | 173.840675 | 0.512 | BB | BB | AB | BB | AA | AB | AB | AB | BB | BB |
| 2 | SNP_A-1743510 | rs2119137 | 174843221 | 174.843221 | 0.333 | AB | AB | AA | BB | AA | AB | AB | AB | BB | BB |
| 2 | SNP_A-1673703 | rs1993385 | 175563974 | 175.563974 | 0.476 | AA | AA | AB | BB | AA | AB | AB | AB | AA | AB |
| 2 | SNP_A-1730586 | rs9287989 | 176543248 | 176.543248 | 0.643 | BB | BB | AA | AA | AA | AA | AA | AA | AA | AB |
| 2 | SNP_A-1676261 | rs6722762 | 177140660 | 177.14066 | 0.345 | AB | AB | BB | BB | BB | BB | AB | AB | AA | AB |
| 2 | SNP_A-1668972 | rs10497467 | 177733918 | 177.733918 | 0.75 | AA | AA | AB | BB | AB | AB | AB | AB | AA | AA |
| 2 | SNP_A-1643400 | rs2008999 | 179796838 | 179.796838 | 0.643 | AA | AA | AB | BB | BB | BB | AA | AA | AA | AA |
| 2 | SNP_A-1721647 | rs259845 | 180560120 | 180.56012 | 0.75 | AA | AA | AA | AA | AA | AA | BB | BB | BB | BB |
| 2 | SNP_A-1643999 | rs9288052 | 181299542 | 181.299542 | 0.488 | BB | BB | BB | BB | BB | BB | BB | BB | BB | BB |
| 2 | SNP_A-1668465 | rs288332 | 183450856 | 183.450856 | 0.262 | BB | BB | AA | AA | AA | AA | AA | AA | AA | AB |
| 2 | SNP_A-1723211 | rs1454042 | 184407382 | 184.407382 | 0.357 | BB | BB | BB | BB | BB | BB | AB | AB | AA | AB |
| 2 | SNP_A-1668055 | rs10490389 | 186428458 | 186.428458 | 0.702 | AA | AA | AA | AA | AA | AA | AA | AA | AA | AA |
| 2 | SNP_A-1678177 | rs2044683 | 187026818 | 187.026818 | 0.366 | BB | BB | BB | BB | BB | BB | AB | AB | BB | BB |
| 2 | SNP_A-1728072 | rs840611 | 188023952 | 188.023952 | 0.583 | BB | BB | BB | BB | BB | BB | BB | BB | AA | AA |
| 2 | SNP_A-1750900 | rs10497725 | 192818722 | 192.818722 | 0.667 | AA | AA | BB | BB | BB | BB | AA | AA | AA | AB |
| 2 | SNP_A-1642958 | rs10497744 | 194316402 | 194.316402 | 0.31 | BB | BB | BB | BB | BB | BB | BB | BB | BB | AB |
| 2 | SNP_A-1669242 | rs1350208 | 198911771 | 198.911771 | 0.571 | AB | AB | AB | BB | AB | AB | AA | AA | AA | AA |
| 2 | SNP_A-1673517 | rs10497821 | 199463403 | 199.463403 | 0.31 | BB | BB | BB | BB | BB | BB | BB | BB | AA | AB |
| 2 | SNP_A-1645863 | rs1376877 | 204097596 | 204.097596 | 0.607 | AA | AA | BB | BB | BB | BB | BB | BB | BB | AB |
| 2 | SNP_A-1650883 | rs6707500 | 204941128 | 204.941128 | 0.667 | AB | AB | AA | AA | AA | AA | AA | AA | AA | AA |
| 2 | SNP_A-1757786 | rs10490293 | 206049378 | 206.049378 | 0.274 | BB | BB | BB | BB | AB | BB | BB | BB | BB | BB |
| 2 | SNP_A-1752790 | rs10490474 | 207934338 | 207.934338 | 0.571 | BB | BB | AB | AA | AB | AB | AB | AB | AA | AA |
| 2 | SNP_A-1642246 | rs10497888 | 208586741 | 208.586741 | 0.679 | AA | AA | BB | BB | BB | BB | AA | AA | AA | AA |
| 2 | SNP_A-1644145 | rs1607181 | 209364109 | 209.364109 | 0.655 | AA | AB | AA | AA | AA | AA | AB | AB | BB | AB |
| 2 | SNP_A-1669816 | rs1816532 | 212093746 | 212.093746 | 0.75 | AA | AA | BB | BB | BB | BB | AA | AA | AA | AA |
| 2 | SNP_A-1661335 | rs1402769 | 212906949 | 212.906949 | 0.274 | BB | BB | BB | BB | BB | BB | BB | BB | BB | AB |
| 2 | SNP_A-1720206 | rs10497986 | 213664725 | 213.664725 | 0.702 | AA | AA | BB | BB | BB | BB | AA | AA | AA | AA |
| 2 | SNP_A-1701518 | rs9283527 | 214674151 | 214.674151 | 0.417 | AA | AA | AB | BB | AB | AB | AA | AA | AA | AA |
| 2 | SNP_A-1692929 | rs2166459 | 215505298 | 215.505298 | 0.31 | AA | AB | BB | BB | BB | BB | AA | AA | BB | AB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 2 | SNP_A-1755667 | rs1250225 | 216151895 | 216.151895 | 0.744 | BB | AB | AA | AA | AA | AA | AA | AA | AA | AA |
| 2 | SNP_A-1705890 | rs1110998 | 217169458 | 217.169458 | 0.429 | BB | BB | AB | AA | AB | AB | BB | BB | BB | BB |
| 2 | SNP_A-1743410 | rs6719545 | 218277340 | 218.27734 | 0.286 | BB | AB | BB | BB | BB | BB | BB | BB | AA | AB |
| 2 | SNP_A-1728154 | rs1344645 | 219363524 | 219.363524 | 0.405 | AA | AB | BB | BB | BB | BB | AA | AA | BB | BB |
| 2 | SNP_A-1726837 | rs715345 | 220649461 | 220.649461 | 0.274 | AA | AA | AB | AB | AB | AB | BB | BB | BB | BB |
| 2 | SNP_A-1721280 | rs1356399 | 221348562 | 221.348562 | 0.702 | AA | AA | AB | AB | AB | AB | BB | AB | AA | AA |
| 2 | SNP_A-1655920 | rs1430234 | 222049201 | 222.049201 | 0.274 | BB | BB | BB | BB | BB | BB | BB | BB | BB | AB |
| 2 | SNP_A-1711521 | rs4673013 | 222802583 | 222.802583 | 0.619 | BB | AB | AB | AB | AB | AB | AA | AA | AA | AB |
| 2 | SNP_A-1695224 | rs1961637 | 223730613 | 223.730613 | 0.452 | AA | AB | AB | AB | AB | AB | BB | BB | BB | BB |
| 2 | SNP_A-1713318 | rs10498158 | 224777152 | 224.777152 | 0.417 | AA | AB | BB | BB | BB | BB | BB | BB | BB | BB |
| 2 | SNP_A-1702406 | rs10498171 | 225622115 | 225.622115 | 0.524 | BB | AB | AA | AA | AA | AA | BB | AB | BB | AB |
| 2 | SNP_A-1643000 | rs1835533 | 226193946 | 226.193946 | 0.738 | AA | AA | AA | AA | AA | AA | AA | AA | AA | AA |
| 2 | SNP_A-1739924 | rs1522804 | 226814661 | 226.814661 | 0.548 | AA | AA | AB | AB | AB | AB | BB | BB | BB | AB |
| 2 | SNP_A-1683533 | rs1950134 | 227888457 | 227.888457 | 0.714 | AA | AA | AA | AA | AA | AA | AA | AA | AA | AA |
| 2 | SNP_A-1663421 | rs1524023 | 228615089 | 228.615089 | 0.75 | AA | AA | AA | AA | AA | AA | AA | AA | AA | AA |
| 2 | SNP_A-1707748 | rs6759815 | 229797926 | 229.797926 | 0.571 | BB | BB | AA | AA | AA | AA | BB | BB | BB | AB |
| 2 | SNP_A-1661533 | rs4973304 | 230936568 | 230.936568 | 0.298 | BB | BB | BB | BB | BB | BB | AA | AA | AA | AB |
| 2 | SNP_A-1727506 | rs10498257 | 231818543 | 231.818543 | 0.702 | BB | AB | AB | AB | AB | AB | BB | AB | AA | AA |
| 2 | SNP_A-1728658 | rs3791711 | 233258388 | 233.258388 | 0.524 | BB | AB | BB | BB | BB | BB | BB | AB | AA | AB |
| 2 | SNP_A-1747120 | rs1880747 | 235240125 | 235.240125 | 0.512 | BB | AB | AA | AA | AA | AA | BB | AB | AA | AA |
| 2 | SNP_A-1738177 | rs103718 | 239180488 | 239.180488 | 0.441 | AA | AA | AA | AA | AA | AA | AB | AB | AA | AA |
| 3 | SNP_A-1675236 | rs1516342 | 147906 | 0.147906 | 0.262 | AB | AB | BB | BB | BB | BB | AA | AB | BB | BB |
| 3 | SNP_A-1754907 | rs10510204 | 981912 | 0.981912 | 0.405 | AA | AA | AA | AA | AA | AA | AA | AB | AA | AA |
| 3 | SNP_A-1726483 | rs1720194 | 2366613 | 2.366613 | 0.631 | AA | AA | AA | AA | AA | AA | AA | AA | AA | AA |
| 3 | SNP_A-1717220 | rs1508734 | 3538991 | 3.538991 | 0.607 | AB | AB | AB | BB | BB | AB | BB | AB | AB | AB |
| 3 | SNP_A-1668475 | rs4684484 | 5437541 | 5.437541 | 0.441 | BB | BB | AA | AA | AA | AA | AA | AA | AA | AA |
| 3 | SNP_A-1646075 | rs9311817 | 6172932 | 6.172932 | 0.72 | AB | AB | AA | AA | AA | AA | AA | AA | AB | AB |
| 3 | SNP_A-1658187 | rs1450097 | 7520521 | 7.520521 | 0.293 | BB | BB | BB | BB | BB | BB | AB | AB | AB | AB |
| 3 | SNP_A-1718736 | rs486012 | 9016299 | 9.016299 | 0.56 | AA | AA | AA | AA | AA | AA | AB | AB | AA | AB |
| 3 | SNP_A-1679373 | rs2160871 | 10421826 | 10.421826 | 0.75 | AB | AB | AB | BB | BB | AB | AA | AA | AB | AB |
| 3 | SNP_A-1649097 | rs6792718 | 11409380 | 11.40938 | 0.429 | AB | AB | AA | AA | AA | AA | AA | AA | AA | AA |
| 3 | SNP_A-1713577 | rs172429 | 14880517 | 14.880517 | 0.25 | BB | BB | BB | BB | BB | BB | BB | BB | BB | BB |
| 3 | SNP_A-1719120 | rs1983085 | 15504547 | 15.504547 | 0.56 | AA | AA | BB | BB | BB | BB | AB | AB | AA | AA |
| 3 | SNP_A-1701284 | rs2733528 | 17211259 | 17.211259 | 0.571 | AB | AB | AA | AA | AA | AA | AA | AA | BB | BB |
| 3 | SNP_A-1653347 | rs336615 | 18605807 | 18.605807 | 0.619 | AA | AA | AB | BB | BB | AB | AB | AB | BB | AB |
| 3 | SNP_A-1753110 | rs2053506 | 19350795 | 19.350795 | 0.595 | AA | AA | AA | AA | AA | AA | AA | AA | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 3 | SNP_A-1649119 | rs6770717 | 20406548 | 20.406548 | 0.726 | AB | AB | AA | AA | AA | AA | AA | AA | AA | AA |
| 3 | SNP_A-1685927 | rs365392 | 21465872 | 21.465872 | 0.583 | BB | BB | AB | BB | BB | AB | AB | AB | BB | AB |
| 3 | SNP_A-1738848 | rs3732395 | 23209622 | 23.209622 | 0.378 | AA | AB | BB | BB | BB | BB | BB | BB | BB | AB |
| 3 | SNP_A-1730534 | rs10510568 | 25577736 | 25.577736 | 0.679 | BB | AB | AA | AA | AA | AA | AB | AB | AA | AB |
| 3 | SNP_A-1725077 | rs9284859 | 26883268 | 26.883268 | 0.655 | BB | BB | AB | BB | BB | AB | AB | AB | BB | AB |
| 3 | SNP_A-1647333 | rs7639905 | 27951868 | 27.951868 | 0.429 | BB | AB | BB | BB | BB | BB | BB | BB | AA | AA |
| 3 | SNP_A-1744932 | rs9310901 | 29477393 | 29.477393 | 0.274 | BB | AB | AA | AA | AA | AA | AA | AA | AB | AB |
| 3 | SNP_A-1741570 | rs795347 | 30720945 | 30.720945 | 0.369 | AA | AB | AB | AB | AB | AB | BB | BB | BB | BB |
| 3 | SNP_A-1747050 | rs347163 | 32435579 | 32.435579 | 0.393 | BB | BB | BB | BB | BB | BB | BB | BB | AB | AB |
| 3 | SNP_A-1735191 | rs1376015 | 35274750 | 35.27475 | 0.595 | BB | AB | AB | AB | AB | AB | AB | AB | BB | BB |
| 3 | SNP_A-1717686 | rs10510667 | 35834447 | 35.834447 | 0.476 | BB | BB | AA | AA | AA | AA | BB | BB | AB | AB |
| 3 | SNP_A-1643995 | rs10510695 | 37621200 | 37.6212 | 0.738 | AA | AA | AA | AA | AA | AA | AA | AA | AA | AA |
| 3 | SNP_A-1649705 | rs2220345 | 41411812 | 41.411812 | 0.429 | AA | AB | AA | AA | AA | AA | AB | AB | AB | AB |
| 3 | SNP_A-1699750 | rs531888 | 43047989 | 43.047989 | 0.476 | BB | AB | AB | AB | AB | AB | AB | AB | AA | AA |
| 3 | SNP_A-1722715 | rs2742393 | 45732421 | 45.732421 | 0.417 | AA | AA | AB | AB | AB | AB | BB | BB | AA | AA |
| 3 | SNP_A-1694360 | rs7620394 | 55206368 | 55.206368 | 0.345 | BB | BB | AA | AA | AA | AA | BB | BB | AB | AB |
| 3 | SNP_A-1643909 | rs6445844 | 57028961 | 57.028961 | 0.726 | BB | BB | AB | AB | AB | AB | AB | AB | AA | AA |
| 3 | SNP_A-1652229 | rs10510803 | 59329572 | 59.329572 | 0.488 | BB | BB | AB | AB | AB | AB | AB | AB | AB | AB |
| 3 | SNP_A-1669748 | rs3843360 | 60016727 | 60.016727 | 0.393 | BB | BB | AB | AB | AB | AB | AB | AB | AA | AA |
| 3 | SNP_A-1678019 | rs1996520 | 61592725 | 61.592725 | 0.488 | BB | BB | BB | BB | BB | BB | AB | AB | AB | AB |
| 3 | SNP_A-1665709 | rs7650561 | 62466087 | 62.466087 | 0.643 | AA | AA | AB | AB | AB | AB | AA | AA | AB | AB |
| 3 | SNP_A-1684953 | rs10510929 | 64709076 | 64.709076 | 0.583 | BB | BB | BB | BB | BB | BB | AA | AA | BB | AB |
| 3 | SNP_A-1688393 | rs725160 | 66943022 | 66.943022 | 0.464 | AA | AA | BB | BB | BB | BB | AB | AB | BB | BB |
| 3 | SNP_A-1678015 | rs4145917 | 68099517 | 68.099517 | 0.679 | AB | AB | AA | AA | AA | AA | AA | AA | AA | AA |
| 3 | SNP_A-1707438 | rs2872939 | 69802192 | 69.802192 | 0.405 | AB | AB | AA | AA | AA | AA | AB | AB | BB | BB |
| 3 | SNP_A-1663707 | rs10510996 | 70545357 | 70.545357 | 0.75 | AA | AA | AA | AA | AB | AB | AA | AA | AA | AB |
| 3 | SNP_A-1650625 | rs830644 | 71748249 | 71.748249 | 0.5 | AB | AB | BB | BB | BB | BB | BB | BB | AA | AB |
| 3 | SNP_A-1713028 | rs4677226 | 73154304 | 73.154304 | 0.613 | BB | BB | BB | BB | BB | BB | AB | AB | AA | AA |
| 3 | SNP_A-1685633 | rs1107768 | 73959415 | 73.959415 | 0.726 | AB | AB | AA | AA | AA | AA | BB | AB | AA | AA |
| 3 | SNP_A-1722733 | rs10511039 | 76184447 | 76.184447 | 0.583 | AA | AA | BB | BB | BB | BB | AA | AA | BB | BB |
| 3 | SNP_A-1648479 | rs251552 | 76852596 | 76.852596 | 0.539 | AB | AB | AA | AA | AA | AA | AA | AB | BB | AB |
| 3 | SNP_A-1642486 | rs9309840 | 80029943 | 80.029943 | 0.588 | BB | BB | BB | BB | BB | BB | BB | BB | BB | BB |
| 3 | SNP_A-1685115 | rs2639611 | 81623522 | 81.623522 | 0.274 | BB | BB | BB | BB | BB | BB | BB | BB | AA | AA |
| 3 | SNP_A-1642250 | rs9309888 | 82418655 | 82.418655 | 0.262 | BB | BB | BB | BB | BB | BB | BB | BB | BB | AB |
| 3 | SNP_A-1732971 | rs10511085 | 85614577 | 85.614577 | 0.619 | BB | AB | BB | AB | BB | AB | AA | AA | AA | AB |
| 3 | SNP_A-1731608 | rs1509783 | 87634505 | 87.634505 | 0.476 | BB | BB | BB | BB | BB | BB | AA | AB | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 3 | SNP_A-1721601 | rs9310061 | 88146455 | 88.146455 | 0.631 | AA | AA | BB | BB | BB | AB | AA | AA | AA | AB |
| 3 | SNP_A-1715294 | rs724972 | 89664098 | 89.664098 | 0.607 | AA | AB | AA | AA | AA | AA | AA | AA | AA | AA |
| 3 | SNP_A-1648583 | rs10511152 | 96638708 | 96.638708 | 0.381 | BB | BB | AA | AA | AB | AA | AB | AA | BB | AB |
| 3 | SNP_A-1701406 | rs3856571 | 99031739 | 99.031739 | 0.298 | BB | AB | BB | BB | BB | BB | BB | BB | BB | BB |
| 3 | SNP_A-1643841 | rs10511169 | 100116062 | 100.116062 | 0.691 | AA | AA | AA | AA | AA | AA | AA | AA | BB | AB |
| 3 | SNP_A-1697988 | rs2700633 | 100643241 | 100.643241 | 0.643 | AA | AB | AA | AA | AA | AA | AA | AA | BB | AB |
| 3 | SNP_A-1740468 | rs10511183 | 102046105 | 102.046105 | 0.738 | AA | AA | AA | AA | AA | AA | AA | AA | AA | AA |
| 3 | SNP_A-1746982 | rs974059 | 103277828 | 103.277828 | 0.25 | BB | BB | BB | BB | BB | BB | AA | AB | BB | AB |
| 3 | SNP_A-1687227 | rs1391423 | 103923668 | 103.923668 | 0.732 | AA | AA | AA | AA | AA | AA | AA | AA | AA | AA |
| 3 | SNP_A-1677819 | rs10511221 | 105099054 | 105.099054 | 0.726 | BB | AB | AA | AA | AB | AB | AA | AA | AA | AB |
| 3 | SNP_A-1663937 | rs6783422 | 106031580 | 106.03158 | 0.393 | AA | AA | AA | AA | AA | AA | BB | BB | AA | AA |
| 3 | SNP_A-1674588 | rs10511243 | 106653352 | 106.653352 | 0.667 | AA | AA | AA | AA | AA | AA | BB | AB | AA | AB |
| 3 | SNP_A-1652015 | rs2222039 | 108202685 | 108.202685 | 0.691 | BB | AB | AA | AA | AA | AA | AA | AA | AA | AA |
| 3 | SNP_A-1722407 | rs1525873 | 111232702 | 111.232702 | 0.702 | BB | AB | BB | BB | BB | BB | AA | AA | AA | AB |
| 3 | SNP_A-1674512 | rs1512514 | 111766406 | 111.766406 | 0.488 | BB | AB | AA | AA | AA | AA | AA | AA | AA | AA |
| 3 | SNP_A-1747616 | rs1797626 | 114308943 | 114.308943 | 0.702 | AA | AA | BB | BB | AB | AB | AA | AA | AA | AA |
| 3 | SNP_A-1668954 | rs1553209 | 116705663 | 116.705663 | 0.476 | BB | AB | AA | AA | AA | AA | BB | BB | BB | BB |
| 3 | SNP_A-1674292 | rs7621196 | 117804184 | 117.804184 | 0.321 | BB | BB | AA | AA | AA | AA | BB | AB | AA | AB |
| 3 | SNP_A-1643903 | rs1218621 | 118459636 | 118.459636 | 0.31 | AA | AA | BB | BB | BB | BB | BB | BB | BB | BB |
| 3 | SNP_A-1728638 | rs950649 | 121567065 | 121.567065 | 0.691 | BB | AB | AA | AA | AA | AA | AA | AA | AA | AA |
| 3 | SNP_A-1730195 | rs2126140 | 122627958 | 122.627958 | 0.5 | BB | AB | AB | AA | AB | AB | AB | AB | AA | AA |
| 3 | SNP_A-1741126 | rs10511409 | 123610479 | 123.610479 | 0.738 | BB | AB | AA | AA | AA | AA | AB | AA | BB | AB |
| 3 | SNP_A-1739520 | rs1373606 | 125496637 | 125.496637 | 0.342 | AA | AA | BB | BB | BB | BB | AA | AA | AA | AA |
| 3 | SNP_A-1727336 | rs1374804 | 127391196 | 127.391196 | 0.524 | AA | AB | AA | AA | AB | AB | BB | BB | AA | AA |
| 3 | SNP_A-1683659 | rs2718880 | 132343455 | 132.343455 | 0.75 | AA | AA | AA | AA | AA | AA | AB | AB | AA | AA |
| 3 | SNP_A-1747192 | rs1553975 | 132999274 | 132.999274 | 0.369 | BB | BB | AB | AB | AB | AB | AB | AB | BB | BB |
| 3 | SNP_A-1744702 | rs2310229 | 133541978 | 133.541978 | 0.691 | AA | AA | AA | AA | AA | AA | AA | AA | AA | AA |
| 3 | SNP_A-1730051 | rs711923 | 136539253 | 136.539253 | 0.744 | AA | AA | AA | AA | AA | AA | AA | AA | AA | AA |
| 3 | SNP_A-1654278 | rs838623 | 144671624 | 144.671624 | 0.619 | AA | AA | AA | AA | AA | AA | AA | AA | BB | AB |
| 3 | SNP_A-1730514 | rs4610179 | 146387799 | 146.387799 | 0.726 | AB | AB | AA | AA | AA | AA | AA | AA | AA | AA |
| 3 | SNP_A-1700733 | rs4592991 | 147111601 | 147.111601 | 0.393 | BB | BB | BB | BB | BB | BB | AA | AA | AB | AB |
| 3 | SNP_A-1744174 | rs7645488 | 149410366 | 149.410366 | 0.31 | AB | AB | BB | BB | BB | BB | BB | BB | AB | AB |
| 3 | SNP_A-1718574 | rs2130319 | 150976344 | 150.976344 | 0.333 | AB | AB | BB | BB | BB | BB | AA | AA | AB | AB |
| 3 | SNP_A-1718772 | rs7648424 | 151906089 | 151.906089 | 0.488 | AB | AB | BB | BB | BB | BB | AA | AA | AB | AB |
| 3 | SNP_A-1663723 | rs10513399 | 152600180 | 152.60018 | 0.488 | BB | BB | BB | BB | BB | BB | BB | BB | AB | AB |
| 3 | SNP_A-1746211 | rs2418925 | 155234610 | 155.23461 | 0.524 | AA | AA | AB | AB | AA | AB | BB | BB | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 3 | SNP_A-1658251 | rs6772323 | 157710345 | 157.710345 | 0.667 | AA | AA | AA | AA | AA | AA | AA | AA | AA | AA |
| 3 | SNP_A-1736960 | rs4679851 | 160261035 | 160.261035 | 0.274 | AB | AB | BB | BB | BB | BB | BB | AB | AB | AB |
| 3 | SNP_A-1716368 | rs10513549 | 161237209 | 161.237209 | 0.25 | BB | BB | AB | AB | AA | AB | BB | AB | AB | AB |
| 3 | SNP_A-1726685 | rs336583 | 162564683 | 162.564683 | 0.417 | AA | AA | BB | BB | BB | BB | BB | BB | BB | BB |
| 3 | SNP_A-1721879 | rs7635791 | 163720371 | 163.720371 | 0.655 | AA | AA | AB | AB | AB | AB | BB | AB | AB | AB |
| 3 | SNP_A-1745785 | rs9290201 | 164397051 | 164.397051 | 0.31 | AB | AB | AB | AB | AA | AB | BB | AB | AB | AB |
| 3 | SNP_A-1697475 | rs4352381 | 165179142 | 165.179142 | 0.369 | BB | BB | AA | AA | AA | AA | AA | AA | AB | AB |
| 3 | SNP_A-1748578 | rs2643191 | 165861395 | 165.861395 | 0.524 | AA | AA | AA | AA | AA | AA | BB | BB | BB | BB |
| 3 | SNP_A-1687865 | rs1371900 | 167443656 | 167.443656 | 0.286 | AB | AB | AB | AB | AA | AB | AB | AB | AB | AB |
| 3 | SNP_A-1680949 | rs1877269 | 170109722 | 170.109722 | 0.548 | AB | AB | AB | AB | AA | AB | AB | AB | AB | AB |
| 3 | SNP_A-1731022 | rs8192675 | 172207585 | 172.207585 | 0.732 | AB | AB | AB | AB | BB | AB | AA | AA | AA | AA |
| 3 | SNP_A-1656780 | rs7627220 | 173288405 | 173.288405 | 0.441 | AB | AB | AA | AA | AA | AA | BB | BB | AB | AB |
| 3 | SNP_A-1720350 | rs792354 | 174456847 | 174.456847 | 0.357 | BB | BB | AA | AA | AA | AA | BB | BB | BB | BB |
| 3 | SNP_A-1662989 | rs1377828 | 177727744 | 177.727744 | 0.286 | AA | AA | BB | BB | BB | BB | BB | BB | BB | BB |
| 3 | SNP_A-1651103 | rs2160836 | 179192927 | 179.192927 | 0.662 | AB | AB | BB | BB | BB | BB | AA | AA | AA | AA |
| 3 | SNP_A-1699226 | rs6762743 | 180494702 | 180.494702 | 0.667 | AA | AA | AA | AA | AA | AA | AA | AA | AB | AB |
| 3 | SNP_A-1655724 | rs262958 | 184975690 | 184.97569 | 0.583 | AB | AB | AA | AA | AA | AA | BB | BB | AB | AB |
| 3 | SNP_A-1726281 | rs10513799 | 186032241 | 186.032241 | 0.75 | AB | AB | AA | AA | AA | AA | AB | AB | AB | AB |
| 3 | SNP_A-1649485 | rs1962838 | 189742951 | 189.742951 | 0.405 | AB | AB | AB | AB | AB | AB | AA | AA | AB | AB |
| 3 | SNP_A-1756920 | rs2378464 | 190305279 | 190.305279 | 0.262 | AB | AB | BB | BB | BB | BB | AB | AB | BB | BB |
| 3 | SNP_A-1734403 | rs3773928 | 191066407 | 191.066407 | 0.405 | BB | BB | AB | AB | AB | AB | BB | BB | AB | AB |
| 3 | SNP_A-1720858 | rs1405036 | 192749559 | 192.749559 | 0.262 | AB | AB | AA | AA | AA | AB | BB | BB | BB | BB |
| 3 | SNP_A-1706600 | rs1403033 | 193538911 | 193.538911 | 0.441 | AB | AB | AA | AA | AA | AA | AB | AB | AB | AB |
| 3 | SNP_A-1643612 | rs587612 | 195020261 | 195.020261 | 0.369 | AA | AA | BB | BB | BB | BB | AA | AA | BB | BB |
| 4 | SNP_A-1669560 | rs1059159 | 5647306 | 5.647306 | 0.683 | AB | AB | AA | AA | AA | AA | AA | AA | BB | BB |
| 4 | SNP_A-1743690 | rs10489076 | 9947117 | 9.947117 | 0.691 | AB | AB | AA | AA | AA | AA | AB | AB | AA | AB |
| 4 | SNP_A-1736300 | rs959233 | 10578428 | 10.578428 | 0.452 | AA | AA | AA | AA | AA | AB | AB | AB | BB | BB |
| 4 | SNP_A-1750658 | rs10516254 | 12310930 | 12.31093 | 0.714 | AA | AA | AB | AB | AB | AB | BB | BB | BB | BB |
| 4 | SNP_A-1712820 | rs10489092 | 13327021 | 13.327021 | 0.286 | AB | AB | AA | AA | AA | AA | AB | AB | AA | AB |
| 4 | SNP_A-1709160 | rs10488982 | 14088975 | 14.088975 | 0.5 | AB | AB | AA | AA | AA | AA | BB | BB | BB | BB |
| 4 | SNP_A-1748456 | rs1496747 | 16275503 | 16.275503 | 0.476 | BB | BB | AB | AB | AB | AB | AB | AB | BB | BB |
| 4 | SNP_A-1674656 | rs10516339 | 19549340 | 19.54934 | 0.725 | AA | AB | AA | AA | AA | AA | AA | AA | AA | AA |
| 4 | SNP_A-1659171 | rs6834573 | 20123113 | 20.123113 | 0.298 | BB | BB | BB | BB | BB | BB | BB | BB | BB | BB |
| 4 | SNP_A-1687559 | rs10516397 | 21369936 | 21.369936 | 0.405 | BB | BB | AB | AB | AB | AB | AB | AB | AA | AA |
| 4 | SNP_A-1695570 | rs2036713 | 22984189 | 22.984189 | 0.357 | BB | AB | AB | BB | AB | AB | BB | BB | BB | AB |
| 4 | SNP_A-1649429 | rs1527354 | 24561836 | 24.561836 | 0.655 | BB | AB | BB | BB | BB | BB | AA | AA | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 4 | SNP_A-1710973 | rs7697266 | 25453418 | 25.453418 | 0.393 | BB | BB | BB | BB | BB | BB | BB | BB | BB | BB |
| 4 | SNP_A-1748352 | rs9291495 | 27032051 | 27.032051 | 0.75 | AA | AA | AA | AA | AA | AA | AA | AA | AA | AB |
| 4 | SNP_A-1737486 | rs1397438 | 28093488 | 28.093488 | 0.463 | BB | BB | BB | BB | BB | BB | BB | BB | AA | AA |
| 4 | SNP_A-1660740 | rs939573 | 28670407 | 28.670407 | 0.75 | AA | AA | AA | AA | AA | AA | AA | AA | AA | AA |
| 4 | SNP_A-1659069 | rs1441691 | 29221732 | 29.221732 | 0.274 | BB | BB | AB | BB | AB | AB | BB | BB | BB | AB |
| 4 | SNP_A-1731582 | rs2571468 | 29891942 | 29.891942 | 0.667 | AA | AA | AB | AA | AB | AB | AB | AB | AA | AA |
| 4 | SNP_A-1666099 | rs412253 | 31119019 | 31.119019 | 0.72 | AA | AA | AB | BB | AB | AB | AB | AB | AA | AA |
| 4 | SNP_A-1659419 | rs10517232 | 31725815 | 31.725815 | 0.321 | BB | BB | AA | AA | AA | AA | BB | BB | AA | AA |
| 4 | SNP_A-1743944 | rs2588544 | 36822899 | 36.822899 | 0.281 | AA | AB | BB | BB | BB | BB | BB | BB | BB | BB |
| 4 | SNP_A-1650541 | rs7693744 | 42094241 | 42.094241 | 0.488 | AA | AA | AB | AA | AA | AB | AA | AB | AA | AA |
| 4 | SNP_A-1651577 | rs10517054 | 42743857 | 42.743857 | 0.726 | AA | AA | AA | AA | AA | AA | AA | AA | AA | AA |
| 4 | SNP_A-1708293 | rs10517094 | 44153139 | 44.153139 | 0.31 | BB | BB | BB | BB | BB | BB | BB | BB | BB | BB |
| 4 | SNP_A-1672145 | rs10517121 | 44712712 | 44.712712 | 0.583 | AA | AA | AB | AA | AB | AA | AB | AA | BB | AB |
| 4 | SNP_A-1742914 | rs1552419 | 45366813 | 45.366813 | 0.583 | AA | AB | AA | AA | AA | AA | BB | AB | AA | AA |
| 4 | SNP_A-1741538 | rs279842 | 46181884 | 46.181884 | 0.439 | BB | BB | BB | BB | BB | BB | BB | AB | AA | AB |
| 4 | SNP_A-1726797 | rs3934674 | 46854066 | 46.854066 | 0.305 | BB | BB | BB | BB | BB | BB | BB | BB | BB | BB |
| 4 | SNP_A-1734487 | rs6447614 | 47908885 | 47.908885 | 0.549 | AA | AB | AA | AA | AB | AA | AA | AA | BB | AB |
| 4 | SNP_A-1659623 | rs6850277 | 54268853 | 54.268853 | 0.667 | AB | AB | AA | AA | AA | AA | AA | AB | AA | AA |
| 4 | SNP_A-1724073 | rs2726610 | 55528245 | 55.528245 | 0.548 | BB | BB | BB | BB | BB | BB | BB | AB | AA | AB |
| 4 | SNP_A-1643184 | rs4580704 | 56167635 | 56.167635 | 0.643 | AB | AB | AA | AA | AA | AA | AA | AA | AA | AB |
| 4 | SNP_A-1647321 | rs10517400 | 58338522 | 58.338522 | 0.679 | AB | AB | BB | BB | AB | AB | AB | AB | BB | BB |
| 4 | SNP_A-1685901 | rs10517453 | 60065841 | 60.065841 | 0.679 | AA | AA | BB | BB | BB | BB | AB | AB | BB | BB |
| 4 | SNP_A-1660836 | rs2129274 | 61712878 | 61.712878 | 0.613 | BB | BB | BB | BB | BB | BB | BB | BB | AA | AA |
| 4 | SNP_A-1712860 | rs2345043 | 62476674 | 62.476674 | 0.619 | AA | AA | AA | AA | AA | AA | BB | BB | BB | BB |
| 4 | SNP_A-1706808 | rs2199219 | 63012534 | 63.012534 | 0.321 | AB | AB | AA | AA | AA | AA | BB | BB | AA | AB |
| 4 | SNP_A-1657186 | rs7674285 | 65578799 | 65.578799 | 0.536 | BB | BB | BB | BB | BB | BB | AA | AA | AA | AA |
| 4 | SNP_A-1701798 | rs1450036 | 67486005 | 67.486005 | 0.619 | AA | AA | AA | AA | AB | AB | AA | AA | AA | AB |
| 4 | SNP_A-1734479 | rs2736466 | 70507268 | 70.507268 | 0.679 | AB | AB | AA | AA | AA | AA | AA | AA | AB | AB |
| 4 | SNP_A-1645045 | rs3775745 | 71293834 | 71.293834 | 0.536 | BB | BB | AA | AA | AA | AA | AA | AA | AB | AB |
| 4 | SNP_A-1741102 | rs7678694 | 75663264 | 75.663264 | 0.476 | BB | BB | AA | AA | AA | AA | BB | BB | AA | AA |
| 4 | SNP_A-1670999 | rs925454 | 77604654 | 77.604654 | 0.595 | AA | AA | AA | AB | AB | AA | AA | AB | AB | AB |
| 4 | SNP_A-1738063 | rs2703134 | 78171011 | 78.171011 | 0.691 | AB | AB | AA | AA | AA | AA | AA | AA | AA | AA |
| 4 | SNP_A-1654306 | rs10518188 | 79483184 | 79.483184 | 0.405 | AB | AB | BB | BB | BB | BB | BB | AB | BB | BB |
| 4 | SNP_A-1661108 | rs2119421 | 80807501 | 80.807501 | 0.714 | AA | AA | AA | AA | AA | AA | AA | AA | BB | BB |
| 4 | SNP_A-1703940 | rs9307787 | 83047673 | 83.047673 | 0.75 | AA | AA | AA | AA | AA | AA | AA | AA | AA | AA |
| 4 | SNP_A-1650367 | rs6813014 | 84235884 | 84.235884 | 0.548 | AB | AB | AA | AA | BB | AB | BB | BB | AA | AA |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 4 | SNP_A-1752998 | rs10516708 | 85194717 | 85.194717 | 0.643 | AA | AA | AA | AA | AA | AA | AA | AA | AB | AB |
| 4 | SNP_A-1669642 | rs10516739 | 86522131 | 86.522131 | 0.655 | AB | AB | BB | BB | AA | AB | AA | AA | AB | AB |
| 4 | SNP_A-1725569 | rs10516760 | 87083328 | 87.083328 | 0.25 | BB | BB | BB | BB | BB | BB | AA | AA | AA | AA |
| 4 | SNP_A-1732366 | rs4693803 | 88425710 | 88.42571 | 0.5 | AA | AA | AA | AA | BB | AB | AA | AA | AB | AB |
| 4 | SNP_A-1657663 | rs10516796 | 89213912 | 89.213912 | 0.634 | AA | AA | AA | AA | AA | AA | BB | AB | BB | BB |
| 4 | SNP_A-1718322 | rs1903002 | 90098072 | 90.098072 | 0.464 | BB | BB | AA | AA | BB | AB | AA | AA | AB | AB |
| 4 | SNP_A-1659867 | rs7693500 | 90643667 | 90.643667 | 0.691 | AA | AA | AA | AA | AA | AA | AA | AA | BB | BB |
| 4 | SNP_A-1705800 | rs4694023 | 91613152 | 91.613152 | 0.393 | AB | AB | BB | BB | BB | BB | AA | AA | AB | AB |
| 4 | SNP_A-1757446 | rs7696847 | 92155216 | 92.155216 | 0.714 | AA | AA | BB | BB | AA | AB | AA | AA | AB | AB |
| 4 | SNP_A-1749382 | rs6827937 | 94157783 | 94.157783 | 0.452 | BB | BB | BB | BB | BB | BB | AA | AB | AB | AB |
| 4 | SNP_A-1727842 | rs10516919 | 94713877 | 94.713877 | 0.667 | AB | AB | AA | AA | AA | AA | AA | AA | AA | AA |
| 4 | SNP_A-1745861 | rs1048627 | 95944765 | 95.944765 | 0.595 | AA | AA | AA | AA | BB | AB | AA | AA | AA | AA |
| 4 | SNP_A-1683945 | rs1384869 | 96613355 | 96.613355 | 0.274 | BB | BB | AA | AA | AA | AA | BB | AB | BB | BB |
| 4 | SNP_A-1756011 | rs6853079 | 99800789 | 99.800789 | 0.286 | BB | BB | BB | BB | BB | BB | BB | BB | AA | AA |
| 4 | SNP_A-1703546 | rs1230164 | 100343201 | 100.343201 | 0.274 | AB | AB | BB | BB | AA | AB | BB | AB | BB | BB |
| 4 | SNP_A-1740940 | rs238486 | 103377982 | 103.377982 | 0.595 | AA | AA | AA | AA | BB | AB | AA | AA | BB | BB |
| 4 | SNP_A-1684917 | rs227284 | 103964838 | 103.964838 | 0.655 | AA | AA | AA | AA | BB | AB | BB | BB | AB | AB |
| 4 | SNP_A-1753948 | rs445761 | 104804695 | 104.804695 | 0.679 | AB | AB | AA | AA | AA | AA | AA | AA | AA | AA |
| 4 | SNP_A-1747884 | rs2866685 | 105649408 | 105.649408 | 0.5 | BB | BB | AA | AA | BB | AB | AB | AB | AB | AB |
| 4 | SNP_A-1720092 | rs1873361 | 106282703 | 106.282703 | 0.345 | BB | BB | AA | AA | AA | AA | BB | BB | BB | BB |
| 4 | SNP_A-1721929 | rs715706 | 106873632 | 106.873632 | 0.286 | BB | BB | BB | BB | BB | BB | BB | BB | AA | AA |
| 4 | SNP_A-1662125 | rs1468221 | 108745388 | 108.745388 | 0.31 | AA | AA | BB | BB | BB | BB | AB | AB | BB | BB |
| 4 | SNP_A-1642856 | rs7654940 | 110143969 | 110.143969 | 0.524 | AB | AB | BB | BB | AA | AB | AB | AB | AB | AB |
| 4 | SNP_A-1686749 | rs6841595 | 113711446 | 113.711446 | 0.317 | BB | BB | BB | BB | BB | BB | BB | BB | AB | AB |
| 4 | SNP_A-1736814 | rs10516593 | 114436416 | 114.436416 | 0.524 | BB | BB | BB | BB | AB | AB | AA | AA | AA | AA |
| 4 | SNP_A-1732667 | rs998359 | 116228635 | 116.228635 | 0.441 | BB | BB | BB | BB | BB | BB | BB | BB | AB | AB |
| 4 | SNP_A-1671469 | rs292910 | 117406405 | 117.406405 | 0.607 | AA | AA | AA | AA | AA | AA | AA | AA | AB | AB |
| 4 | SNP_A-1696003 | rs2125710 | 118964366 | 118.964366 | 0.25 | BB | BB | BB | BB | BB | BB | BB | BB | BB | AB |
| 4 | SNP_A-1695754 | rs10518293 | 119688966 | 119.688966 | 0.691 | AA | AA | BB | BB | BB | BB | AA | AA | AB | AB |
| 4 | SNP_A-1745189 | rs10518336 | 120880537 | 120.880537 | 0.536 | AA | AA | BB | BB | AB | AB | BB | BB | AB | AB |
| 4 | SNP_A-1648947 | rs2036696 | 121573324 | 121.573324 | 0.667 | AA | AA | BB | BB | BB | BB | BB | BB | AB | AB |
| 4 | SNP_A-1702984 | rs998327 | 122441717 | 122.441717 | 0.726 | AA | AA | AA | AA | AA | AB | AB | AA | AA | AA |
| 4 | SNP_A-1733111 | rs4833836 | 123858274 | 123.858274 | 0.381 | BB | BB | BB | BB | BB | BB | AB | AB | BB | BB |
| 4 | SNP_A-1643743 | rs444646 | 124370464 | 124.370464 | 0.548 | AB | AB | AB | AB | AB | AB | BB | BB | AA | AA |
| 4 | SNP_A-1746251 | rs10518307 | 125084153 | 125.084153 | 0.262 | AB | AB | BB | BB | BB | BB | BB | BB | BB | BB |
| 4 | SNP_A-1648121 | rs7682791 | 125875709 | 125.875709 | 0.631 | AA | AA | AA | AA | AA | AA | AA | AA | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 4 | SNP_A-1699868 | rs953211 | 126708654 | 126.708654 | 0.488 | AB | AB | AA | AA | AA | AA | AB | AB | AA | AA |
| 4 | SNP_A-1706772 | rs4834083 | 127331109 | 127.331109 | 0.726 | AA | AA | BB | BB | AB | AB | AA | AA | AB | AB |
| 4 | SNP_A-1653649 | rs318510 | 130173248 | 130.173248 | 0.571 | AA | AA | BB | BB | BB | BB | AA | AA | AA | AA |
| 4 | SNP_A-1655974 | rs2969001 | 131140397 | 131.140397 | 0.643 | AA | AA | AA | AA | AA | AA | AB | AB | AA | AA |
| 4 | SNP_A-1694056 | rs6846560 | 131988611 | 131.988611 | 0.357 | BB | BB | BB | BB | BB | BB | AB | AB | BB | AB |
| 4 | SNP_A-1719820 | rs10518609 | 133609659 | 133.609659 | 0.658 | AA | AA | BB | BB | BB | BB | AA | AA | AA | AA |
| 4 | SNP_A-1721507 | rs9307688 | 134441091 | 134.441091 | 0.726 | BB | BB | AA | AA | AA | AA | AA | AA | BB | AB |
| 4 | SNP_A-1716218 | rs9307703 | 135374277 | 135.374277 | 0.321 | BB | BB | BB | BB | BB | BB | AB | AB | BB | BB |
| 4 | SNP_A-1719154 | rs6535037 | 135968531 | 135.968531 | 0.691 | AB | AB | AA | AA | AA | AA | AB | AB | AA | AB |
| 4 | SNP_A-1718316 | rs10519369 | 137048788 | 137.048788 | 0.619 | AB | AB | AA | AB | AB | AB | AB | AB | AA | AB |
| 4 | SNP_A-1643751 | rs7692053 | 138020209 | 138.020209 | 0.631 | AB | AB | BB | BB | BB | BB | AA | AA | AA | AA |
| 4 | SNP_A-1712218 | rs1376088 | 139852726 | 139.852726 | 0.357 | BB | BB | BB | BB | BB | BB | AB | AB | BB | BB |
| 4 | SNP_A-1688437 | rs10519540 | 141950175 | 141.950175 | 0.429 | AB | AB | BB | BB | BB | BB | AA | AB | AA | AB |
| 4 | SNP_A-1669152 | rs2062597 | 143153292 | 143.153292 | 0.61 | AA | AA | AA | AA | AA | AA | BB | BB | AA | AA |
| 4 | SNP_A-1651007 | rs331963 | 144031456 | 144.031456 | 0.369 | AA | AA | AB | AB | AB | AB | AA | AA | BB | AB |
| 4 | SNP_A-1705078 | rs789351 | 146225975 | 146.225975 | 0.679 | BB | BB | AA | AA | AA | AA | AA | AA | AA | AA |
| 4 | SNP_A-1700284 | rs10519824 | 148107681 | 148.107681 | 0.658 | AA | AA | AA | AA | AA | AA | AA | AA | AA | AA |
| 4 | SNP_A-1655082 | rs6810951 | 149441717 | 149.441717 | 0.333 | BB | BB | AB | AB | AB | AB | BB | AB | BB | BB |
| 4 | SNP_A-1650743 | rs10489053 | 150276232 | 150.276232 | 0.643 | AB | AB | AA | AA | AA | AA | AA | AA | AA | AB |
| 4 | SNP_A-1695870 | rs991529 | 151852936 | 151.852936 | 0.488 | BB | BB | BB | BB | BB | BB | AA | AA | AA | AA |
| 4 | SNP_A-1750768 | rs361101 | 153131731 | 153.131731 | 0.631 | BB | BB | AB | AB | AA | AB | AA | AA | BB | AB |
| 4 | SNP_A-1694614 | rs7662116 | 154375569 | 154.375569 | 0.691 | AA | AA | AA | AA | AA | AA | BB | AB | AA | AA |
| 4 | SNP_A-1651497 | rs1125228 | 155126657 | 155.126657 | 0.738 | AA | AA | BB | BB | BB | BB | BB | BB | BB | BB |
| 4 | SNP_A-1732214 | rs6536240 | 158751762 | 158.751762 | 0.381 | AB | AB | BB | BB | BB | BB | AB | AB | BB | AB |
| 4 | SNP_A-1721547 | rs7678486 | 159498426 | 159.498426 | 0.25 | BB | BB | BB | BB | BB | BB | BB | BB | AA | AB |
| 4 | SNP_A-1695472 | rs7665879 | 160305968 | 160.305968 | 0.31 | AB | AB | BB | BB | BB | BB | AB | AB | BB | AB |
| 4 | SNP_A-1653797 | rs6856295 | 160845965 | 160.845965 | 0.595 | BB | BB | AB | AB | AA | AB | AB | AB | AA | AA |
| 4 | SNP_A-1705238 | rs9308000 | 161359479 | 161.359479 | 0.655 | AA | AA | AA | AA | AA | AA | AA | AA | AA | AA |
| 4 | SNP_A-1679349 | rs195894 | 163885040 | 163.88504 | 0.366 | BB | BB | AB | AB | BB | AB | BB | BB | BB | BB |
| 4 | SNP_A-1719176 | rs4057797 | 164602658 | 164.602658 | 0.381 | BB | BB | AB | AB | AB | AB | BB | BB | BB | AB |
| 4 | SNP_A-1657975 | rs4404502 | 165513434 | 165.513434 | 0.738 | AA | AA | AA | AA | AA | AA | AB | AB | AA | AB |
| 4 | SNP_A-1669824 | rs4691246 | 167437606 | 167.437606 | 0.402 | BB | BB | AB | AB | AB | AB | AB | AB | BB | BB |
| 4 | SNP_A-1701924 | rs7435411 | 169800826 | 169.800826 | 0.524 | BB | BB | AB | AB | BB | AB | AB | AB | AA | AB |
| 4 | SNP_A-1673825 | rs13212 | 170689681 | 170.689681 | 0.274 | BB | BB | BB | BB | BB | BB | BB | BB | BB | BB |
| 4 | SNP_A-1736222 | rs449424 | 171884933 | 171.884933 | 0.631 | AA | AA | AB | AB | AA | AB | AA | AA | AA | AA |
| 4 | SNP_A-1745583 | rs1485870 | 173125585 | 173.125585 | 0.744 | BB | AB | AA | AA | AA | AA | AA | AA | AA | AA |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 4 | SNP_A-1717120 | rs10520252 | 174445689 | 174.445689 | 0.619 | AA | AA | AB | AB | AA | AB | AB | AB | AA | AA |
| 4 | SNP_A-1714548 | rs10520282 | 175752491 | 175.752491 | 0.738 | AA | AA | AB | AB | AA | AB | AA | AA | AA | AA |
| 4 | SNP_A-1662283 | rs393279 | 177816548 | 177.816548 | 0.488 | AA | AA | BB | BB | BB | BB | BB | BB | BB | AB |
| 4 | SNP_A-1675843 | rs10520383 | 178915654 | 178.915654 | 0.357 | BB | BB | BB | BB | BB | BB | AB | AB | BB | AB |
| 4 | SNP_A-1737632 | rs2706012 | 179727204 | 179.727204 | 0.718 | AA | AA | AA | AA | AA | AA | AA | AA | BB | AB |
| 4 | SNP_A-1720252 | rs10520430 | 180911694 | 180.911694 | 0.679 | AA | AA | AB | AB | AA | AB | AA | AA | BB | BB |
| 4 | SNP_A-1644751 | rs7667245 | 181665445 | 181.665445 | 0.695 | AA | AB | AB | AB | BB | AB | AA | AA | AA | AA |
| 4 | SNP_A-1649573 | rs10520479 | 182667862 | 182.667862 | 0.702 | AA | AA | AA | AA | AA | AA | BB | BB | AA | AA |
| 4 | SNP_A-1689263 | rs10520518 | 183365702 | 183.365702 | 0.369 | BB | AB | AB | AB | BB | AB | AA | AA | BB | BB |
| 4 | SNP_A-1738928 | rs830838 | 187288258 | 187.288258 | 0.333 | BB | AB | BB | AB | AB | AB | BB | BB | AB | AB |
| 4 | SNP_A-1713082 | rs1280100 | 187913282 | 187.913282 | 0.345 | AA | AB | AA | AA | AA | AB | AB | AB | BB | BB |
| 4 | SNP_A-1654608 | rs1505509 | 188945352 | 188.945352 | 0.345 | AA | AB | BB | BB | BB | BB | AA | AA | BB | BB |
| 4 | SNP_A-1680395 | rs2376743 | 189829781 | 189.829781 | 0.679 | AA | AA | AA | AA | AA | AB | AB | AB | AB | AB |
| 5 | SNP_A-1689409 | rs10512651 | 1816661 | 1.816661 | 0.405 | BB | BB | AB | AB | BB | AB | AA | AA | AB | AB |
| 5 | SNP_A-1642488 | rs1445862 | 3675257 | 3.675257 | 0.25 | BB | BB | AB | AB | BB | AB | BB | AB | BB | BB |
| 5 | SNP_A-1651781 | rs272190 | 5103830 | 5.10383 | 0.25 | AB | AB | AA | AA | AA | AA | AB | AB | BB | BB |
| 5 | SNP_A-1663379 | rs2560294 | 5619114 | 5.619114 | 0.726 | AA | AA | AA | AA | AA | AB | AB | AB | AB | AB |
| 5 | SNP_A-1643560 | rs10512858 | 6486915 | 6.486915 | 0.613 | BB | BB | AB | AB | AA | AA | AA | AA | AB | AB |
| 5 | SNP_A-1651637 | rs4629562 | 7847326 | 7.847326 | 0.619 | AB | AB | AB | AB | AB | AA | AA | AB | AB | AB |
| 5 | SNP_A-1693207 | rs9313236 | 8348429 | 8.348429 | 0.25 | BB | BB | BB | BB | BB | BB | BB | BB | BB | BB |
| 5 | SNP_A-1744546 | rs12515692 | 9883408 | 9.883408 | 0.357 | AB | AB | BB | BB | BB | BB | BB | BB | AB | AB |
| 5 | SNP_A-1721268 | rs2937513 | 11007551 | 11.007551 | 0.619 | AB | AB | BB | BB | BB | BB | AB | AB | BB | BB |
| 5 | SNP_A-1702624 | rs173671 | 12217918 | 12.217918 | 0.476 | AB | AB | BB | AB | AB | AB | AB | AB | AA | AA |
| 5 | SNP_A-1695478 | rs1476154 | 13000353 | 13.000353 | 0.691 | BB | BB | AA | AA | AA | AA | AA | AA | AA | AA |
| 5 | SNP_A-1757294 | rs3734108 | 13806984 | 13.806984 | 0.56 | AA | AA | AB | BB | AB | AB | AB | AB | AB | AB |
| 5 | SNP_A-1696687 | rs2938832 | 15817866 | 15.817866 | 0.25 | AB | AB | BB | BB | BB | BB | AB | AB | AB | AB |
| 5 | SNP_A-1713461 | rs585991 | 17246633 | 17.246633 | 0.274 | BB | BB | AA | AA | AA | AA | BB | BB | BB | BB |
| 5 | SNP_A-1661473 | rs1394215 | 18359538 | 18.359538 | 0.548 | BB | BB | AA | AA | AA | AA | BB | BB | AA | AA |
| 5 | SNP_A-1646961 | rs2942296 | 19421031 | 19.421031 | 0.429 | BB | BB | AA | AB | AB | AB | AB | AB | AA | AA |
| 5 | SNP_A-1698916 | rs248202 | 21159137 | 21.159137 | 0.274 | BB | BB | BB | BB | BB | BB | BB | BB | AB | AB |
| 5 | SNP_A-1757332 | rs7705523 | 23659025 | 23.659025 | 0.714 | AA | AA | AB | BB | AB | AB | AA | AA | AB | AB |
| 5 | SNP_A-1672683 | rs1995599 | 24552793 | 24.552793 | 0.548 | AB | AB | BB | BB | AB | BB | BB | BB | AB | AB |
| 5 | SNP_A-1660984 | rs9293241 | 26606178 | 26.606178 | 0.56 | AB | AB | AA | AA | AA | AA | AB | AB | AB | AB |
| 5 | SNP_A-1704664 | rs921469 | 29989233 | 29.989233 | 0.583 | AB | AB | AA | AA | AA | AA | AB | AB | AB | AB |
| 5 | SNP_A-1644843 | rs1921111 | 30906615 | 30.906615 | 0.405 | BB | BB | BB | BB | BB | BB | AA | AA | AB | AB |
| 5 | SNP_A-1678791 | rs893551 | 33493407 | 33.493407 | 0.607 | AA | AA | AA | AA | AA | AA | AA | AA | AA | AA |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 5 | SNP_A-1724049 | rs716302 | 35846025 | 35.846025 | 0.357 | AB | AB | AA | AA | AA | AA | AA | AB | BB | BB |
| 5 | SNP_A-1703432 | rs159751 | 37035755 | 37.035755 | 0.464 | AA | AA | BB | BB | BB | BB | BB | BB | AA | AA |
| 5 | SNP_A-1645375 | rs4072686 | 38003109 | 38.003109 | 0.405 | AB | AB | BB | BB | BB | BB | BB | BB | BB | AB |
| 5 | SNP_A-1719252 | rs675502 | 39878266 | 39.878266 | 0.679 | AB | AB | BB | BB | AA | AB | AA | AA | AA | AA |
| 5 | SNP_A-1685613 | rs1697938 | 40890439 | 40.890439 | 0.441 | AA | AA | AA | AA | AA | AA | BB | BB | AA | AA |
| 5 | SNP_A-1731232 | rs276278 | 42016012 | 42.016012 | 0.298 | BB | BB | BB | BB | BB | BB | BB | BB | BB | AB |
| 5 | SNP_A-1694450 | rs1072746 | 43646445 | 43.646445 | 0.441 | AA | AB | BB | BB | BB | BB | BB | AB | BB | AB |
| 5 | SNP_A-1675759 | rs2404958 | 50098792 | 50.098792 | 0.619 | AA | AB | AA | AA | BB | AB | AA | AA | AA | AA |
| 5 | SNP_A-1723309 | rs9283709 | 51510492 | 51.510492 | 0.595 | BB | AB | BB | BB | AB | AB | AA | AA | BB | BB |
| 5 | SNP_A-1728968 | rs10512988 | 52085030 | 52.08503 | 0.357 | BB | AB | AA | AA | AA | AA | BB | AB | AA | AA |
| 5 | SNP_A-1746984 | rs9292039 | 53454075 | 53.454075 | 0.268 | BB | BB | BB | BB | BB | AA | AB | BB | AB | AB |
| 5 | SNP_A-1697874 | rs6450270 | 54287290 | 54.28729 | 0.714 | AA | AA | AA | AA | AA | AA | BB | AB | AA | AA |
| 5 | SNP_A-1684501 | rs889310 | 56000924 | 56.000924 | 0.476 | BB | BB | AB | AB | AB | BB | AB | BB | AA | AB |
| 5 | SNP_A-1673657 | rs2539731 | 57109292 | 57.109292 | 0.475 | BB | BB | BB | BB | BB | BB | AB | AB | BB | BB |
| 5 | SNP_A-1716782 | rs9292159 | 57677129 | 57.677129 | 0.31 | BB | BB | BB | BB | BB | BB | BB | BB | BB | BB |
| 5 | SNP_A-1724117 | rs9292180 | 58192447 | 58.192447 | 0.25 | BB | BB | AB | AA | AB | AB | BB | BB | AA | AB |
| 5 | SNP_A-1755537 | rs10514860 | 58859777 | 58.859777 | 0.726 | AA | AA | AA | AA | AA | AA | AA | AA | AA | AA |
| 5 | SNP_A-1653871 | rs6859376 | 59471964 | 59.471964 | 0.56 | AA | AB | BB | BB | BB | BB | AB | AB | BB | BB |
| 5 | SNP_A-1653455 | rs159375 | 60469024 | 60.469024 | 0.691 | AA | AA | AA | AA | AA | AA | BB | BB | BB | AB |
| 5 | SNP_A-1682537 | rs356598 | 63380121 | 63.380121 | 0.631 | BB | BB | AA | AA | AA | AA | BB | BB | BB | AB |
| 5 | SNP_A-1755307 | rs7704890 | 66151331 | 66.151331 | 0.357 | AA | AB | BB | BB | BB | BB | BB | BB | AA | AB |
| 5 | SNP_A-1671457 | rs6858907 | 67817289 | 67.817289 | 0.417 | BB | BB | AB | BB | AB | AB | BB | BB | BB | BB |
| 5 | SNP_A-1654744 | rs1600073 | 74472493 | 74.472493 | 0.61 | BB | BB | AB | BB | AB | AB | AB | AB | AA | AA |
| 5 | SNP_A-1653531 | rs10514059 | 75460983 | 75.460983 | 0.658 | AA | AA | AA | AA | AA | AA | AA | AA | BB | BB |
| 5 | SNP_A-1720510 | rs2972341 | 76504599 | 76.504599 | 0.536 | AB | AB | AA | AA | AA | AA | AB | AB | AA | AB |
| 5 | SNP_A-1682839 | rs949645 | 78478278 | 78.478278 | 0.564 | AA | AB | BB | BB | AB | AB | BB | BB | AA | AB |
| 5 | SNP_A-1747624 | rs264986 | 79206180 | 79.20618 | 0.31 | BB | BB | BB | BB | BB | BB | BB | BB | BB | BB |
| 5 | SNP_A-1730614 | rs964102 | 80843469 | 80.843469 | 0.679 | AB | AB | AA | AA | AA | AA | AA | AB | BB | BB |
| 5 | SNP_A-1732246 | rs10514249 | 82540612 | 82.540612 | 0.56 | AA | AA | AA | AA | AA | AA | BB | AB | BB | BB |
| 5 | SNP_A-1729977 | rs4639197 | 83381853 | 83.381853 | 0.25 | BB | BB | BB | BB | BB | BB | BB | BB | BB | BB |
| 5 | SNP_A-1742238 | rs323744 | 86861304 | 86.861304 | 0.5 | BB | BB | AA | AA | AA | AA | BB | AB | AA | AB |
| 5 | SNP_A-1751644 | rs819344 | 89093506 | 89.093506 | 0.463 | AA | AA | AB | BB | AB | BB | BB | BB | BB | BB |
| 5 | SNP_A-1690642 | rs2935499 | 89626568 | 89.626568 | 0.548 | AA | AA | BB | BB | BB | BB | AA | AB | AB | AB |
| 5 | SNP_A-1744488 | rs52308 | 90817903 | 90.817903 | 0.512 | BB | BB | AA | AA | AA | AA | BB | BB | AA | AA |
| 5 | SNP_A-1670907 | rs248339 | 95229134 | 95.229134 | 0.643 | AA | AA | BB | BB | BB | BB | BB | AB | AB | AB |
| 5 | SNP_A-1729028 | rs31248 | 96040439 | 96.040439 | 0.275 | BB | BB | AB | BB | AA | AB | AA | AB | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 5 | SNP_A-1657092 | rs10515273 | 97821155 | 97.821155 | 0.75 | AA | AA | AA | AA | AA | AA | AA | AA | AA | AA |
| 5 | SNP_A-1643346 | rs2887526 | 98552712 | 98.552712 | 0.667 | AB | AB | AA | AA | AA | AA | AA | AA | AA | AA |
| 5 | SNP_A-1722905 | rs2369754 | 99184261 | 99.184261 | 0.488 | AA | AA | AB | BB | AA | AB | AA | AB | BB | BB |
| 5 | SNP_A-1664073 | rs1477625 | 101358141 | 101.358141 | 0.271 | BB | BB | BB | BB | BB | BB | BB | BB | BB | BB |
| 5 | SNP_A-1742802 | rs9327861 | 101895776 | 101.895776 | 0.655 | BB | BB | AA | AA | AA | AA | AB | AB | AA | AA |
| 5 | SNP_A-1745283 | rs39984 | 102625191 | 102.625191 | 0.31 | AA | AA | BB | BB | BB | BB | AA | AA | BB | BB |
| 5 | SNP_A-1734843 | rs10515355 | 103975436 | 103.975436 | 0.738 | AB | AB | AA | AA | AA | BB | BB | AA | AA | AA |
| 5 | SNP_A-1730932 | rs4957531 | 106511277 | 106.511277 | 0.463 | AA | AA | AA | AA | AA | AA | AA | AB | AB | AB |
| 5 | SNP_A-1757418 | rs245243 | 109258634 | 109.258634 | 0.714 | AB | AB | AB | AA | BB | AB | AB | AB | AA | AA |
| 5 | SNP_A-1646761 | rs10491424 | 110481705 | 110.481705 | 0.56 | BB | BB | AB | AB | BB | AB | AA | AA | AA | AA |
| 5 | SNP_A-1691719 | rs1213404 | 111130917 | 111.130917 | 0.35 | BB | BB | BB | BB | BB | BB | BB | AB | BB | BB |
| 5 | SNP_A-1747768 | rs971517 | 112050154 | 112.050154 | 0.476 | AA | AA | AA | AA | AA | AA | AA | AA | AA | AA |
| 5 | SNP_A-1726679 | rs10519378 | 113555966 | 113.555966 | 0.738 | AA | AA | AA | AA | AA | AA | AA | AA | AA | AA |
| 5 | SNP_A-1738592 | rs2546480 | 114841054 | 114.841054 | 0.452 | AB | AB | BB | BB | BB | BB | BB | BB | AB | AB |
| 5 | SNP_A-1708792 | rs2662458 | 115402242 | 115.402242 | 0.655 | AB | AB | AB | AB | BB | AB | AA | AA | AB | AB |
| 5 | SNP_A-1720512 | rs1027292 | 116078486 | 116.078486 | 0.548 | BB | BB | AA | AA | AA | AA | AA | AA | AB | AB |
| 5 | SNP_A-1701708 | rs1504978 | 118638459 | 118.638459 | 0.655 | AB | AB | AB | AB | AA | AB | AA | AA | AA | AA |
| 5 | SNP_A-1689317 | rs10519615 | 119189176 | 119.189176 | 0.643 | BB | BB | BB | BB | BB | BB | AB | AB | AB | AB |
| 5 | SNP_A-1751260 | rs6897147 | 119692229 | 119.692229 | 0.691 | AA | AA | AA | AA | AA | AA | BB | BB | AA | AA |
| 5 | SNP_A-1654688 | rs161011 | 123703275 | 123.703275 | 0.286 | AA | AA | AB | AB | AB | AB | BB | BB | BB | BB |
| 5 | SNP_A-1699578 | rs7716491 | 124265772 | 124.265772 | 0.738 | AB | AB | AA | AA | AA | AB | AB | AB | AB | AB |
| 5 | SNP_A-1703238 | rs1826263 | 124839517 | 124.839517 | 0.571 | BB | BB | AA | AA | AA | AA | AB | AB | AB | AB |
| 5 | SNP_A-1715428 | rs964185 | 125631547 | 125.631547 | 0.345 | AA | AA | AA | AB | AB | AB | BB | BB | AB | AB |
| 5 | SNP_A-1751090 | rs1345663 | 126678081 | 126.678081 | 0.31 | BB | AB | AA | AA | AA | AA | AA | AA | AA | AA |
| 5 | SNP_A-1694738 | rs9327460 | 127338947 | 127.338947 | 0.524 | AA | AA | AA | AA | AA | AA | AB | AB | BB | BB |
| 5 | SNP_A-1658519 | rs1181962 | 128414700 | 128.4147 | 0.333 | BB | BB | AA | AA | AA | AA | AB | AB | BB | BB |
| 5 | SNP_A-1677377 | rs25810 | 129015788 | 129.015788 | 0.595 | AA | AA | AA | AA | AA | AA | AA | AA | AB | AB |
| 5 | SNP_A-1673843 | rs10520083 | 129967905 | 129.967905 | 0.345 | AA | AA | AA | AB | AB | AB | AB | AB | AA | AA |
| 5 | SNP_A-1705560 | rs9327673 | 133230970 | 133.23097 | 0.286 | BB | BB | BB | BB | BB | BB | AB | AB | AB | AB |
| 5 | SNP_A-1662391 | rs10515473 | 134961986 | 134.961986 | 0.714 | BB | BB | AA | AA | AA | AA | AA | AA | AB | AB |
| 5 | SNP_A-1707797 | rs10515481 | 136007946 | 136.007946 | 0.536 | BB | AB | AA | AA | AA | AA | AA | AA | BB | BB |
| 5 | SNP_A-1720076 | rs1560930 | 136590879 | 136.590879 | 0.537 | BB | BB | AA | AA | AA | AA | AA | AA | AB | AB |
| 5 | SNP_A-1697724 | rs288019 | 138219292 | 138.219292 | 0.39 | BB | BB | AB | AB | AB | AB | BB | AB | BB | BB |
| 5 | SNP_A-1707038 | rs2336977 | 139130436 | 139.130436 | 0.61 | AA | AB | AB | AB | AB | BB | BB | BB | AA | AA |
| 5 | SNP_A-1703312 | rs6860077 | 139725338 | 139.725338 | 0.31 | BB | AB | BB | BB | BB | BB | BB | BB | AB | AB |
| 5 | SNP_A-1742086 | rs246002 | 140321288 | 140.321288 | 0.5 | BB | BB | AB | AB | AB | AB | AA | AB | AA | AA |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 5 | SNP_A-1730974 | rs32927 | 141102251 | 141.102251 | 0.298 | AA | AB | BB | BB | BB | BB | BB | AB | AB | AB |
| 5 | SNP_A-1736416 | rs997833 | 141815738 | 141.815738 | 0.286 | AA | AB | AB | AB | AB | AB | BB | BB | BB | BB |
| 5 | SNP_A-1722681 | rs325227 | 143131067 | 143.131067 | 0.31 | AA | AB | AA | AA | AA | AA | AA | AA | BB | BB |
| 5 | SNP_A-1749482 | rs10515600 | 147316068 | 147.316068 | 0.548 | AB | AB | AB | AB | AB | AB | AA | AA | BB | BB |
| 5 | SNP_A-1716760 | rs185021 | 148147283 | 148.147283 | 0.524 | AB | AB | AB | AB | AB | AB | BB | BB | AA | AA |
| 5 | SNP_A-1642124 | rs10515632 | 149082624 | 149.082624 | 0.333 | BB | BB | AB | AB | AB | AB | BB | AB | AA | AA |
| 5 | SNP_A-1737743 | rs1277464 | 150234035 | 150.234035 | 0.354 | BB | BB | AB | AB | AB | AB | AB | AB | BB | BB |
| 5 | SNP_A-1678329 | rs2304054 | 150923278 | 150.923278 | 0.548 | AB | AB | AA | AA | AA | AA | BB | BB | AB | AB |
| 5 | SNP_A-1649583 | rs10515686 | 152529312 | 152.529312 | 0.619 | AA | AA | AB | AB | AB | AB | BB | AB | AB | AB |
| 5 | SNP_A-1652471 | rs4129128 | 153102070 | 153.10207 | 0.321 | AB | AB | AA | AA | AA | AA | BB | AB | BB | BB |
| 5 | SNP_A-1700286 | rs991314 | 154438135 | 154.438135 | 0.744 | AA | AA | AA | AA | AA | AA | AA | AA | AA | AA |
| 5 | SNP_A-1752802 | rs2569031 | 155177249 | 155.177249 | 0.488 | AB | AB | AB | AB | AB | AB | AB | AA | AB | AB |
| 5 | SNP_A-1706578 | rs873343 | 157106698 | 157.106698 | 0.25 | AB | AB | AB | AB | AB | AA | AA | AA | BB | BB |
| 5 | SNP_A-1757398 | rs9313777 | 157878177 | 157.878177 | 0.75 | AA | AA | AA | AA | AA | AA | AA | AA | AB | AB |
| 5 | SNP_A-1736540 | rs10515781 | 158633942 | 158.633942 | 0.321 | AB | AB | AB | AB | AB | AB | BB | BB | BB | BB |
| 5 | SNP_A-1647073 | rs411005 | 160517741 | 160.517741 | 0.476 | AB | AB | AA | AA | AA | AA | BB | BB | AA | AA |
| 5 | SNP_A-1724235 | rs2170901 | 161840216 | 161.840216 | 0.429 | BB | BB | AB | AB | AB | AB | BB | BB | AA | AA |
| 5 | SNP_A-1754048 | rs300238 | 162682948 | 162.682948 | 0.452 | AB | AB | AB | AB | AB | AB | AA | AA | AB | AB |
| 5 | SNP_A-1745987 | rs158295 | 163217790 | 163.21779 | 0.25 | BB | BB | BB | BB | BB | BB | AA | AB | BB | BB |
| 5 | SNP_A-1720394 | rs6869856 | 166017651 | 166.017651 | 0.412 | AA | AA | AA | AA | AA | AA | AA | AA | AA | AA |
| 5 | SNP_A-1687531 | rs1911557 | 169681232 | 169.681232 | 0.25 | BB | BB | BB | BB | BB | BB | AB | AB | AB | AB |
| 5 | SNP_A-1749300 | rs10516089 | 171083836 | 171.083836 | 0.726 | AB | AB | AA | AA | AA | AA | AB | AA | AA | AA |
| 5 | SNP_A-1665975 | rs1909706 | 173644330 | 173.64433 | 0.707 | AA | AA | AA | AA | AA | AA | AA | AA | AA | AA |
| 5 | SNP_A-1724885 | rs965017 | 174509108 | 174.509108 | 0.548 | AB | AB | AB | AB | BB | AA | AA | AA | AA | AA |
| 5 | SNP_A-1644515 | rs1071882 | 178068646 | 178.068646 | 0.702 | AA | AA | AA | AB | AA | AB | AA | AA | AA | AA |
| 5 | SNP_A-1748220 | rs2892344 | 180297919 | 180.297919 | 0.536 | AB | AB | BB | BB | BB | BB | BB | BB | AB | AB |
| 6 | SNP_A-1732501 | rs3765437 | 508013 | 0.508013 | 0.536 | AA | AA | BB | BB | BB | BB | BB | BB | AA | AA |
| 6 | SNP_A-1728682 | rs238073 | 1192930 | 1.19293 | 0.381 | AA | AA | BB | BB | BB | BB | AA | AA | AB | AB |
| 6 | SNP_A-1747718 | rs6919059 | 1729095 | 1.729095 | 0.691 | AA | AB | AA | AA | AA | AA | AB | AB | AA | AA |
| 6 | SNP_A-1723553 | rs2326366 | 3923256 | 3.923256 | 0.417 | BB | AB | AA | AA | AB | AB | BB | BB | AB | AB |
| 6 | SNP_A-1747058 | rs10484314 | 5593086 | 5.593086 | 0.333 | BB | BB | BB | BB | BB | BB | BB | BB | AB | AB |
| 6 | SNP_A-1673883 | rs3851514 | 6219569 | 6.219569 | 0.75 | BB | BB | BB | BB | BB | BB | AB | AB | AA | AA |
| 6 | SNP_A-1737825 | rs267202 | 7799235 | 7.799235 | 0.619 | AB | AB | AA | AA | AB | AA | AA | AA | AA | AA |
| 6 | SNP_A-1680945 | rs1543731 | 8355978 | 8.355978 | 0.346 | AA | AA | AA | AA | AA | AA | BB | BB | BB | BB |
| 6 | SNP_A-1702006 | rs9296701 | 9687981 | 9.687981 | 0.536 | AB | AB | BB | BB | BB | BB | BB | BB | AB | AB |
| 6 | SNP_A-1715186 | rs4512212 | 10379387 | 10.379387 | 0.464 | BB | BB | AA | AB | AA | AB | BB | BB | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 6 | SNP_A-1680453 | rs2182335 | 11324963 | 11.324963 | 0.714 | AA | AA | AA | AB | AA | AB | BB | BB | AA | AA |
| 6 | SNP_A-1690060 | rs2841555 | 13574809 | 13.574809 | 0.655 | AA | AA | AA | AA | AA | AA | AB | AB | AB | AB |
| 6 | SNP_A-1646375 | rs2237166 | 16755137 | 16.755137 | 0.536 | AB | AB | AB | AB | BB | AB | BB | BB | AA | AA |
| 6 | SNP_A-1744270 | rs2147211 | 17898170 | 17.89817 | 0.714 | AA | AA | AA | AA | AA | AA | AB | AB | AB | AB |
| 6 | SNP_A-1679405 | rs9297090 | 18873893 | 18.873893 | 0.571 | AB | AB | AA | AA | AA | AA | AA | AA | AB | AB |
| 6 | SNP_A-1717924 | rs971623 | 20437442 | 20.437442 | 0.405 | AB | AB | BB | BB | BB | BB | AB | AB | BB | BB |
| 6 | SNP_A-1749068 | rs10485012 | 22715005 | 22.715005 | 0.595 | AB | AB | AB | AB | AB | AB | BB | BB | AA | AA |
| 6 | SNP_A-1754953 | rs2022330 | 23554534 | 23.554534 | 0.667 | AB | AB | AB | AB | AB | AB | AB | AB | AB | AB |
| 6 | SNP_A-1698352 | rs499466 | 24069410 | 24.06941 | 0.5 | AB | AB | BB | BB | BB | BB | AB | AB | AA | AA |
| 6 | SNP_A-1682833 | rs9295755 | 28141153 | 28.141153 | 0.25 | BB | BB | BB | BB | BB | BB | AB | AB | BB | BB |
| 6 | SNP_A-1656688 | rs2747430 | 29756485 | 29.756485 | 0.702 | AB | AB | AA | AA | AA | AA | AA | AA | AA | AA |
| 6 | SNP_A-1715492 | rs2395173 | 32512837 | 32.512837 | 0.691 | AB | AB | AA | AA | AA | AA | AB | AB | AA | AA |
| 6 | SNP_A-1722893 | rs9296266 | 38990614 | 38.990614 | 0.573 | AA | AA | AB | AB | AB | AB | AA | AA | AA | AB |
| 6 | SNP_A-1724965 | rs2395743 | 40400147 | 40.400147 | 0.488 | BB | AB | BB | BB | BB | BB | BB | BB | BB | AB |
| 6 | SNP_A-1757782 | rs3804281 | 41853967 | 41.853967 | 0.429 | BB | BB | AB | AB | AB | AB | AA | AB | BB | BB |
| 6 | SNP_A-1700088 | rs3763234 | 42725939 | 42.725939 | 0.298 | AA | AB | BB | BB | BB | BB | BB | BB | BB | AB |
| 6 | SNP_A-1748380 | rs525043 | 44511878 | 44.511878 | 0.25 | BB | BB | BB | BB | BB | BB | BB | BB | BB | AB |
| 6 | SNP_A-1685295 | rs9296453 | 45335410 | 45.33541 | 0.429 | AA | AB | BB | BB | BB | BB | AA | AA | AA | AA |
| 6 | SNP_A-1708722 | rs9296468 | 45876662 | 45.876662 | 0.726 | AA | AA | AB | AB | AB | AB | AA | AA | AA | AA |
| 6 | SNP_A-1736458 | rs10498767 | 46471516 | 46.471516 | 0.441 | BB | AB | BB | BB | BB | BB | BB | BB | BB | AB |
| 6 | SNP_A-1642956 | rs9296547 | 47474339 | 47.474339 | 0.643 | AA | AA | BB | BB | BB | BB | BB | AB | AA | AA |
| 6 | SNP_A-1742558 | rs2089505 | 48229201 | 48.229201 | 0.643 | AA | AA | BB | BB | BB | BB | BB | BB | AA | AA |
| 6 | SNP_A-1738582 | rs504213 | 49411897 | 49.411897 | 0.607 | AA | AA | AA | AA | AA | AA | AA | AA | BB | AB |
| 6 | SNP_A-1658085 | rs10484664 | 51124482 | 51.124482 | 0.256 | BB | BB | BB | BB | BB | BB | BB | BB | BB | AB |
| 6 | SNP_A-1723157 | rs913098 | 51750772 | 51.750772 | 0.667 | AA | AB | AA | AA | AA | AA | AA | AA | AA | AA |
| 6 | SNP_A-1726221 | rs509946 | 52411949 | 52.411949 | 0.369 | BB | BB | AA | BB | BB | AB | BB | AB | BB | BB |
| 6 | SNP_A-1717116 | rs10484785 | 53457958 | 53.457958 | 0.476 | BB | AB | BB | BB | BB | BB | AA | AB | BB | BB |
| 6 | SNP_A-1717814 | rs1393779 | 54808762 | 54.808762 | 0.464 | AA | AB | AA | AA | AA | AA | BB | BB | BB | BB |
| 6 | SNP_A-1693069 | rs1925179 | 56129171 | 56.129171 | 0.655 | AA | AA | AA | AA | AA | AA | AA | AA | AA | AB |
| 6 | SNP_A-1664153 | rs6934928 | 58422082 | 58.422082 | 0.714 | BB | AB | AA | AA | AA | AA | BB | AB | AA | AA |
| 6 | SNP_A-1682123 | rs565795 | 62597708 | 62.597708 | 0.61 | AA | AA | AA | AA | AA | AA | BB | BB | AA | AB |
| 6 | SNP_A-1692597 | rs9293849 | 63255396 | 63.255396 | 0.333 | BB | BB | BB | AA | BB | AB | BB | AB | BB | AB |
| 6 | SNP_A-1729072 | rs9294630 | 65677619 | 65.677619 | 0.702 | AA | AB | AA | AA | AA | AA | AA | AA | AA | AB |
| 6 | SNP_A-1685655 | rs2502270 | 67886666 | 67.886666 | 0.488 | AA | AA | AA | AA | AA | AA | AB | AB | AA | AA |
| 6 | SNP_A-1744006 | rs4707479 | 68787830 | 68.78783 | 0.286 | AA | AA | BB | BB | BB | BB | BB | BB | BB | AB |
| 6 | SNP_A-1683273 | rs579588 | 69639537 | 69.639537 | 0.714 | AA | AA | BB | AA | BB | AB | AB | AB | BB | AA |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 6 | SNP_A-1659091 | rs591809 | 72270133 | 72.270133 | 0.524 | BB | BB | BB | BB | BB | BB | BB | BB | AA | AB |
| 6 | SNP_A-1660794 | rs959369 | 74620278 | 74.620278 | 0.607 | AA | AA | AA | AA | AA | AA | AA | AA | AA | AB |
| 6 | SNP_A-1656648 | rs1575856 | 76774483 | 76.774483 | 0.262 | BB | BB | BB | BB | BB | BB | BB | BB | BB | AB |
| 6 | SNP_A-1675424 | rs1457947 | 77533004 | 77.533004 | 0.619 | AA | AA | AA | AA | AA | AA | AB | AB | AA | AA |
| 6 | SNP_A-1657250 | rs236225 | 79172654 | 79.172654 | 0.744 | AA | AA | AA | AA | AA | AA | AB | AB | AA | AA |
| 6 | SNP_A-1646741 | rs239500 | 80761863 | 80.761863 | 0.595 | AB | AB | AA | AA | AA | AA | AB | AB | BB | BB |
| 6 | SNP_A-1733643 | rs310387 | 81832380 | 81.83238 | 0.56 | AA | AA | AA | AA | AA | AA | AA | AA | BB | AB |
| 6 | SNP_A-1684117 | rs2323435 | 82365338 | 82.365338 | 0.417 | BB | BB | BB | BB | BB | BB | BB | BB | BB | BB |
| 6 | SNP_A-1749278 | rs958568 | 83211843 | 83.211843 | 0.417 | BB | BB | BB | BB | BB | BB | BB | BB | BB | AB |
| 6 | SNP_A-1737476 | rs6938512 | 85412591 | 85.412591 | 0.476 | AB | AB | BB | BB | BB | BB | AA | AA | BB | BB |
| 6 | SNP_A-1658179 | rs3966882 | 85938190 | 85.93819 | 0.46 | BB | BB | BB | AA | AB | AB | AB | AB | BB | BB |
| 6 | SNP_A-1704672 | rs3857488 | 88057783 | 88.057783 | 0.548 | AB | AB | BB | BB | BB | BB | AA | AA | AA | AB |
| 6 | SNP_A-1750678 | rs942115 | 90274825 | 90.274825 | 0.691 | AA | AA | BB | BB | BB | AA | AA | AA | AA | AA |
| 6 | SNP_A-1641794 | rs1753826 | 91283465 | 91.283465 | 0.274 | BB | BB | BB | BB | BB | BB | BB | BB | BB | BB |
| 6 | SNP_A-1747902 | rs427118 | 92400922 | 92.400922 | 0.622 | AB | AB | AA | AA | AA | AA | AA | AA | AB | AB |
| 6 | SNP_A-1699604 | rs609590 | 93182864 | 93.182864 | 0.595 | AB | AB | AA | AA | AA | AA | AB | AB | AB | AB |
| 6 | SNP_A-1671865 | rs1906966 | 94362973 | 94.362973 | 0.571 | AA | AA | AA | AA | AA | AA | AB | AB | AB | AB |
| 6 | SNP_A-1672477 | rs2380218 | 95947837 | 95.947837 | 0.643 | AB | AB | BB | AB | AB | AB | AB | AB | AA | AA |
| 6 | SNP_A-1727169 | rs6925466 | 96483564 | 96.483564 | 0.476 | AB | AB | AA | AB | AB | AB | BB | BB | AB | AB |
| 6 | SNP_A-1669372 | rs2206094 | 97681917 | 97.681917 | 0.595 | AB | AB | AA | AA | AA | AA | AB | AB | AB | AB |
| 6 | SNP_A-1754567 | rs10484477 | 103889951 | 103.889951 | 0.738 | AA | AA | AA | AA | AA | AA | BB | BB | AB | AB |
| 6 | SNP_A-1687147 | rs1341123 | 104971433 | 104.971433 | 0.274 | BB | BB | BB | BB | BB | BB | BB | BB | AB | AB |
| 6 | SNP_A-1696467 | rs1325421 | 105998201 | 105.998201 | 0.643 | AB | AB | AB | AB | AB | AB | AA | AA | AA | AA |
| 6 | SNP_A-1733167 | rs1462145 | 107068713 | 107.068713 | 0.357 | AB | AB | BB | BB | BB | BB | BB | BB | BB | BB |
| 6 | SNP_A-1650105 | rs7740028 | 110825873 | 110.825873 | 0.393 | AA | AA | BB | BB | BB | BB | AA | AA | BB | BB |
| 6 | SNP_A-1680493 | rs2010315 | 112529340 | 112.52934 | 0.679 | AA | AA | AA | AA | AA | AA | AA | AA | AA | AA |
| 6 | SNP_A-1735595 | rs1378682 | 113188320 | 113.18832 | 0.405 | AA | AA | BB | BB | BB | BB | AA | AA | AB | AB |
| 6 | SNP_A-1712634 | rs2810160 | 114329403 | 114.329403 | 0.548 | AB | AB | BB | BB | BB | BB | AB | AB | AB | AB |
| 6 | SNP_A-1687581 | rs1748168 | 114955404 | 114.955404 | 0.56 | BB | AB | AA | AA | AA | AA | AB | AB | BB | BB |
| 6 | SNP_A-1738139 | rs2250263 | 116940700 | 116.9407 | 0.679 | AA | AB | AA | AA | AA | AA | AA | AA | BB | BB |
| 6 | SNP_A-1729937 | rs929122 | 117712442 | 117.712442 | 0.726 | AA | AA | AA | AA | AA | AA | AA | AA | AB | AB |
| 6 | SNP_A-1661803 | rs9285429 | 118811259 | 118.811259 | 0.619 | AA | AA | AB | AB | AB | AB | AA | AA | BB | BB |
| 6 | SNP_A-1665123 | rs1873553 | 120164641 | 120.164641 | 0.429 | BB | BB | BB | BB | BB | BB | AB | AB | AA | AA |
| 6 | SNP_A-1679087 | rs6906196 | 122713901 | 122.713901 | 0.369 | BB | BB | BB | BB | BB | BB | BB | BB | BB | BB |
| 6 | SNP_A-1707510 | rs6924068 | 124232587 | 124.232587 | 0.345 | BB | BB | AB | AB | AB | AB | BB | BB | BB | BB |
| 6 | SNP_A-1745119 | rs484510 | 125528599 | 125.528599 | 0.691 | AA | AA | AA | AA | AA | AA | AA | AA | AB | AB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 6 | SNP_A-1685381 | rs9321057 | 126198636 | 126.198636 | 0.405 | AA | AB | BB | BB | BB | BB | AB | AB | AB | AB |
| 6 | SNP_A-1751986 | rs270044 | 128228176 | 128.228176 | 0.405 | AA | AB | BB | BB | BB | BB | BB | BB | AB | AB |
| 6 | SNP_A-1721422 | rs1508439 | 129073191 | 129.073191 | 0.655 | AA | AB | AA | AA | AA | AA | AB | AB | AA | AA |
| 6 | SNP_A-1707720 | rs10484282 | 130107771 | 130.107771 | 0.321 | BB | AB | BB | BB | BB | BB | AB | AB | BB | BB |
| 6 | SNP_A-1652817 | rs766967 | 130912718 | 130.912718 | 0.488 | AA | AA | AB | AB | AB | AB | AB | AB | BB | BB |
| 6 | SNP_A-1653251 | rs170881 | 132358254 | 132.358254 | 0.655 | AA | AA | BB | BB | BB | BB | AB | AB | BB | BB |
| 6 | SNP_A-1723663 | rs2745426 | 133045037 | 133.045037 | 0.287 | BB | BB | BB | BB | BB | BB | BB | BB | BB | BB |
| 6 | SNP_A-1751418 | rs509904 | 133558775 | 133.558775 | 0.713 | AA | AB | AA | AA | AA | AA | AA | AA | BB | BB |
| 6 | SNP_A-1735812 | rs6570091 | 137092589 | 137.092589 | 0.464 | BB | BB | AA | AA | AA | AB | BB | BB | AB | AB |
| 6 | SNP_A-1669540 | rs662100 | 137931606 | 137.931606 | 0.512 | AA | AA | AA | AA | AA | AA | BB | AB | AA | AA |
| 6 | SNP_A-1692831 | rs2473522 | 139472945 | 139.472945 | 0.274 | BB | BB | AB | AB | AB | AB | AA | AA | BB | BB |
| 6 | SNP_A-1729139 | rs9321743 | 140005650 | 140.00565 | 0.655 | AA | AA | AA | AA | AA | AA | AA | AA | AB | AB |
| 6 | SNP_A-1668519 | rs225710 | 142582952 | 142.582952 | 0.548 | AB | AB | BB | BB | BB | BB | BB | AB | AA | AA |
| 6 | SNP_A-1741850 | rs10484804 | 143972461 | 143.972461 | 0.262 | AB | AB | BB | BB | BB | BB | BB | BB | BB | BB |
| 6 | SNP_A-1699598 | rs4243477 | 145767511 | 145.767511 | 0.655 | AA | AA | AA | AA | AA | AA | AB | AB | AB | AB |
| 6 | SNP_A-1714061 | rs6923545 | 146286436 | 146.286436 | 0.417 | AB | AB | BB | BB | BB | BB | BB | AB | AB | AB |
| 6 | SNP_A-1643757 | rs2025157 | 146851348 | 146.851348 | 0.607 | AA | AA | AA | AA | AA | AA | AB | BB | BB | BB |
| 6 | SNP_A-1746680 | rs10484677 | 148334072 | 148.334072 | 0.702 | AA | AA | AA | AA | AA | AA | AA | AA | AB | AB |
| 6 | SNP_A-1674099 | rs997682 | 149708313 | 149.708313 | 0.293 | BB | BB | AB | AB | AB | AB | BB | AB | BB | BB |
| 6 | SNP_A-1742378 | rs1933079 | 151696424 | 151.696424 | 0.464 | AA | AA | BB | BB | BB | BB | AA | AB | BB | BB |
| 6 | SNP_A-1664463 | rs872371 | 153469676 | 153.469676 | 0.732 | AA | AA | BB | BB | BB | BB | AA | AB | AA | AA |
| 6 | SNP_A-1706738 | rs612450 | 154306471 | 154.306471 | 0.56 | AB | AB | AB | AB | AB | AB | AA | AA | AA | AA |
| 6 | SNP_A-1661002 | rs1980602 | 155248334 | 155.248334 | 0.429 | AB | AB | AA | AA | AA | AA | BB | AB | AB | AB |
| 6 | SNP_A-1700465 | rs1391655 | 156092837 | 156.092837 | 0.298 | BB | AB | BB | BB | BB | BB | BB | BB | BB | BB |
| 6 | SNP_A-1660620 | rs7770496 | 156806897 | 156.806897 | 0.372 | AA | AB | AA | AB | AB | AB | AA | AB | AB | AB |
| 6 | SNP_A-1712976 | rs4709298 | 157885415 | 157.885415 | 0.262 | BB | AB | BB | AB | AB | AB | AA | AB | AA | AA |
| 6 | SNP_A-1676117 | rs7753885 | 158892133 | 158.892133 | 0.488 | BB | AB | AA | AB | AB | AB | BB | BB | BB | BB |
| 6 | SNP_A-1669774 | rs923459 | 159532261 | 159.532261 | 0.513 | BB | AB | AA | AA | AA | AA | BB | AB | AB | AB |
| 6 | SNP_A-1659978 | rs927450 | 160152507 | 160.152507 | 0.583 | AA | AA | AA | AA | AA | AA | BB | AB | AB | AB |
| 6 | SNP_A-1670969 | rs598969 | 160664317 | 160.664317 | 0.425 | BB | AB | AA | AA | AA | AA | BB | BB | BB | BB |
| 6 | SNP_A-1697554 | rs6910079 | 164339862 | 164.339862 | 0.441 | AA | AB | BB | AB | AB | AB | BB | BB | AB | AB |
| 6 | SNP_A-1641972 | rs907223 | 165179009 | 165.179009 | 0.702 | AA | AA | AA | AA | AA | AA | AA | AA | AB | AB |
| 6 | SNP_A-1698488 | rs162293 | 167420582 | 167.420582 | 0.75 | AA | AA | AA | AA | AA | AA | AA | AA | AA | AA |
| 7 | SNP_A-1647507 | rs1637750 | 2001052 | 2.001052 | 0.655 | AA | AA | AA | AA | AA | AA | AB | AB | AA | AA |
| 7 | SNP_A-1710599 | rs10257982 | 3107838 | 3.107838 | 0.452 | AA | AB | AA | AA | AA | AA | BB | BB | AB | AB |
| 7 | SNP_A-1675597 | rs10488360 | 4184450 | 4.18445 | 0.317 | BB | BB | BB | BB | BB | BB | BB | BB | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 7 | SNP_A-1712104 | rs719423 | 7128355 | 7.128355 | 0.667 | AA | AA | BB | BB | BB | BB | BB | BB | AB | AB |
| 7 | SNP_A-1649251 | rs38012 | 7815795 | 7.815795 | 0.464 | AB | AB | AB | AB | BB | AB | AB | AB | AB | AB |
| 7 | SNP_A-1714013 | rs10253058 | 10364900 | 10.3649 | 0.738 | AA | AA | AA | AA | AA | AA | AA | AA | AB | AB |
| 7 | SNP_A-1656052 | rs7785008 | 10921568 | 10.921568 | 0.452 | AB | AB | BB | BB | BB | BB | AA | AA | AB | AB |
| 7 | SNP_A-1678735 | rs10270630 | 11629477 | 11.629477 | 0.738 | BB | BB | AB | AB | BB | AA | AA | AA | AB | AB |
| 7 | SNP_A-1672885 | rs1036667 | 12197823 | 12.197823 | 0.488 | BB | BB | AB | AB | AA | AB | AA | AA | AA | AA |
| 7 | SNP_A-1707354 | rs2214867 | 13507965 | 13.507965 | 0.417 | AA | AA | AA | AA | AA | AA | BB | BB | AB | AB |
| 7 | SNP_A-1724539 | rs7793372 | 14320689 | 14.320689 | 0.619 | BB | BB | BB | BB | BB | BB | AA | AA | AB | AB |
| 7 | SNP_A-1756798 | rs1527203 | 15931001 | 15.931001 | 0.643 | AA | AA | AB | AB | AB | AA | AA | AA | AA | AA |
| 7 | SNP_A-1755023 | rs706057 | 16577230 | 16.57723 | 0.56 | AB | AB | AB | AB | AB | AB | AB | AB | AB | AB |
| 7 | SNP_A-1647845 | rs4721619 | 17291814 | 17.291814 | 0.667 | AB | AB | AA | AA | AA | AA | AB | AB | AA | AA |
| 7 | SNP_A-1693824 | rs2731551 | 18050825 | 18.050825 | 0.25 | BB | BB | AB | AB | AB | AB | BB | BB | BB | BB |
| 7 | SNP_A-1724213 | rs10486334 | 18974842 | 18.974842 | 0.726 | BB | BB | AB | AB | AB | AB | BB | BB | AA | AA |
| 7 | SNP_A-1716746 | rs2248634 | 21065118 | 21.065118 | 0.262 | BB | BB | BB | BB | BB | BB | AB | AB | BB | BB |
| 7 | SNP_A-1706218 | rs7781044 | 21636203 | 21.636203 | 0.61 | AA | AA | AA | AA | AA | AA | AB | AB | AB | AB |
| 7 | SNP_A-1718088 | rs2286497 | 22701238 | 22.701238 | 0.305 | BB | BB | AB | AB | AB | AB | AB | AB | AB | AB |
| 7 | SNP_A-1755947 | rs2521642 | 24200036 | 24.200036 | 0.31 | BB | BB | BB | BB | BB | BB | AB | AB | BB | BB |
| 7 | SNP_A-1751950 | rs4275130 | 26366016 | 26.366016 | 0.75 | AB | AB | AA | AA | AA | AA | AA | AA | AA | AA |
| 7 | SNP_A-1725907 | rs6953785 | 27237607 | 27.237607 | 0.536 | AB | AB | AB | BB | AB | AB | AB | AB | AA | AA |
| 7 | SNP_A-1729503 | rs4498447 | 28177012 | 28.177012 | 0.524 | BB | BB | AB | AB | AB | AB | BB | BB | AB | AB |
| 7 | SNP_A-1663287 | rs1859681 | 28699408 | 28.699408 | 0.275 | BB | BB | BB | BB | BB | BB | BB | BB | BB | BB |
| 7 | SNP_A-1728544 | rs1476991 | 29293282 | 29.293282 | 0.571 | AA | AA | AA | AA | AA | AA | AA | AA | AB | AB |
| 7 | SNP_A-1718026 | rs997349 | 29955684 | 29.955684 | 0.357 | BB | BB | BB | BB | BB | BB | BB | BB | BB | BB |
| 7 | SNP_A-1695134 | rs10487729 | 31345524 | 31.345524 | 0.726 | AA | AA | AA | AA | AA | AA | AB | AB | BB | BB |
| 7 | SNP_A-1694740 | rs215675 | 32156237 | 32.156237 | 0.286 | AA | AB | BB | BB | BB | BB | BB | BB | AB | AB |
| 7 | SNP_A-1717858 | rs10254116 | 33010729 | 33.010729 | 0.631 | BB | AB | AA | AA | AA | AA | AA | AA | AA | AA |
| 7 | SNP_A-1678175 | rs10486619 | 33600838 | 33.600838 | 0.262 | BB | BB | BB | BB | BB | BB | BB | BB | AB | AB |
| 7 | SNP_A-1749566 | rs741202 | 35093154 | 35.093154 | 0.262 | BB | BB | BB | BB | AB | AB | BB | BB | AA | AA |
| 7 | SNP_A-1731924 | rs4720228 | 36725169 | 36.725169 | 0.476 | BB | AB | BB | BB | BB | BB | BB | BB | BB | BB |
| 7 | SNP_A-1671783 | rs2893552 | 37928803 | 37.928803 | 0.679 | AA | AA | AA | AA | AA | AA | BB | BB | AA | AA |
| 7 | SNP_A-1730217 | rs4723791 | 38613746 | 38.613746 | 0.56 | BB | AB | AA | AA | AA | AA | AA | AA | AA | AA |
| 7 | SNP_A-1669882 | rs10486802 | 39497008 | 39.497008 | 0.571 | AA | AA | BB | BB | BB | BB | AA | AA | AA | AA |
| 7 | SNP_A-1721388 | rs7807596 | 40599281 | 40.599281 | 0.417 | AA | AA | BB | BB | AB | AB | AB | AB | AA | AA |
| 7 | SNP_A-1750290 | rs384469 | 41099793 | 41.099793 | 0.702 | AA | AB | AA | AA | AB | AB | AB | AB | AA | AA |
| 7 | SNP_A-1695614 | rs721273 | 42867596 | 42.867596 | 0.702 | AA | AA | BB | BB | AB | AB | AA | AA | AA | AA |
| 7 | SNP_A-1736506 | rs2330918 | 43444472 | 43.444472 | 0.75 | AA | AB | AA | AA | AA | AA | AA | AA | AA | AA |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 7 | SNP_A-1732094 | rs10253161 | 46769632 | 46.769632 | 0.714 | AA | AA | AA | AA | AA | AA | AA | AA | BB | AB |
| 7 | SNP_A-1710294 | rs7357251 | 47841498 | 47.841498 | 0.417 | AA | AA | AA | AA | AA | AB | BB | BB | BB | BB |
| 7 | SNP_A-1669906 | rs3923511 | 48463293 | 48.463293 | 0.688 | AA | AA | AA | AA | AA | AB | AB | BB | AB | |
| 7 | SNP_A-1748806 | rs716719 | 50102978 | 50.102978 | 0.262 | AA | AA | BB | BB | BB | BB | BB | BB | BB | BB |
| 7 | SNP_A-1646085 | rs2159809 | 52287324 | 52.287324 | 0.39 | AA | AB | BB | BB | BB | BB | BB | BB | BB | BB |
| 7 | SNP_A-1655668 | rs6955211 | 63316490 | 63.31649 | 0.464 | BB | AB | AA | AA | AA | AA | AA | AB | BB | BB |
| 7 | SNP_A-1695272 | rs9638255 | 67214110 | 67.21411 | 0.655 | AA | AA | AA | AA | AA | AA | AB | AA | AA | |
| 7 | SNP_A-1673105 | rs1699443 | 68224124 | 68.224124 | 0.583 | AA | AB | AA | AA | AA | AA | AA | BB | AB | |
| 7 | SNP_A-1667673 | rs10499812 | 69098641 | 69.098641 | 0.333 | AA | AB | BB | BB | BB | BB | BB | BB | BB | |
| 7 | SNP_A-1757146 | rs6976144 | 77019455 | 77.019455 | 0.5 | AA | AB | BB | BB | BB | BB | AB | AB | AA | AB |
| 7 | SNP_A-1741890 | rs10485887 | 77712706 | 77.712706 | 0.548 | AA | AA | AA | AB | AA | AB | BB | BB | AA | AB |
| 7 | SNP_A-1663217 | rs984312 | 78285441 | 78.285441 | 0.631 | AA | AA | BB | AB | AB | AB | AA | AA | BB | AB |
| 7 | SNP_A-1676663 | rs3211816 | 79922641 | 79.922641 | 0.39 | BB | BB | BB | BB | BB | BB | AB | AB | BB | BB |
| 7 | SNP_A-1724625 | rs3801720 | 81447606 | 81.447606 | 0.595 | AA | AB | BB | AB | AB | AB | AB | AB | BB | AB |
| 7 | SNP_A-1701440 | rs1693380 | 82818863 | 82.818863 | 0.738 | AA | AA | AA | AA | AA | AA | AB | AB | AA | AA |
| 7 | SNP_A-1690947 | rs10499889 | 84765715 | 84.765715 | 0.369 | BB | BB | BB | BB | BB | BB | AB | AB | AA | AA |
| 7 | SNP_A-1722683 | rs1063964 | 87480120 | 87.48012 | 0.607 | AA | AA | AA | AA | AA | AA | AA | AA | BB | AB |
| 7 | SNP_A-1697794 | rs7799830 | 88761617 | 88.761617 | 0.429 | BB | BB | AA | AA | AA | AA | AB | AB | AA | AA |
| 7 | SNP_A-1692549 | rs3802029 | 90126750 | 90.12675 | 0.595 | AB | AB | AA | AB | AB | AB | BB | BB | BB | AB |
| 7 | SNP_A-1721485 | rs1468180 | 92759526 | 92.759526 | 0.441 | BB | BB | AA | AA | AA | AA | AA | AA | AA | AB |
| 7 | SNP_A-1705566 | rs6465448 | 94217939 | 94.217939 | 0.548 | AB | AB | BB | BB | BB | BB | AA | AA | BB | AB |
| 7 | SNP_A-1644895 | rs1403179 | 96113755 | 96.113755 | 0.75 | AB | AB | AA | AA | AA | AA | AB | AA | AA | |
| 7 | SNP_A-1698924 | rs7779090 | 96790254 | 96.790254 | 0.345 | BB | BB | BB | BB | BB | BB | AB | AB | BB | AB |
| 7 | SNP_A-1755481 | rs2572009 | 99133656 | 99.133656 | 0.524 | AA | AA | BB | AB | AB | AB | AA | AA | AA | AA |
| 7 | SNP_A-1669180 | rs10487284 | 102064226 | 102.064226 | 0.667 | AA | AA | AA | AA | AA | AA | AA | AA | AA | AB |
| 7 | SNP_A-1730488 | rs10487162 | 102860400 | 102.8604 | 0.256 | AB | AB | AB | AB | AB | AB | BB | BB | BB | AB |
| 7 | SNP_A-1715320 | rs2519681 | 105578447 | 105.578447 | 0.369 | AB | AB | AA | AB | AB | AB | AB | AB | AA | AB |
| 7 | SNP_A-1657867 | rs997381 | 106280867 | 106.280867 | 0.524 | AB | AB | BB | BB | BB | BB | AA | AA | BB | BB |
| 7 | SNP_A-1703262 | rs3801948 | 106832398 | 106.832398 | 0.643 | AA | AA | BB | AB | AB | AB | AA | AA | BB | AB |
| 7 | SNP_A-1687475 | rs1015422 | 107930809 | 107.930809 | 0.298 | BB | AB | AA | AA | AA | AA | BB | BB | BB | AB |
| 7 | SNP_A-1643849 | rs2106442 | 108493824 | 108.493824 | 0.476 | AA | AA | BB | BB | BB | BB | AB | AB | AA | AA |
| 7 | SNP_A-1688527 | rs10487320 | 109537858 | 109.537858 | 0.619 | BB | AB | BB | BB | BB | BB | AA | AA | AA | AA |
| 7 | SNP_A-1641802 | rs10500003 | 110076704 | 110.076704 | 0.702 | AA | AB | AA | AA | AA | AA | AA | AA | AA | |
| 7 | SNP_A-1740412 | rs10487331 | 110945463 | 110.945463 | 0.726 | AA | AA | AA | AB | AA | AA | AA | BB | AB | AB |
| 7 | SNP_A-1745955 | rs2529588 | 111697006 | 111.697006 | 0.726 | AA | AA | AA | AA | AA | AA | AA | AB | AA | AB |
| 7 | SNP_A-1724315 | rs1548395 | 112947523 | 112.947523 | 0.298 | BB | BB | BB | BB | BB | BB | BB | AB | AA | AB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 7 | SNP_A-1719538 | rs6973150 | 114297804 | 114.297804 | 0.45 | BB | BB | AB | AB | AB | AB | BB | BB | BB | BB |
| 7 | SNP_A-1736164 | rs10500054 | 115247129 | 115.247129 | 0.5 | BB | BB | BB | BB | BB | BB | AA | AB | BB | BB |
| 7 | SNP_A-1733815 | rs7783832 | 116468422 | 116.468422 | 0.298 | BB | BB | AB | AB | AB | AB | AB | AB | BB | AB |
| 7 | SNP_A-1676935 | rs10487392 | 117466579 | 117.466579 | 0.488 | BB | BB | AB | AB | AB | AB | AA | AA | AA | AB |
| 7 | SNP_A-1647647 | rs10488301 | 119761267 | 119.761267 | 0.262 | AA | AB | BB | BB | BB | BB | AA | AB | BB | BB |
| 7 | SNP_A-1655036 | rs1206486 | 121146345 | 121.146345 | 0.441 | BB | BB | BB | BB | BB | BB | AA | AB | BB | BB |
| 7 | SNP_A-1643783 | rs10487974 | 122442567 | 122.442567 | 0.381 | AA | AB | AB | AB | AB | AB | BB | BB | BB | BB |
| 7 | SNP_A-1690238 | rs6948425 | 123386447 | 123.386447 | 0.476 | AA | AA | AB | AB | AB | AB | AA | AB | BB | AB |
| 7 | SNP_A-1745008 | rs723444 | 124253175 | 124.253175 | 0.417 | BB | BB | AB | AB | AB | AB | BB | BB | BB | BB |
| 7 | SNP_A-1675675 | rs2107098 | 124969695 | 124.969695 | 0.488 | BB | AB | AA | AA | AA | AA | BB | AB | BB | AB |
| 7 | SNP_A-1678693 | rs2299447 | 125743520 | 125.74352 | 0.738 | AA | AA | AA | AA | AA | AA | AA | AA | AA | AA |
| 7 | SNP_A-1670675 | rs6467115 | 126530478 | 126.530478 | 0.643 | AA | AA | AA | AA | AA | AA | AA | AA | BB | BB |
| 7 | SNP_A-1708033 | rs10487505 | 127454114 | 127.454114 | 0.464 | BB | BB | AB | AB | AB | AB | BB | BB | BB | AB |
| 7 | SNP_A-1656498 | rs10488628 | 127961843 | 127.961843 | 0.405 | AA | AB | AB | AB | AB | AB | AA | AA | AA | AB |
| 7 | SNP_A-1742598 | rs7803075 | 130199321 | 130.199321 | 0.726 | AA | AA | BB | BB | BB | BB | BB | AB | AA | AA |
| 7 | SNP_A-1695048 | rs1790998 | 133595635 | 133.595635 | 0.476 | AA | AA | AB | AB | AB | AB | BB | BB | BB | BB |
| 7 | SNP_A-1721434 | rs2551778 | 134556904 | 134.556904 | 0.548 | AA | AA | AA | AA | AA | AA | AA | AA | AA | AA |
| 7 | SNP_A-1669022 | rs10253975 | 135674764 | 135.674764 | 0.662 | BB | AB | AA | AA | AA | AA | AA | AA | AA | AA |
| 7 | SNP_A-1715624 | rs2253729 | 139396073 | 139.396073 | 0.583 | AA | AB | BB | BB | BB | BB | AA | AA | BB | BB |
| 7 | SNP_A-1652925 | rs1527304 | 141162389 | 141.162389 | 0.571 | AA | AA | BB | BB | BB | BB | AA | AA | AA | AB |
| 7 | SNP_A-1715016 | rs6949653 | 143162918 | 143.162918 | 0.691 | AA | AB | AB | AB | AB | AB | AA | AA | AA | AA |
| 7 | SNP_A-1666637 | rs4725680 | 144870787 | 144.870787 | 0.369 | AA | AB | BB | BB | BB | BB | AA | AA | AA | AA |
| 7 | SNP_A-1681703 | rs10487936 | 145527849 | 145.527849 | 0.732 | AA | AA | AA | AA | AA | AA | AA | AA | BB | AB |
| 7 | SNP_A-1680321 | rs10278315 | 146403556 | 146.403556 | 0.726 | AA | AA | AA | AA | AA | AA | AA | AA | AA | AA |
| 7 | SNP_A-1720798 | rs1177946 | 147495250 | 147.49525 | 0.643 | AA | AA | AA | AA | AA | AA | AA | AA | BB | BB |
| 7 | SNP_A-1713513 | rs1403222 | 149691561 | 149.691561 | 0.536 | AB | AB | AA | AA | AA | AA | BB | BB | AA | AB |
| 7 | SNP_A-1736364 | rs306293 | 154243700 | 154.2437 | 0.643 | AA | AA | BB | BB | BB | BB | AA | AA | AB | AB |
| 7 | SNP_A-1691199 | rs2301916 | 156473603 | 156.473603 | 0.369 | AB | AB | AB | AB | BB | BB | AB | AB | AB | AB |
| 8 | SNP_A-1659972 | rs747351 | 228574 | 0.228574 | 0.369 | AB | AB | AB | AB | AA | AB | AB | AB | AA | AB |
| 8 | SNP_A-1725579 | rs4876153 | 2291741 | 2.291741 | 0.691 | BB | BB | AA | AA | AA | AA | AA | AA | AA | AB |
| 8 | SNP_A-1651465 | rs9314492 | 3332437 | 3.332437 | 0.476 | AA | AA | BB | BB | BB | BB | BB | BB | BB | AB |
| 8 | SNP_A-1695486 | rs10503246 | 4117771 | 4.117771 | 0.714 | AB | AB | AA | AA | AA | AA | BB | BB | BB | AB |
| 8 | SNP_A-1650643 | rs4146469 | 5253259 | 5.253259 | 0.441 | AB | AB | AB | AB | AB | AB | BB | AB | BB | BB |
| 8 | SNP_A-1714359 | rs6559072 | 5839489 | 5.839489 | 0.679 | AB | AB | AA | AA | AA | AA | BB | BB | AA | AA |
| 8 | SNP_A-1660050 | rs3020252 | 6450411 | 6.450411 | 0.634 | AB | AB | BB | BB | BB | BB | AA | AA | BB | AB |
| 8 | SNP_A-1757262 | rs2409113 | 8849712 | 8.849712 | 0.72 | AB | AB | AA | AA | AA | AA | AA | AA | AA | AA |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 8 | SNP_A-1680667 | rs1588198 | 9929939 | 9.929939 | 0.655 | AB | AB | AB | AB | AB | AB | AA | AB | AA | AA |
| 8 | SNP_A-1679891 | rs2278335 | 10740863 | 10.740863 | 0.702 | AB | AB | AA | AA | AA | AA | AA | AA | AA | AB |
| 8 | SNP_A-1715348 | rs10503478 | 13876453 | 13.876453 | 0.607 | AA | AA | AB | AB | AB | AA | AB | AB | BB | BB |
| 8 | SNP_A-1659353 | rs2410193 | 14445035 | 14.445035 | 0.738 | AA | AA | AA | AA | AA | AA | BB | RB | AA | AB |
| 8 | SNP_A-1756484 | rs351572 | 16065839 | 16.065839 | 0.595 | AA | AA | AA | AA | AA | AA | AA | AA | BB | AB |
| 8 | SNP_A-1750990 | rs7003503 | 17226143 | 17.226143 | 0.25 | BB | BB | AB | AA | AB | AB | BB | BB | BB | AB |
| 8 | SNP_A-1688509 | rs7006702 | 19316813 | 19.316813 | 0.333 | AA | AB | AB | BB | AB | AB | BB | BB | BB | AB |
| 8 | SNP_A-1747706 | rs2083637 | 19909455 | 19.909455 | 0.738 | AA | AB | AB | BB | AB | AB | AB | AB | AA | AA |
| 8 | SNP_A-1646595 | rs2306518 | 22526253 | 22.526253 | 0.357 | BB | AB | BB | BB | BB | BB | BB | BB | AA | AA |
| 8 | SNP_A-1699334 | rs10503733 | 23589963 | 23.589963 | 0.714 | AA | AB | AA | AA | AA | AA | AB | AB | AA | AA |
| 8 | SNP_A-1752532 | rs2976457 | 24923988 | 24.923988 | 0.548 | BB | AB | AA | AA | AA | AA | AB | AB | BB | BB |
| 8 | SNP_A-1746191 | rs10503776 | 25765786 | 25.765786 | 0.671 | BB | BB | AA | AA | AA | AA | AB | AB | AA | AA |
| 8 | SNP_A-1742962 | rs10503872 | 30556573 | 30.556573 | 0.476 | AA | AB | BB | AA | AA | AB | AA | AA | BB | BB |
| 8 | SNP_A-1710298 | rs10503907 | 32291552 | 32.291552 | 0.607 | AA | AA | AA | BB | BB | AB | AB | AB | AA | AB |
| 8 | SNP_A-1646333 | rs1551652 | 34443033 | 34.443033 | 0.662 | AA | AA | BB | AA | AA | AB | BB | BB | AA | AA |
| 8 | SNP_A-1679337 | rs10503970 | 34985910 | 34.98591 | 0.262 | BB | BB | BB | AA | AA | AB | AB | AB | BB | BB |
| 8 | SNP_A-1701068 | rs581187 | 37119893 | 37.119893 | 0.286 | BB | BB | AA | AA | AA | AA | BB | BB | BB | AB |
| 8 | SNP_A-1747018 | rs3935233 | 39307991 | 39.307991 | 0.31 | AA | AB | BB | BB | BB | BB | BB | BB | BB | BB |
| 8 | SNP_A-1730295 | rs9298596 | 40431722 | 40.431722 | 0.333 | AA | AA | BB | AA | AA | AB | BB | BB | BB | BB |
| 8 | SNP_A-1664173 | rs341817 | 50186153 | 50.186153 | 0.56 | AA | AA | AA | BB | BB | AB | AA | AB | BB | AB |
| 8 | SNP_A-1712754 | rs318913 | 51075845 | 51.075845 | 0.262 | BB | BB | BB | BB | BB | BB | BB | BB | BB | BB |
| 8 | SNP_A-1716236 | rs10504120 | 52554998 | 52.554998 | 0.726 | AA | AA | AA | AA | AA | AA | AA | AA | AA | AA |
| 8 | SNP_A-1645251 | rs2249236 | 53110767 | 53.110767 | 0.286 | AA | AB | AA | BB | AB | AB | AA | AB | BB | BB |
| 8 | SNP_A-1674928 | rs360956 | 54063839 | 54.063839 | 0.61 | BB | BB | BB | AA | AB | AB | AA | AA | BB | BB |
| 8 | SNP_A-1661925 | rs7824078 | 55966296 | 55.966296 | 0.631 | AA | AA | BB | AA | AB | AB | AA | AA | AA | AB |
| 8 | SNP_A-1734483 | rs2670052 | 57666163 | 57.666163 | 0.583 | AA | AB | AA | BB | AB | AB | AA | AA | AA | AA |
| 8 | SNP_A-1649879 | rs9297980 | 58641477 | 58.641477 | 0.476 | AA | AA | AB | BB | AB | AB | AA | AB | AB | AB |
| 8 | SNP_A-1689109 | rs7012230 | 62449232 | 62.449232 | 0.31 | BB | BB | BB | BB | BB | BB | BB | BB | AB | AB |
| 8 | SNP_A-1729837 | rs874777 | 65147501 | 65.147501 | 0.583 | BB | BB | BB | BB | BB | BB | AA | AA | AA | AA |
| 8 | SNP_A-1688563 | rs977467 | 67469418 | 67.469418 | 0.56 | BB | AB | AA | AA | AA | AA | AA | AA | AA | AB |
| 8 | SNP_A-1656454 | rs900896 | 68690751 | 68.690751 | 0.702 | AA | AA | AB | AA | AB | AB | AA | AA | AA | AA |
| 8 | SNP_A-1673083 | rs1404605 | 69369253 | 69.369253 | 0.585 | BB | AB | AA | AA | AA | AA | BB | BB | AA | AA |
| 8 | SNP_A-1673921 | rs10504451 | 70626182 | 70.626182 | 0.524 | AA | AB | BB | BB | BB | BB | AA | AA | AB | AB |
| 8 | SNP_A-1660240 | rs10504477 | 71500739 | 71.500739 | 0.487 | BB | AB | AB | AB | BB | BB | AB | AB | AB | AB |
| 8 | SNP_A-1698932 | rs2732090 | 72080811 | 72.080811 | 0.5 | AA | AB | AA | AA | AA | AA | AA | AB | AB | AB |
| 8 | SNP_A-1710462 | rs10504526 | 73129106 | 73.129106 | 0.548 | AA | AA | AA | AA | AA | AA | BB | AB | AA | AA |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 8 | SNP_A-1684163 | rs10504552 | 75038119 | 75.038119 | 0.286 | BB | BB | AA | AA | AA | AA | AA | AA | AA | AA |
| 8 | SNP_A-1673775 | rs1375646 | 76679672 | 76.679672 | 0.321 | BB | BB | BB | BB | BB | BB | BB | BB | AB | AB |
| 8 | SNP_A-1753574 | rs1993196 | 78213269 | 78.213269 | 0.583 | BB | BB | AA | AA | AA | AA | AB | AB | AA | AA |
| 8 | SNP_A-1713893 | rs2461063 | 80781668 | 80.781668 | 0.631 | AA | AA | AB | BB | AB | AB | AB | AB | AB | AB |
| 8 | SNP_A-1650035 | rs1199030 | 81917969 | 81.917969 | 0.357 | BB | BB | AA | AA | AA | AA | BB | BB | BB | BB |
| 8 | SNP_A-1709456 | rs1525339 | 83916405 | 83.916405 | 0.738 | AA | AA | AA | AA | AA | AA | BB | BB | AA | AA |
| 8 | SNP_A-1747972 | rs1465809 | 85243012 | 85.243012 | 0.25 | BB | BB | BB | BB | BB | BB | BB | BB | BB | AB |
| 8 | SNP_A-1690861 | rs3808538 | 86308563 | 86.308563 | 0.738 | AA | AA | AB | BB | BB | BB | AA | AA | AB | AB |
| 8 | SNP_A-1642120 | rs10504819 | 87183400 | 87.1834 | 0.369 | BB | BB | AA | AA | AA | AA | AA | AA | BB | BB |
| 8 | SNP_A-1704458 | rs997597 | 88259667 | 88.259667 | 0.274 | BB | BB | BB | BB | BB | BB | BB | BB | BB | BB |
| 8 | SNP_A-1731702 | rs10504855 | 88844371 | 88.844371 | 0.345 | BB | BB | BB | BB | BB | BB | AB | AB | AB | AB |
| 8 | SNP_A-1669078 | rs160410 | 90717844 | 90.717844 | 0.658 | AA | AA | BB | BB | BB | BB | AA | AA | AA | AA |
| 8 | SNP_A-1713264 | rs1818193 | 91886818 | 91.886818 | 0.631 | AA | AA | AA | AA | AA | AA | AA | AA | AB | AB |
| 8 | SNP_A-1679699 | rs2245797 | 95329376 | 95.329376 | 0.31 | BB | BB | BB | BB | BB | BB | AB | AB | AB | AB |
| 8 | SNP_A-1738642 | rs962451 | 101400186 | 101.400186 | 0.583 | AA | AA | AA | AA | AA | AA | AA | AA | BB | BB |
| 8 | SNP_A-1677965 | rs4495397 | 103476369 | 103.476369 | 0.268 | BB | BB | AA | AA | AA | AA | BB | BB | BB | BB |
| 8 | SNP_A-1718730 | rs543736 | 104082125 | 104.082125 | 0.619 | AB | AB | BB | BB | BB | BB | AA | AB | AA | AA |
| 8 | SNP_A-1724051 | rs10505064 | 105831730 | 105.83173 | 0.345 | AB | AB | BB | BB | BB | BB | BB | AB | BB | BB |
| 8 | SNP_A-1691919 | rs2930485 | 107881851 | 107.881851 | 0.607 | AB | AB | AB | BB | AB | AA | AB | BB | BB | BB |
| 8 | SNP_A-1652191 | rs10505107 | 108392560 | 108.39256 | 0.619 | AA | AA | AB | AA | AB | AB | AA | AA | AA | AA |
| 8 | SNP_A-1756952 | rs1353298 | 108959098 | 108.959098 | 0.321 | BB | BB | BB | BB | BB | BB | BB | BB | AB | AB |
| 8 | SNP_A-1695466 | rs5772 | 110167808 | 110.167808 | 0.571 | AB | AB | AB | AB | AB | AA | AB | AA | AB | AB |
| 8 | SNP_A-1747370 | rs10505135 | 111120579 | 111.120579 | 0.345 | AA | AA | BB | BB | BB | BB | AA | AB | AB | AB |
| 8 | SNP_A-1745327 | rs10505156 | 112369457 | 112.369457 | 0.25 | AB | AB | BB | BB | BB | BB | BB | BB | BB | BB |
| 8 | SNP_A-1681911 | rs10505180 | 113392265 | 113.392265 | 0.726 | AB | AB | AA | AA | AA | AA | AA | AA | AA | AA |
| 8 | SNP_A-1694542 | rs2125552 | 113984509 | 113.984509 | 0.274 | BB | BB | AB | AB | AB | AB | BB | AB | BB | BB |
| 8 | SNP_A-1713409 | rs9297496 | 114629527 | 114.629527 | 0.321 | BB | BB | BB | BB | BB | BB | BB | BB | AB | AB |
| 8 | SNP_A-1725803 | rs7828185 | 116438576 | 116.438576 | 0.286 | BB | BB | BB | BB | BB | BB | BB | BB | BB | BB |
| 8 | SNP_A-1698988 | rs10505328 | 119219639 | 119.219639 | 0.441 | AB | AB | BB | BB | BB | BB | BB | BB | BB | BB |
| 8 | SNP_A-1753414 | rs3924784 | 121618858 | 121.618858 | 0.667 | AA | AA | AA | AA | AA | AA | BB | BB | AB | AB |
| 8 | SNP_A-1735413 | rs17478 | 122793072 | 122.793072 | 0.595 | AA | AA | AB | AA | AB | AB | BB | AB | AB | AB |
| 8 | SNP_A-1655430 | rs6470143 | 124219594 | 124.219594 | 0.345 | BB | BB | BB | BB | BB | BB | BB | AA | AA | AA |
| 8 | SNP_A-1754805 | rs3909562 | 124803864 | 124.803864 | 0.405 | AA | AB | AA | AA | AA | AA | BB | BB | AB | AB |
| 8 | SNP_A-1696789 | rs2382993 | 125770106 | 125.770106 | 0.345 | BB | AB | BB | BB | BB | BB | BB | BB | BB | BB |
| 8 | SNP_A-1686811 | rs897153 | 126747483 | 126.747483 | 0.643 | BB | AB | AB | BB | AB | AB | AA | AB | AB | AB |
| 8 | SNP_A-1753008 | rs2091933 | 127485749 | 127.485749 | 0.679 | AA | AB | BB | BB | BB | BB | AA | AA | AB | AB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 8 | SNP_A-1651085 | rs10505486 | 128074016 | 128.074016 | 0.441 | BB | BB | BB | BB | BB | BB | BB | AB | AB | AB |
| 8 | SNP_A-1682761 | rs4123791 | 129288419 | 129.288419 | 0.417 | BB | BB | AA | AA | AA | AA | AA | AA | AA | AA |
| 8 | SNP_A-1692841 | rs9297775 | 129805894 | 129.805894 | 0.333 | BB | AB | BB | BB | BB | BB | BB | BB | BB | BB |
| 8 | SNP_A-1653731 | rs10505545 | 130646449 | 130.646449 | 0.538 | AA | AA | AB | AB | AB | AB | BB | BB | BB | BB |
| 8 | SNP_A-1655374 | rs7460225 | 131408555 | 131.408555 | 0.464 | AA | AB | AB | AB | AB | AA | AB | AB | AB | AA |
| 8 | SNP_A-1672735 | rs7008202 | 132143592 | 132.143592 | 0.357 | BB | AB | AA | AA | AA | AA | BB | BB | AB | AB |
| 8 | SNP_A-1725115 | rs4736424 | 133782292 | 133.782292 | 0.31 | BB | BB | BB | BB | BB | BB | AA | AB | BB | BB |
| 8 | SNP_A-1647079 | rs10505607 | 134527931 | 134.527931 | 0.441 | AA | AB | BB | BB | BB | BB | BB | BB | AB | AB |
| 8 | SNP_A-1700220 | rs4909801 | 135948341 | 135.948341 | 0.702 | AA | AB | BB | BB | BB | BB | AA | AB | AA | AA |
| 8 | SNP_A-1675316 | rs4909582 | 137288153 | 137.288153 | 0.488 | AA | AA | BB | AB | AB | AB | BB | BB | AA | AA |
| 8 | SNP_A-1661056 | rs9324439 | 138086052 | 138.086052 | 0.452 | BB | AB | BB | BB | BB | BB | BB | BB | AB | AB |
| 8 | SNP_A-1689603 | rs1325053 | 139156386 | 139.156386 | 0.732 | AA | AA | AA | AB | AB | AB | BB | BB | AA | AA |
| 8 | SNP_A-1710354 | rs2468705 | 140618265 | 140.618265 | 0.75 | AB | AB | BB | AB | AB | AB | AA | AA | AA | AA |
| 9 | SNP_A-1643050 | rs10491691 | 336963 | 0.336963 | 0.655 | AB | AB | AA | AA | AA | AA | AB | AB | BB | BB |
| 9 | SNP_A-1704718 | rs2370220 | 907667 | 0.907667 | 0.726 | AA | AA | AB | AB | AB | AB | AA | AA | AA | AA |
| 9 | SNP_A-1681445 | rs7040916 | 2645520 | 2.64552 | 0.726 | BB | BB | AA | AA | AA | AA | AA | AA | AA | AA |
| 9 | SNP_A-1734535 | rs1358908 | 3162093 | 3.162093 | 0.524 | AA | AA | BB | BB | BB | BB | BB | BB | AA | AA |
| 9 | SNP_A-1685961 | rs1455177 | 3782613 | 3.782613 | 0.488 | BB | BB | BB | BB | BB | BB | AB | AB | AB | AB |
| 9 | SNP_A-1642494 | rs10491650 | 5193054 | 5.193054 | 0.354 | BB | BB | BB | BB | BB | BB | BB | BB | BB | BB |
| 9 | SNP_A-1696419 | rs1407473 | 7989681 | 7.989681 | 0.31 | BB | BB | BB | BB | BB | BB | BB | BB | BB | BB |
| 9 | SNP_A-1709516 | rs1433548 | 8927116 | 8.927116 | 0.31 | AB | AB | AB | AB | AB | AB | BB | BB | BB | BB |
| 9 | SNP_A-1682679 | rs1613507 | 9791755 | 9.791755 | 0.563 | AB | AB | AA | AA | AA | AA | BB | BB | AA | AA |
| 9 | SNP_A-1673445 | rs10511545 | 10341048 | 10.341048 | 0.726 | AA | AA | AA | AA | AA | AA | AA | AA | AA | AA |
| 9 | SNP_A-1679185 | rs4740473 | 11080005 | 11.080005 | 0.369 | AB | AB | AA | AA | AA | AA | BB | BB | BB | BB |
| 9 | SNP_A-1744452 | rs1825739 | 11777410 | 11.77741 | 0.429 | BB | BB | BB | BB | BB | BB | AB | AB | AA | AB |
| 9 | SNP_A-1714556 | rs1086377 | 12824688 | 12.824688 | 0.702 | AA | AA | BB | BB | BB | BB | AB | AB | AA | AA |
| 9 | SNP_A-1672461 | rs7038474 | 13355816 | 13.355816 | 0.702 | AB | AB | AA | AA | AA | AA | BB | BB | BB | AB |
| 9 | SNP_A-1704214 | rs10511587 | 13970584 | 13.970584 | 0.738 | AB | AB | AB | AB | AB | AB | AA | AA | AA | AA |
| 9 | SNP_A-1714243 | rs4615688 | 14495861 | 14.495861 | 0.714 | AA | AA | AA | AA | AA | AA | AA | AA | AA | AA |
| 9 | SNP_A-1741448 | rs10511603 | 15006475 | 15.006475 | 0.536 | BB | BB | BB | BB | BB | BB | BB | BB | AA | AA |
| 9 | SNP_A-1742240 | rs1001265 | 17618726 | 17.618726 | 0.726 | BB | BB | AA | AA | AA | AA | AA | AA | AA | AA |
| 9 | SNP_A-1675206 | rs7862683 | 18257947 | 18.257947 | 0.427 | BB | BB | AB | AB | AB | AB | AB | AB | BB | BB |
| 9 | SNP_A-1706426 | rs7859334 | 20660966 | 20.660966 | 0.56 | AA | AA | BB | BB | AB | AB | AB | AB | AB | AB |
| 9 | SNP_A-1669996 | rs871024 | 21793880 | 21.79388 | 0.441 | AA | AA | AA | AA | AA | AA | AA | AA | BB | AB |
| 9 | SNP_A-1662201 | rs10511705 | 22537789 | 22.537789 | 0.512 | BB | BB | BB | BB | AB | AB | AB | AB | BB | AB |
| 9 | SNP_A-1673761 | rs9298846 | 23216243 | 23.216243 | 0.655 | AB | AB | AA | AA | AA | AA | AA | AA | AA | AB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 9 | SNP_A-1752066 | rs10511761 | 25602704 | 25.602704 | 0.441 | BB | BB | BB | BB | BB | BB | AA | AA | AA | AA |
| 9 | SNP_A-1690106 | rs4978049 | 26131011 | 26.131011 | 0.381 | AB | AB | BB | BB | BB | BB | BB | BB | BB | BB |
| 9 | SNP_A-1700687 | rs983863 | 26681668 | 26.681668 | 0.345 | BB | BB | BB | AB | AB | AA | AA | AA | AA | AA |
| 9 | SNP_A-1690672 | rs1452357 | 28090846 | 28.090846 | 0.707 | BB | BB | BB | BB | AB | AB | AA | AA | AA | AA |
| 9 | SNP_A-1693514 | rs824257 | 28765262 | 28.765262 | 0.655 | AA | AA | AA | AA | AA | AA | AA | AA | BB | BB |
| 9 | SNP_A-1665553 | rs10511842 | 30009704 | 30.009704 | 0.25 | AA | AB | BB | BB | AB | AB | BB | BB | AA | AB |
| 9 | SNP_A-1724125 | rs10511886 | 31826555 | 31.826555 | 0.607 | BB | AB | BB | AB | AB | AB | AB | AB | BB | BB |
| 9 | SNP_A-1648177 | rs20583 | 33016572 | 33.016572 | 0.452 | AA | AB | BB | BB | BB | BB | AA | AA | AA | AB |
| 9 | SNP_A-1717742 | rs6476493 | 35884737 | 35.884737 | 0.691 | AA | AA | AA | AA | AA | AA | AA | AA | AA | AA |
| 9 | SNP_A-1671263 | rs4880042 | 36940301 | 36.940301 | 0.393 | AA | AA | BB | BB | BB | BB | BB | BB | BB | BB |
| 9 | SNP_A-1681599 | rs2181139 | 38364977 | 38.364977 | 0.25 | BB | AB | AA | AA | AA | AA | AB | AB | BB | AB |
| 9 | SNP_A-1666811 | rs4111409 | 40345280 | 40.34528 | 0.262 | BB | BB | BB | BB | BB | BB | BB | BB | BB | BB |
| 9 | SNP_A-1727790 | rs7864775 | 69030853 | 69.030853 | 0.548 | BB | BB | BB | BB | BB | BB | BB | BB | AA | AB |
| 9 | SNP_A-1699350 | rs10511972 | 69672094 | 69.672094 | 0.619 | BB | BB | AA | AA | AA | AB | BB | AB | BB | BB |
| 9 | SNP_A-1753754 | rs10511984 | 70399849 | 70.399849 | 0.75 | AA | AA | AA | AA | AA | AA | AB | AA | AA | AA |
| 9 | SNP_A-1748876 | rs10511999 | 71526051 | 71.526051 | 0.595 | AA | AA | AA | AA | AA | AA | AA | AA | BB | AB |
| 9 | SNP_A-1750024 | rs1998372 | 72123726 | 72.123726 | 0.369 | BB | BB | BB | BB | BB | AB | BB | BB | BB | BB |
| 9 | SNP_A-1733975 | rs2377524 | 76002013 | 76.002013 | 0.321 | BB | BB | BB | BB | BB | BB | BB | BB | BB | AB |
| 9 | SNP_A-1707951 | rs10512079 | 78602073 | 78.602073 | 0.25 | AA | AA | AA | AA | AB | AB | AA | AB | BB | BB |
| 9 | SNP_A-1655498 | rs1316823 | 79531349 | 79.531349 | 0.643 | AB | AB | AA | AA | AA | AA | AA | AA | AA | AA |
| 9 | SNP_A-1721234 | rs1572147 | 80160841 | 80.160841 | 0.634 | AA | AA | AB | AA | AB | AB | AA | AA | BB | AB |
| 9 | SNP_A-1757764 | rs7873639 | 80780459 | 80.780459 | 0.286 | BB | BB | BB | BB | BB | BB | AA | AA | AA | AB |
| 9 | SNP_A-1685995 | rs2774635 | 82184146 | 82.184146 | 0.286 | BB | BB | BB | BB | BB | BB | BB | BB | AA | AB |
| 9 | SNP_A-1698246 | rs1436932 | 83903397 | 83.903397 | 0.476 | AB | AB | AA | AA | AA | AA | AA | AA | AA | AB |
| 9 | SNP_A-1743644 | rs7030902 | 85064645 | 85.064645 | 0.548 | AA | AA | AB | BB | AB | AB | BB | BB | AA | AB |
| 9 | SNP_A-1642838 | rs1475524 | 87362117 | 87.362117 | 0.357 | BB | BB | AB | AA | AB | AA | AB | AA | AA | AA |
| 9 | SNP_A-1683979 | rs4744114 | 91732136 | 91.732136 | 0.452 | BB | BB | AB | AA | AA | AB | BB | BB | AA | AA |
| 9 | SNP_A-1645449 | rs1547201 | 95896039 | 95.896039 | 0.548 | AA | AA | BB | BB | BB | BB | AB | AB | AB | AB |
| 9 | SNP_A-1751508 | rs1924001 | 102134812 | 102.134812 | 0.643 | BB | BB | AA | AA | AA | AA | AB | AA | AA | AA |
| 9 | SNP_A-1724479 | rs1463983 | 105506339 | 105.506339 | 0.429 | BB | BB | AB | AB | AB | AB | AB | AB | AB | AB |
| 9 | SNP_A-1653563 | rs2418076 | 110092906 | 110.092906 | 0.298 | BB | BB | AA | AA | AA | AA | BB | BB | BB | BB |
| 9 | SNP_A-1744924 | rs1813202 | 111767658 | 111.767658 | 0.286 | AB | AB | BB | BB | BB | BB | BB | BB | BB | BB |
| 9 | SNP_A-1731818 | rs10513222 | 113757379 | 113.757379 | 0.321 | BB | BB | AB | BB | AB | AB | AA | AA | BB | BB |
| 9 | SNP_A-1733479 | rs10513267 | 115067920 | 115.06792 | 0.75 | AA | AB | AA | AA | AA | AA | AA | AA | AA | AA |
| 9 | SNP_A-1643236 | rs4112759 | 117313823 | 117.313823 | 0.75 | AA | AA | AA | AA | AA | AA | AA | AA | AA | AA |
| 9 | SNP_A-1750306 | rs7849366 | 118191918 | 118.191918 | 0.286 | AA | AA | AB | BB | AB | AB | AB | AB | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 9 | SNP_A-1686447 | rs10514837 | 118919482 | 118.919482 | 0.321 | BB | BB | BB | BB | BB | BB | BB | BB | BB | BB |
| 9 | SNP_A-1656426 | rs10491529 | 120012279 | 120.012279 | 0.25 | BB | AB | AB | AB | AB | AB | BB | BB | BB | BB |
| 9 | SNP_A-1677789 | rs306796 | 121206889 | 121.206889 | 0.631 | AA | AA | AA | AA | AA | AA | AA | AA | AB | AB |
| 9 | SNP_A-1705544 | rs7043602 | 126285054 | 126.285054 | 0.738 | AA | AA | AA | AA | AA | AA | AB | AB | AA | AA |
| 9 | SNP_A-1653355 | rs883335 | 129165519 | 129.165519 | 0.595 | BB | BB | AB | AB | AB | AA | AB | AB | AA | AB |
| 9 | SNP_A-1699424 | rs2269337 | 130602238 | 130.602238 | 0.742 | BB | AB | AA | AA | AA | AA | AA | AA | AA | AA |
| 9 | SNP_A-1747024 | rs2809243 | 132799854 | 132.799854 | 0.298 | BB | BB | AA | AA | AA | AA | AA | AA | AA | AA |
| 10 | SNP_A-1659685 | rs1392827 | 1234414 | 1.234414 | 0.667 | AA | AA | AB | AB | AB | AB | AB | AB | AA | AA |
| 10 | SNP_A-1753764 | rs4880915 | 1747289 | 1.747289 | 0.293 | BB | BB | BB | BB | BB | BB | BB | BB | BB | BB |
| 10 | SNP_A-1727231 | rs9329289 | 2532389 | 2.532389 | 0.405 | AA | AA | AB | AB | AB | AB | AB | AB | AB | AB |
| 10 | SNP_A-1732637 | rs2388557 | 3181527 | 3.181527 | 0.321 | BB | BB | BB | BB | BB | AB | AB | BB | BB | BB |
| 10 | SNP_A-1679829 | rs1679440 | 4468715 | 4.468715 | 0.286 | BB | BB | BB | BB | BB | BB | BB | BB | BB | BB |
| 10 | SNP_A-1713889 | rs946785 | 7041660 | 7.04166 | 0.595 | AA | AA | AB | AB | AB | AB | BB | BB | AB | AB |
| 10 | SNP_A-1717612 | rs4385796 | 8539643 | 8.539643 | 0.286 | BB | BB | BB | BB | BB | BB | BB | BB | AA | AB |
| 10 | SNP_A-1740604 | rs1762757 | 9449776 | 9.449776 | 0.726 | AA | AA | AA | AA | AA | AA | BB | BB | AA | AA |
| 10 | SNP_A-1686911 | rs10508380 | 10003736 | 10.003736 | 0.738 | AA | AA | AB | AB | AA | AB | BB | BB | AA | AA |
| 10 | SNP_A-1739848 | rs1041044 | 10644387 | 10.644387 | 0.5 | BB | BB | AB | AB | BB | AB | AB | AB | BB | BB |
| 10 | SNP_A-1721418 | rs4750093 | 11829643 | 11.829643 | 0.429 | BB | BB | BB | BB | BB | BB | BB | BB | BB | BB |
| 10 | SNP_A-1739768 | rs1108131 | 12537753 | 12.537753 | 0.75 | AB | AB | AB | AB | AA | AB | BB | BB | AA | AA |
| 10 | SNP_A-1737160 | rs564166 | 13110955 | 13.110955 | 0.738 | AB | AB | AA | AA | AA | AA | AA | AA | AA | AA |
| 10 | SNP_A-1678303 | rs10508465 | 13725194 | 13.725194 | 0.429 | AA | AA | AB | AB | BB | AB | AB | AB | AA | AA |
| 10 | SNP_A-1669628 | rs10508473 | 14241057 | 14.241057 | 0.417 | BB | BB | BB | BB | BB | BB | AB | AB | AA | AA |
| 10 | SNP_A-1714770 | rs1361588 | 16119457 | 16.119457 | 0.298 | BB | BB | BB | BB | BB | BB | BB | BB | BB | AB |
| 10 | SNP_A-1700268 | rs10490962 | 17240369 | 17.240369 | 0.56 | AB | AB | BB | BB | BB | BB | AB | AB | BB | BB |
| 10 | SNP_A-1744374 | rs10508555 | 18316688 | 18.316688 | 0.441 | AB | AB | AB | AB | BB | AB | BB | BB | BB | BB |
| 10 | SNP_A-1748644 | rs984292 | 19028813 | 19.028813 | 0.393 | BB | BB | AB | AB | AA | AB | BB | BB | AA | AB |
| 10 | SNP_A-1686549 | rs2358348 | 19533421 | 19.533421 | 0.643 | AA | AA | BB | BB | BB | BB | AA | AA | AA | AA |
| 10 | SNP_A-1678189 | rs788977 | 21229153 | 21.229153 | 0.262 | BB | BB | AB | AB | BB | AB | BB | BB | BB | BB |
| 10 | SNP_A-1672001 | rs1417374 | 23168481 | 23.168481 | 0.298 | BB | BB | AA | AA | AA | AA | AA | AA | AA | AB |
| 10 | SNP_A-1726471 | rs2150651 | 24829491 | 24.829491 | 0.321 | BB | BB | BB | BB | BB | BB | BB | BB | BB | BB |
| 10 | SNP_A-1751938 | rs10508686 | 25367068 | 25.367068 | 0.714 | AA | AA | AB | AB | AA | AB | AA | AA | AA | AA |
| 10 | SNP_A-1713661 | rs4747530 | 25876455 | 25.876455 | 0.56 | AB | AB | BB | BB | BB | BB | AA | AA | AA | AA |
| 10 | SNP_A-1706402 | rs10508717 | 26712334 | 26.712334 | 0.524 | AA | AA | AB | AB | AA | AB | BB | BB | BB | BB |
| 10 | SNP_A-1713649 | rs1970631 | 28271741 | 28.271741 | 0.452 | AA | AA | BB | BB | BB | BB | AA | AA | AA | AB |
| 10 | SNP_A-1707064 | rs703041 | 29265782 | 29.265782 | 0.25 | BB | BB | AB | AB | BB | AB | BB | BB | BB | AB |
| 10 | SNP_A-1755663 | rs2776644 | 30294654 | 30.294654 | 0.488 | AB | AB | AB | AB | BB | AB | BB | AB | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 10 | SNP_A-1679427 | rs2490527 | 32711123 | 32.711123 | 0.631 | BB | AB | AB | BB | BB | AB | AA | AB | AA | AA |
| 10 | SNP_A-1678169 | rs2269101 | 33546185 | 33.546185 | 0.286 | AA | AB | AB | AA | AA | AB | BB | AB | BB | AB |
| 10 | SNP_A-1674978 | rs224750 | 34271036 | 34.271036 | 0.619 | AA | AA | AA | AA | AA | AA | BB | AB | AA | AA |
| 10 | SNP_A-1722205 | rs1032408 | 43808849 | 43.808849 | 0.738 | AA | AA | BB | BB | BB | BB | AA | AA | AA | AA |
| 10 | SNP_A-1700828 | rs1583421 | 45099157 | 45.099157 | 0.583 | BB | AB | AA | AA | AA | AA | AA | AA | AA | AA |
| 10 | SNP_A-1718604 | rs10508908 | 49643864 | 49.643864 | 0.5 | BB | BB | AA | BB | BB | AB | AA | AB | AB | AB |
| 10 | SNP_A-1741518 | rs10508929 | 51841987 | 51.841987 | 0.423 | AA | AB | AA | BB | BB | BB | BB | BB | AA | AA |
| 10 | SNP_A-1674358 | rs2339628 | 52548976 | 52.548976 | 0.679 | AA | AB | BB | BB | BB | BB | BB | BB | AB | AB |
| 10 | SNP_A-1665161 | rs1937666 | 53326630 | 53.32663 | 0.464 | AB | AB | AA | BB | BB | AB | AA | AB | BB | BB |
| 10 | SNP_A-1648887 | rs10508976 | 54302305 | 54.302305 | 0.56 | BB | BB | BB | AA | AB | AB | AB | AB | BB | BB |
| 10 | SNP_A-1660432 | rs422296 | 54965065 | 54.965065 | 0.714 | AA | AA | BB | AA | AB | AB | AA | AA | AB | AB |
| 10 | SNP_A-1642640 | rs6481257 | 58608558 | 58.608558 | 0.274 | BB | BB | BB | BB | BB | BB | BB | BB | BB | BB |
| 10 | SNP_A-1697033 | rs10509093 | 60193775 | 60.193775 | 0.452 | AA | AA | BB | BB | BB | AA | AA | AA | AA | AA |
| 10 | SNP_A-1723683 | rs4245585 | 61596196 | 61.596196 | 0.286 | BB | BB | BB | AA | AB | AB | BB | BB | BB | BB |
| 10 | SNP_A-1653973 | rs10509139 | 62150158 | 62.150158 | 0.691 | AB | AB | AA | AA | AA | AA | AA | AA | AA | AA |
| 10 | SNP_A-1713014 | rs2787720 | 63018471 | 63.018471 | 0.488 | BB | BB | BB | BB | BB | BB | BB | BB | BB | BB |
| 10 | SNP_A-1667099 | rs1255484 | 65108003 | 65.108003 | 0.488 | BB | BB | BB | BB | BB | BB | AB | AB | AA | AA |
| 10 | SNP_A-1658163 | rs7073489 | 67452445 | 67.452445 | 0.274 | AB | AB | BB | BB | BB | BB | BB | BB | BB | BB |
| 10 | SNP_A-1642112 | rs4746654 | 68476694 | 68.476694 | 0.441 | AB | AB | BB | BB | BB | BB | BB | BB | AB | AB |
| 10 | SNP_A-1720304 | rs7918860 | 70340702 | 70.340702 | 0.583 | BB | BB | AA | BB | AB | AB | AA | AA | AB | AB |
| 10 | SNP_A-1729287 | rs10509321 | 71655739 | 71.655739 | 0.298 | AB | AB | AA | AA | AA | AA | BB | BB | AB | AB |
| 10 | SNP_A-1707688 | rs10509334 | 73110058 | 73.110058 | 0.427 | BB | BB | BB | BB | BB | BB | AB | AB | AA | AA |
| 10 | SNP_A-1654508 | rs1865636 | 77473753 | 77.473753 | 0.5 | AA | AA | BB | AA | AB | AB | BB | BB | BB | BB |
| 10 | SNP_A-1697249 | rs10509384 | 78693188 | 78.693188 | 0.726 | AB | AB | AA | AA | AA | AA | AB | AB | AB | AB |
| 10 | SNP_A-1679101 | rs1344967 | 79197624 | 79.197624 | 0.262 | AA | AA | BB | BB | BB | BB | BB | BB | AB | AB |
| 10 | SNP_A-1748530 | rs10509397 | 79905374 | 79.905374 | 0.476 | BB | BB | AA | AB | AB | AB | AB | AB | AA | AA |
| 10 | SNP_A-1736610 | rs7914988 | 80540330 | 80.54033 | 0.441 | AB | AB | AA | BB | AB | AB | AA | AA | AB | AB |
| 10 | SNP_A-1665139 | rs342372 | 84579316 | 84.579316 | 0.536 | AB | AB | BB | AA | AB | AB | AA | AA | AB | AB |
| 10 | SNP_A-1715818 | rs2067731 | 86973180 | 86.97318 | 0.381 | BB | BB | AB | AA | AB | AB | BB | BB | AA | AA |
| 10 | SNP_A-1689101 | rs2949392 | 87497414 | 87.497414 | 0.5 | AA | AA | AA | AA | AA | AA | BB | BB | AB | AB |
| 10 | SNP_A-1657815 | rs391683 | 90510663 | 90.510663 | 0.679 | BB | BB | AB | AA | AB | AB | AB | AB | AA | AA |
| 10 | SNP_A-1706118 | rs303212 | 91151335 | 91.151335 | 0.298 | AB | AB | BB | BB | BB | BB | BB | BB | BB | BB |
| 10 | SNP_A-1703070 | rs747334 | 92734724 | 92.734724 | 0.476 | AA | AA | AA | AB | AB | AB | AB | AB | AA | AA |
| 10 | SNP_A-1717632 | rs716361 | 93308518 | 93.308518 | 0.321 | AB | AB | BB | BB | BB | BB | BB | BB | AB | AB |
| 10 | SNP_A-1713435 | rs2490739 | 94587885 | 94.587885 | 0.631 | AA | AA | AA | AA | AA | AA | AA | AA | AA | AA |
| 10 | SNP_A-1642080 | rs3781270 | 95520148 | 95.520148 | 0.607 | AA | AA | AA | AA | AA | AA | BB | BB | AB | AB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 10 | SNP_A-1680183 | rs10509692 | 97226588 | 97.226588 | 0.583 | AB | AB | AB | AB | AB | AB | AA | AA | AB | AB |
| 10 | SNP_A-1705694 | rs10509700 | 97884521 | 97.884521 | 0.5 | AA | AA | AB | AB | AB | AB | AA | AA | BB | BB |
| 10 | SNP_A-1753314 | rs793515 | 98978459 | 98.978459 | 0.345 | BB | BB | BB | BB | BB | BB | BB | BB | BB | BB |
| 10 | SNP_A-1742188 | rs10509754 | 103711687 | 103.711687 | 0.262 | AB | AB | BB | BB | BB | BB | BB | BB | AB | AB |
| 10 | SNP_A-1716744 | rs2451500 | 106622867 | 106.622867 | 0.707 | AA | AA | AA | AA | AA | AA | AB | AB | BB | BB |
| 10 | SNP_A-1684935 | rs10509832 | 109070424 | 109.070424 | 0.667 | AA | AA | BB | BB | BB | BB | BB | BB | AB | AB |
| 10 | SNP_A-1676403 | rs4113 | 111223756 | 111.223756 | 0.369 | AA | AA | AB | AB | AB | BB | BB | BB | BB | BB |
| 10 | SNP_A-1726183 | rs7099088 | 114343455 | 114.343455 | 0.631 | AB | AB | AB | AB | AB | AB | AB | AB | AA | AA |
| 10 | SNP_A-1732939 | rs10509976 | 115170888 | 115.170888 | 0.286 | BB | BB | BB | BB | BB | BB | BB | BB | AB | AB |
| 10 | SNP_A-1675599 | rs2420070 | 116671318 | 116.671318 | 0.548 | AB | AB | BB | BB | BB | BB | BB | BB | BB | BB |
| 10 | SNP_A-1700278 | rs4447088 | 117536799 | 117.536799 | 0.274 | BB | BB | BB | BB | BB | BB | AB | AB | AB | AB |
| 10 | SNP_A-1660760 | rs880977 | 118409221 | 118.409221 | 0.452 | AB | AB | AA | AA | AA | AA | AB | AB | AB | AB |
| 10 | SNP_A-1747698 | rs2619111 | 118956986 | 118.956986 | 0.702 | AA | AA | AB | AB | AB | AA | AA | AA | AA | AA |
| 10 | SNP_A-1682085 | rs10490913 | 120144426 | 120.144426 | 0.537 | AB | AB | BB | BB | BB | BB | AB | AB | AB | AB |
| 10 | SNP_A-1731688 | rs1980030 | 120960017 | 120.960017 | 0.393 | AB | AB | BB | BB | BB | BB | AB | AB | BB | BB |
| 10 | SNP_A-1641760 | rs1326654 | 122305416 | 122.305416 | 0.405 | AB | AB | BB | BB | BB | BB | BB | BB | BB | BB |
| 10 | SNP_A-1741090 | rs2420995 | 123842994 | 123.842994 | 0.393 | BB | BB | BB | BB | BB | BB | AB | AB | AB | AB |
| 10 | SNP_A-1751948 | rs845101 | 125180422 | 125.180422 | 0.631 | AB | AB | AA | AA | AA | AA | AA | AA | AA | AA |
| 10 | SNP_A-1711689 | rs1278305 | 127801415 | 127.801415 | 0.524 | BB | BB | BB | BB | BB | BB | AB | AB | BB | BB |
| 10 | SNP_A-1715610 | rs10510154 | 128412532 | 128.412532 | 0.738 | AA | AA | AA | AA | AA | AA | AA | AA | AA | AA |
| 10 | SNP_A-1706112 | rs2251104 | 130003906 | 130.003906 | 0.333 | AA | AA | BB | BB | BB | BB | AB | AB | AB | AB |
| 10 | SNP_A-1712012 | rs1886380 | 130596834 | 130.596834 | 0.702 | AA | AA | AA | BB | AA | AA | AA | AA | AB | AB |
| 10 | SNP_A-1652639 | rs4077516 | 133237947 | 133.237947 | 0.369 | AA | AB | BB | BB | BB | BB | BB | BB | AB | AB |
| 11 | SNP_A-1727870 | rs2499935 | 5066470 | 5.06647 | 0.417 | BB | BB | AA | AB | BB | AB | BB | BB | BB | BB |
| 11 | SNP_A-1656094 | rs2001778 | 5575584 | 5.575584 | 0.452 | BB | BB | BB | BB | BB | BB | BB | BB | AB | AB |
| 11 | SNP_A-1680969 | rs10500667 | 6284499 | 6.284499 | 0.274 | BB | BB | AA | BB | AB | BB | BB | BB | BB | BB |
| 11 | SNP_A-1656388 | rs2595456 | 6841339 | 6.841339 | 0.524 | BB | BB | BB | BB | BB | BB | BB | AB | AB | AB |
| 11 | SNP_A-1649885 | rs3884596 | 7488751 | 7.488751 | 0.571 | AB | AB | BB | BB | BB | BB | AA | AA | AB | AB |
| 11 | SNP_A-1663461 | rs3993279 | 10627568 | 10.627568 | 0.321 | BB | BB | AB | AB | AA | AB | BB | BB | BB | BB |
| 11 | SNP_A-1723239 | rs10500740 | 11167698 | 11.167698 | 0.274 | AB | AB | BB | BB | BB | BB | AB | AB | AB | AB |
| 11 | SNP_A-1712474 | rs1344613 | 12408280 | 12.40828 | 0.31 | AB | AB | BB | BB | BB | BB | AB | AB | BB | BB |
| 11 | SNP_A-1705810 | rs1894131 | 15104916 | 15.104916 | 0.441 | AA | AB | AA | AA | AA | AA | AB | AB | BB | BB |
| 11 | SNP_A-1674594 | rs2190454 | 17490211 | 17.490211 | 0.333 | AA | AB | BB | BB | BB | BB | BB | BB | AB | AB |
| 11 | SNP_A-1701156 | rs211102 | 18003069 | 18.003069 | 0.25 | BB | BB | AB | AA | AB | BB | BB | BB | AB | AB |
| 11 | SNP_A-1685951 | rs894556 | 19822510 | 19.82251 | 0.56 | BB | BB | AB | AB | AB | AB | AA | AA | AB | AB |
| 11 | SNP_A-1685201 | rs10500886 | 20976742 | 20.976742 | 0.607 | BB | AB | AA | AA | AA | AA | AA | AA | AA | AA |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 11 | SNP_A-1668135 | rs6483807 | 21873219 | 21.873219 | 0.5 | BB | BB | AA | AB | AB | AB | BB | BB | AA | AA |
| 11 | SNP_A-1713403 | rs10500927 | 22398998 | 22.398998 | 0.262 | BB | AB | BB | BB | BB | BB | AB | AB | AB | AB |
| 11 | SNP_A-1697826 | rs1600958 | 23180524 | 23.180524 | 0.388 | BB | BB | BB | AB | AB | AB | AA | AA | AA | AA |
| 11 | SNP_A-1753516 | rs975980 | 24515539 | 24.515539 | 0.441 | AA | AB | BB | BB | BB | BB | AA | AA | AB | AB |
| 11 | SNP_A-1652525 | rs10501011 | 25497059 | 25.497059 | 0.417 | AA | AB | BB | BB | BB | BB | AA | AA | AB | AB |
| 11 | SNP_A-1665219 | rs980562 | 30413393 | 30.413393 | 0.726 | AA | AB | AA | AB | AB | AB | AB | AB | AA | AA |
| 11 | SNP_A-1720570 | rs1848394 | 30965654 | 30.965654 | 0.619 | BB | BB | BB | AB | AB | AB | BB | BB | BB | BB |
| 11 | SNP_A-1749112 | rs10488689 | 31659092 | 31.659092 | 0.286 | BB | BB | AA | AA | AA | AA | BB | BB | AB | AB |
| 11 | SNP_A-1701102 | rs1033717 | 33023147 | 33.023147 | 0.342 | BB | BB | BB | BB | BB | BB | BB | BB | BB | BB |
| 11 | SNP_A-1752850 | rs2136509 | 34753380 | 34.75338 | 0.537 | BB | BB | BB | AB | AB | AB | AA | AA | AB | AB |
| 11 | SNP_A-1691121 | rs10501163 | 36830990 | 36.83099 | 0.286 | AA | AA | AA | AA | AA | AA | AA | AA | BB | BB |
| 11 | SNP_A-1725595 | rs992118 | 40016469 | 40.016469 | 0.286 | BB | AB | AA | AB | AB | AA | AB | AA | BB | BB |
| 11 | SNP_A-1667717 | rs7102885 | 40922404 | 40.922404 | 0.655 | AA | AA | AA | AB | AB | AB | BB | AB | BB | AB |
| 11 | SNP_A-1717738 | rs1531932 | 41781058 | 41.781058 | 0.643 | AA | AA | BB | AB | AA | AB | AA | AA | AA | AA |
| 11 | SNP_A-1709380 | rs692726 | 50396846 | 50.396846 | 0.321 | AA | AA | BB | BB | BB | BB | BB | AB | BB | BB |
| 11 | SNP_A-1752494 | rs629948 | 55113024 | 55.113024 | 0.643 | AA | AA | AA | BB | BB | AB | AA | AA | AA | AA |
| 11 | SNP_A-1697650 | rs1080800 | 56067666 | 56.067666 | 0.381 | AA | AB | BB | AA | AA | AB | BB | AB | BB | BB |
| 11 | SNP_A-1658985 | rs540505 | 56621831 | 56.621831 | 0.536 | AA | AB | BB | BB | BB | BB | BB | AB | BB | AB |
| 11 | SNP_A-1749414 | rs612688 | 57333672 | 57.333672 | 0.25 | BB | BB | BB | BB | BB | BB | AA | AA | BB | BB |
| 11 | SNP_A-1698180 | rs10501369 | 57870148 | 57.870148 | 0.512 | AA | AA | AA | AA | AA | AA | BB | BB | AA | AA |
| 11 | SNP_A-1729269 | rs1941030 | 59982334 | 59.982334 | 0.56 | BB | BB | AA | BB | BB | AB | AB | AB | AA | AA |
| 11 | SNP_A-1656934 | rs528736 | 65461684 | 65.461684 | 0.393 | BB | AB | AB | BB | BB | AB | AA | AA | BB | BB |
| 11 | SNP_A-1738462 | rs624765 | 69826722 | 69.826722 | 0.714 | AA | AB | AA | AA | AA | AA | AA | AA | AA | AA |
| 11 | SNP_A-1645461 | rs527529 | 74298448 | 74.298448 | 0.573 | AA | AA | BB | BB | BB | BB | AB | AB | AA | AA |
| 11 | SNP_A-1711405 | rs1793483 | 76653115 | 76.653115 | 0.583 | AA | AA | AA | AA | AA | AA | AA | AA | AA | AB |
| 11 | SNP_A-1739334 | rs3819256 | 77379509 | 77.379509 | 0.571 | BB | BB | AB | BB | AB | AB | BB | BB | AA | AB |
| 11 | SNP_A-1712184 | rs7128417 | 77883622 | 77.883622 | 0.25 | BB | BB | BB | BB | BB | BB | BB | BB | BB | BB |
| 11 | SNP_A-1734963 | rs483089 | 78543310 | 78.54331 | 0.655 | AA | AA | AB | BB | AB | AB | AA | AA | AA | AB |
| 11 | SNP_A-1695384 | rs1569168 | 79525377 | 79.525377 | 0.441 | AB | AB | AB | AA | AB | AB | AA | AA | BB | AB |
| 11 | SNP_A-1695760 | rs10501496 | 80598450 | 80.59845 | 0.298 | AB | AB | AA | AA | AA | AA | AA | AA | AB | AB |
| 11 | SNP_A-1679629 | rs666649 | 81460553 | 81.460553 | 0.56 | AB | AB | AB | BB | AB | AB | AB | AB | BB | AB |
| 11 | SNP_A-1674894 | rs2000922 | 82720260 | 82.72026 | 0.619 | AA | AA | AA | AA | AA | AA | AA | AB | AA | AA |
| 11 | SNP_A-1645839 | rs7924334 | 83853909 | 83.853909 | 0.714 | AA | AA | AA | AA | AA | AA | AA | AA | AA | AA |
| 11 | SNP_A-1654894 | rs10501586 | 84433725 | 84.433725 | 0.726 | AA | AA | AA | AA | AA | AA | AA | AA | AA | AB |
| 11 | SNP_A-1756404 | rs10501612 | 85594787 | 85.594787 | 0.342 | BB | BB | BB | BB | BB | BB | AB | AB | BB | BB |
| 11 | SNP_A-1722491 | rs503952 | 86520236 | 86.520236 | 0.268 | AB | AB | BB | BB | BB | BB | BB | BB | AA | AB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 11 | SNP_A-1740548 | rs10501723 | 89922680 | 89.92268 | 0.5 | AB | AB | AB | AA | AB | AB | AA | AA | AA | AB |
| 11 | SNP_A-1741388 | rs1528760 | 90459676 | 90.459676 | 0.738 | AA | AA | AA | AA | AA | AA | AA | AA | AA | AB |
| 11 | SNP_A-1755135 | rs10501759 | 91082163 | 91.082163 | 0.537 | BB | BB | BB | BB | BB | BB | AA | AA | AA | AA |
| 11 | SNP_A-1656446 | rs554735 | 91994827 | 91.994827 | 0.524 | AB | AB | AA | AA | AA | AA | BB | BB | AA | AB |
| 11 | SNP_A-1720756 | rs2605592 | 92842667 | 92.842667 | 0.702 | AA | AA | AA | AA | AA | AA | AB | AB | BB | AB |
| 11 | SNP_A-1672903 | rs609493 | 93708735 | 93.708735 | 0.286 | BB | BB | BB | BB | BB | BB | AA | AB | BB | AB |
| 11 | SNP_A-1659851 | rs12627 | 94442268 | 94.442268 | 0.607 | AA | AA | AB | AB | AB | AB | BB | BB | AA | AB |
| 11 | SNP_A-1649021 | rs1940201 | 95387950 | 95.38795 | 0.31 | AB | AB | AB | AA | AB | AB | BB | BB | AB | AB |
| 11 | SNP_A-1706350 | rs10501859 | 95973889 | 95.973889 | 0.298 | AB | AB | BB | BB | BB | BB | AB | AB | AB | AB |
| 11 | SNP_A-1670058 | rs1939713 | 99567868 | 99.567868 | 0.631 | AA | AA | AB | AA | AB | AB | BB | AB | AA | AA |
| 11 | SNP_A-1712712 | rs667504 | 100221671 | 100.221671 | 0.738 | AA | AA | AA | AA | AA | AA | AA | AA | AB | AB |
| 11 | SNP_A-1729283 | rs313403 | 102697742 | 102.697742 | 0.524 | AA | AA | BB | BB | BB | BB | AA | AB | AA | AA |
| 11 | SNP_A-1643334 | rs260818 | 103425315 | 103.425315 | 0.417 | BB | BB | BB | BB | BB | BB | BB | BB | AB | AB |
| 11 | SNP_A-1690312 | rs10502051 | 104808805 | 104.808805 | 0.286 | BB | BB | BB | BB | BB | BB | BB | AB | BB | BB |
| 11 | SNP_A-1746850 | rs10502080 | 106341710 | 106.34171 | 0.346 | BB | BB | BB | BB | BB | BB | BB | BB | BB | BB |
| 11 | SNP_A-1718590 | rs2640757 | 107936868 | 107.936868 | 0.31 | AA | AA | BB | BB | BB | BB | BB | BB | BB | BB |
| 11 | SNP_A-1739572 | rs2298501 | 109571744 | 109.571744 | 0.56 | AA | AA | BB | BB | BB | BB | BB | BB | BB | BB |
| 11 | SNP_A-1742110 | rs170486 | 110202174 | 110.202174 | 0.452 | AB | AB | AA | AA | AA | AA | AA | AA | AA | AA |
| 11 | SNP_A-1720008 | rs10502152 | 111296905 | 111.296905 | 0.321 | BB | BB | BB | BB | BB | BB | AA | AB | BB | BB |
| 11 | SNP_A-1658493 | rs7118530 | 113395335 | 113.395335 | 0.357 | AA | AB | BB | BB | BB | BB | AA | AA | AA | AA |
| 11 | SNP_A-1689389 | rs2247060 | 114257194 | 114.257194 | 0.536 | BB | AB | BB | BB | BB | BB | BB | AB | BB | BB |
| 11 | SNP_A-1652091 | rs572619 | 115738853 | 115.738853 | 0.619 | AA | AA | BB | BB | BB | BB | AA | AB | AA | AA |
| 11 | SNP_A-1737192 | rs660443 | 116265903 | 116.265903 | 0.362 | AA | AA | AB | AB | AB | AB | AA | AA | AA | AA |
| 11 | SNP_A-1643985 | rs1219410 | 121294459 | 121.294459 | 0.691 | BB | AB | AA | AA | AA | AA | AA | AA | BB | BB |
| 11 | SNP_A-1728568 | rs872414 | 122170647 | 122.170647 | 0.452 | AA | AA | AA | AB | AB | AB | BB | AB | BB | BB |
| 11 | SNP_A-1696469 | rs2078158 | 122950070 | 122.95007 | 0.333 | BB | BB | AA | AB | AB | AB | BB | BB | BB | BB |
| 11 | SNP_A-1748196 | rs1940751 | 127447038 | 127.447038 | 0.683 | AA | AA | AA | AA | AA | AA | AA | AA | BB | BB |
| 11 | SNP_A-1741458 | rs1368850 | 130433518 | 130.433518 | 0.598 | AA | AB | AB | AB | AB | AB | BB | BB | AA | AA |
| 11 | SNP_A-1732434 | rs748807 | 131232636 | 131.232636 | 0.452 | AA | AB | BB | BB | BB | BB | BB | BB | AB | AB |
| 12 | SNP_A-1644365 | rs7973282 | 1095178 | 1.095178 | 0.738 | AA | AA | AA | AA | AA | AA | AA | AA | AB | AA |
| 12 | SNP_A-1716332 | rs215994 | 2587421 | 2.587421 | 0.274 | BB | BB | BB | BB | BB | BB | AA | AB | BB | BB |
| 12 | SNP_A-1708039 | rs4625554 | 4286565 | 4.286565 | 0.298 | AB | BB | BB | BB | BB | BB | BB | BB | BB | BB |
| 12 | SNP_A-1727428 | rs1861584 | 5578079 | 5.578079 | 0.702 | AA | AA | AB | AB | AB | AB | AA | AB | AB | AB |
| 12 | SNP_A-1708085 | rs4883241 | 9384549 | 9.384549 | 0.369 | AA | AA | AA | AA | AA | AA | AA | AA | AB | AB |
| 12 | SNP_A-1709352 | rs560444 | 9940542 | 9.940542 | 0.321 | BB | AB | BB | BB | BB | BB | BB | BB | BB | BB |
| 12 | SNP_A-1667917 | rs1009954 | 11789366 | 11.789366 | 0.333 | BB | BB | AB | AB | AB | AB | BB | BB | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 12 | SNP_A-1749536 | rs10505774 | 13327672 | 13.327672 | 0.714 | AA | AB | AA | AA | AA | AA | BB | BB | AA | AA |
| 12 | SNP_A-1696855 | rs10492150 | 14935164 | 14.935164 | 0.333 | BB | BB | BB | BB | BB | BB | BB | BB | BB | BB |
| 12 | SNP_A-1680095 | rs4366546 | 18267461 | 18.267461 | 0.75 | AA | AA | AA | AA | AA | AA | AA | AA | AA | AA |
| 12 | SNP_A-1714486 | rs10505845 | 19976927 | 19.976927 | 0.714 | AA | AA | AA | AA | AA | AA | BB | BB | BB | AB |
| 12 | SNP_A-1729086 | rs4131935 | 20632200 | 20.6322 | 0.738 | BB | BB | AA | AA | AA | AA | AB | AB | BB | AB |
| 12 | SNP_A-1673313 | rs2417981 | 21483114 | 21.483114 | 0.5 | BB | BB | AB | BB | AB | AB | AA | AA | AA | AA |
| 12 | SNP_A-1645425 | rs3884510 | 24249990 | 24.24999 | 0.512 | AA | AA | AB | BB | AB | AB | AB | AB | AA | AA |
| 12 | SNP_A-1672243 | rs10505945 | 24803300 | 24.8033 | 0.381 | BB | AB | BB | BB | BB | BB | BB | BB | BB | BB |
| 12 | SNP_A-1692085 | rs10505972 | 25379461 | 25.379461 | 0.393 | BB | AB | AB | AA | AB | AB | AB | AB | BB | AB |
| 12 | SNP_A-1674778 | rs9300175 | 27617467 | 27.617467 | 0.417 | BB | BB | BB | BB | BB | BB | BB | BB | AA | AB |
| 12 | SNP_A-1649795 | rs148898 | 29606383 | 29.606383 | 0.691 | AA | AA | AA | AA | AA | AA | AB | AA | AB | |
| 12 | SNP_A-1658781 | rs10506065 | 30342307 | 30.342307 | 0.417 | BB | AB | BB | BB | BB | BB | BB | BB | BB | BB |
| 12 | SNP_A-1722521 | rs7979386 | 30966129 | 30.966129 | 0.464 | AA | AB | AA | BB | BB | AB | AA | AB | AA | AA |
| 12 | SNP_A-1705996 | rs2593998 | 32333520 | 32.33352 | 0.714 | AA | AA | AA | AA | AA | AA | AA | AB | AA | AB |
| 12 | SNP_A-1644085 | rs1905428 | 33450742 | 33.450742 | 0.512 | AA | AA | AA | AA | AA | AA | BB | AB | BB | AB |
| 12 | SNP_A-1711331 | rs2389276 | 33989158 | 33.989158 | 0.595 | AA | AB | BB | AA | AA | AB | BB | AB | BB | AB |
| 12 | SNP_A-1692149 | rs10506124 | 37305503 | 37.305503 | 0.571 | BB | AB | AA | BB | BB | AB | AA | AB | AA | AA |
| 12 | SNP_A-1720482 | rs7969928 | 39561348 | 39.561348 | 0.393 | AA | AA | BB | BB | BB | BB | BB | BB | BB | AB |
| 12 | SNP_A-1659791 | rs7309345 | 40585255 | 40.585255 | 0.75 | BB | BB | AA | AA | AA | AA | AA | AA | AA | AA |
| 12 | SNP_A-1754513 | rs1369610 | 41755818 | 41.755818 | 0.369 | AA | AB | AA | BB | AB | AB | BB | AB | AA | AB |
| 12 | SNP_A-1693494 | rs1506678 | 43535759 | 43.535759 | 0.631 | AA | AB | AA | AA | AA | AA | AA | AA | AA | AA |
| 12 | SNP_A-1702318 | rs7310869 | 44951653 | 44.951653 | 0.536 | AA | AB | BB | BB | BB | BB | AA | AA | BB | BB |
| 12 | SNP_A-1748898 | rs10506292 | 49031020 | 49.03102 | 0.381 | BB | BB | BB | BB | BB | BB | BB | BB | BB | BB |
| 12 | SNP_A-1733843 | rs7968810 | 52445260 | 52.44526 | 0.738 | AA | AA | AA | AA | AA | AA | AA | AA | AA | AA |
| 12 | SNP_A-1712318 | rs10506393 | 56672989 | 56.672989 | 0.691 | AA | AB | BB | AA | AA | AB | BB | BB | BB | AB |
| 12 | SNP_A-1657234 | rs3913094 | 57197682 | 57.197682 | 0.655 | AA | AA | AA | BB | BB | AB | AA | AA | AA | AB |
| 12 | SNP_A-1662747 | rs10506408 | 58834234 | 58.834234 | 0.512 | AA | AB | AA | AA | AA | AA | BB | AB | AA | AB |
| 12 | SNP_A-1688045 | rs7308021 | 61145687 | 61.145687 | 0.571 | BB | AB | AA | BB | BB | AB | AA | AB | BB | BB |
| 12 | SNP_A-1749010 | rs513203 | 62226007 | 62.226007 | 0.56 | BB | BB | BB | AA | AA | AB | AB | AB | AB | AB |
| 12 | SNP_A-1730271 | rs1596727 | 63609374 | 63.609374 | 0.583 | AA | AA | AA | AA | AA | AA | BB | BB | BB | AA |
| 12 | SNP_A-1716970 | rs8756 | 64646019 | 64.646019 | 0.595 | AA | AA | BB | BB | BB | BB | BB | BB | AB | AB |
| 12 | SNP_A-1721334 | rs10506514 | 65583191 | 65.583191 | 0.298 | AB | AA | BB | BB | BB | BB | BB | AA | AA | AA |
| 12 | SNP_A-1646303 | rs7313431 | 66378203 | 66.378203 | 0.631 | AA | AA | AA | AA | AA | AA | AA | AA | AA | AA |
| 12 | SNP_A-1695666 | rs710779 | 68249633 | 68.249633 | 0.476 | AB | BB | AB | AB | AB | AB | BB | AB | BB | BB |
| 12 | SNP_A-1700862 | rs2567134 | 69233806 | 69.233806 | 0.31 | BB | BB | BB | BB | BB | BB | AB | AB | BB | BB |
| 12 | SNP_A-1757570 | rs7960254 | 70109323 | 70.109323 | 0.405 | AB | AB | BB | AA | AA | AB | BB | BB | BB | BB |

TABLE 18-continued

Database S2.
Database S2 Heterozygosity or phESC (Abbreviated as "pC") Lines

| chromosome | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 12 | SNP_A-1676631 | rs10506645 | 70671767 | 70.671767 | 0.31 | BB | BB | BB | AA | AA | AB | AB | AB | BB | BB |
| 12 | SNP_A-1743470 | rs7964705 | 72103027 | 72.103027 | 0.31 | AA | AA | BB | AA | AA | AB | AB | AB | BB | BB |
| 12 | SNP_A-1660536 | rs1396226 | 73586112 | 73.586112 | 0.429 | BB | BB | AA | BB | BB | AB | AB | AB | AB | AB |
| 12 | SNP_A-1662713 | rs1275643 | 74439702 | 74.439702 | 0.393 | AB | AB | BB | AA | AA | AB | AB | AB | AA | AA |
| 12 | SNP_A-1667227 | rs310877 | 75889008 | 75.889008 | 0.274 | BB | BB | BB | BB | BB | BB | BB | BB | AB | AB |
| 12 | SNP_A-1732426 | rs7315131 | 76389953 | 76.389953 | 0.381 | AB | AB | AA | AA | AA | AA | AA | AB | AA | AA |
| 12 | SNP_A-1667491 | rs1796135 | 77491016 | 77.491016 | 0.524 | BB | BB | BB | AA | AA | AB | AA | AA | AB | AB |
| 12 | SNP_A-1643877 | rs1244908 | 79104469 | 79.104469 | 0.631 | AA | AA | BB | BB | BB | BB | AA | AB | AB | AB |
| 12 | SNP_A-1737202 | rs10506839 | 79948071 | 79.948071 | 0.31 | AA | AA | BB | BB | BB | BB | AA | AA | AB | AB |
| 12 | SNP_A-1700433 | rs10506846 | 80609736 | 80.609736 | 0.655 | AA | AA | AA | BB | BB | AB | AA | AB | AB | AB |
| 12 | SNP_A-1738317 | rs892540 | 81919943 | 81.919943 | 0.667 | AB | AB | BB | AA | AA | AB | AA | AA | AA | AA |
| 12 | SNP_A-1688895 | rs7960510 | 82715458 | 82.715458 | 0.274 | AB | AB | BB | BB | BB | BB | BB | BB | AB | AB |
| 12 | SNP_A-1675076 | rs839159 | 85096176 | 85.096176 | 0.726 | AB | AB | BB | BB | BB | BB | AA | AA | AB | AB |
| 12 | SNP_A-1663055 | rs2635067 | 85762474 | 85.762474 | 0.571 | AB | AB | AB | AA | AA | AB | AA | AA | BB | BB |
| 12 | SNP_A-1727255 | rs1019206 | 87893500 | 87.8935 | 0.333 | BB | BB | BB | BB | BB | BB | BB | BB | BB | BB |
| 12 | SNP_A-1657981 | rs2731240 | 89061896 | 89.061896 | 0.31 | BB | BB | BB | BB | BB | BB | AA | AB | AA | AA |
| 12 | SNP_A-1696519 | rs924328 | 91753976 | 91.753976 | 0.31 | BB | BB | BB | BB | BB | BB | AA | AA | BB | BB |
| 12 | SNP_A-1747554 | rs4761590 | 93076279 | 93.076279 | 0.655 | BB | BB | AA | AA | AA | AA | BB | AB | AB | AB |
| 12 | SNP_A-1701918 | rs759572 | 95985503 | 95.985503 | 0.524 | BB | BB | AB | AA | AB | AB | AB | AB | BB | BB |
| 12 | SNP_A-1734475 | rs1394380 | 97055132 | 97.055132 | 0.75 | AA | AA | AA | AA | AA | AA | AB | AB | AA | AA |
| 12 | SNP_A-1690482 | rs10492276 | 97699500 | 97.6995 | 0.691 | AA | AA | AB | BB | AB | AB | AA | AA | AB | AB |
| 12 | SNP_A-1704900 | rs1718312 | 101743655 | 101.743655 | 0.393 | BB | BB | BB | BB | BB | BB | BB | BB | BB | BB |
| 12 | SNP_A-1698694 | rs10507166 | 102367680 | 102.36768 | 0.369 | BB | BB | BB | BB | BB | BB | BB | BB | BB | BB |
| 12 | SNP_A-1731482 | rs7954946 | 103966503 | 103.966503 | 0.333 | AA | AA | AA | AA | AA | AA | AA | AA | AA | AA |
| 12 | SNP_A-1689283 | rs10507197 | 104564170 | 104.56417 | 0.583 | AA | AA | AA | AA | AA | AA | BB | BB | AB | AB |
| 12 | SNP_A-1723539 | rs1444581 | 105816718 | 105.816718 | 0.488 | BB | BB | AA | AA | AA | AA | AA | AA | BB | BB |
| 12 | SNP_A-1676727 | rs715447 | 107449185 | 107.449185 | 0.464 | BB | BB | AB | AB | AB | AB | BB | BB | AB | AB |
| 12 | SNP_A-1742456 | rs10507234 | 108519202 | 108.519202 | 0.714 | AB | AB | AA | AA | AA | AA | AA | AA | AA | AA |
| 12 | SNP_A-1655216 | rs4767550 | 116413870 | 116.41387 | 0.595 | AA | AA | AA | AB | AB | AA | AA | AA | AB | AB |
| 12 | SNP_A-1673501 | rs1726392 | 117061645 | 117.061645 | 0.321 | BB | AB | BB | BB | BB | BB | BB | BB | BB | BB |
| 12 | SNP_A-1748666 | rs3858710 | 118701913 | 118.701913 | 0.573 | AA | AB | AA | AA | AA | AA | AA | AA | AB | AB |
| 12 | SNP_A-1708029 | rs1558062 | 124778387 | 124.778387 | 0.524 | AA | AA | AA | AA | AA | AA | AA | AA | AA | AA |
| 12 | SNP_A-1716508 | rs345676 | 126581103 | 126.581103 | 0.643 | AA | AB | BB | BB | BB | BB | BB | AB | AA | AA |
| 12 | SNP_A-1664795 | rs1983314 | 129393207 | 129.393207 | 0.333 | BB | AB | BB | BB | BB | AB | AB | BB | BB | BB |
| 13 | SNP_A-1652867 | rs7985257 | 18787997 | 18.787997 | 0.524 | BB | BB | AA | AA | AA | AA | BB | AB | AA | AA |
| 13 | SNP_A-1686943 | rs535233 | 20445317 | 20.445317 | 0.321 | AB | AB | BB | BB | BB | BB | BB | BB | AA | AB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 13 | SNP_A-1745741 | rs2862901 | 23933239 | 23.933239 | 0.571 | AB | AB | AA | AA | AA | AA | BB | AB | AA | AA |
| 13 | SNP_A-1642868 | rs10507349 | 25679528 | 25.679528 | 0.274 | BB | BB | AA | AA | AA | AB | BB | BB | AB | AB |
| 13 | SNP_A-1702806 | rs1161470 | 28322644 | 28.322644 | 0.31 | BB | BB | BB | BB | BB | BB | BB | BB | BB | BB |
| 13 | SNP_A-1664657 | rs213611 | 30348913 | 30.348913 | 0.705 | AA | AA | AA | AA | AA | AA | AB | AB | AB | AB |
| 13 | SNP_A-1658585 | rs206079 | 31818618 | 31.818618 | 0.417 | BB | BB | BB | BB | BB | BB | AB | AB | AB | AB |
| 13 | SNP_A-1685897 | rs4941700 | 32383381 | 32.383381 | 0.262 | BB | BB | BB | BB | BB | BB | BB | BB | BB | BB |
| 13 | SNP_A-1664201 | rs1538001 | 33683068 | 33.683068 | 0.274 | BB | BB | BB | BB | BB | BB | BB | BB | BB | BB |
| 13 | SNP_A-1742432 | rs6563348 | 35588714 | 35.588714 | 0.397 | AA | AA | BB | BB | BB | BB | AB | AB | BB | BB |
| 13 | SNP_A-1709846 | rs2224655 | 36217500 | 36.2175 | 0.298 | BB | BB | BB | BB | BB | BB | AB | AB | AA | AA |
| 13 | SNP_A-1719156 | rs1359214 | 36774982 | 36.774982 | 0.452 | AB | AB | AA | AA | AA | AA | AB | AB | AB | AB |
| 13 | SNP_A-1699940 | rs10507466 | 37361657 | 37.361657 | 0.75 | AA | AA | AA | AA | AA | AA | AB | AB | AB | AB |
| 13 | SNP_A-1757710 | rs2197879 | 38143188 | 38.143188 | 0.286 | AB | AB | BB | BB | BB | BB | BB | BB | AA | AA |
| 13 | SNP_A-1725889 | rs4566029 | 39136387 | 39.136387 | 0.691 | AA | AA | AA | AA | AA | AA | AB | AB | AA | AA |
| 13 | SNP_A-1648291 | rs7322754 | 40220977 | 40.220977 | 0.31 | BB | BB | BB | AB | AB | AB | BB | BB | BB | BB |
| 13 | SNP_A-1644487 | rs1409075 | 42143450 | 42.14345 | 0.5 | AB | AB | AB | AB | AB | AB | AA | AA | AA | AA |
| 13 | SNP_A-1692131 | rs9316020 | 42892291 | 42.892291 | 0.274 | BB | BB | AB | AB | AB | AB | BB | BB | BB | BB |
| 13 | SNP_A-1683729 | rs9285153 | 43710570 | 43.71057 | 0.536 | BB | BB | BB | BB | BB | BB | AB | AB | AB | AB |
| 13 | SNP_A-1675092 | rs10507544 | 46298746 | 46.298746 | 0.286 | BB | BB | BB | BB | BB | BB | AB | AB | AB | AB |
| 13 | SNP_A-1706220 | rs1983805 | 48609971 | 48.609971 | 0.655 | AA | AA | AA | AA | AA | AA | BB | AB | AA | AA |
| 13 | SNP_A-1656586 | rs1359613 | 49664241 | 49.664241 | 0.381 | AA | AB | AA | AA | AA | AA | BB | BB | AB | AB |
| 13 | SNP_A-1687875 | rs9316513 | 50452286 | 50.452286 | 0.643 | AA | AB | AA | AA | AA | AA | BB | AB | AA | AA |
| 13 | SNP_A-1699260 | rs1891948 | 52537146 | 52.537146 | 0.429 | BB | BB | AA | AA | AA | AA | AB | BB | BB | BB |
| 13 | SNP_A-1670827 | rs9316642 | 53093973 | 53.093973 | 0.571 | AA | AB | BB | BB | BB | BB | BB | BB | BB | BB |
| 13 | SNP_A-1664927 | rs1010947 | 53921670 | 53.92167 | 0.702 | AA | AB | AA | AA | AA | AA | AA | AA | AA | AA |
| 13 | SNP_A-1686045 | rs10507599 | 54585799 | 54.585799 | 0.286 | AA | AB | BB | BB | BB | BB | BB | BB | BB | BB |
| 13 | SNP_A-1686285 | rs2253408 | 55216697 | 55.216697 | 0.75 | AA | AA | AB | AB | AB | AB | AB | AB | BB | BB |
| 13 | SNP_A-1668215 | rs959745 | 56718869 | 56.718869 | 0.274 | BB | BB | BB | BB | BB | BB | BB | AB | BB | BB |
| 13 | SNP_A-1706400 | rs10492603 | 57769822 | 57.769822 | 0.679 | AA | AA | BB | BB | BB | BB | AA | AA | AA | AA |
| 13 | SNP_A-1695368 | rs2786664 | 59574054 | 59.574054 | 0.417 | BB | BB | BB | BB | BB | BB | BB | BB | AA | AA |
| 13 | SNP_A-1690895 | rs3102221 | 60652316 | 60.652316 | 0.488 | AA | AB | AB | AB | AB | AB | AA | AA | AA | AA |
| 13 | SNP_A-1731184 | rs7323089 | 61693413 | 61.693413 | 0.56 | AA | AA | AA | AA | AA | AA | AA | AB | AA | AA |
| 13 | SNP_A-1697063 | rs2134898 | 62767058 | 62.767058 | 0.25 | BB | BB | AA | AA | AA | AA | BB | BB | BB | BB |
| 13 | SNP_A-1707522 | rs9317406 | 63717021 | 63.717021 | 0.417 | BB | AB | BB | BB | BB | BB | BB | BB | AB | AB |
| 13 | SNP_A-1645393 | rs7321823 | 65570977 | 65.570977 | 0.679 | BB | BB | AA | AA | AA | AA | AA | AA | AA | AA |
| 13 | SNP_A-1726077 | rs10492592 | 66385683 | 66.385683 | 0.714 | AA | AB | AB | AB | AB | AB | AA | AA | AB | AB |
| 13 | SNP_A-1650731 | rs176343 | 68069259 | 68.069259 | 0.702 | AA | AB | AA | AA | AA | AA | AA | AA | AA | AA |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 13 | SNP_A-1705084 | rs2782448 | 68801734 | 68.801734 | 0.643 | AA | AA | AA | AA | AA | AA | AA | AA | AA | AA |
| 13 | SNP_A-1715042 | rs3909263 | 71753222 | 71.753222 | 0.321 | BB | BB | AB | AB | AB | AB | AA | AA | BB | BB |
| 13 | SNP_A-1732673 | rs10507812 | 72886773 | 72.886773 | 0.75 | AA | AA | AB | AB | AB | AB | BB | BB | AA | AA |
| 13 | SNP_A-1713643 | rs9318226 | 73391987 | 73.391987 | 0.419 | BB | BB | AA | AA | AA | AA | AA | AA | BB | BB |
| 13 | SNP_A-1756880 | rs9318324 | 74649787 | 74.649787 | 0.658 | AA | AA | BB | BB | BB | BB | AA | AA | AB | AB |
| 13 | SNP_A-1685215 | rs10507835 | 75353682 | 75.353682 | 0.691 | AA | AA | AA | AA | AA | AA | BB | AB | AA | AA |
| 13 | SNP_A-1679595 | rs1952548 | 76037205 | 76.037205 | 0.333 | BB | BB | BB | BB | BB | BB | BB | BB | BB | BB |
| 13 | SNP_A-1687191 | rs7326108 | 77781442 | 77.781442 | 0.393 | AB | AB | AA | AA | AA | AA | BB | BB | AB | AB |
| 13 | SNP_A-1680379 | rs3903388 | 78802822 | 78.802822 | 0.393 | BB | BB | AB | AB | AB | AB | AA | AA | BB | BB |
| 13 | SNP_A-1664955 | rs1215462 | 79594011 | 79.594011 | 0.536 | BB | BB | AB | AB | AB | AB | AB | AB | BB | BB |
| 13 | SNP_A-1727874 | rs1744600 | 80158809 | 80.158809 | 0.631 | AB | AB | AB | AB | AB | AB | BB | BB | AA | AA |
| 13 | SNP_A-1710116 | rs10507917 | 80741431 | 80.741431 | 0.488 | AA | AA | AA | AA | AA | AA | BB | BB | AB | AB |
| 13 | SNP_A-1663633 | rs9318868 | 81947326 | 81.947326 | 0.643 | AB | AB | AA | AA | AA | AA | AA | AA | AB | AB |
| 13 | SNP_A-1693530 | rs9319022 | 83601961 | 83.601961 | 0.345 | BB | BB | AB | AB | AB | AB | AB | AB | AB | AB |
| 13 | SNP_A-1706422 | rs1331567 | 84793816 | 84.793816 | 0.56 | AA | AA | AA | AA | AA | AA | AA | AA | AA | AA |
| 13 | SNP_A-1733077 | rs995475 | 87558036 | 87.558036 | 0.357 | AB | AB | BB | BB | BB | BB | AB | AB | BB | BB |
| 13 | SNP_A-1679861 | rs1113478 | 88908389 | 88.908389 | 0.417 | AA | AA | AB | AB | AB | AB | AB | AB | AB | AB |
| 13 | SNP_A-1649205 | rs665530 | 90571947 | 90.571947 | 0.726 | AA | AA | AA | AA | AA | AA | AB | AB | AA | AA |
| 13 | SNP_A-1726887 | rs1926489 | 91465990 | 91.46599 | 0.524 | AB | AB | AA | AA | AA | AA | AA | AA | AB | AB |
| 13 | SNP_A-1714183 | rs913005 | 92275844 | 92.275844 | 0.607 | AB | AB | BB | BB | BB | BB | AA | AA | AA | AA |
| 13 | SNP_A-1701716 | rs9301876 | 92819688 | 92.819688 | 0.56 | AA | AA | BB | BB | BB | BB | AA | AA | AA | AA |
| 13 | SNP_A-1681625 | rs1412938 | 93661657 | 93.661657 | 0.726 | AA | AA | AA | AA | AA | AA | AA | AA | AA | AA |
| 13 | SNP_A-1648409 | rs9302001 | 94261393 | 94.261393 | 0.274 | AA | AA | BB | BB | BB | BB | AB | AB | BB | BB |
| 13 | SNP_A-1741482 | rs7324781 | 95032754 | 95.032754 | 0.405 | AB | AB | BB | BB | AB | AB | BB | BB | BB | BB |
| 13 | SNP_A-1661319 | rs4603415 | 96610639 | 96.610639 | 0.631 | AB | AB | AA | AA | AA | AA | AB | AB | AA | AB |
| 13 | SNP_A-1664929 | rs285067 | 97536416 | 97.536416 | 0.691 | AA | AA | BB | BB | BB | BB | AA | AA | AA | AA |
| 13 | SNP_A-1709292 | rs1886553 | 98448739 | 98.448739 | 0.486 | BB | BB | AA | AA | AB | AB | AA | AA | BB | AB |
| 13 | SNP_A-1749428 | rs2760306 | 99841672 | 99.841672 | 0.298 | BB | BB | BB | BB | BB | BB | AB | AB | BB | BB |
| 13 | SNP_A-1703098 | rs10508075 | 101237184 | 101.237184 | 0.464 | AA | AB | AA | AA | AB | AB | AB | AB | AA | AA |
| 13 | SNP_A-1680317 | rs1015795 | 102023701 | 102.023701 | 0.488 | AA | AB | BB | BB | BB | BB | AA | AA | BB | BB |
| 13 | SNP_A-1704124 | rs279927 | 102539019 | 102.539019 | 0.643 | AA | AA | AA | AA | AA | AA | AA | AA | BB | AB |
| 13 | SNP_A-1752530 | rs1033147 | 103460337 | 103.460337 | 0.333 | AA | AA | BB | BB | BB | BB | BB | BB | BB | BB |
| 13 | SNP_A-1654228 | rs9300981 | 104440279 | 104.440279 | 0.286 | BB | AB | BB | BB | BB | BB | AB | AB | BB | AB |
| 13 | SNP_A-1715354 | rs7318881 | 105459909 | 105.459909 | 0.671 | BB | BB | AA | AA | AA | AA | BB | BB | BB | BB |
| 13 | SNP_A-1645715 | rs7327250 | 106243682 | 106.243682 | 0.329 | BB | AB | BB | BB | BB | BB | BB | AB | BB | BB |
| 13 | SNP_A-1756346 | rs1320446 | 106965333 | 106.965333 | 0.679 | BB | BB | BB | BB | AB | AB | BB | AB | AA | AA |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 13 | SNP_A-1732084 | rs231604 | 107524007 | 107.524007 | 0.381 | AA | AA | BB | BB | BB | BB | BB | BB | BB | BB |
| 13 | SNP_A-1681321 | rs4772985 | 108080882 | 108.080882 | 0.25 | BB | BB | BB | BB | BB | BB | BB | BB | BB | BB |
| 13 | SNP_A-1648777 | rs10492480 | 108947427 | 108.947427 | 0.333 | BB | BB | AA | AA | AA | AA | AA | AA | BB | BB |
| 13 | SNP_A-1654860 | rs2183850 | 110513987 | 110.513987 | 0.714 | BB | BB | AA | AA | AA | AA | BB | BB | AA | AA |
| 14 | SNP_A-1733261 | rs1952805 | 19586195 | 19.586195 | 0.345 | BB | BB | BB | BB | BB | BB | BB | BB | AB | AB |
| 14 | SNP_A-1702470 | rs1923 | 22511019 | 22.511019 | 0.429 | BB | AB | AA | AA | AA | AA | AB | AB | AA | AA |
| 14 | SNP_A-1645139 | rs4983041 | 24495978 | 24.495978 | 0.595 | BB | AB | AB | AB | AB | AB | AA | AB | AB | AB |
| 14 | SNP_A-1676969 | rs10483331 | 26546808 | 26.546808 | 0.417 | AB | AB | BB | BB | BB | BB | AB | AB | AA | AA |
| 14 | SNP_A-1680111 | rs4981658 | 27234585 | 27.234585 | 0.732 | AA | AA | AA | AA | AA | AA | AB | AB | AA | AA |
| 14 | SNP_A-1734437 | rs2333423 | 28146939 | 28.146939 | 0.381 | AB | AB | BB | BB | BB | BB | BB | BB | BB | BB |
| 14 | SNP_A-1669916 | rs10483350 | 28885906 | 28.885906 | 0.738 | AA | AA | BB | BB | BB | AA | AA | AA | AA | AA |
| 14 | SNP_A-1732697 | rs225842 | 29622687 | 29.622687 | 0.441 | AB | AB | BB | BB | BB | BB | AB | AB | AB | AB |
| 14 | SNP_A-1656700 | rs1278891 | 31464813 | 31.464813 | 0.595 | AA | AA | AB | AA | AB | AB | BB | BB | AB | AB |
| 14 | SNP_A-1740154 | rs9322929 | 33377471 | 33.377471 | 0.345 | AB | AB | AB | BB | AB | AB | BB | BB | BB | BB |
| 14 | SNP_A-1757044 | rs799493 | 34621626 | 34.621626 | 0.691 | AB | AB | AB | BB | AB | AB | AA | AA | AA | AA |
| 14 | SNP_A-1676887 | rs847498 | 35546428 | 35.546428 | 0.607 | AA | AA | AA | AA | AA | AA | AA | AA | AA | AA |
| 14 | SNP_A-1665507 | rs1950361 | 36101975 | 36.101975 | 0.329 | AB | AB | BB | BB | BB | BB | AB | AB | AB | AB |
| 14 | SNP_A-1705178 | rs4901596 | 37659956 | 37.659956 | 0.667 | AB | AB | AA | AA | AA | AA | AB | AB | BB | BB |
| 14 | SNP_A-1654996 | rs6571869 | 38248210 | 38.24821 | 0.679 | AA | AA | AB | AB | AB | AB | AB | AB | AA | AA |
| 14 | SNP_A-1708854 | rs10483511 | 39587714 | 39.587714 | 0.571 | AB | AB | AB | AB | AB | AB | AB | AB | AB | AB |
| 14 | SNP_A-1653001 | rs10498360 | 40670723 | 40.670723 | 0.476 | AB | AB | BB | BB | BB | BB | BB | BB | AB | AB |
| 14 | SNP_A-1753660 | rs1951874 | 41387217 | 41.387217 | 0.345 | AA | AA | AB | AB | AB | AB | BB | BB | AA | AA |
| 14 | SNP_A-1653419 | rs2010338 | 45895631 | 45.895631 | 0.655 | AA | AA | BB | BB | BB | BB | AA | AA | AA | AA |
| 14 | SNP_A-1663303 | rs10483573 | 46932227 | 46.932227 | 0.357 | BB | BB | AA | AA | AA | AA | AA | AA | AB | AB |
| 14 | SNP_A-1664801 | rs698340 | 47611853 | 47.611853 | 0.585 | AB | AB | AA | AA | AA | AA | AA | AA | BB | BB |
| 14 | SNP_A-1722201 | rs7146291 | 48172131 | 48.172131 | 0.274 | BB | BB | BB | BB | BB | BB | BB | BB | AB | AB |
| 14 | SNP_A-1650017 | rs8006972 | 48690753 | 48.690753 | 0.31 | BB | BB | AB | AB | AA | AB | AA | AA | AB | AB |
| 14 | SNP_A-1720778 | rs10498420 | 49483793 | 49.483793 | 0.476 | AB | AB | AB | AB | BB | AB | AB | AB | BB | BB |
| 14 | SNP_A-1743320 | rs963626 | 50157439 | 50.157439 | 0.691 | AA | AA | AA | AA | AA | AA | AB | AB | AA | AA |
| 14 | SNP_A-1641756 | rs1956574 | 51163026 | 51.163026 | 0.655 | AA | AA | AA | AA | AA | AA | AA | AA | AB | AB |
| 14 | SNP_A-1669704 | rs7151306 | 52273870 | 52.27387 | 0.607 | AB | AB | BB | BB | BB | BB | AA | AA | AB | AB |
| 14 | SNP_A-1748272 | rs877018 | 52892776 | 52.892776 | 0.451 | BB | BB | AB | AA | AA | AA | AB | AB | AB | AB |
| 14 | SNP_A-1714357 | rs1382978 | 55788938 | 55.788938 | 0.536 | AA | AA | BB | BB | BB | BB | AA | AA | AA | AA |
| 14 | SNP_A-1714205 | rs10483679 | 56503799 | 56.503799 | 0.61 | BB | AB | AB | AB | AB | AB | AB | AB | AB | AB |
| 14 | SNP_A-1654106 | rs238376 | 57129665 | 57.129665 | 0.357 | AA | AB | BB | BB | BB | BB | AA | AB | AB | AB |
| 14 | SNP_A-1690578 | rs10498488 | 58658876 | 58.658876 | 0.451 | BB | BB | AB | AB | BB | AB | AA | AA | AA | AA |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 14 | SNP_A-1690058 | rs9323353 | 59240800 | 59.2408 | 0.619 | AA | AA | AB | AB | AA | AB | AA | AA | AA | AA |
| 14 | SNP_A-1671347 | rs2296274 | 60986931 | 60.986931 | 0.75 | BB | AB | AA | AA | AA | AA | AA | AA | AB | AB |
| 14 | SNP_A-1755551 | rs9285590 | 61521469 | 61.521469 | 0.417 | AA | AA | AA | AA | AA | AA | BB | AB | BB | BB |
| 14 | SNP_A-1707294 | rs1271582 | 64634456 | 64.634456 | 0.441 | BB | BB | AA | AA | AA | AA | BB | BB | BB | BB |
| 14 | SNP_A-1648725 | rs10483805 | 67325404 | 67.325404 | 0.329 | BB | AB | AB | AB | BB | AB | BB | BB | AB | AB |
| 14 | SNP_A-1699466 | rs1956528 | 67858721 | 67.858721 | 0.631 | BB | BB | AA | AA | AA | AA | BB | AB | AB | AB |
| 14 | SNP_A-1682431 | rs749397 | 69414068 | 69.414068 | 0.262 | BB | BB | AA | AA | AA | AA | BB | BB | BB | BB |
| 14 | SNP_A-1674164 | rs2215132 | 71545542 | 71.545542 | 0.262 | AA | AB | BB | BB | BB | BB | AA | AA | AB | AB |
| 14 | SNP_A-1672631 | rs2803971 | 72182227 | 72.182227 | 0.713 | AA | AA | AA | AA | AA | AA | AA | AA | AB | AB |
| 14 | SNP_A-1648423 | rs1028258 | 75447775 | 75.447775 | 0.726 | AA | AA | AB | AB | BB | AB | AA | AA | AA | AA |
| 14 | SNP_A-1700204 | rs7152153 | 76265708 | 76.265708 | 0.286 | BB | BB | BB | BB | BB | BB | AA | AA | BB | BB |
| 14 | SNP_A-1701478 | rs7156671 | 76991628 | 76.991628 | 0.7 | AA | AA | AB | AB | BB | AB | AA | AA | BB | BB |
| 14 | SNP_A-1706776 | rs10483905 | 78043978 | 78.043978 | 0.429 | BB | BB | AA | AA | AA | AA | BB | BB | BB | BB |
| 14 | SNP_A-1667157 | rs997842 | 78614233 | 78.614233 | 0.679 | AA | AA | AA | AA | AA | AA | AB | AB | AB | AB |
| 14 | SNP_A-1722889 | rs2049826 | 79383063 | 79.383063 | 0.345 | BB | BB | BB | BB | BB | BB | BB | BB | BB | BB |
| 14 | SNP_A-1645339 | rs2372083 | 81860288 | 81.860288 | 0.452 | AB | AB | AA | AA | AA | AA | BB | AB | AB | AB |
| 14 | SNP_A-1704748 | rs2372424 | 83017248 | 83.017248 | 0.438 | AA | AA | BB | BB | BB | BB | AA | AA | BB | BB |
| 14 | SNP_A-1757272 | rs8003423 | 83533541 | 83.533541 | 0.643 | BB | BB | AB | AB | AA | AB | AA | AA | AA | AA |
| 14 | SNP_A-1644835 | rs1530325 | 84781909 | 84.781909 | 0.702 | AB | AB | AA | AA | AA | AA | AA | AB | AB | AB |
| 14 | SNP_A-1680733 | rs10498604 | 86238836 | 86.238836 | 0.298 | BB | BB | BB | BB | BB | BB | BB | BB | AB | AB |
| 14 | SNP_A-1702796 | rs8018273 | 86867956 | 86.867956 | 0.524 | AA | AA | BB | BB | BB | BB | AA | AA | AA | AA |
| 14 | SNP_A-1687761 | rs429923 | 87481126 | 87.481126 | 0.405 | BB | BB | AA | AA | AA | AA | AA | AA | BB | BB |
| 14 | SNP_A-1725723 | rs1742083 | 90256423 | 90.256423 | 0.321 | AB | AB | AB | AB | AB | AB | AB | AB | AB | AB |
| 14 | SNP_A-1661389 | rs10498627 | 91041872 | 91.041872 | 0.583 | AA | AA | BB | BB | BB | BB | AA | AA | AB | AB |
| 14 | SNP_A-1705392 | rs2148567 | 93244403 | 93.244403 | 0.286 | BB | BB | BB | BB | BB | BB | AA | AA | BB | BB |
| 14 | SNP_A-1734665 | rs1456988 | 97557760 | 97.55776 | 0.679 | AB | AB | AA | AA | AA | AA | AA | AA | BB | BB |
| 14 | SNP_A-1684765 | rs200331 | 98457298 | 98.457298 | 0.488 | AB | AB | AA | AA | AA | AA | AB | AB | AA | AA |
| 14 | SNP_A-1682935 | rs3918051 | 99023837 | 99.023837 | 0.61 | BB | BB | AA | AA | AA | AA | AB | AB | AA | AA |
| 14 | SNP_A-1734911 | rs10484072 | 102695759 | 102.695759 | 0.631 | AA | AA | AB | AB | AB | AB | BB | BB | AB | AB |
| 14 | SNP_A-1659209 | rs1048257 | 104475429 | 104.475429 | 0.667 | AA | AA | AB | AB | AB | AB | BB | BB | AB | AB |
| 15 | SNP_A-1669336 | rs1405186 | 21306806 | 21.306806 | 0.441 | BB | AB | BB | BB | BB | BB | BB | BB | BB | BB |
| 15 | SNP_A-1690082 | rs2169637 | 25517776 | 25.517776 | 0.262 | BB | BB | AA | AA | AA | AA | BB | BB | BB | BB |
| 15 | SNP_A-1643639 | rs10519635 | 27330404 | 27.330404 | 0.607 | BB | AB | AB | AB | AB | AB | BB | AB | AB | AB |
| 15 | SNP_A-1740804 | rs4779462 | 28026287 | 28.026287 | 0.598 | BB | BB | AB | AB | AB | AB | AA | AA | AA | AA |
| 15 | SNP_A-1722463 | rs2219507 | 29646927 | 29.646927 | 0.691 | AA | AA | AA | AA | AA | AA | BB | AB | AA | AA |
| 15 | SNP_A-1730684 | rs10519737 | 30756749 | 30.756749 | 0.381 | BB | BB | BB | BB | BB | BB | BB | BB | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 15 | SNP_A-1648795 | rs1343900 | 31431890 | 31.43189 | 0.667 | AA | AA | AB | AB | AB | AB | AA | AB | BB | BB |
| 15 | SNP_A-1755583 | rs10519956 | 32849133 | 32.849133 | 0.345 | AB | AB | BB | BB | BB | BB | BB | BB | AA | AB |
| 15 | SNP_A-1699406 | rs1948650 | 33827340 | 33.82734 | 0.738 | AA | AA | AA | AA | AA | AA | AB | AB | AA | AB |
| 15 | SNP_A-1645977 | rs10518868 | 34381353 | 34.381353 | 0.655 | AA | AA | AB | AB | AB | AB | AB | AB | AA | AA |
| 15 | SNP_A-1665819 | rs471122 | 41345866 | 41.345866 | 0.3 | AA | AA | BB | BB | BB | BB | BB | BB | AA | AB |
| 15 | SNP_A-1673073 | rs10519044 | 44169166 | 44.169166 | 0.381 | BB | BB | AB | AB | AB | AB | BB | BB | BB | BB |
| 15 | SNP_A-1740676 | rs493728 | 48678247 | 48.678247 | 0.441 | BB | BB | BB | BB | BB | BB | BB | BB | BB | BB |
| 15 | SNP_A-1709940 | rs1478200 | 51948279 | 51.948279 | 0.357 | BB | AB | BB | BB | BB | BB | AB | AB | BB | BB |
| 15 | SNP_A-1720532 | rs2553222 | 52657040 | 52.65704 | 0.691 | BB | BB | AA | AA | AA | AA | AB | AB | AA | AB |
| 15 | SNP_A-1654466 | rs4534776 | 55408068 | 55.408068 | 0.463 | AA | AA | AB | AB | AB | AB | AB | BB | BB | AB |
| 15 | SNP_A-1752856 | rs1550574 | 56000660 | 56.00066 | 0.536 | AA | AA | BB | BB | BB | BB | AA | AA | AA | AA |
| 15 | SNP_A-1735597 | rs2033721 | 58609267 | 58.609267 | 0.714 | AA | AB | AB | AB | AB | AB | AA | AA | AA | AB |
| 15 | SNP_A-1642536 | rs3935962 | 59611593 | 59.611593 | 0.536 | AA | AB | AA | AA | AA | AA | AA | AA | AA | AB |
| 15 | SNP_A-1726387 | rs10519148 | 60507655 | 60.507655 | 0.25 | BB | BB | BB | BB | BB | BB | BB | BB | BB | BB |
| 15 | SNP_A-1750348 | rs2652824 | 61207054 | 61.207054 | 0.286 | BB | BB | BB | BB | BB | BB | BB | BB | BB | BB |
| 15 | SNP_A-1741266 | rs10518707 | 65152676 | 65.152676 | 0.488 | AA | AB | AB | AB | AB | AB | AA | AA | AA | AA |
| 15 | SNP_A-1739192 | rs305002 | 67928959 | 67.928959 | 0.595 | AA | AA | AA | AA | AA | AA | BB | BB | BB | BB |
| 15 | SNP_A-1677047 | rs2128112 | 69973340 | 69.97334 | 0.262 | BB | BB | BB | BB | BB | BB | BB | BB | BB | BB |
| 15 | SNP_A-1698770 | rs3898352 | 74308825 | 74.308825 | 0.631 | BB | AB | AB | AB | AB | AB | BB | BB | AA | AA |
| 15 | SNP_A-1654378 | rs1446312 | 75199244 | 75.199244 | 0.738 | AA | AA | AA | AA | AA | AA | AB | AB | AA | AB |
| 15 | SNP_A-1657306 | rs7163689 | 76352533 | 76.352533 | 0.488 | AA | AB | AA | AA | AB | AB | AB | AB | BB | BB |
| 15 | SNP_A-1701268 | rs1001460 | 77291934 | 77.291934 | 0.56 | AA | AA | AB | AB | BB | AB | AB | AB | AA | AB |
| 15 | SNP_A-1689635 | rs1320323 | 79128502 | 79.128502 | 0.59 | AA | AA | AA | AA | AA | AA | AA | AA | AA | AA |
| 15 | SNP_A-1749864 | rs1846911 | 80255705 | 80.255705 | 0.329 | AA | AA | BB | BB | BB | BB | AB | AB | BB | BB |
| 15 | SNP_A-1714319 | rs10520585 | 83462510 | 83.46251 | 0.286 | BB | AB | AB | AB | AA | AB | BB | BB | BB | AB |
| 15 | SNP_A-1654264 | rs1961601 | 84030610 | 84.03061 | 0.31 | BB | BB | AB | AB | AA | AB | BB | BB | BB | AB |
| 15 | SNP_A-1650691 | rs1122907 | 84708371 | 84.708371 | 0.691 | AA | AA | AB | AB | BB | AB | AA | AA | AA | AA |
| 15 | SNP_A-1665669 | rs10520655 | 85887415 | 85.887415 | 0.595 | BB | AB | AA | AA | AA | AA | AA | AA | AA | AB |
| 15 | SNP_A-1694944 | rs3817428 | 87216251 | 87.216251 | 0.75 | AA | AA | AA | AA | AA | AA | AB | AB | AA | AA |
| 15 | SNP_A-1683397 | rs1079537 | 89675287 | 89.675287 | 0.452 | AB | AB | AB | AB | AA | AB | BB | BB | BB | BB |
| 15 | SNP_A-1752072 | rs10520710 | 90688998 | 90.688998 | 0.287 | BB | BB | BB | BB | BB | BB | AB | BB | AB | AB |
| 15 | SNP_A-1731798 | rs1989269 | 91611056 | 91.611056 | 0.305 | BB | BB | BB | BB | BB | BB | BB | BB | BB | BB |
| 15 | SNP_A-1728656 | rs10520754 | 92760413 | 92.760413 | 0.548 | AA | AA | AA | AA | AA | AA | AA | AA | AA | AA |
| 15 | SNP_A-1700188 | rs4321143 | 93957372 | 93.957372 | 0.262 | BB | BB | BB | BB | BB | BB | BB | BB | BB | BB |

TABLE 18-continued

Database S2.
Database S2 Heterozygosity or phESC (Abbreviated as "pC") Lines

| chromo-some | SNP ID | RS ID (dbSNP) | basepair | basepair (Mb) | Freq A in Caucasian | pC-1 | pC-1 donor | pC-3 | pC-4 | pC-5 | N3-5 donor | pC-6 | pC-6 donor | pC-7 | pC-7 donor |
|---|---|---|---|---|---|---|---|---|---|---|---|---|---|---|---|
| 15 | SNP_A-1686439 | rs1551466 | 99344619 | 99.344619 | 0.345 | AB | AB | AB | AB | AB | AB | BB | BB | AB | AB |
| 15 | SNP_A-1647533 | rs352716 | 100155950 | 100.15595 | 0.31 | AA | AA | BB | BB | BB | BB | BB | AB | AA | AA |

The results show heterozygosity of derived phESC lines and displays changes in genotype by comparison with the related donor genotype. Portions of heterozygous segments of the donor genome became homozygous in phESC. Chromosome-chromosome number; RS ID-RS number in dbSNP database; Base pair-base pair distance as recorded by Affimetrix GeneChip; Freq A in Cauc-the frequency of A allele in Caucasian population.

In prior research, parthenogenetic activation of mouse oocytes has resulted in homozygous embryonic stem cell lines (Lin et al., Stem Cells (2003) 21:152). In human oocytes, the suppression of the second meiotic division after oocyte parthenogenetic activation and the generation of diploid embryos does not lead to the derivation of wholly homozygous hES cells.

Based on the HLA-typing results, differentiated cells derived from all phESC lines should be wholly histocompatible with the oocyte donors, making this a method to create cells of therapeutic use (Table 19).

for neuron specific markers neurofiliment 68 (FIG. 4A), NCAM (FIG. 4B), beta III-tubulin (FIG. 4C) and the glial cell marker GFAP (FIGS. 4D, M). Differentiated cells were positive for mesoderm markers including alpha-actinin (FIG. 4G) and desmin (FIG. 4J), which are muscle specific markers, and the endothelial markers PECAM-1 (FIG. 4E) and VE-Cadherin (FIG. 4F). Endoderm differentiation is presented by positive staining of differentiated derivatives for alpha-feto-protein. These data demonstrate that phESC can be differentiated into the three germ layers that lead to all cell types of a human body.

TABLE 19

HLA-typing for phESC cell lines

| | MHC I | | | MHC II | | |
|---|---|---|---|---|---|---|
| | HLA-A | HLA-B | HLA-C | DRB1 | DQB1 | DQA1 |
| phESC-1 | A*01 | B*15(63) | Cw*04 | DRB1*12 | DQB1*06 | DQA1*01 |
| | A*02 | B*35 | Cw*0708 | DRB1*13 | DQB1*03 | DQA1*0505 |
| phESC-1 donor | A*01 | B*15(63) | Cw*04 | DRB1*12 | DQB1*06 | DQA1*01 |
| | A*02 | B*35 | Cw*0708 | DRB1*13 | DQB1*03 | DQA1*0505 |
| phESC-3, 4, 5 | A*02 | B*52 | Cw*03 | DRB1*01 | DQB1*05 | DQA1*0101 |
| | A*03 | B*22 | Cw*04 | DRB1*03 | DQB1*02 | DQA1*05 |
| phESC-3, 4, 5 donor | A*02 | B*52 | Cw*03 | DRB1*01 | DQB1*05 | DQA1*0101 |
| | A*03 | B*22 | Cw*04 | DRB1*03 | DQB1*02 | DQA1*05 |
| phESC-6 | A*02 | B*07 | Cw*04 | DRB1*04 | DQB1*06 | DQA1*01 |
| | A*03 | B*27 | Cw*07 | DRB1*15 | DQB1*03 | DQA1*03 |
| phESC-6 donor | A*02 | B*07 | Cw*04 | DRB1*04 | DQB1*06 | DQA1*01 |
| | A*03 | B*27 | Cw*07 | DRB1*15 | DQB1*03 | DQA1*03 |
| phESC-7 | A*01 | B*38 | Cw*06 | DRB1*13 | DQB1*06 | DQA1*0106 |
| | A*02 | B*57 | Cw*12 | DRB1*14 | DQB1*06 | DQA1*0103 |
| phESC-7 donor | A*01 | B*38 | Cw*06 | DRB1*13 | DQB1*06 | DQA1*0106 |
| | A*02 | B*57 | Cw*12 | DRB1*14 | DQB1*06 | DQA1*0103 |
| NSF | A*25 | B*15(62) | Cw*12 | DRB1*04 | DQB1*06 | DQA1*01 |
| | A*32 | B*18 | Cw*12 | DRB1*15 | DQB1*03 | DQA1*03 |

DNA-profiling of the genetic material derived from the human fibroblasts used as feeder cells revealed no contamination of the phESC cell lines with material from the human fibroblasts (Table 19).

The phESC-1 line remained undifferentiated during ten months of culture, spanning 35 passages. The other cell lines were successfully cultivated over at least 21 passages. The cells from all phESC lines formed cystic embryoid bodies in suspension culture and gave rise to derivatives of all three germ layers: ectoderm, mesoderm, and endoderm, after differentiation in vitro (FIG. 4). Approximately 5% of embryoid bodies from the phESC-1 line gave rise to beating cells five days following plating. The phESC-6 line produced pigmented epithelial-like cells (FIG. 4I, K). Ectoderm differentiation is presented by positive immunocytochemical staining The altered karyotype of phESC-7 may be a reason to exclude it form clinical use. Alterations of genomic imprinting in human embryos can contribute to the development of disorders linked to maternally or paternally expressed genes (Gabriel et al., Proc Natl Acad Sci USA (1998) 95:14857). In order to investigate other characteristics of the phESC lines, and to determine their suitability for use in cell therapy, imprinting analysis was performed.

Figure 3:
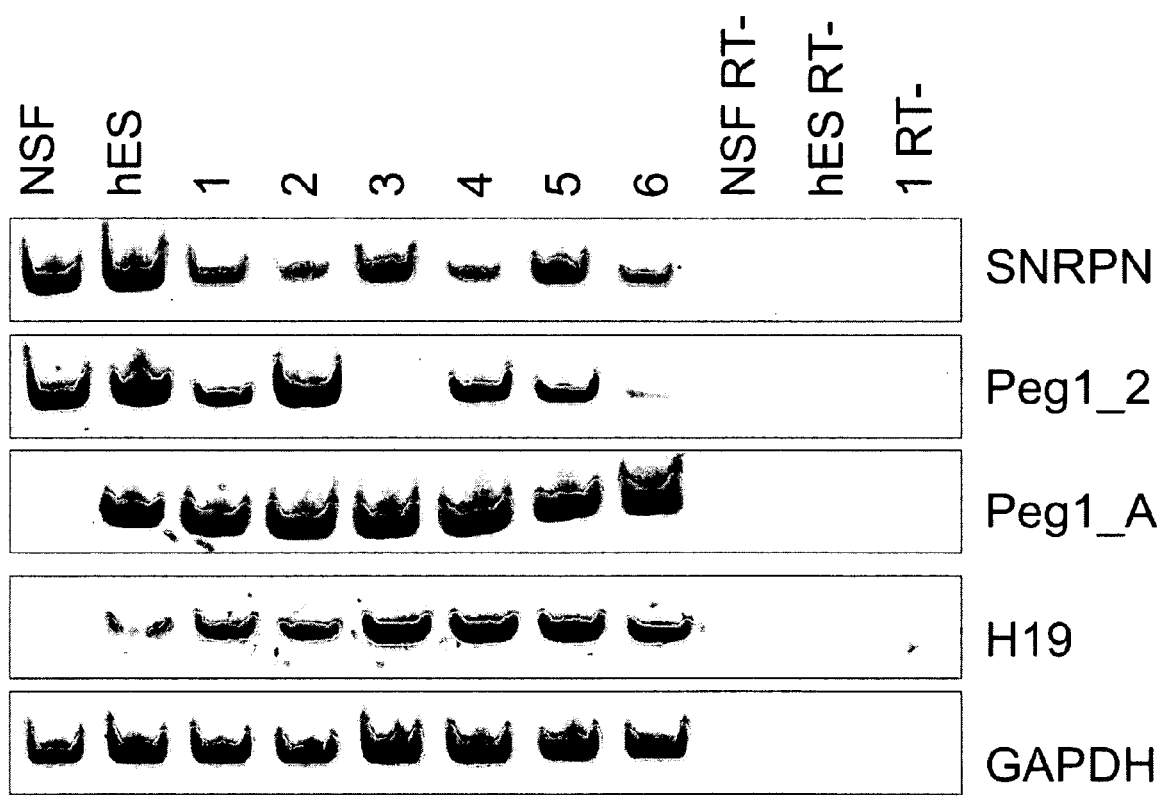
FIG. 3 shows a Northern blot characterizing the expression of genes associated with genomic imprinting. DNA probes: SNRPN, Peg1_2, Peg1_A, H19, and GAPDH (as an internal control). NSF, neonatal skin fibroblasts; hES, human embryonic stem cell line derived from fertilized oocytes; 1, phESC- 1; 2, phESC-3, 3, phESC-4, 4, phESC-5; 5, phESC-6; 6 phESC-7. NSF RT–, hES RT–, 1 RT– are negative controls.

Northern blots were made and screened with DNA probes SNRPN, Peg1_2, Peg1_A, H19, and GAPDH (as an internal control) as outlined above. Blotted nucleic acids were obtained from NSF, neonatal skin fibroblasts; hES, human embryonic stem cell line derived from fertilized oocytes; 1, phESC-1; 2, phESC-3, 3, phESC-4, 4, phESC-5; 5, phESC-6; 6 phESC-7. NSF RT-, hES RT-, 1 RT- are negative controls. FIG. 3 shows the results of the imprinting blot.

The maternal imprinting gene, Peg1_A shows strong binding in all of the cell lines tested. Weaker (relative to Peg1_A), but consistent binding was observed in all of the cell lines for the maternal imprinting gene H19. SNRPN shows binding predominantly in NSF, hES, phESC-4, and phESC-6. Peg1_2 shows binding predominantly in NSF, hES, phESC-1 (weaker signal), phESC-3, phESC-5, and phESC-6. GAPDH binding confirmed similar loading of RNA in all lanes.

Although the invention has been described with reference to the above examples, it will be understood that modifications and variations are encompassed within the spirit and scope of the invention. Accordingly, the invention is limited only by the following claims.

REFERENCES

1. J. Cibelli et al., Methods for making and using reprogrammed human somatic cell nuclei and autologous and isogenic human stem cells. US Patent Application No. 20030232430, Dec. 18, 2003.
2. H. Lin et al., Multilineage potential of homozygous stem cells derived from metaphase II oocytes. Stem Cells (2003) 21:153-161
3. K. E. Vrana et al., Nonhuman primate parthenogenetic stem cells. PNAS (2003) 100 (Suppl 1):11911-11916.
4. J. P. M. Dumoulin et al., Effect of oxygen concentration on human in vitro fertilization and embryo culture. Human Reproduction. (1999) 14(2):465-469.
5. B.Fischer and B. D. Bavister, Oxygen tension in the oviduct and uterus of rhesus monkeys, hamsters and rabbits. J Reprod Fertil (1993) 99:673-679.
6. D. I. Kaufman and J. A. Mitchell, Intauterine oxygen tension during oestrous cycle in the hamster: patterns of change. Comp Biochem Physiol Comp Physiol (1994) 107 (4): 673-678.
7. F. D. Houghton et al., Oxygen consumption and energy metabolism of the early mouse embryo. Mol Reprod Dev (1996) 44:476-485.
8. A. Van Soom et al., Prevalence of apoptosis and inner cell allocation in bovine embryos cultured under different oxygen tension with or without cysteine addition. Theriogenology (2002) 57(5):1453-1465.

What is claimed is:

1. A method of producing human stem cells comprising:
a) parthenogenetically activating a human oocyte, wherein activating comprises: i) contacting the oocyte with an ionophore at high $O_2$ tension and ii) contacting the oocyte with a serine-threonine kinase inhibitor under low $O_2$ tension;
b) cultivating the activated oocyte of step (a) at low $O_2$ tension until blastocyst formation;
c) transferring the blastocyst to a layer of feeder cells, and culturing the transferred blastocyst under high $O_2$ tension;
d) mechanically isolating an inner cell mass (ICM) from trophectoderm of the blastocyst of step (c); and
e) culturing the cells of the ICM of step (d) on a layer of feeder cells, wherein culturing step (e) is carried out under high $O_2$ tension, thereby producing human stem cells.

2. The method of claim 1, wherein low $O_2$ tension is maintained by incubation in a gas mixture environment comprising an $O_2$ concentration of about 2% $O_2$ to about 5% $O_2$.

3. The method of claim 2, wherein the gas mixture environment further comprises about 5% $CO_2$ and about 90% $N_2$ to 93% $N_2$.

4. The method of claim 1, wherein high $O_2$ tension is maintained by incubation in a gas mixture environment comprising about 5% $CO_2$ and about 20% $O_2$.

5. The method of claim 1, wherein the ionophore is selected from the group consisting of ionomycin and A23187.

6. The method of claim 1, wherein the serine-threonine kinase inhibitor is selected from the group consisting of staurosporine, 2-aminopurine, sphingosine, and 6-dimethylaminopurine (DMAP).

7. The method of claim 1, wherein the activating, isolating, and culturing steps are carried out under defined media conditions for therapeutic applications.

8. The method of claim 7, wherein the media comprises human umbilical cord serum.

9. The method of claim 8, wherein the media comprises about 10% human umbilical cord serum.

10. The method of claim 1, wherein the layer of feeder cells comprises human fibroblasts.

11. The method of claim 10, wherein the fibroblasts are postnatal human dermal fibroblasts.

12. The method of claim 10, wherein the feeder cells are inactivated with an antibiotic.

13. The method of claim 12, wherein the antibiotic is mitomycin C.

14. A method of activating a human metaphase II oocyte comprising;
a) incubating a human metaphase II oocyte in in vitro fertilization (IYF) media;
b) incubating the cell of step (a) in IVF media comprising an ionophore;
c) incubating the cell of step (b) in IYF media comprising a serine-threonine kinase inhibitor; and
d) incubating the cells of step (c) in fresh IVF medium until blastocyst formation,
wherein the incubating steps (a) and (b) are carried out under high $O_2$ tension, and wherein an inner cell mass (ICM) obtained from the blastocyst at step (d) produce culturable stem cells.

15. The method of claim 14, wherein the $O_2$ tension for incubating steps (c) and (d) is maintained by incubating the cells in a gas mixture environment comprising an $O_2$ concentration of about 2% $O_2$ to 5% $O_2$.

16. The method of claim 15, wherein the gas mixture environment further comprises about 5% $CO_2$ and about 90% $N_2$ to 93% $N_2$.

17. The method of claim 14, further comprising incubating the oocytes with hyaluronidase.

18. The method of claim 14, wherein incubating step (a) is carried out for about 2 hours at about 37° C.

19. The method of claim 14, wherein incubating step (b) is carried out for about 5 minutes at about 37° C.

20. The method of claim 14, wherein incubating step (c) is carried out for about 4 hours at about 37° C.

21. The method of claim 14, wherein incubating step (d) is carried out for about 24 hours at about 37° C.

22. The method of claim 14, wherein the IVF media is free of non-human products.

23. The method of claim 22, wherein the ionophore is selected from the group consisting of ionomycin and A23187.

24. The method of claim 23, wherein the ionophore is ionomycin.

25. The method of claim 22, wherein the serine-threonine kinase inhibitor is selected from the group consisting of staurosporine, 2-aminopurine, sphingosine, and 6- dimethylaminopurine (DMAP).

26. The method of claim 25, wherein the serine-threonine kinase inhibitor is DMAP.

* * * * *

```
                        SEQUENCE LISTING

<160> NUMBER OF SEQ ID NOS: 8

<210> SEQ ID NO 1
<211> LENGTH: 1650
<212> TYPE: DNA
<213> ORGANISM: Homo sapiens

<400> SEQUENCE: 1
tataattaaa tattttataa ttaaaatatt tataattaaa tattttataa ttaaaatatt      60
tataattaaa tattttataa ttaaaatatt tataattaaa tattttataa ttaaaatatt     120
tataattaaa tattttataa ttaaaatatt tataattaaa tattttataa ttaaaatatt     180
tataattaaa tattttataa ttaaaatatt tataattaaa tattttataa ttaaaatatt     240
tataattaaa tattttataa ttaaaatatt tataattaaa tattttataa ttaaaatatt     300
tataattaaa tattttataa ttaaaatatt tataattaaa tattttataa ttaaaatatt     360
tataattaaa tattttataa ttaaaatatt tataattaaa tattttataa ttaaaatatt     420
tataattaaa tattttataa ttaaaatatt tataattaaa tattttataa ttaaaatatt     480
tataattaaa tattttataa ttaaaatatt tataattaaa tattttataa ttaaaatatt     540
tataattaaa tattttataa ttaaaatatt tataattaaa tattttataa ttaaaatatt     600
tataattaaa tattttataa ttaaaatatt tataattaaa tattttataa ttaaaatatt     660
tataattaaa tattttataa ttaaaatatt tataattaaa tattttataa ttaaaatatt     720
tataattaaa tattttataa ttaaaatatt tataattaaa tattttataa ttaaaatatt     780
tataattaaa tattttataa ttaaaatatt tataattaaa tattttataa ttaaaatatt     840
tataattaaa tattttataa ttaaaatatt tataattaaa tattttataa ttaaaatatt     900
tataattaaa tattttataa ttaaaatatt tataattaaa tattttataa ttaaaatatt     960
tataattaaa tattttataa ttaaaatatt tataattaaa tattttataa ttaaaatatt    1020
tataattaaa tattttataa ttaaaatatt tataattaaa tattttataa ttaaaatatt    1080
tataattaaa tattttataa ttaaaatatt tataattaaa tattttataa ttaaaatatt    1140
```

| | |
|---|---|
| tataattaaa tattttataa ttaaaatatt tataattaaa tattttataa ttaaaatatt | 1200 |
| tataattaaa tattttataa ttaaaatatt tataattaaa tattttataa ttaaaatatt | 1260 |
| tataattaaa tattttataa ttaaaatatt tataattaaa tattttataa ttaaaatatt | 1320 |
| tataattaaa tattttataa ttaaaatatt tataattaaa tattttataa ttaaaatatt | 1380 |
| tataattaaa tattttataa ttaaaatatt tataattaaa tattttataa ttaaaatatt | 1440 |
| tataattaaa tattttataa ttaaaatatt tataattaaa tattttataa ttaaaatatt | 1500 |
| tataattaaa tattttataa ttaaaatatt tataattaaa tattttataa ttaaaatatt | 1560 |
| tataattaaa tattttataa ttaaaatatt tataattaaa tattttataa ttaaaatatt | 1620 |
| tataattaaa tattttataa ttaaaatatt | 1650 |

<210> SEQ ID NO 2
<211> LENGTH: 615
<212> TYPE: DNA
<213> ORGANISM: Homo sapiens

<400> SEQUENCE: 2

| | |
|---|---|
| gaagacagac cacaggaaga cagaccacag gaagacagac cacaggaaga cagaccacag | 60 |
| gaagacagac cacaggaaga cagaccacag gaagacagac cacaggaaga cagaccacag | 120 |
| gaagacagac cacaggaaga cagaccacag gaagacagac cacaggaaga cagaccacag | 180 |
| gaagacagac cacaggaaga cagaccacag gaagacagac cacaggaaga cagaccacag | 240 |
| gaagacagac cacaggaaga cagaccacag gaagacagac cacaggaaga cagaccacag | 300 |
| gaagacagac cacaggaaga cagaccacag gaagacagac cacaggaaga cagaccacag | 360 |
| gaagacagac cacaggaaga cagaccacag gaagacagac cacaggaaga cagaccacag | 420 |
| gaagacagac cacaggaaga cagaccacag gaagacagac cacaggaaga cagaccacag | 480 |
| gaagacagac cacaggaaga cagaccacag gaagacagac cacaggaaga cagaccacag | 540 |
| gaagacagac cacaggaaga cagaccacag gaagacagac cacaggaaga cagaccacag | 600 |
| gaagacagac cacag | 615 |

<210> SEQ ID NO 3
<211> LENGTH: 60
<212> TYPE: DNA
<213> ORGANISM: Homo sapiens

<400> SEQUENCE: 3

| | |
|---|---|
| agatagatag atagatagat agatagatag atagatagat agatagatag atagatagat | 60 |

<210> SEQ ID NO 4
<211> LENGTH: 56
<212> TYPE: DNA
<213> ORGANISM: Homo sapiens

<400> SEQUENCE: 4

| | |
|---|---|
| agatagatag atagatagat agatagatag atagatagat agatagatag atagat | 56 |

<210> SEQ ID NO 5
<211> LENGTH: 60
<212> TYPE: DNA
<213> ORGANISM: Homo sapiens

<400> SEQUENCE: 5

| | |
|---|---|
| atctatctat ctatctatct atctatctat ctatctatct atctatctat ctatctatct | 60 |

```
<210> SEQ ID NO 6
<211> LENGTH: 84
<212> TYPE: DNA
<213> ORGANISM: Homo sapiens

<400> SEQUENCE: 6
agatagatag atagatagat agatagatag atagatagat agatagatag atagatagat        60
agatagatag atagatagat agat                                                84

<210> SEQ ID NO 7
<211> LENGTH: 52
<212> TYPE: DNA
<213> ORGANISM: Homo sapiens

<400> SEQUENCE: 7
aatgaatgaa tgaatgaatg aatgaatgaa tgaatgaatg aatgaatgaa tg                 52

<210> SEQ ID NO 8
<211> LENGTH: 44
<212> TYPE: DNA
<213> ORGANISM: Homo sapiens

<400> SEQUENCE: 8
aatgaatgaa tgaatgaatg aatgaatgaa tgaatgaatg aatg                         44
```